US008673896B2

(12) United States Patent
Bunnelle et al.

(10) Patent No.: US 8,673,896 B2
(45) Date of Patent: Mar. 18, 2014

(54) BENZODIAZEPINE AND PYRIDODIAZEPINE DERIVATIVES

(75) Inventors: William H. Bunnelle, Mundelein, IL (US); Marc Scanio, Lindenhurst, IL (US); Jason T. Brewer, Zion, IL (US); Ying Wang, Lake Villa, IL (US); Irini Akritopoulou-Zanze, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/092,332

(22) Filed: Apr. 22, 2011

(65) Prior Publication Data

US 2011/0288069 A1 Nov. 24, 2011

Related U.S. Application Data

(60) Provisional application No. 61/326,696, filed on Apr. 22, 2010, provisional application No. 61/366,959, filed on Jul. 23, 2010.

(51) Int. Cl.
*A61K 31/55* (2006.01)
*C07D 491/00* (2006.01)
*C07D 487/12* (2006.01)

(52) U.S. Cl.
USPC .......................... 514/220; 540/497; 540/559

(58) Field of Classification Search
USPC .................. 540/497, 559; 514/220
See application file for complete search history.

(56) References Cited

FOREIGN PATENT DOCUMENTS

WO 2008067863 A2 6/2008

OTHER PUBLICATIONS

Mueller et al. (Helvetica Chimica Acta (1982), 65(7), 2118-32). Abstract.*
Bachurin S. et al., "Antihistamine Agent Dimebon as a Novel Neuroprotector and a Cognition Enhancer," Annals of the New York Academy of Sciences, 2001, vol. 939, pp. 425-435.
Beal M.F., "Mitochondria and Neurodegeneration," Novartis Foundation Symposium, 2007, vol. 287, pp. 183-196.
Berge, S. M. et al., "Pharmaceutical Salts," Journal of Pharmaceutical Sciences, 1977, vol. 66 (1), pp. 1-19.
Bitner R.S., et al., "Broad-Spectrum Efficacy Across Cognitive Domains by Alpha7 Nicotinic Acetylcholine Receptor Agonism Correlates with Activation of ERK1/2 and CREB Phosphorylation Pathways," The Journal of Neuroscience, 2007, vol. 27 (39), pp. 10578-10587.
Borroni B., et al., "Combined Biomarkers for Early Alzheimer Disease Diagnosis," Current Medicinal Chemistry, 2007, vol. 14 (11), pp. 1171-1178.
Bouwman F.H., et al., "Longitudinal Changes of CSF Biomarkers in Memory Clinic Patients," Neurology, 2007, vol. 69 (10), pp. 1006-1011.

Buccafusco J.J., et al., "Profile of Nicotinic Acetylcholine Receptor Agonists ABT-594 and A-582941, with Differential Subtype Selectivity, on Delayed Matching Accuracy by Young Monkeys," Biochemical Pharmacology, 2007, vol. 74 (8), pp. 1202-1211.
Burns A., et al., "Dimebon in Alzheimer's Disease: Old Drug for New Indication," Lancet, 2008, vol. 372 (9634), pp. 179-180.
Cavalli A., et al., "Multi-Target Directed Ligands to Combat Neurodegenerative Diseases," Journal of Medicinal Chemistry, 2008, vol. 51 (3), pp. 347-372.
Chaplan S.R., et al., "Quantitative Assessment of Tactile Allodynia in the Rat Paw," Journal of Neuroscience Methods, 1994, vol. 53 (1), pp. 55-63.
Chauvier D., et al., "Upstream Control of Apoptosis by Caspase-2 in Serum-Deprived Primary Neurons.," Apoptosis, 2005, vol. 10 (6), pp. 1243-1259.
Chu W., et al., "N-Benzylisatin Sulfonamide Analogues As Potent Caspase-3 Inhibitors: Synthesis, in Vitro Activity, and Molecular Modeling Studies," Journal of Medicinal Chemistry, 2005, vol. 48 (24), pp. 7637-7647.
Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
Csermely P., et al., "The Efficiency of Multi-Target Drugs: The Network Approach Might Help Drug Design," Trends in Pharmacological Sciences, 2005, vol. 26 (4), pp. 178-182.
Cummings, J. et al., "18-month data from an open-label extension of a one-year controlled trial of dimebon in patients with mild-to-moderate Alzheimer's disease," Presented at the International Conference on Alzheimer's Disease (ICAD), Chicago, IL, USA, 2.
Cummings J. I., et al., "Disease-Modifying Therapies for Alzheimer Disease: Challenges to Early Intervention," Neurology, 2007, vol. 69 (16), pp. 1622-1634.
Dixon W.J., "Efficient Analysis of Experimental Observations," Annual Review of Pharmacology and Toxicology, 1980, vol. 20, pp. 441-462.
Doody R.S., et al., "Effect of Dimebon on Cognition, Activities of Daily Living, Behaviour, and Global Function in Patients with Mild-to-Moderate Alzheimer's Disease: A Randomised, Double-Blind, Placebo-Controlled Study," Lancet, 2008, vol. 372 (9634), pp. 207-215.

(Continued)

Primary Examiner — Bruck Kifle
(74) Attorney, Agent, or Firm — Lisa V. Mueller; Michael Best & Friedrich LLP

(57) ABSTRACT

The present application relates to benzodiazepine and pyridodiazepine derivatives of formula (I)

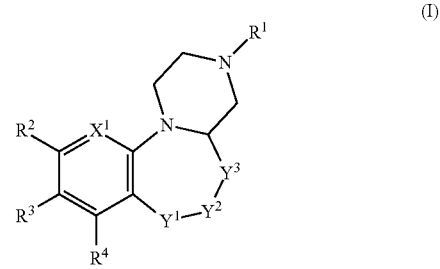

wherein $R^1$, $R^2$, $R^3$, $R^4$, $X^1$, $Y^1$, $Y^2$, and $Y^3$ are as defined in the specification. The present application also relates to compositions comprising such compounds, and methods of treating disease conditions using such compounds and compositions, and methods for identifying such compounds.

18 Claims, No Drawings

(56) References Cited

OTHER PUBLICATIONS

Goetz J., et al., "Animal Models of Alzheimer's Disease and Frontotemporal Dementia," Nature Reviews Neuroscience, 2008, vol. 9 (7), pp. 532-544.

Green K.N., et al., "Linking Calcium to A Beta and Alzheimer's Disease," Neuron, 2008, vol. 59 (2), pp. 190-194.

Greene T.W., et al., in: Protective Groups in Organic Synthesis, 3rd Edition, John Wiley and Sons, Inc., 1999, Preface, Table of Contents, Abbreviations.

Grigore V.V., et al., "Comparative Study of Action Mechanisms of Dimebon and Memantine on AMPA- and NMDA-Subtypes Glutamate Receptors in Rat Cerebral Neurons," Bulletin of Experimental Biology and Medicine, 2003, vol. 136(5), pp. 474-477.

Hu M., et al., "High Content Screen Microscopy Analysis of A Beta 1-42-Induced Neurite Outgrowth Reduction in Rat Primary Cortical Neurons: Neuroprotective Effects of Alpha 7 Neuronal Nicotinic Acetylcholine Receptor Ligands," Brain Research, 2007, vol. 1151, pp. 227-235.

Hu M., et al., "Role of GSK-3Beta Activation and Alpha7 nAChRs in Abeta(1-42)-Induced Tau Phosphorylation in PC12 Cells," Journal of Neurochemistry, 2008, vol. 106 (3), pp. 1371-1377.

Hung, D. et al., "Dimebon: A phase 3 investigational agent for Alzheimer's disease with a novel mitochondrial mechanism of action," Presented at the International Conference on Alzheimer's Disease, Chicago, IL, USA, 2008, pp. S4-04-05.

Juhaszova M., et al., "Glycogen Synthase Kinase-3beta Mediates Convergence of Protection Signaling to Inhibit the Mitochondrial Permeability Transition Pore," The Journal of Clinical Investigation, 2004, vol. 113 (11), pp. 1535-1549.

Juhaszova M., et al., "The Identity and Regulation of the Mitochondrial Permeability Transition Pore: where the Known Meets the Unknown," Annals of the New York Academy of Sciences, 2008, vol. 1123, pp. 197-212.

Kar S., et al., "Amyloid Beta Peptides and Central Cholinergic Neurons: Functional Interrelationship and Relevance to Alzheimer's Disease Pathology," Progress in brain research, 2004, vol. 145, pp. 261-274.

Kim S.H., et al., "An Experimental Model for Peripheral Neuropathy Produced by Segmental Spinal Nerve Ligation in the Rat," Pain, 1992, vol. 50 (3), pp. 355-363.

King J.A., et al., "The Preparation of Some Pyridazonyl Acids," Journal of the American Chemical Society, 1952, vol. 74, pp. 3222-3224.

Lermontova N.N., et al., "Dimebon and Tacrine Inhibit Neurotoxic Action of Beta-Amyloid in Culture and Block L-Type Ca(2+) Channels," Bulletin of Experimental Biology and Medicine, 2001, vol. 132 (11), pp. 1079-1078.

Lermontova N.N., et al., "Dimebon Improves Learning in Animals with Experimental Alzheimer's Disease," Bulletin of Experimental Biology and Medicine, 2000, vol. 129 (6), pp. 544-546.

Lin C.H., et al., "Bax-Regulated Mitochondrial-Mediated Apoptosis is Responsible for the in Vitro Ischemia Induced Neuronal Cell Death of SPRAGUE Dawley Rat," Neuroscience Letter, 2005, vol. 387 (1), pp. 22-27.

Linseman D.A., et al., "Glycogen Synthase Kinase-3beta Phosphorylates Bax and Promotes Its Mitochondrial Localization During Neuronal Apoptosis," The Journal of Neuroscience, 2004, vol. 24 (44), pp. 9993-10002.

Moreira, P. I. et al., "Is mitochondrial impairment a common link between Alzheimer's disease and diabetes" A matter under discussion, Trends Alzheimer's Dis. Res., 2006, pp. 259-279.

Oddo S., et al., "Temporal Profile of Amyloid-Beta (ABeta) Oligomerization in an Invivo Model of Alzheimer Disease. A Link Between Abeta and Tau Pathology," The Journal of Biological Chemistry, 2006, vol. 281 (3), pp. 1599-1604.

Olson J., et al., "Customization of a Commercially Available Prep Scale SFC System to Provide Enhanced Capabilities," Jala, 2002, vol. 7 (4), pp. 69-74.

Phillips K. A., et al., "Diagnostics and Biomarker Development: Priming the Pipeline," Nature Reviews, 2006, vol. 5 (6), pp. 463-469.

Poste G. et al., "Lipid Vesicles as Carriers for Introducing Biologically Active Materials into Cells," Methods in Cell Biology, 1976, vol. 14, pp. 33-71.

Ray S., et al., "Classification and Prediction of Clinical Alzheimer's Diagnosis Based on Plasma Signaling Proteins," Nature Medicine, 2007, vol. 13 (11), pp. 1359-1362.

Reddy P.H., et al., "Amyloid Beta, Mitochondrial Dysfunction and Synaptic Damage: Implications for Cognitive Decline in Aging and Alzheimer's Disease," Trends in Molecular Medicine, 2008, vol. 14 (2), pp. 45-53.

Shaw L.M., et al., "Biomarkers of Neurode Generation for Diagnosis and Monitoring Therapeutics," Nature Reviews, 2007, vol. 6 (4), pp. 295-303.

Shekhar S., et al., "Reevaluation of the Mechanism of the Amination of Aryl Halides Catalyzed by BINAP-ligated Palladium Complexes," Journal of the American Chemical Society, 2006, vol. 128 (11), pp. 3584-3591.

Soskic V., et al., "A Connection Between the Mitochondrial Permeability Transition Pore, Autophagy, and Cerebral Amyloidogenesis," Journal of Proteome Research, 2008, vol. 7 (6), pp. 2262-2269.

Sullivan P.G., et al., "Mitochondrial Permeability Transition in CNS Trauma: Cause or Effect of Neuronal Cell Death," Journal of Neuroscience Research, 2005, vol. 79 (1-2), pp. 231-239.

Timmermann D.B., et al., "An Allosteric Modulator of the Alpha7 Nicotinic Acetylcholine Receptor Possessing Cognition-Enhancing Properties in Vivo," Journal of Pharmacology and Experimental Therapeutics, 2007, vol. 323 (1), pp. 294-307.

Tkachenko S., "Discovery and in vivo evaluation of potent 5-ht6 receptor antagonists for cognition enhancement in treating Alzheimer's disease," International Conference on Alzheimer's Disease, Chicago, IL, USA, 2008, paper P2-47.

Walsh D.M., et al., "Deciphering the Molecular Basis of Memory Failure in Alzheimer's Disease," Neuron, 2004, vol. 44 (1), pp. 181-193.

Youdim M.B., et al., "Multi-Functional Drugs for Various CNS Targets in the Treatment of Neurodegenerative Disorders," Trends in Pharmacological Sciences, 2005, vol. 26 (1), pp. 27-35.

Zhang H.Y., "One-Compound-Multiple-Targets Strategy to Combat Alzheimer's Disease," FEBS Letters, 2005, vol. 579 (24), pp. 5260-5264.

* cited by examiner

BENZODIAZEPINE AND PYRIDODIAZEPINE DERIVATIVES

CROSS-REFERENCE TO RELATED APPLICATION

This application claims the benefit of U.S. Provisional Patent Application No. 61/326,696, filed on Apr. 22, 2010, and U.S. Provisional Patent Application No. 61/366,959, filed on Jul. 23, 2010, each of which is herein incorporated by reference in its entirety.

STATEMENT REGARDING FEDERALLY SPONSORED RESEARCH OR DEVELOPMENT

Not applicable.

FIELD OF THE INVENTION

The present invention relates to benzodiazepine and pyridodiazepine derivatives, compositions comprising these benzodiazepine and pyridodiazepine derivatives, methods of preventing or treating disease conditions such as neurodegeneration or neuropsychiatric disorders using such compounds and compositions, and processes for preparing such compounds and compositions.

BACKGROUND OF THE INVENTION

Treatment of dementias of various types, such as but not limited to, Alzheimer's disease (AD), Parkinson's disease, Huntington's disease and other forms, continue to be unmet medical needs. Alzheimer's disease is the most common form of dementia, wherein loss of memory and other intellectual abilities are serious enough to interfere with daily living. Alzheimer's disease is an age-related neurodegenerative disorder characterized by progressive loss of memory accompanied with cholinergic neurodegeneration (Kar, S.; Quirion, R. Amyloid β peptides and central cholinergic neurons: functional interrelationship and relevance to Alzheimer's disease pathology. *Prog. Brain Res.* 2004, 145 (Acetylcholine in the Cerebral Cortex), 261-274.). This disease accounts for over 50% of all progressive cognitive impairment in elderly patients. The prevalence increases with age. Alzheimer's disease is classified by its severity as mild, moderate and severe. The pathological hallmarks of AD include neuronal dysfunction/death, accumulation of senile plaques extracellularly and neurofibrillary tangles (NFTs) intraneuronally. Several hypotheses have been put forth to explain the pathophysiology of this disease, including aberrant β-amyloid (Aβ) metabolism, hyperphosphorylation of cytoskeletal proteins, genetic predisposition such as mutations in genes coding for presenilin-1 and -2 (PS-1 and PS-2) and amyloid precursor protein (APP), apolipoprotein E genotype, oxidative stress, excitotoxicity, inflammation and abnormal cell cycle re-entry. However to date, none of these hypotheses is sufficient to explain the diversity of biochemical and pathological abnormalities in AD.

Two pathological hallmarks of AD are generally recognized: senile plaques composed of β-amyloid peptide 1-42 ($A\beta_{1-42}$) and neurofibrillary tangles (NFTs) formed by abnormal polymerization of microtubule-associated protein tau (Walsh, D. M.; Selkoe, D. J. Deciphering the molecular basis of memory failure in Alzheimer's disease. *Neuron* 2004, 44(1), 181-193.). While the precise cause underlying AD-related memory loss and cognitive changes remains to be fully elucidated, there is evidence indicating that pathological assemblies of $A\beta_{1-42}$ cause diverse forms of AD and that tau plays a role including in mechanisms leading to $A\beta_{1-42}$-induced neurodegeneration. More recent evidence from studies using transgenic animals suggests that tau pathology exacerbates neurodegenerative and cognitive processes in the presence of $A\beta_{1-42}$ (Oddo, S.; Caccamo, A.; et al. Temporal Profile of Amyloid-β(Aβ) Oligomerization in an in Vivo Model of Alzheimer Disease: a link between Aβ and tau pathology. *J. Biol. Chem.* 2006, 281(3), 1599-1604.). In addition to Aβ and tau, dysregulation of calcium homeostasis also plays an integral role in the pathophysiology of AD (Green, K. N.; LaFerla, F. M. Linking calcium to Aβ and Alzheimer's disease. *Neuron* 2008, 59(2), 190-194.). It is becoming evident that dysregulation of mitochondrial function and resultant altered cellular homeostasis increasingly contributes to the pathology of neurodegenerative diseases such as AD (Moreira, P. I.; Santos, M. S.; et al. Is mitochondrial impairment a common link between Alzheimer's disease and diabetes? A matter under discussion. *Trends Alzheimer's Dis. Res.* 2006, 259-279. Beal, M. F. Mitochondria and neurodegeneration. Novartis Found. Symp. 2007, 287 (Mitochondrial Biology), 183-196. Reddy, P. H.; Beal, M. F. Amyloid beta, mitochondrial dysfunction and synaptic damage: implications for cognitive decline in aging and Alzheimer's disease. *Trends Mol. Med.* 2008, 14(2), 45-53.).

Mitochondria play major roles in bioenergetics and cell death/survival signaling of the mammalian cell as they are 'gatekeepers of life and death'. Mitochondrial dysfunction contributes to the pathogenesis of various neurodegenerative diseases with pathophysiological consequences at multiple levels including at the level of calcium-driven excitotoxicity. One of the primary mitochondrial mechanisms is the mitochondrial permeability transition pores (MPTP) that represent a multiprotein complex derived from components of inner and outer mitochondrial membrane. The pores regulate transport of ions and peptides in and out of mitochondria, and their regulation is associated with mechanisms for maintaining cellular calcium homeostasis. A deficit in mitochondria is the earliest feature of neurodegenerative diseases. One general characteristic of aging and neurodegeneration is an increase in the number of neuronal cells undergoing signs of apoptotic degeneration. A key role for this apoptotic process is attributable to the mitochondrial permeability transition pore, which provides transport in and out of mitochondria for both calcium ions and compounds with low molecular weight. It has been proposed that MPTP is a multiprotein complex with the outer membrane fragment including porin (a voltage-dependent ion channel), anti-apoptotic proteins of the Bcl-2 family, and the peripheral benzodiazepine receptor. The inner fragment of MPTP contains an adenine nucleotide translocator and cyclophilin, which may interact with proapoptotic proteins of the Bax family. Inhibition of mitochondrial calcium uptake and/or blocking of MPTP may protect cells against the development of apoptosis in the presence of pathological factors such as excitotoxins and anti-oxidants. Indirect modulation of MPTP via kinase pathways is also known wherein glycogen synthase kinase-3β (GSK3β) mediates convergence of protection signaling to inhibit the mitochondrial MPTP (Juhaszova, M.; Zorov, D. B.; et al. Glycogen synthase kinase-3β mediates convergence of protection signaling to inhibit the mitochondrial permeability transition pore. *J. Clin. Invest.* 2004, 113(11), 1535-1549. Juhaszova, M.; Wang, S.; et al. The identity and regulation of the mitochondrial permeability transition pore: where the known meets the unknown. *Ann. N.Y. Acad. Sci.* 2008, 1123 (Control and Regulation of Transport Phenomena in the Cardiac System), 197-212.) and mitochondrial localization during apoptosis (Linseman, D. A.; Butts, B. D.; et al. Glycogen synthase kinase-3β phosphorylates Bax and promotes its mitochondrial localization during neuronal apoptosis. *J. Neurosci.* 2004, 24(44), 9993-10002.). Furthermore, calcium-dependent activation of MPTP in brain mitochondria enhances with age and may play an important role in age related neurodegenerative disorders.

Neuroprotective effects of agents have been linked to various cellular processes including inhibition of mitochondrial MPTPs. For example, the neuroprotective effects of 4-azasteroids parallel the inhibition of the mitochondrial transition pore (Soskic, V.; Klemm, M.; et al. A connection between the mitochondrial permeability transition pore, autophagy, and cerebral amyloidogenesis. *J. Proteome Res.* 2008, 7(6): 2262-2269.). In vivo administration of MPTP inhibitor, 1-(3-chlorophenyl)-3-phenyl-pyrrole-2,5-dione to a mouse model of multiple sclerosis significantly prevented the development of the disease (Pelicci, P., Giorgio, M.; et al. MPTP inhibitors for blockade of degenerative tissue damages. WO 2008067863A2).

SUMMARY OF THE INVENTION

In one aspect, the present invention relates to compounds of having a formula of (I):

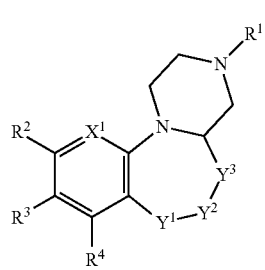

(I)

or a pharmaceutically acceptable salt or prodrug thereof, wherein $R^1$ is selected from the group consisting of hydrogen, alkyl, alkylcarbonyl, haloalkyl, $G^1$, —$(CR^{4a}R^{5a})_m$-$G^1$, —C(O)-$G^1$, —$S(O)_2G^1$, —$C(O)OR^6$ and —$C(O)NR^7R^8$; wherein $R^1$ is other than hydrogen, alkyl, alkylcarbonyl, haloalkyl when one of $Y^1$ or $Y^2$ is $CH_2$ and the other is $NR^9$;

$R^2$, $R^3$, $R^4$, and $R^5$ are each independently hydrogen, alkyl, alkenyl, alkynyl, halogen, cyano, —$NO_2$, —$OR^{1a}$, —$S(O)_2R^{2a}$, —$C(O)OR^{1a}$, or haloalkyl;

$R^6$ is alkyl or —$(CR^{4a}R^{5a})_m$-$G^1$;

$R^7$ and $R^8$ are independently hydrogen, alkyl, $G^1$, or —$(CR^{4a}R^{5a})_m$-$G^1$;

$R^9$ is hydrogen or alkyl;

$R^{1a}$, at each occurrence, is independently hydrogen, alkyl, haloalkyl, or —$(CR^{4a}R^{5a})_m$-$G^1$;

$R^{2a}$, at each occurrence, is independently alkyl, haloalkyl, or $G^1$;

$R^{4a}$ and $R^{5a}$, at each occurrence, are each independently hydrogen, halogen, alkyl, or haloalkyl, or $R^{4a}$ and $R^{5a}$ together with the carbon to which they are attached form a cycloalkyl;

$R^{1b}$, at each occurrence, is independently hydrogen, alkyl, or haloalkyl;

$R^{2b}$, at each occurrence, is independently alkyl, cyanoalkyl or haloalkyl;

$G^1$, at each occurrence, is independently aryl or heteroaryl, wherein each $G^1$ is independently unsubstituted or substituted with 1, 2, 3, 4, or 5 substituents selected from the group consisting of alkyl, alkenyl, halogen, cyano, —$NO_2$, —$OR^{1b}$, —$S(O)_2R^{2b}$, —$C(O)OR^{1b}$, —$(CR^{4a}R^{5a})_m$—$N(R^{1b})_2$, and haloalkyl;

$G^2$, at each occurrence, is independently cycloalkyl or heterocycle, wherein each $G^2$ is independently unsubstituted or substituted with 1, 2, 3, 4, or 5 substituents selected from the group consisting of alkyl, alkenyl, halogen, cyano, —$NO_2$, —$OR^{1b}$, —$S(O)_2R^{2b}$, —$C(O)OR^{1b}$, —$C(O)R^{2b}$, —$C(O)N(R^{1b})_2$, haloalkyl, and oxo;

m, at each occurrence, is independently 1, 2, 3, 4, or 5;

$X^1$ is N or $CR^5$;

one of $Y^1$ or $Y^2$ is $CH_2$ and the other is selected from the group consisting of $NR^9$, N-$G^1$, N—$(CR^{4a}R^{5a})_m$-$G^1$, $N^+$—$[CR^{4a}R^{5a})_m$-$G^1]_2$, NC(O)—$R^{2b}$, NC(O)—$(CR^{4a}R^{5a})_m$-$G^1$, NC(O)—$(CR^{4a}R^{5a})_m$—$W^1$, NC(O)—CH=CH-$G^1$, NC(O)-$G^1$, NC(O)-$G^2$-$G^1$, N-$G^2$, N-$G^2$-C(O)-$G^1$, N—$(CR^{4a}R^{5a})_m$-$G^2$, NC(O)—$(CR^{4a}R^{5a})_m$-$G^2$, NC(O)-$G^2$, NC(O)NH—$W^3$, NC(O)N($R^{2b}$)—$W^3$, and NC(O)N($R^{1b}$)—$(CR^{4a}R^{5a})_m$—$W^2$; wherein $W^1$ is NHC(O)$G^1$ or —O—$(CR^{4a}R^{5a})_m$—$R^{1b}$;

$W^2$ is $G^1$, $G^2$, $N(R^{1b})_2$, $R^{1b}$, or —O—$(CR^{4a}R^{5a})_m$—$R^{1b}$;

$W^3$ is $R^{1b}$, $G^1$ or $G^2$; and $Y^3$ is $CH_2$ or C(O).

In another aspect, the present invention relates to pharmaceutical compositions comprising a therapeutically effective amount of at least one compound(s) having a formula of (I), described above or pharmaceutically acceptable salts thereof, in combination with at least one pharmaceutically acceptable carrier.

The present invention can also include use of a compound of formula (I) as neuroprotective agent for the prevention or treatment of a neurological disorder or condition. The method includes administering a therapeutically effective amount of at least one compound of formula (I), to a subject in need of treatment thereof. The neurological disorder or condition can include, but is not limited to, neurodegeneration disorders, neuropsychiatric disorder and pain conditions, brain injuries, stroke and other acute and chronic neuronal injuries or degenerative conditions. The neurological disorder or condition can include, for example, conditions associated, at least in part, with mitochondrial dysfunction and/or neuronal apoptosis in the central nervous system.

In still yet another aspect, the present invention relates to the use of a compound of formula (I), or a pharmaceutically acceptable salt thereof in the manufacture of a medicament for the prevention or treatment of the neurodegeneration disorders described above, alone or in combination with at least one pharmaceutically acceptable carrier.

The compounds of formula (I), compositions comprising these compounds, and methods for preventing or treating neurodegenerative or neuropsychiatric disorders by administering these compounds or pharmaceutical compositions are further described herein.

These and other objects of the invention are described in the following paragraphs. These objects should not be deemed to narrow the scope of the invention.

DETAILED DESCRIPTION

In one aspect, the present invention relates to compounds having a formula (I) as shown below:

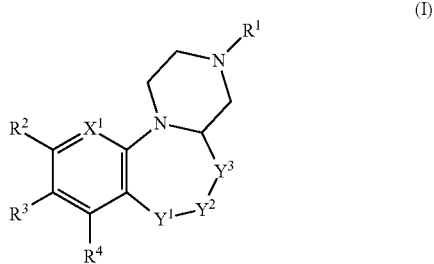

wherein $R^1$, $R^2$, $R^3$, $R^4$, $X^1$, $Y^1$, $Y^2$ and $Y^3$ are as defined above in the Summary of the Invention.

In another aspect, the present invention relates to composition comprising compounds having a formula (I) as described above and at least one pharmaceutically acceptable carrier.

In still yet another aspect, the present invention relates to methods for preventing and treating disease conditions, such as neurodegeneration disorders or neuropsychiatric disorders, using compounds having a formula of formula (I) as described above.

In still yet another aspect, the present invention relates to the use of compounds having a formula (I) in the manufacture of a medicament for the prevention or treatment of the disease conditions, such as neurodegeneration disorders or neuropsychiatric disorders, described above, alone or in combination with at least one pharmaceutically acceptable carrier.

In various embodiments, the present invention provides at least one variable that occurs more than one time in any substituent or in the compound of the present invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

a. DEFINITIONS

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" denotes a divalent group derived from a straight or branched chain hydrocarbon of 2 to 4 carbon atoms and contains at least one carbon-carbon double. Representative examples of alkenylene include, but are not limited to, —CH=CH— and —CH$_2$CH=CH—.

The term "alkyl" as used herein, means a straight or branched, saturated hydrocarbon chain containing from 1 to 10 carbon atoms. The term "lower alkyl" or "$C_{1-6}$ alkyl" means a straight or branched chain hydrocarbon containing 1 to 6 carbon atoms. The term "$C_{1-3}$ alkyl" means a straight or branched chain hydrocarbon containing 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylene" denotes a divalent group derived from a straight or branched chain hydrocarbon 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "arylalkyl" as used herein, means an aryl group, as defined herein, appended to the parent molecular moiety through an alkylene group, as defined herein. Representative examples of arylalkyl include, but are not limited to, benzyl, 2-phenylethyl, 3-phenylpropyl, and 2-naphth-2-ylethyl.

The term "cyano" as used herein, means a —CN group.

The term "cyanoalkyl" as used herein, means a cyano group, as defined herein, appended to the parent molecular moiety through an alkylene group, as defined herein. Representative examples of cyanoalkyl include, but are not limited to, cyanomethyl, 2-cyanoethyl, and 3-cyanopropyl.

The term "cycloalkenyl" as used herein, means a monocyclic or bicyclic ring system containing from 3 to 10 carbons and containing at least one carbon-carbon double bond formed by the removal of two hydrogens. Representative examples of monocyclic ring systems include, but are not limited to, 2-cyclohexen-1-yl, 3-cyclohexen-1-yl, 2,4-cyclohexadien-1-yl and 3-cyclopenten-1-yl. Bicyclic ring systems are exemplified by a monocyclic cycloalkenyl ring system which is fused to another monocyclic cycloalkyl ring as defined herein, a monocyclic aryl ring as defined herein, a monocyclic heterocycle as defined herein or a monocyclic heteroaryl as defined herein. The bicyclic ring systems of the present invention must be appended to the parent molecular moiety through an available carbon atom within the cycloalkenyl ring. Representative examples of bicyclic ring systems include, but are not limited to, 4,5-dihydro-benzo[1,2,5]oxadiazole, 3a,4,5,6,7,7a-hexahydro-1H-indenyl, 1,2,3,4,5,6-hexahydro-pentalenyl, 1,2,3,4,4a,5,6,8a-octahydro-pentalenyl.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1] nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. Representative examples of haloalkyl include, but are not limited to, fluoromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyridazin-3 (2H)-onyl, pyridin-2(1H)-onyl, pyrrolinyl, pyrrolidinyl, tetrahydrofuranyl, tetrahydropyranyl, tetrahydropyridinyl, tetrahydropyrimidinyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, 1,4-benzoxazinyl, benzothiopyranyl, chromanyl, 2,3-dihydrobenzofuranyl, 2,3-dihydrobenzothienyl, azabicyclo [2.2.1]heptyl (including 2-azabicyclo[2.2.1]hept-2-yl), 2,3-dihydro-1H-indolyl, isoindolinyl, octahydrocyclopenta[c] pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-admantane (1-azatricyclo [3.3.1.1$^{3,7}$]decane), and oxa-adamantane (2-oxatricyclo [3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "heteroaryl" as used herein, means a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,2-oxazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzodiazepinyl, benzofuranyl, benzothienyl, benzoxazolyl, benzimidazolyl, benzoxadiazolyl, 6,7-dihydro-1,3-benzothiazolyl, imidazo[1,2-b]pyridazinyl, imidazo[1,2-a]pyridinyl, imidazo[1,2-a]pyrimidinyl, indazolyl, indolyl, isoindolyl, isoquinolinyl, naphthyridinyl, pyridodiazepinyl, pyridoimidazolyl, pyrido[1,2-a]pyrimidin-4-onyl, quinoxalinyl, quinazolinyl, quinolinyl, thiazolo[5,4-b]pyridin-2-yl, thiazolo[5,4d]pyrimidin-2-yl, and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heteroatom" as used herein, means a nitrogen, oxygen, or sulfur atom.

The term "hydroxyl" or "hydroxy" as used herein, means an —OH group.

The term "oxo" as used herein, means a =O group.

The term "pain", as used herein, is understood to mean nociceptive pain and neuropathic pain, both chronic and acute pain, including but not limited to, osteoarthritis or rheumatoid arthritis pain, ocular pain, pains associated with intestinal inflammation, pains associated with cardiac muscle inflammation, pains associated with multiple sclerosis, pains associated with neuritis, pains associated with carcinomas and sarcomas, pains associated with AIDS, pains associated with chemotherapy, amputation pain, trigeminus neuralgia, headaches, such as migraine cephalalgia, or neuropathic pains, such as post-herpes zoster neuralgia, post-injury pains and post-operative pains.

The term "sulfonyl" as used herein, means a —$SO_2$— group.

b. COMPOUNDS

Compounds of the present invention have the formula (I) as described above.

Particular values of variable groups in compounds of formula (I) are as follows. Such values may be used where appropriate with any of the other values, definitions, claims or embodiments defined hereinbefore or hereinafter.

In one embodiment, $R^1$ is selected from the group consisting of hydrogen, alkyl, alkylcarbonyl, haloalkyl, $G^1$, —$(CR^{4a}R^{5a})_m$-$G^1$, —C(O)-$G^1$, —$S(O)_2G^1$, —$C(O)OR^6$ and —$C(O)NR^7R^8$; wherein $R^1$ is other than hydrogen, alkyl, alkylcarbonyl, or haloalkyl when one of $Y^1$ or $Y^2$ is $CH_2$ and the other is $NR^9$; $G^1$, at each occurrence, is independently aryl or heteroaryl, wherein each $G^1$ is independently unsubstituted or substituted with 1, 2, 3, 4, or 5 substituents selected from the group consisting of alkyl, alkenyl, halogen, cyano, —$NO_2$, —$OR^{1b}$, —$S(O)_2R^{2b}$, —$C(O)OR^{1b}$, —$(CR^{4a}R^{5a})_m$—$N(R^{1b})_2$, and haloalkyl; $R^{4a}$ and $R^{5a}$, at each occurrence, are each independently hydrogen, halogen, alkyl, or haloalkyl, or $R^{4a}$ and $R^{5a}$ together with the carbon to which they are attached form a cycloalkyl; m, at each occurrence, is independently 1, 2, 3, 4, or 5; $R^6$ is alkyl or —$(CR^{4a}R^{5a})_m$-$G^1$; $R^7$ and $R^8$ are independently hydrogen, alkyl, $G^1$, or —$(CR^{4a}R^{5a})_m$-$G^1$; $R^9$ is hydrogen or alkyl; $R^{1b}$, at each occurrence, is independently hydrogen, alkyl, or haloalkyl; and $R^{2b}$, at each occurrence, is independently alkyl, cyanoalkyl or haloalkyl.

In another embodiment, $R^1$ is hydrogen, alkyl, alkylcarbonyl, or haloalkyl.

In a further embodiment, $R^1$ is hydrogen, alkyl, or alkylcarbonyl.

In another embodiment, $R^1$ is $G^1$, —$(CR^{4a}R^{5a})_m$-$G^1$, —C(O)-$G^1$, —$S(O)_2G^1$, —$C(O)OR^6$ or —$C(O)NR^7R^8$.

In another embodiment, $R^1$ is $G^1$, —$(CR^{4a}R^{5a})_m$-$G^1$, —C(O)-$G^1$, —$S(O)_2G^1$, or —$C(O)OR^6$.

In one embodiment, $R^2$, $R^3$, and $R^4$ are each independently hydrogen, alkyl, alkenyl, alkynyl, halogen, cyano, —$NO_2$, —$OR^{1a}$, —$S(O)_2R^{2a}$, —$C(O)OR^{1a}$, or haloalkyl; wherein $R^{1a}$, at each occurrence, is independently hydrogen, alkyl, haloalkyl, or —$(CR^{4a}R^{5a})_m$-$G^1$; and $R^{2a}$, at each occurrence, is independently alkyl, haloalkyl, or $G^1$.

In another embodiment, $R^2$, $R^3$, and $R^4$ are each independently hydrogen, alkyl, alkenyl, alkynyl, halogen, cyano, —$NO_2$, —$OR^{1a}$, or haloalkyl.

In another embodiment, $R^2$, $R^3$, and $R^4$ are each independently —$S(O)_2R^{2a}$ or —$C(O)OR^{1a}$.

In a further embodiment, $R^2$, $R^3$, and $R^4$ are each hydrogen.

In one embodiment, $R^5$ is hydrogen, alkyl, alkenyl, alkynyl, halogen, cyano, —$NO_2$, —$OR^{1a}$, —$S(O)_2R^{2a}$, —$C(O)OR^{1a}$, or haloalkyl; wherein $R^{1a}$, at each occurrence, is independently hydrogen, alkyl, haloalkyl, or —$(CR^{4a}R^{5a})_m$-$G^1$; and $R^{2a}$, at each occurrence, is independently alkyl, haloalkyl, or $G^1$.

In another embodiment, $R^5$ is hydrogen, alkyl, alkenyl, alkynyl, halogen, cyano, —$NO_2$, —$OR^{1a}$, or haloalkyl.

In another embodiment, $R^5$ is —$S(O)_2R^{2a}$ or —$C(O)OR^{1a}$.

In a further embodiment, $R^5$ is hydrogen.

In one embodiment, $R^{1a}$, at each occurrence, is independently hydrogen, alkyl, haloalkyl, or —$(CR^{4a}R^{5a})_m$-$G^1$.

In another embodiment, $R^{1a}$ is hydrogen.
In another embodiment, $R^{1a}$ is alkyl.
In another embodiment, $R^{1a}$ is haloalkyl.
In another embodiment, $R^{1a}$ is —$(CR^{4a}R^{5a})_m$-$G^1$.

In one embodiment, $R^{2a}$, at each occurrence, is independently alkyl, haloalkyl, or $G^1$.
In another embodiment, $R^{2a}$ is alkyl.
In another embodiment, $R^{2a}$ is haloalkyl.
In another embodiment, $R^{2a}$ is $G^1$.

In one embodiment, $R^{4a}$ and $R^{5a}$, at each occurrence, are each independently hydrogen, halogen, alkyl, or haloalkyl, or $R^{4a}$ and $R^{5a}$ together with the carbon to which they are attached form a cycloalkyl.

In another embodiment, $R^{4a}$ and $R^{5a}$, at each occurrence, are each hydrogen.

In another embodiment, $R^{4a}$ and $R^{5a}$, at each occurrence, are each independently hydrogen or alkyl.

In another embodiment, $R^{4a}$ and $R^{5a}$, together with the carbon to which they are attached form a cycloalkyl.

In one embodiment, $R^{1b}$, at each occurrence, is independently hydrogen, alkyl, or haloalkyl.
In another embodiment, $R^{1b}$ is hydrogen.
In another embodiment, $R^{1b}$ is alkyl.
In another embodiment, $R^{1b}$ is haloalkyl.

In one embodiment, $R^{2b}$, at each occurrence, is independently alkyl, cyanoalkyl or haloalkyl.
In another embodiment, $R^{2b}$ is alkyl.
In another embodiment, $R^{2b}$ is cyanoalkyl.
In another embodiment, $R^{2b}$ is haloalkyl.

In one embodiment, $G^1$, at each occurrence, is independently aryl or heteroaryl, wherein each $G^1$ is independently unsubstituted or substituted with 1, 2, 3, 4, or 5 substituents selected from the group consisting of alkyl, alkenyl, halogen, cyano, —$NO_2$, —$OR^{1b}$, —$S(O)_2R^{2b}$, —$C(O)OR^{1b}$, —$(CR^{4a}R^{5a})_m$—$N(R^{1b})_2$, and haloalkyl.

In another embodiment, $G^1$ is aryl, wherein each $G^1$ is independently unsubstituted or substituted with 1, 2, 3, 4, or 5 substituents selected from the group consisting of alkyl, alkenyl, halogen, cyano, —$NO_2$, —$OR^{1b}$, —$S(O)_2R^{2b}$, —$C(O)OR^{1b}$, —$(CR^{4a}R^{5a})_m$—$N(R^{1b})_2$, and haloalkyl.

In another embodiment, $G^1$ is heteroaryl, wherein each $G^1$ is independently unsubstituted or substituted with 1, 2, 3, 4, or 5 substituents selected from the group consisting of alkyl, alkenyl, halogen, cyano, —$NO_2$, —$OR^{1b}$, —$S(O)_2R^{2b}$, C(O)$OR^{1b}$, —$(CR^{4a}R^{5a})_m$—$N(R^{1b})_2$, and haloalkyl.

In one embodiment, $G^2$, at each occurrence, is independently cycloalkyl or heterocycle, wherein each $G^2$ is independently unsubstituted or substituted with 1, 2, 3, 4, or 5 substituents selected from the group consisting of alkyl, alkenyl, halogen, cyano, —$NO_2$, —$OR^{1b}$, —$S(O)_2R^{2b}$, —$C(O)OR^{1b}$, —$C(O)R^{2b}$, —$C(O)N(R^{1b})_2$, haloalkyl, and oxo.

In another embodiment, $G^2$, at each occurrence, is cycloalkyl, wherein each $G^2$ is independently unsubstituted or substituted with 1, 2, 3, 4, or 5 substituents selected from the group consisting of alkyl, alkenyl, halogen, cyano, —$NO_2$, —$OR^{1b}$, —$S(O)_2R^{2b}$, —$C(O)OR^{1b}$, —$C(O)R^{2b}$, —$C(O)N(R^{1b})_2$, haloalkyl, and oxo.

In another embodiment, $G^2$, at each occurrence, is heterocycle, wherein each $G^2$ is independently unsubstituted or substituted with 1, 2, 3, 4, or 5 substituents selected from the group consisting of alkyl, alkenyl, halogen, cyano, —$NO_2$, —$OR^{1b}$, —$S(O)_2R^{2b}$, —$C(O)OR^{1b}$, —$C(O)R^{2b}$, —$C(O)N(R^{1b})_2$, haloalkyl, and oxo.

In one embodiment, m, at each occurrence is 1, 2, 3, 4, or 5.

In another embodiment, m, at each occurrence is 1, 2, or 3.

In a further embodiment, m, at each occurrence is 1 or 2.

In one embodiment, $W^1$ is $NHC(O)G^1$ or $-O-(CR^{4a}R^{5a})_m-R^{1b}$.

In another embodiment, $W^1$ is $NHC(O)G^1$.

In another embodiment, $W^1$ is $-O-(CR^{4a}R^{5a})_m-R^{1b}$.

In one embodiment, $W^2$ is $G^1$, $G^2$, $N(R^{1b})_2$, $R^{1b}$, or $-O-(CR^{4a}R^{5a})_m-R^{1b}$.

In another embodiment, $W^2$ is $G^1$.

In another embodiment, $W^2$ is $G^2$.

In another embodiment, $W^2$ is $N(R^{1b})_2$.

In another embodiment, $W^2$ is $R^{1b}$.

In another embodiment, $W^2$ is $-O-(CR^{4a}R^{5a})_m-R^{1b}$.

In one embodiment, $X^1$ is N or $CR^5$.

In another embodiment, $X^1$ is $CR^5$.

In a further embodiment, $X^1$ is CH.

In a further embodiment, $X^1$ is N.

In one embodiment, one of $Y^1$ or $Y^2$ is $CH_2$ and the other is selected from the group consisting of $NR^9$, $N-G^1$, $N-(CR^{4a}R^{5a})_m-G^1$, $N^+-[(CR^{4a}R^{5a})_m-G^1]_2$, $NC(O)-R^{2b}$, $NC(O)-(CR^{4a}R^{5a})_m-G^1$, $NC(O)-(CR^{4a}R^{5a})_m-W^1$, $NC(O)-CH=CH-G^1$, $NC(O)-G^1$, $NC(O)-G^2-G^1$, $N-G^2$, $N-G^2-C(O)-G^1$, $N-(CR^{4a}R^{5a})_m-G^2$, $NC(O)-(CR^{4a}R^{5a})_m-G^2$, $NC(O)-G^2$, $NC(O)NH-W^3$, $NC(O)N(R^{2b})-W^3$, and $NC(O)N(R^{1b})-(CR^{4a}R^{5a})_m-W^2$; wherein $R^9$ is hydrogen or alkyl; $G^1$, at each occurrence, is independently aryl or heteroaryl, wherein each $G^1$ is independently unsubstituted or substituted with 1, 2, 3, 4, or 5 substituents selected from the group consisting of alkyl, alkenyl, halogen, cyano, $-NO_2$, $-OR^{1b}$, $-S(O)_2R^{2b}$, $-C(O)OR^{1b}$, $-(CR^{4a}R^{5a})_m-N(R^{1b})_2$, and haloalkyl; $R^{4a}$ and $R^{5a}$, at each occurrence, are each independently hydrogen, halogen, alkyl, or haloalkyl, or $R^{4a}$ and $R^{5a}$ together with the carbon to which they are attached form a cycloalkyl; m, at each occurrence, is independently 1, 2, 3, 4, or 5; $G^2$, at each occurrence, is independently cycloalkyl or heterocycle, wherein each $G^2$ is independently unsubstituted or substituted with 1, 2, 3, 4, or 5 substituents selected from the group consisting of alkyl, alkenyl, halogen, cyano, $-NO_2$, $-OR^{1b}$, $-S(O)_2R^{2b}$, $-C(O)OR^{1b}$, $-C(O)R^{2b}$, $-C(O)N(R^{1b})_2$, haloalkyl, and oxo; $R^{1b}$, at each occurrence, is independently hydrogen, alkyl, or haloalkyl; $R^{2b}$, at each occurrence, is independently alkyl, cyanoalkyl, or haloalkyl; $W^1$ is $NHC(O)G^1$ or $-O-(CR^{4a}R^{5a})_m-R^{1b}$; $W^2$ is $G^1$, $G^2$, $N(R^{1b})_2$, $R^{1b}$, or $-O-(CR^{4a}R^{5a})_m-R^{1b}$; and $W^3$ is $R^{1b}$, $G^1$ or $G^2$.

In one embodiment, $Y^1$ is $CH_2$ and $Y^2$ is $NR^9$ wherein $R^9$ is hydrogen or alkyl.

In another embodiment, $Y^1$ is $CH_2$ and $Y^2$ is $NR^9$ wherein $R^9$ is hydrogen.

In a further embodiment, $Y^1$ is $CH_2$ and $Y^2$ is $NR^9$ wherein $R^9$ is alkyl.

In one embodiment, $Y^1$ is $NR^9$, wherein $R^9$ is hydrogen or alkyl, and $Y^2$ is $CH_2$.

In another embodiment, $Y^1$ is $NR^9$, wherein $R^9$ is hydrogen, and $Y^2$ is $CH_2$.

In a further embodiment, $Y^1$ is $NR^9$, wherein $R^9$ is alkyl, and $Y^2$ is $CH_2$.

In one embodiment, $Y^1$ is $CH_2$ and $Y^2$ is $N-G^1$, $N-(CR^{4a}R^{5a})_m-G^1$, $N^+-[(CR^{4a}R^{5a})_m-G^1]_2$, $NC(O)-R^{2b}$, $NC(O)-(CR^{4a}R^{5a})_m-G^1$, $NC(O)-(CR^{4a}R^{5a})_m-W^1$, $NC(O)-CH=CH-G^1$, $NC(O)-G^1$, $NC(O)-G^2-G^1$, $N-G^2$, $N-G^2-C(O)-G^1$, $N-(CR^{4a}R^{5a})_m-G^2$, $NC(O)-(CR^{4a}R^{5a})_m-G^2$, $NC(O)-G^2$, $NC(O)NH-W^3$, $NC(O)N(R^{2b})-W^3$, or $NC(O)N(R^{1b})-(CR^{4a}R^{5a})_m-W^2$.

In another embodiment, $Y^1$ is $CH_2$ and $Y^2$ is $N-G^1$, $N-(CR^{4a}R^{5a})_m-G^1$, $N^+-[(CR^{4a}R^{5a})_m-G^1]_2$, $NC(O)-R^{2b}$, $NC(O)-(CR^{4a}R^{5a})_m-G^1$, $NC(O)-(CR^{4a}R^{5a})_m-W^1$, $NC(O)-CH=CH-G^1$, $NC(O)-G^1$, $NC(O)-G^2-G^1$, $N-G^2$-C(O)-G^1$, $NC(O)-G^2$, $NC(O)NH-W^3$, $NC(O)N(R^{2b})-W^3$, or $NC(O)N(R^{1b})-(CR^{4a}R^{5a})_m-W^2$.

In another embodiment, $Y^1$ is $CH_2$ and $Y^2$ is $N-G^1$.

In another embodiment, $Y^1$ is $CH_2$ and $Y^2$ is $N-(CR^{4a}R^{5a})_m-G^1$, wherein $R^{4a}$ and $R^{5a}$, at each occurrence, are each hydrogen, or $R^{4a}$ and $R^{5a}$ together with the carbon to which they are attached form a cycloalkyl, and m is 1 or 2.

In another embodiment, $Y^1$ is $CH_2$ and $Y^2$ is $N^+-[(CR^{4a}R^{5a})_m-G^1]_2$, wherein $R^{4a}$ and $R^{5a}$, at each occurrence, are each hydrogen, and m is 1 or 2.

In another embodiment, $Y^1$ is $CH_2$ and $Y^2$ is $NC(O)-R^{2b}$, wherein $R^{2b}$ is alkyl or haloalkyl.

In another embodiment, $Y^1$ is $CH_2$ and $Y^2$ is $NC(O)-(CR^{4a}R^{5a})_m-G^1$, wherein $R^{4a}$ and $R^{5a}$, at each occurrence, are each hydrogen, or $R^{4a}$ and $R^{5a}$ together with the carbon to which they are attached form a cycloalkyl, and m is 1 or 2.

In another embodiment, $Y^1$ is $CH_2$ and $Y^2$ is $NC(O)-(CR^{4a}R^{5a})_m-W^1$, wherein $R^{4a}$ and $R^{5a}$, at each occurrence, are each hydrogen, m is 1 or 2, and $W^1$ is $NHC(O)G^1$ or $-O-(CR^{4a}R^{5a})-m-R^{1b}$.

In another embodiment, $Y^1$ is $CH_2$ and $Y^2$ is $NC(O)-CH=CH-G^1$.

In another embodiment, $Y^1$ is $CH_2$ and $Y^2$ is $NC(O)-G^1$.

In another embodiment, $Y^1$ is $CH_2$ and $Y^2$ is $NC(O)-G^2-G^1$.

In a further embodiment, $Y^1$ is $CH_2$ and $Y^2$ is $NC(O)-G^2-G^1$, wherein $G^2$ is cyclopropyl.

In another embodiment, $Y^1$ is $CH_2$ and $Y^2$ is $N-G^2$.

In another embodiment, $Y^1$ is $CH_2$ and $Y^2$ is $N-G^2-C(O)-G^1$.

In a further embodiment, $Y^1$ is $CH_2$ and $Y^2$ is $N-G^2-C(O)-G^1$, wherein $G^2$ is piperidinyl.

In another embodiment, $Y^1$ is $CH_2$ and $Y^2$ is $N-(CR^{4a}R^{5a})-G^2$.

In another embodiment, $Y^1$ is $CH_2$ and $Y^2$ is $NC(O)-(CR^{4a}R^{5a})-G^2$.

In another embodiment, $Y^1$ is $CH_2$ and $Y^2$ is $NC(O)-G^2$.

In another embodiment, $Y^1$ is $CH_2$ and $Y^2$ is $NC(O)NH-W^3$.

In a further embodiment, $Y^1$ is $CH_2$ and $Y^2$ is $NC(O)NH-W^3$, wherein $W^3$ is $R^{1b}$, $G^1$ or $G^2$.

In another embodiment, $Y^1$ is $CH_2$ and $Y^2$ is $NC(O)N(R^{2b})-W^3$.

In a further embodiment, $Y^1$ is $CH_2$ and $Y^2$ is $NC(O)N(R^{2b})-W^3$, wherein $R^{2b}$ is alkyl, cyanoalkyl or haloalkyl and $W^3$ is $R^{1b}$, $G^1$ or $G^2$.

In another embodiment, $Y^1$ is $CH_2$ and $Y^2$ is $NC(O)N(R^{1b})-(CR^{4a}R^{5a})_m-W^2$.

In a further embodiment, $Y^1$ is $CH_2$ and $Y^2$ is $NC(O)N(R^{1b})-(CR^{4a}R^{5a})_m-W^2$, wherein $R^{1b}$ is hydrogen, alkyl, or haloalkyl, $R^{4a}$ and $R^{5a}$ are each hydrogen, m is 1, and $W^2$ is $G^1$, $G^2$, $N(R^{1b})_2$, or $-O-(CR^{4a}R^{5a})_m-R^{1b}$.

In another embodiment, $Y^1$ is $N-G^1$, $N-(CR^{4a}R^{5a})_m-G^1$, $N^+-[(CR^{4a}R^{5a})_m-G^1]_2$, $NC(O)-R^{2b}$, $NC(O)-(CR^{4a}R^{5a})_m-G^1$, $NC(O)-(CR^{4a}R^{5a})_m-W^1$, $NC(O)-CH=CH-G^1$, $NC(O)-G^1$, $NC(O)-G^2-G^1$, $N-G^2$, $N-G^2-C(O)-G^1$, $N-(CR^{4a}R^{5a})_m-G^2$, $NC(O)-(CR^{4a}R^{5a})_m-G^2$, $NC(O)-G^2$, $NC(O)NH-W^3$, $NC(O)N(R^{2b})-W^3$, or $NC(O)N(R^{1b})-(CR^{4a}R^{5a})_m-W^2$ and $Y^2$ is $CH_2$.

In another embodiment, $Y^1$ is $N-G^1$ and $Y^2$ is $CH_2$.

In another embodiment, $Y^1$ is $N-(CR^{4a}R^{5a})_m-G^1$, wherein $R^{4a}$ and $R^{5a}$, at each occurrence, are each hydrogen, and m is 1 or 2, and $Y^2$ is $CH_2$.

In another embodiment, $Y^1$ is $N^+-[(CR^{4a}R^{5a})_m-G^1]_2$, wherein $R^{4a}$ and $R^{5a}$, at each occurrence, are each hydrogen, and m is 1 or 2, and $Y^2$ is $CH_2$.

In another embodiment, $Y^1$ is $NC(O)$—$R^{2b}$, wherein $R^{2b}$ is alkyl, cyanoalkyl or haloalkyl, and $Y^2$ is $CH_2$.

In another embodiment, $Y^1$ is $NC(O)$—$(CR^{4a}R^{5a})_m$-$G^1$, wherein $R^{4a}$ and $R^{5a}$, at each occurrence, are each hydrogen, and m is 1 or 2, and $Y^2$ is $CH_2$.

In another embodiment, $Y^1$ is $NC(O)$—$(CR^{4a}R^{5a})_m$—$W^1$, wherein $R^{4a}$ and $R^{5a}$, at each occurrence, are each hydrogen, and m is 1 or 2, $W^1$ is $NHC(O)G^1$ or —O—$(CR^{4a}R^{5a})_m$—$R^{1b}$, and $Y^2$ is $CH_2$.

In another embodiment, $Y^1$ is $NC(O)$—$CH$=$CH$-$G^1$ and $Y^2$ is $CH_2$.

In another embodiment, $Y^1$ is $NC(O)$-$G^1$ and $Y^2$ is $CH_2$.

In another embodiment, $Y^1$ is $NC(O)$-$G^2$-$G^1$ and $Y^2$ is $CH_2$.

In another embodiment, $Y^1$ is N-$G^2$ and $Y^2$ is $CH_2$.

In another embodiment, $Y^1$ is N-$G^2$-$C(O)$-$G^1$ and $Y^2$ is $CH_2$.

In another embodiment, $Y^1$ is $NC(O)$-$G^2$ and $Y^2$ is $CH_2$.

In another embodiment, $Y^1$ is N—$(CR^{4a}R^{5a})_m$-$G^2$, wherein $R^{4a}$ and $R^{5a}$, at each occurrence, are each hydrogen, m is 1 or 2, and $Y^2$ is $CH_2$.

In another embodiment, $Y^1$ is $NC(O)$—$(CR^{4a}R^{5a})_m$-$G^2$, wherein $R^{4a}$ and $R^{5a}$, at each occurrence, are each hydrogen, m is 1 or 2, and $Y^2$ is $CH_2$.

In another embodiment, $Y^1$ is $NC(O)NH$—$W^3$, wherein $W^3$ is $R^{1b}$, $G^1$ or $G^2$, and $Y^2$ is $CH_2$.

In another embodiment, $Y^1$ is $NC(O)N(R^{2b})$—$W^3$, wherein $W^3$ is $R^{1b}$, $G^1$ or $G^2$, $R^{2b}$ is alkyl, cyanoalkyl or haloalkyl, and $Y^2$ is $CH_2$.

In another embodiment, $Y^1$ is $NC(O)N(R^{1b})$—$(CR^{4a}R^{5a})_m$—$W^2$, wherein $W^2$ is $G^1$, $G^2$, $N(R^{1b})_2$, $R^{1b}$ or —O—$(CR^{4a}R^{5a})_m$—$R^{1b}$, and $Y^2$ is $CH_2$.

In one embodiment, $Y^3$ is $CH_2$ or $C(O)$.

In another embodiment, $Y^3$ is $C(O)$.

In a further embodiment, $Y^3$ is $CH_2$.

In one embodiment, compounds of formula (I) can include compounds of formula (Ia):

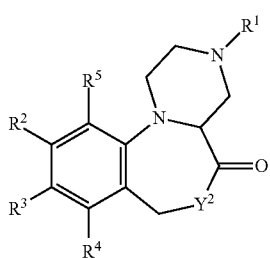

(Ia)

wherein $R^1$, $R^2$, $R^3$, $R^4$, $R^5$ and $Y^2$ are as described above.

In another embodiment, compounds of formula (Ia) are disclosed wherein $Y^2$ is selected from the group consisting of $NR^9$, N—$(CR^{4a}R^{5a})_m$-$G^2$, or N—$(CR^{4a}R^{5a})_m$-$G^1$, wherein $R^9$, $R^{4a}$, $R^{5a}$, m, $G^2$ and $G^1$ are as described in the Summary of the Invention.

In a further embodiment, compounds of formula (Ia) are disclosed wherein $Y^2$ is selected from the group consisting of NH, N—$(CR^{4a}R^{5a})_m$-$G^2$ or N—$(CR^{4a}R^{5a})_m$-$G^1$, wherein $R^{4a}$, $R^{5a}$, m, $G^2$ and $G^1$ are as described in the Summary of the Invention.

In one embodiment, compounds of formula (I) can include compounds of formula (Ib):

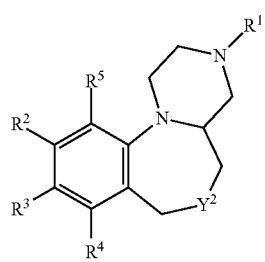

(Ib)

wherein $R^1$, $R^2$, $R^3$, $R^4$, $R^5$ and $Y^2$ are as described above.

In another embodiment, compounds of formula (Ib) are disclosed wherein $Y^2$ is $NR^9$, N-$G^1$, N—$(CR^{4a}R^{5a})_m$-$G^1$, $N^+$—$[(CR^{4a}R^{5a})_m$-$G^1]_2$, $NC(O)$—$R^{2b}$, $NC(O)$—$(CR^{4a}R^{5a})_m$-$G^1$, $NC(O)$—$CH$=$CH$-$G^1$, $NC(O)$-$G^1$, $NC(O)$-$G^2$-$G^1$, N-$G^2$, N-$G^2$-$C(O)$-$G^1$, N—$(CR^{4a}R^{5a})_m$-$G^2$, $NC(O)$—$(CR^{4a}R^{5a})_m$-$G^2$, $NC(O)$-$G^2$, $NC(O)$—$(CR^{4a}R^{5a})_m$—$W^1$, $NC(O)N(R^{1b})$—$(CR^{4a}R^{5a})_m$—$W^2$, or $NC(O)N(R^{2b})$—$W^3$, wherein $R^9$, $R^{4a}$, $R^{5a}$, $R^{1b}$, $R^{2b}$, $W^1$, $W^2$, $W^3$, m, $G^1$ and $G^2$ are as described in the Summary of the Invention.

In another embodiment, compounds of formula (Ib) are disclosed wherein $Y^2$ is $NR^9$, wherein $R^9$ is hydrogen or alkyl.

In a further embodiment, compounds of formula (Ib) are disclosed wherein $Y^2$ is N-$G^1$, N—$(CR^{4a}R^{5a})_m$-$G^1$, $N^+$—$[(CR^{4a}R^{5a})_m$-$G^1]_2$, $NC(O)$—$R^{2b}$, $NC(O)$—$(CR^{4a}R^{5a})_m$-$G^1$, $NC(O)$—$CH$=$CH$-$G^1$, $NC(O)$-$G^1$, $NC(O)$-$G^2$-$G^1$, N-$G^2$-$C(O)$-$G^1$, N—$(CR^{4a}R^{5a})_m$-$G^2$, $NC(O)$—$(CR^{4a}R^{5a})_m$-$G^2$, $NC(O)$-$G^2$, $NC(O)$—$(CR^{4a}R^{5a})_m$—$W^1$, $NC(O)N(R^{1b})$—$(CR^{4a}R^{5a})_m$—$W^2$, $NC(O)N(R^{2b})$—$W^3$, wherein $R^{4a}$, $R^{5a}$, $R^{1b}$, $R^{2b}$, $W^1$, $W^2$, $W^3$, m, $G^1$ and $G^2$ are as described in the Summary of the Invention.

In one embodiment, compounds of formula (I) can include compounds of formula (Ic):

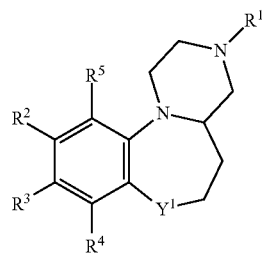

(Ic)

wherein $R^1$, $R^2$, $R^3$, $R^4$, $R^5$ and $Y^1$ are as described above.

In another embodiment, compounds of formula (Ic) are disclosed wherein $Y^1$ is $NR^9$, N-$G^1$, N—$(CR^{4a}R^{5a})_m$-$G^1$, $N^+$—$[(CR^{4a}R^{5a})_m$-$G^1]_2$, $NC(O)$—$(CR^{4a}R^{5a})_m$-$G^1$, $NC(O)$—$CH$=$CH$-$G^1$, $NC(O)$-$G^1$, $NC(O)$-$G^2$-$G^1$, N-$G^2$, N—$(CR^{4a}R^{5a})_m$-$G^2$, $NC(O)$—$(CR^{4a}R^{5a})_m$-$G^2$, or $NC(O)$-$G^2$, wherein $R^9$, $R^{4a}$, $R^{5a}$, m, $G^1$ and $G^2$ are as described in the Summary of the Invention.

In another embodiment, compounds of formula (Ic) are disclosed wherein $Y^1$ is $NR^9$, wherein $R^9$ is hydrogen or alkyl.

In a further embodiment, compounds of formula (Ic) are disclosed wherein $Y^1$ is N-$G^1$, N—$(CR^{4a}R^{5a})_m$-$G^1$, $N^+$—$[(CR^{4a}R^{5a})_m$-$G^1]_2$, $NC(O)$—$(CR^{4a}R^{5a})_m$-$G^1$, $NC(O)$—$CH$=$CH$-$G^1$, $NC(O)$-$G^1$, $NC(O)$-$G^2$-$G^1$, N-$G^2$, N—(CR$^{4a}$R$^{5a}$)$_m$-G$^2$, NC(O)—(CR$^{4a}$R$^{5a}$)$_m$-G$^2$, or NC(O)-G$^2$, wherein R$^{4a}$, R$^{5a}$, m, G$^1$ and G$^2$ are as described in the Summary of the Invention.

In one embodiment, compounds of formula (I) can include compounds of formula (Id):

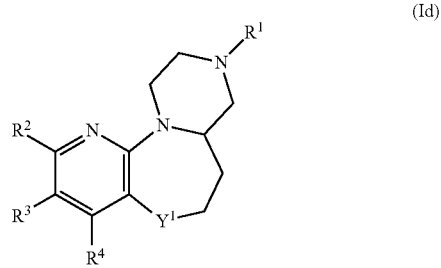

(Id)

wherein R$^1$, R$^2$, R$^3$, R$^4$, and Y$^1$ are as described above.

In another embodiment, compounds of formula (Id) are disclosed wherein Y$^1$ is NR$^9$, N-G$^1$, N—(CR$^{4a}$R$^{5a}$)$_m$-G$^1$, N$^+$—[(CR$^{4a}$R$^{5a}$)$_m$-G$^1$]$_2$, NC(O)—(CR$^{4a}$R$^{5a}$)$_m$-G$^1$, NC(O)—CH=CH-G$^1$, NC(O)-G$^1$, NC(O)-G$^2$-G$^1$, N-G$^2$, N—(CR$^{4a}$R$^{5a}$)$_m$-G$^2$, NC(O)—(CR$^{4a}$R$^{5a}$)$_m$-G$^2$, or NC(O)-G$^2$, wherein R$^9$, R$^{4a}$, R$^{5a}$, m, G$^1$ and G$^2$ are as described in the Summary of the Invention.

In another embodiment, compounds of formula (Id) are disclosed wherein Y$^1$ is NR$^9$, wherein R$^9$ is hydrogen or alkyl.

In a further embodiment, compounds of formula (Id) are disclosed wherein Y$^1$ is N—(CR$^{4a}$R$^{5a}$)$_m$-G$^1$, NC(O)—(CR$^{4a}$R$^{5a}$)$_m$-G$^1$, N—(CR$^{4a}$R$^{5a}$)$_m$-G$^2$, or NC(O)-G$^2$, wherein R$^{4a}$, R$^{5a}$, m, G$^1$ and G$^2$ are as described in the Summary of the Invention.

Specific embodiments of compounds contemplated as part of the invention include, but are not limited to:

tert-butyl 5-oxo-1,2,4a,5,6,7-hexahydropyrazino[1,2-a][1,4]benzodiazepine-3(4H)-carboxylate;
3-benzyl-1,2,3,4,4a,5,6,7-octahydropyrazino[1,2-a][1,4]benzodiazepine;
3-benzyl-6-(4-bromobenzyl)-1,2,3,4,4a,5,6,7-octahydropyrazino[1,2-a][1,4]benzodiazepine;
1-(3-benzyl-1,2,3,4,4a,5-hexahydropyrazino[1,2-a][1,4]benzodiazepin-6(7H)-yl)-2-phenylethanone;
(3-benzyl-1,2,3,4,4a,5-hexahydropyrazino[1,2-a][1,4]benzodiazepin-6(7H)-yl)(phenyl)methanone;
3,6,6-tribenzyl-1,2,3,4,4a,5,6,7-octahydropyrazino[1,2-a][1,4]benzodiazepin-6-ium;
3,6-dibenzyl-1,2,3,4,4a,5,6,7-octahydropyrazino[1,2-a][1,4]benzodiazepine;
3-benzyl-6-methyl-1,2,3,4,4a,5,6,7-octahydropyrazino[1,2-a][1,4]benzodiazepine;
3-benzyl-6-(pyrimidin-2-yl)-1,2,3,4,4a,5,6,7-octahydropyrazino[1,2-a][1,4]benzodiazepine;
(3-benzyl-1,2,3,4,4a,5-hexahydropyrazino[1,2-a][1,4]benzodiazepin-6(7H)-yl)(4-fluorophenyl)methanone;
3-benzyl-6-(pyrazin-2-yl)-1,2,3,4,4a,5,6,7-octahydropyrazino[1,2-a][1,4]benzodiazepine;
(3-benzyl-1,2,3,4,4a,5-hexahydropyrazino[1,2-a][1,4]benzodiazepin-6(7H)-yl)(pyrazin-2-yl)methanone;
(3-benzyl-1,2,3,4,4a,5-hexahydropyrazino[1,2-a][1,4]benzodiazepin-6(7H)-yl)(1-phenylcyclopropyl)methanone;
(3-benzyl-1,2,3,4,4a,5-hexahydropyrazino[1,2-a][1,4]benzodiazepin-6(7H)-yl)(morpholin-4-yl)methanone;
(3-benzyl-1,2,3,4,4a,5-hexahydropyrazino[1,2-a][1,4]benzodiazepin-6(7H)-yl) [trans-2-phenylcyclopropyl]methanone;
3-benzyl-6-(pyridin-2-yl)-1,2,3,4,4a,5,6,7-octahydropyrazino[1,2-a][1,4]benzodiazepine;
3-benzyl-6-(4-fluorobenzyl)-1,2,3,4,4a,5,6,7-octahydropyrazino[1,2-a][1,4]benzodiazepine;
(−)-3-benzyl-6-(4-bromobenzyl)-1,2,3,4,4a,5,6,7-octahydropyrazino[1,2-a][1,4]benzodiazepine;
(+)-3-benzyl-6-(4-bromobenzyl)-1,2,3,4,4a,5,6,7-octahydropyrazino[1,2-a][1,4]benzodiazepine;
(2E)-1-(3-benzyl-1,2,3,4,4a,5-hexahydropyrazino[1,2-a][1,4]benzodiazepin-6(7H)-yl)-3-phenylprop-2-en-1-one;
3-benzyl-6-[4-(trifluoromethyl)benzyl]-1,2,3,4,4a,5,6,7-octahydropyrazino[1,2-a][1,4]benzodiazepine;
7-(4-bromobenzyl)-3-methyl-1,2,3,4,4a,5,6,7-octahydropyrazino[1,2-a][1,5]benzodiazepine;
3-benzyl-6-(4-bromo-3-fluorobenzyl)-1,2,3,4,4a,5,6,7-octahydropyrazino[1,2-a][1,4]benzodiazepine;
3-benzyl-6-(3,5-difluorobenzyl)-1,2,3,4,4a,5,6,7-octahydropyrazino[1,2-a][1,4]benzodiazepine;
3-benzyl-6-(3,4-difluorobenzyl)-1,2,3,4,4a,5,6,7-octahydropyrazino[1,2-a][1,4]benzodiazepine;
3-benzyl-1,2,3,4,4a,5,6,7-octahydropyrazino[1,2-a][1,5]benzodiazepine;
1-(3-benzyl-2,3,4,4a,5,6-hexahydropyrazino[1,2-a][1,5]benzodiazepin-7(1H)-yl)-2-(4-chlorophenyl)ethanone;
3-benzyl-6-(pyridin-3-ylmethyl)-1,2,3,4,4a,5,6,7-octahydropyrazino[1,2-a][1,4]benzodiazepine;
3-benzyl-6-(pyridin-2-ylmethyl)-1,2,3,4,4a,5,6,7-octahydropyrazino[1,2-a][1,4]benzodiazepine;
3-benzyl-6-(pyridin-4-ylmethyl)-1,2,3,4,4a,5,6,7-octahydropyrazino[1,2-a][1,4]benzodiazepine;
(3-benzyl-1,2,3,4,4a,5-hexahydropyrazino[1,2-a][1,4]benzodiazepin-6(7H)-yl)(4-bromophenyl)methanone;
3-benzyl-6-[(6-methylpyridin-3-yl)methyl]-1,2,3,4,4a,5,6,7-octahydropyrazino[1,2-a][1,4]benzodiazepine;
3-benzyl-6-(quinolin-3-ylmethyl)-1,2,3,4,4a,5,6,7-octahydropyrazino[1,2-a][1,4]benzodiazepine;
3-benzyl-6-[(6-chloropyridin-3-yl)methyl]-1,2,3,4,4a,5,6,7-octahydropyrazino[1,2-a][1,4]benzodiazepine;
3-benzyl-6-{[6-(trifluoromethyl)pyridin-3-yl]methyl}-1,2,3,4,4a,5,6,7-octahydropyrazino[1,2-a][1,4]benzodiazepine;
3-benzyl-6-(quinolin-4-ylmethyl)-1,2,3,4,4a,5,6,7-octahydropyrazino[1,2-a][1,4]benzodiazepine;
3-benzyl-6-(isoquinolin-4-ylmethyl)-1,2,3,4,4a,5,6,7-octahydropyrazino[1,2-a][1,4]benzodiazepine;
3-(4-fluorobenzyl)-2,3,4,4a,6,7-hexahydropyrazino[1,2-a][1,4]benzodiazepin-5(1H)-one;
3-benzyl-6-[(6-bromopyridin-3-yl)methyl]-1,2,3,4,4a,5,6,7-octahydropyrazino[1,2-a][1,4]benzodiazepine;
3-(4-fluorobenzyl)-1,2,3,4,4a,5,6,7-octahydropyrazino[1,2-a][1,4]benzodiazepine;
(3-benzyl-2,3,4,4a,5,6-hexahydropyrazino[1,2-a][1,5]benzodiazepin-7(1H)-yl)(4-bromophenyl)methanone;
3-benzyl-6-[(5-bromopyridin-2-yl)methyl]-1,2,3,4,4a,5,6,7-octahydropyrazino[1,2-a][1,4]benzodiazepine;
(3-benzyl-2,3,4,4a,5,6-hexahydropyrazino[1,2-a][1,5]benzodiazepin-7(1H)-yl)(pyridin-4-yl)methanone;
3-benzyl-7-[2-(4-chlorophenyl)ethyl]-1,2,3,4,4a,5,6,7-octahydropyrazino[1,2-a][1,5]benzodiazepine;
3,7-dibenzyl-1,2,3,4,4a,5,6,7-octahydropyrazino[1,2-a][1,5]benzodiazepine;
3-benzyl-6-(4-iodobenzyl)-1,2,3,4,4a,5,6,7-octahydropyrazino[1,2-a][1,4]benzodiazepine;
3-benzyl-7-(4-bromobenzyl)-1,2,3,4,4a,5,6,7-octahydropyrazino[1,2-a][1,5]benzodiazepine;
3-benzyl-7-(pyridin-4-ylmethyl)-1,2,3,4,4a,5,6,7-octahydropyrazino[1,2-a][1,5]benzodiazepine;

3-benzyl-7-methyl-1,2,3,4,4a,5,6,7-octahydropyrazino[1,2-a][1,5]benzodiazepine;

4-[(3-benzyl-1,2,3,4,4a,5-hexahydropyrazino[1,2-a][1,4]benzodiazepin-6(7H)-yl)methyl]phenol;

9-benzyl-7,7a,8,9,10,11-hexahydropyrazino[1,2-d]pyrido[3,2-b][1,4]diazepin-6 (5H)-one;

9-benzyl-5,6,7,7a,8,9,10,11-octahydropyrazino[1,2-d]pyrido[3,2-b][1,4]diazepine;

1-(9-benzyl-7,7a,8,9,10,11-hexahydropyrazino[1,2-d]pyrido[3,2-b][1,4]diazepin-5(6H)-yl)-2-(4-chlorophenyl)ethanone;

9-benzyl-5-[2-(4-chlorophenyl)ethyl]-5,6,7,7a,8,9,10,11-octahydropyrazino[1,2-d]pyrido[3,2-b][1,4]diazepine;

9-benzyl-5-methyl-5,6,7,7a,8,9,10,11-octahydropyrazino[1,2-d]pyrido[3,2-b][1,4]diazepine;

6-(4-bromobenzyl)-3-(4-fluorobenzyl)-1,2,3,4,4a,5,6,7-octahydropyrazino[1,2-a][1,4]benzodiazepine;

6-(4-bromobenzyl)-3-methyl-1,2,3,4,4a,5,6,7-octahydropyrazino[1,2-a][1,4]benzodiazepine;

(9-benzyl-7,7a,8,9,10,11-hexahydropyrazino[1,2-d]pyrido[3,2-b][1,4]diazepin-5(6H)-yl)(2,2,3,3-tetramethylcyclopropyl)methanone;

9-benzyl-5-[(2,2,3,3-tetramethylcyclopropyl)methyl]-5,6,7,7a,8,9,10,11-octahydropyrazino[1,2-d]pyrido[3,2-b][1,4]diazepine;

1-(3-benzyl-1,2,3,4,4a,5-hexahydropyrazino[1,2-a][1,4]benzodiazepin-6(7H)-yl)-2-(6-chloropyridin-3-yl)ethanone;

(+)-(4aS)-6-(4-bromobenzyl)-3-(4-fluorobenzyl)-1,2,3,4,4a,5,6,7-octahydropyrazino[1,2-a][1,4]benzodiazepine;

(−)-(4aR)-6-(4-bromobenzyl)-3-(4-fluorobenzyl)-1,2,3,4,4a,5,6,7-octahydropyrazino[1,2-a][1,4]benzodiazepine;

3-benzyl-6-[2-(6-chloropyridin-3-yl)ethyl]-1,2,3,4,4a,5,6,7-octahydropyrazino[1,2-a][1,4]benzodiazepine;

5-(cyclopropylmethyl)-9-(4-fluorobenzyl)-5,6,7,7a,8,9,10,11-octahydropyrazino[1,2-d]pyrido[3,2-b][1,4]diazepine;

5-(cyclobutylmethyl)-9-(4-fluorobenzyl)-5,6,7,7a,8,9,10,11-octahydropyrazino[1,2-d]pyrido[3,2-b][1,4]diazepine;

tert-butyl 6-(4-bromobenzyl)-1,2,4a,5,6,7-hexahydropyrazino[1,2-a][1,4]benzodiazepine-3(4H)-carboxylate;

tert-butyl 6-(4-bromobenzyl)-5-oxo-1,2,4a,5,6,7-hexahydropyrazino[1,2-a][1,4]benzodiazepine-3(4H)-carboxylate;

5-[(2S)-azetidin-2-ylmethyl]-9-(4-fluorobenzyl)-5,6,7,7a,8,9,10,11-octahydropyrazino[1,2-d]pyrido[3,2-b][1,4]diazepine;

5-(azetidin-3-ylmethyl)-9-(4-fluorobenzyl)-5,6,7,7a,8,9,10,11-octahydropyrazino[1,2-d]pyrido[3,2-b][1,4]diazepine;

6-(4-bromobenzyl)-2,3,4,4a,6,7-hexahydropyrazino[1,2-a][1,4]benzodiazepin-5(1H)-one;

6-(4-bromobenzyl)-1,2,3,4,4a,5,6,7-octahydropyrazino[1,2-a][1,4]benzodiazepine;

cyclopropyl(7,7a,8,9,10,11-hexahydropyrazino[1,2-d]pyrido[3,2-b][1,4]diazepin-5(6H)-yl)methanone;

6-(4-bromobenzyl)-3-(4-fluorobenzyl)-2,3,4,4a,6,7-hexahydropyrazino[1,2-a][1,4]benzodiazepin-5(1H)-one;

[5-(cyclopropylmethyl)-6,7,7a,8,10,11-hexahydropyrazino[1,2-d]pyrido[3,2-b][1,4]diazepin-9(5H)-yl](pyridin-3-yl)methanone;

1,2,3,4,4a,5-hexahydropyrazino[1,2-a][1,4]benzodiazepin-6(7H)-yl(morpholin-4-yl)methanone;

[3-(4-fluorobenzyl)-1,2,3,4,4a,5-hexahydropyrazino[1,2-a][1,4]benzodiazepin-6(7H)-yl](morpholin-4-yl)methanone;

(3-methyl-1,2,3,4,4a,5-hexahydropyrazino[1,2-a][1,4]benzodiazepin-6(7H)-yl)(morpholin-4-yl)methanone;

2-[2-(3-benzyl-2,3,4,4a,5,6-hexahydropyrazino[1,2-a][1,5]benzodiazepin-7(1H)-yl)-2-oxoethyl]pyridazin-3(2H)-one;

(3-benzoyl-1,2,3,4,4a,5-hexahydropyrazino[1,2-a][1,4]benzodiazepin-6(7H)-yl)(morpholin-4-yl)methanone;

morpholin-4-yl[3-(pyrimidin-2-yl)-1,2,3,4,4a,5-hexahydropyrazino[1,2-a][1,4]benzodiazepin-6(7H)-yl]methanone;

morpholin-4-yl[3-(phenylsulfonyl)-1,2,3,4,4a,5-hexahydropyrazino[1,2-a][1,4]benzodiazepin-6(7H)-yl]methanone;

[3-(4-chlorophenyl)-1,2,3,4,4a,5-hexahydropyrazino[1,2-a][1,4]benzodiazepin-6(7H)-yl](morpholin-4-yl)methanone;

1-[6-(morpholin-4-ylcarbonyl)-1,2,4a,5,6,7-hexahydropyrazino[1,2-a][1,4]benzodiazepin-3(4H)-yl]ethanone;

1-{4-[(3-benzyl-1,2,3,4,4a,5-hexahydropyrazino[1,2-a][1,4]benzodiazepin-6(7H)-yl)carbonyl]piperidin-1-yl}ethanone;

(3-benzyl-1,2,3,4,4a,5-hexahydropyrazino[1,2-a][1,4]benzodiazepin-6(7H)-yl)(1H-pyrazol-4-yl)methanone;

(3-benzyl-1,2,3,4,4a,5-hexahydropyrazino[1,2-a][1,4]benzodiazepin-6(7H)-yl)(1H-pyrazol-5-yl)methanone;

1-(3-benzyl-1,2,3,4,4a,5-hexahydropyrazino[1,2-a][1,4]benzodiazepin-6(7H)-yl)-2-(morpholin-4-yl)ethanone;

(3-benzyl-1,2,3,4,4a,5-hexahydropyrazino[1,2-a][1,4]benzodiazepin-6(7H)-yl)(1,3-thiazol-4-yl)methanone;

(3-benzyl-1,2,3,4,4a,5-hexahydropyrazino[1,2-a][1,4]benzodiazepin-6(7H)-yl)(1,3-thiazol-5-yl)methanone;

(3-benzyl-1,2,3,4,4a,5-hexahydropyrazino[1,2-a][1,4]benzodiazepin-6(7H)-yl)(1,2-oxazol-5-yl)methanone;

1-(3-benzyl-1,2,3,4,4a,5-hexahydropyrazino[1,2-a][1,4]benzodiazepin-6(7H)-yl)-3-(pyrrolidin-1-yl)propan-1-one;

1-(3-benzyl-1,2,3,4,4a,5-hexahydropyrazino[1,2-a][1,4]benzodiazepin-6(7H)-yl)-2-cyclopropylethanone;

(3-benzyl-1,2,3,4,4a,5-hexahydropyrazino[1,2-a][1,4]benzodiazepin-6(7H)-yl)(1H-pyrrol-2-yl)methanone;

(3-benzyl-1,2,3,4,4a,5-hexahydropyrazino[1,2-a][1,4]benzodiazepin-6(7H)-yl)(3-furyl)methanone;

(3-benzyl-1,2,3,4,4a,5-hexahydropyrazino[1,2-a][1,4]benzodiazepin-6(7H)-yl)(1,2,5-trimethyl-1H-pyrrol-3-yl)methanone;

(3-benzyl-1,2,3,4,4a,5-hexahydropyrazino[1,2-a][1,4]benzodiazepin-6(7H)-yl)(2,5-dimethyl-1H-pyrrol-3-yl)methanone;

1-[(3-benzyl-1,2,3,4,4a,5-hexahydropyrazino[1,2-a][1,4]benzodiazepin-6(7H)-yl)carbonyl]cyclopropanecarboxamide;

1-(3-benzyl-1,2,3,4,4a,5-hexahydropyrazino[1,2-a][1,4]benzodiazepin-6(7H)-yl)-2-(pyridin-3-yl)ethanone;

N-[2-(3-benzyl-1,2,3,4,4a,5-hexahydropyrazino[1,2-a][1,4]benzodiazepin-6(7H)-yl)-2-oxoethyl]-2-furamide;

1-(3-benzyl-1,2,3,4,4a,5-hexahydropyrazino[1,2-a][1,4]benzodiazepin-6(7H)-yl)-2-methylpropan-1-one;

(3-benzyl-1,2,3,4,4a,5-hexahydropyrazino[1,2-a][1,4]benzodiazepin-6(7H)-yl)(3,5-dimethyl-1,2-oxazol-4-yl)methanone;

(3-benzyl-1,2,3,4,4a,5-hexahydropyrazino[1,2-a][1,4]benzodiazepin-6(7H)-yl)(5-methylpyrazin-2-yl)methanone;

1-(3-benzyl-1,2,3,4,4a,5-hexahydropyrazino[1,2-a][1,4]benzodiazepin-6(7H)-yl)-2-(4-methylpiperazin-1-yl)ethanone;

(3-benzyl-1,2,3,4,4a,5-hexahydropyrazino[1,2-a][1,4]benzodiazepin-6(7H)-yl)(2-furyl)methanone;

(3-benzyl-1,2,3,4,4a,5-hexahydropyrazino[1,2-a][1,4]benzodiazepin-6(7H)-yl)(1-methyl-1H-pyrrol-2-yl)methanone;

1-(3-benzyl-1,2,3,4,4a,5-hexahydropyrazino[1,2-a][1,4]
benzodiazepin-6(7H)-yl)propan-1-one;
(3-benzyl-1,2,3,4,4a,5-hexahydropyrazino[1,2-a][1,4]ben-
zodiazepin-6(7H)-yl)(pyridin-4-yl)methanone;
1-(3-benzyl-1,2,3,4,4a,5-hexahydropyrazino[1,2-a][1,4]
benzodiazepin-6(7H)-yl)butan-1-one;
(3-benzyl-1,2,3,4,4a,5-hexahydropyrazino[1,2-a][1,4]ben-
zodiazepin-6(7H)-yl)(tetrahydrofuran-3-yl)methanone;
(3-benzyl-1,2,3,4,4a,5-hexahydropyrazino[1,2-a][1,4]ben-
zodiazepin-6(7H)-yl)(pyridin-3-yl)methanone;
1-(3-benzyl-1,2,3,4,4a,5-hexahydropyrazino[1,2-a][1,4]
benzodiazepin-6(7H)-yl)-3-(piperidin-1-yl)propan-1-one;
(3-benzyl-1,2,3,4,4a,5-hexahydropyrazino[1,2-a][1,4]ben-
zodiazepin-6(7H)-yl)(cyclopropyl)methanone;
1-(3-benzyl-1,2,3,4,4a,5-hexahydropyrazino[1,2-a][1,4]
benzodiazepin-6(7H)-yl)-2-ethoxyethanone;
(3-benzyl-1,2,3,4,4a,5-hexahydropyrazino[1,2-a][1,4]ben-
zodiazepin-6(7H)-yl)(1-methylcyclopropyl)methanone;
(3-benzyl-1,2,3,4,4a,5-hexahydropyrazino[1,2-a][1,4]ben-
zodiazepin-6(7H)-yl)(cyclobutyl)methanone;
(3-benzyl-1,2,3,4,4a,5-hexahydropyrazino[1,2-a][1,4]ben-
zodiazepin-6(7H)-yl)(2-methylcyclopropyl)methanone;
1-(3-benzyl-1,2,3,4,4a,5-hexahydropyrazino[1,2-a][1,4]
benzodiazepin-6(7H)-yl)-3,3,3-trifluoropropan-1-one;
(3-benzyl-1,2,3,4,4a,5-hexahydropyrazino[1,2-a][1,4]ben-
zodiazepin-6(7H)-yl)(tetrahydrofuran-2-yl)methanone;
3-benzyl-6-(4-methoxy-3-methylbenzyl)-1,2,3,4,4a,5,6,7-
octahydropyrazino[1,2-a][1,4]benzodiazepine;
3-benzyl-6-[(4,5-dimethyl-2-furyl)methyl]-1,2,3,4,4a,5,6,7-
octahydropyrazino[1,2-a][1,4]benzodiazepine;
3-benzyl-6-(4-ethoxybenzyl)-1,2,3,4,4a,5,6,7-octahydropy-
razino[1,2-a][1,4]benzodiazepine;
3-benzyl-6-[(5-methyl-2-thienyl)methyl]-1,2,3,4,4a,5,6,7-
octahydropyrazino[1,2-a][1,4]benzodiazepine;
3-benzyl-6-(4-bromobenzyl)-1,2,3,4,4a,5,6,7-octahydropy-
razino[1,2-a][1,4]benzodiazepine;
3-benzyl-6-(2-naphthylmethyl)-1,2,3,4,4a,5,6,7-octahydro-
pyrazino[1,2-a][1,4]benzodiazepine;
3-benzyl-6-(cyclopentylmethyl)-1,2,3,4,4a,5,6,7-octahydro-
pyrazino[1,2-a][1,4]benzodiazepine;
3-benzyl-6-(quinolin-2-ylmethyl)-1,2,3,4,4a,5,6,7-octahy-
dropyrazino[1,2-a][1,4]benzodiazepine;
3-benzyl-6-[(5-ethyl-2-furyl)methyl]-1,2,3,4,4a,5,6,7-oc-
tahydropyrazino[1,2-a][1,4]benzodiazepine;
4-[(3-benzyl-1,2,3,4,4a,5-hexahydropyrazino[1,2-a][1,4]
benzodiazepin-6(7H)-yl)methyl]benzonitrile;
3-benzyl-6-butyl-1,2,3,4,4a,5,6,7-octahydropyrazino[1,2-a]
[1,4]benzodiazepine;
3-benzyl-6-(4-chlorobenzyl)-1,2,3,4,4a,5,6,7-octahydropy-
razino[1,2-a][1,4]benzodiazepine;
3-benzyl-6-(2-methylbenzyl)-1,2,3,4,4a,5,6,7-octahydropy-
razino[1,2-a][1,4]benzodiazepine;
3-benzyl-6-(2-bromobenzyl)-1,2,3,4,4a,5,6,7-octahydropy-
razino[1,2-a][1,4]benzodiazepine;
3-benzyl-6-(2-methoxybenzyl)-1,2,3,4,4a,5,6,7-octahydro-
pyrazino[1,2-a][1,4]benzodiazepine;
3-benzyl-6-(4-methoxybenzyl)-1,2,3,4,4a,5,6,7-octahydro-
pyrazino[1,2-a][1,4]benzodiazepine;
3-benzyl-6-(3-methoxybenzyl)-1,2,3,4,4a,5,6,7-octahydro-
pyrazino[1,2-a][1,4]benzodiazepine;
3-benzyl-6-(3-bromobenzyl)-1,2,3,4,4a,5,6,7-octahydropy-
razino[1,2-a][1,4]benzodiazepine;
3-benzyl-6-(4-methylbenzyl)-1,2,3,4,4a,5,6,7-octahydropy-
razino[1,2-a][1,4]benzodiazepine;
3-benzyl-6-(1-naphthylmethyl)-1,2,3,4,4a,5,6,7-octahydro-
pyrazino[1,2-a][1,4]benzodiazepine;
3-benzyl-6-(2-chlorobenzyl)-1,2,3,4,4a,5,6,7-octahydropy-
razino[1,2-a][1,4]benzodiazepine;
3-benzyl-6-(3-chlorobenzyl)-1,2,3,4,4a,5,6,7-octahydropy-
razino[1,2-a][1,4]benzodiazepine;
3-benzyl-6-(2,2-dimethylpropyl)-1,2,3,4,4a,5,6,7-octahy-
dropyrazino[1,2-a][1,4]benzodiazepine;
3-benzyl-6-[(3-methyl-2-thienyl)methyl]-1,2,3,4,4a,5,6,7-
octahydropyrazino[1,2-a][1,4]benzodiazepine;
3-benzyl-6-(3-methylbutyl)-1,2,3,4,4a,5,6,7-octahydropy-
razino[1,2-a][1,4]benzodiazepine;
3-benzyl-6-(cyclohexylmethyl)-1,2,3,4,4a,5,6,7-octahydro-
pyrazino[1,2-a][1,4]benzodiazepine;
3-benzyl-6-(3-methylbenzyl)-1,2,3,4,4a,5,6,7-octahydropy-
razino[1,2-a][1,4]benzodiazepine;
3-[(3-benzyl-1,2,3,4,4a,5-hexahydropyrazino[1,2-a][1,4]
benzodiazepin-6(7H)-yl)methyl]benzonitrile;
3-benzyl-6-(2-thienylmethyl)-1,2,3,4,4a,5,6,7-octahydropy-
razino[1,2-a][1,4]benzodiazepine;
3-benzyl-6-isobutyl-1,2,3,4,4a,5,6,7-octahydropyrazino[1,
2-a][1,4]benzodiazepine;
3-benzyl-N-(2-methoxyethyl)-N-methyl-1,2,3,4,4a,5-
hexahydropyrazino[1,2-a][1,4]benzodiazepine-6(7H)-
carboxamide;
3-benzyl-N-[2-(pyridin-3-yl)ethyl]-1,2,3,4,4a,5-hexahydro-
pyrazino[1,2-a][1,4]benzodiazepine-6(7H)-carboxamide;
3-benzyl-N-[2-(pyridin-2-yl)ethyl]-1,2,3,4,4a,5-hexahydro-
pyrazino[1,2-a][1,4]benzodiazepine-6(7H)-carboxamide;
3-benzyl-N-[2-(pyridin-4-yl)ethyl]-1,2,3,4,4a,5-hexahydro-
pyrazino[1,2-a][1,4]benzodiazepine-6(7H)-carboxamide;
3-benzyl-N-(2-cyanoethyl)-N-cyclopropyl-1,2,3,4,4a,5-
hexahydropyrazino[1,2-a][1,4]benzodiazepine-6(7H)-
carboxamide;
[4-(2-aminoethyl)-1H-imidazol-1-yl](3-benzyl-1,2,3,4,4a,
5-hexahydropyrazino[1,2-a][1,4]benzodiazepin-6(7H)-
yl)methanone;
3-benzyl-N-(pyridin-4-ylmethyl)-1,2,3,4,4a,5-hexahydro-
pyrazino[1,2-a][1,4]benzodiazepine-6(7H)-carboxamide;
3-benzyl-N-[(5-methyl-2-furyl)methyl]-1,2,3,4,4a,5-
hexahydropyrazino[1,2-a][1,4]benzodiazepine-6(7H)-
carboxamide;
3-benzyl-N-ethyl-N-(2-methoxyethyl)-1,2,3,4,4a,5-hexahy-
dropyrazino[1,2-a][1,4]benzodiazepine-6(7H)-carboxam-
ide;
3-benzyl-N,N-diethyl-1,2,3,4,4a,5-hexahydropyrazino[1,2-
a][1,4]benzodiazepine-6(7H)-carboxamide;
3-benzyl-N-(1,3-thiazol-2-yl)-1,2,3,4,4a,5-hexahydropy-
razino[1,2-a][1,4]benzodiazepine-6(7H)-carboxamide;
3-benzyl-N-(cyclopropylmethyl)-1,2,3,4,4a,5-hexahydropy-
razino[1,2-a][1,4]benzodiazepine-6(7H)-carboxamide;
(3-benzyl-1,2,3,4,4a,5-hexahydropyrazino[1,2-a][1,4]ben-
zodiazepin-6(7H)-yl)(4-isopropylpiperazin-1-yl)metha-
none;
3-benzyl-N-isobutyl-1,2,3,4,4a,5-hexahydropyrazino[1,2-a]
[1,4]benzodiazepine-6(7H)-carboxamide;
3-benzyl-N-(pyridin-3-ylmethyl)-1,2,3,4,4a,5-hexahydro-
pyrazino[1,2-a][1,4]benzodiazepine-6(7H)-carboxamide;
3-benzyl-N-[3-(dimethylamino)propyl]-1,2,3,4,4a,5-
hexahydropyrazino[1,2-a][1,4]benzodiazepine-6(7H)-
carboxamide;
3-benzyl-N-butyl-N-(cyanomethyl)-1,2,3,4,4a,5-hexahy-
dropyrazino[1,2-a][1,4]benzodiazepine-6(7H)-carboxam-
ide;
3-benzyl-N-(3-methoxypropyl)-1,2,3,4,4a,5-hexahydropy-
razino[1,2-a][1,4]benzodiazepine-6(7H)-carboxamide;
3-benzyl-N-(2-methoxyethyl)-1,2,3,4,4a,5-hexahydropy-
razino[1,2-a][1,4]benzodiazepine-6(7H)-carboxamide;

3-benzyl-N-(pyridin-2-ylmethyl)-1,2,3,4,4a,5-hexahydropyrazino[1,2-a][1,4]benzodiazepine-6(7H)-carboxamide;
3-benzyl-N-cyclobutyl-1,2,3,4,4a,5-hexahydropyrazino[1,2-a][1,4]benzodiazepine-6(7H)-carboxamide;
3-benzyl-N-methyl-N-propyl-1,2,3,4,4a,5-hexahydropyrazino[1,2-a][1,4]benzodiazepine-6(7H)-carboxamide;
(3-benzyl-1,2,3,4,4a,5-hexahydropyrazino[1,2-a][1,4]benzodiazepin-6(7H)-yl)(piperidin-1-yl)methanone;
6-(cyclopropylmethyl)-2,3,4,4a,6,7-hexahydropyrazino[1,2-a][1,4]benzodiazepin-5(1H)-one;
[4-(3-methyl-1,2,3,4,4a,5-hexahydropyrazino[1,2-a][1,4]benzodiazepin-6(7H)-yl)piperidin-1-yl](phenyl)methanone;
(2-chlorophenyl)(3-methyl-1,2,3,4,4a,5-hexahydropyrazino[1,2-a][1,4]benzodiazepin-6(7H)-yl)methanone;
(3-chlorophenyl)(3-methyl-1,2,3,4,4a,5-hexahydropyrazino[1,2-a][1,4]benzodiazepin-6(7H)-yl)methanone; or
(4-chlorophenyl)(3-methyl-1,2,3,4,4a,5-hexahydropyrazino[1,2-a][1,4]benzodiazepin-6(7H)-yl)methanone.

Compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

The present application contemplates various stereoisomers and mixtures thereof and these are specifically included within the scope of this application. Stereoisomers include enantiomers and diastereomers, and mixtures of enantiomers or diastereomers. Individual stereoisomers of compounds of the present application may be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers may exist in the compounds of the present invention. The present invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

Within the present invention it is to be understood that compounds disclosed herein may exhibit the phenomenon of tautomerism.

Thus, the formulae drawings within this specification can represent only one of the possible tautomeric or stereoisomeric forms. It is to be understood that the present invention encompasses any tautomeric or stereoisomeric form, and mixtures thereof, and is not to be limited merely to any one tautomeric or stereoisomeric form utilized within the naming of the compounds or formulae drawings.

The present invention also includes isotopically-labeled compounds, which are identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, fluorine, and chlorine, such as, but not limited to $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Compounds incorporating positron-emitting isotopes are useful in medical imaging and positron-emitting tomography (PET) studies for determining the distribution of receptors. Suitable positron-emitting isotopes that can be incorporated in compounds of formula (I) are $^{13}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

c. BIOLOGICAL DATA

To determine the effectiveness of compounds having a formula (I), these compounds can be evaluated in in vitro models of cellular function and in vivo models of pro-cognitive effects.

Abbreviations which have been used in the descriptions of Biological Data that follow are: DMEM for Dulbecco's modified Eagle's medium; DMSO for dimethyl sulfoxide; FBS for fetal bovine serum; FLIPR for fluorometric imaging plate reader; GFAP for glial fibrillary acidic protein; HBSS for Hank's balanced salt solution; i.p. for intraperitoneal; NGF for nerve growth factor; PBS for phosphate buffered saline; and TRITC for tetramethylrhodamine isothiocyanate.

(i) Effects on Neurite Outgrowth in Neurons and Neuronal Cell Lines:

Effects on cellular properties such as neurite outgrowth and neuronal or neuronal-like cell number, etc. can be measured either using rat or human neuronal/neuroblastoma cell lines (e.g., SH-SY5Y, PC12, IMR-32, etc.) or using primary cells (e.g., rat cortical neurons).

For example, studies can be conducted using PC12 cells plated in 96-well plates, treated with or without nerve growth factor (100 ng/mL) for 6 days. Compounds are then added at various concentrations (ranging from 0.1 nM to 30 μM), and incubated for 24 hours. Cells are then fixed and stained by neuron marker β-tubulin (green), and nuclei were stained by Hoechst 33342 (blue). Images are collected using the ImageXpress Micro automatic fluorescent microscopy system (Molecular Devices, Sunnyvale, Calif.) employing a Nikon 10× Plan Fluor objective and Cool Snap HQ CCD camera. The Neurite Outgrowth module in the MetaMorph Imaging software can be used to automatically count neuron-like number, and the extent of neurite outgrowth.

In addition to PC12 cells, other cellular model systems may also be used. Rat cortical cells can be cultured and prepared for high content microscopy analysis as previously described (Hu, M.; Schurdak, M. E.; et al. High content screen microscopy analysis of Aβ$_{1-42}$-induced neurite outgrowth reduction in rat primary cortical neurons: Neuroprotective effects of α7 neuronal nicotinic acetylcholine receptor ligands. *Brain Res.* 2007, 1151, 227-235.). Briefly, cortical cell cultures are plated at density of 5×10$^{5}$ cells/mL onto poly-D-lysine coated 96-well plates and maintained in a cell incubator at 37° C. with 5% CO$_2$. Experiments are performed using 6-7 day-old cortical cell cultures by treating with test compounds. In some experiments, the effect of test compounds on reversing Aβ toxicity can also be measured (Hu, M.; Schurdak, M. E.; et al. High content screen microscopy analysis of $A\beta_{1-42}$-induced neurite outgrowth reduction in rat primary cortical neurons: Neuroprotective effects of α7 neuronal nicotinic acetylcholine receptor ligands. *Brain Res.* 2007, 1151, 227-235.). For assessment of neuroprotective effects, cells are first pretreated with test compounds for about 5 hours. Medium is then replaced with the medium containing freshly prepared about 5 μM $A\beta_{1-42}$ peptide in the absence or presence of the test compounds for 3 days. The untreated group contains the same percentage of vehicle (DMSO) as in the treatment groups. Cells are fixed with approximately 4% paraformaldehyde containing 0.5% Hoechst 33342 for about 15 minutes, followed by three washes using PBS (pH 7.4) and blocked with 10% donkey serum in PBS for 1 hour at room temperature. The cells are then incubated overnight at about 4° C. with mouse anti-tubulin monoclonal antibody (1:100) for staining neurons and rabbit anti-GFAP (1:1000) for staining glia. In the next day, cells are incubated with FITC-labeled anti-mouse and TRITC-labeled anti-rabbit antibodies (1:1000) for about 1 hour at room temperature. After fixing and staining the cells, nuclei (360/400 nm excitation and 465/300 nm emission filters), neuron (475/350 nm excitation and 535/400 nm emission filters) and glial cell (535 nm excitation and 610 nm emission filters) images are collected using the ImageExpress Micro automatic fluorescent microscopy system (Molecular Devices, Sunnyvale, Calif.) employing a Nikon 10× Plan Fluor objective and Cool Snap HQ CCD camera. The Neurite Outgrowth module in the MetaMorph Imaging software can be used to automatically count total cell number, number of neuron cells, and the extent of neurite outgrowth.

(ii) Effects on $A\beta_{1-42}$ Induced Tau Phosphorylation in PC12 Cells

The effect of test compound(s) on $A\beta_{1-42}$ induced tau phosphorylation can be assessed in a cell line such as PC12 as previously described (Hu, M.; Waring, J. F.; et al. Role of GSK-3β activation and α7 nAChRs in $A\beta_{1-42}$-induced tau phosphorylation in PC12 cells. *J. Neurochem.* 2008, 106(3), 1371-1377.). Briefly, PC12 cells are plated on poly-D-lysine coated 96-well plates, cultured in Ham's F12K medium supplemented with 15% horse serum, 2.5% FBS, 2 mM L-glutamine, 100 U/mL penicillin and 100 μg/mL streptomycin at 37° C. with 5% $CO_2$ and differentiated with 100 ng/mL NGF for approximately 6 days. Cells are pretreated with test compounds for 30 minutes at about 37° C. The medium is then replaced with that containing freshly prepared $A\beta_{1-42}$ or control peptide in the absence or presence of the test compounds and the cells are incubated at 37° C. for 24 hours. Cells are fixed with 3.7% formaldehyde in PBS (pH 7.4) for about 1 hour at room temperature followed by permeabilization by three washes with 0.1% Triton-X 100 in PBS. The fixed cells are incubated with blocking buffer for about 2 hours at room temperature followed by overnight incubation with primary antibodies AT8 (for phosphorylated tau), anti-human tau (for total Tau), or anti-GSK-3β. On the next day, cells are washed 3 times with 0.1% Tween-20 in PBS, then incubated with IRDye® 800CW anti-mouse IgG antibodies (1:100) for 1 hour at room temperature for detection of phosphorylated tau (p-tau) or GSK-3β, or with the Alexa Fluor® 680 anti-rabbit antibodies (1:100) for detection of total tau (t-tau). Cells are then washed three times, and the target signals are simultaneously visualized using Odyssey Infrared Imaging Scanner with the 680-nm fluorophore emitting an image of red color and the 800-nm fluorophore emitting an image of green color. The integrated fluorescence intensities are calculated and analyzed using the Odyssey Infrared Imaging System Application Software version 1.2.15 (Li-Cor Biosciences (Lincoln, Nebr.). The p-tau and t-tau levels are typically presented as the ratio p-tau/t-tau (Hu, M.; Waring, J. F.; et al. Role of GSK-3β activation and α7 nAChRs in $A\beta_{1-42}$-induced tau phosphorylation in PC12 cells. *J. Neurochem.* 2008, 106(3), 1371-1377.).

(iii) Effects on Mitochondrial Function

The method also involves a high-throughput assay using serum-deprivation conditions involving neuronal cells to screen for compounds that increase or preserve mitochondrial membrane potential. Such compounds can be found to aid in rescuing cells from energy-depletion that occurs in several neurodegenerative states. Mitochondrial-mediated apoptosis occurs in response to a wide range of apoptotic stimuli including p53, c-myc, DNA damage, prooxidants, chemotherapeutic agents, serum starvation and death receptor activation (Lin C-H., Lu Y-Z., Cheng, F-C., Chu L-F. and Hsueh C-M. Bax-regulated mitochondrial-mediated apoptosis is responsible for the in vitro ischemia induced neuronal cell death of Sprague Dawley rat. *Neuroscience Lett.* 2005, 387, 22-27).

Serum deprivation for 16-18 hours initiates the early stages of apoptosis (Chavier D, Lecoeur H, Langonne A, Borgne-Sanchez A, Mariani J., Martinou J-C, Rebouillat D and Jacotot E. Upstream control of apoptosis by caspase-2 in serum-deprived neurons. Apoptosis 10:1243-1259, 2005) and induces stress on a cell before full commitment to cell death. Mitochondria play a critical role in the cell for survival or death due to their regulation of both energy metabolism as well as apoptosis (Sullivan P G, Rabchevsky A G, Waldmeirer P C and Springer J E. Mitochondrial Permeability Transition in CNS Trauma: Cause or Effect of Neuronal Cell Death. *J. Neuroscience Res.* 2005, 79, 231-239). One of the first major events to occur in apoptosis is the breakdown of the membranes of the mitochondria to release cytochrome c, activate caspases, change electron transport and cause a decrease in mitochondrial membrane potential ($\Delta\psi_m$). A change in $\Delta\psi_m$ therefore serves as a measure of mitochondrial function and indicator of cell health.

Thus, this stress inducer, serum deprivation, combined with monitoring changes in the mitochondrial membrane potential in a 96-well format allows for the establishment of an efficient high-throughput screen (HTS) in order to evaluate the ability of compounds to increase mitochondrial membrane potential in the presence of stress and preserve health of the cell. Exemplary procedures for conducting such high-throughput assay are provided below.

Tissue Culture:

SK-N-SH human neuroblastoma cells obtained from American Type Culture Collection (Rockville, Md.) were maintained in the log phase of growth in Minimal Essential Media (MEM), 10% heat inactivated fetal calf serum and 100 units/mL antibiotic-antimycotic (AA). Cells were cultured and maintained in a humidified incubator at 37° C. under 5% $CO_2$ and 95% air. Cells were trypsinized (0.25%) and subcultured every 3 days and used from 15-18 passages. All cell culture supplies were obtained from Invitrogen (Carlsbad, Calif.).

Serum Deprivation/JC-1 Mitochondrial Membrane Potential (MMP) Assay.

SK-N-SH cells were plated 2-3 days in advance at a concentration of 50,000 cells/well onto collagen coated black-walled 96 well plates (Becton-Dickinson, Bedford, Mass.) in a total volume of 200 μL. On day of experimental treatment, the media containing serum was aspirated from each well and rinsed once with MEM/1% AA without serum. The cells then were incubated overnight in 100 μL of MEM/1% AA (no serum) with and without dimebolin or novel chemical entities overnight for ~18 hours. The following day, JC-1 dye (5,5',6, 6'-tetrachloro-1,1',3,3'-tetraethylbenzimidazolcarbocyanide) was diluted 1:10 into MEM media according to the JC-1 Mitochondrial Membrane Potential Assay Kit: (Cayman Chemical Company, Ann Arbor, Mich.) and then 10 μL of the JC-1 dye solution was added to each well. The plates were centrifuged for 5 minutes at 400×g at room temperature followed by 40 minute incubation at 37° C. The plates were washed twice with 200 μL of provided Assay Buffer followed an addition of 100 μL of Assay Buffer to each well. The plates were read with an excitation and emission of 560 nM and 595 nM for red fluorescence and with an excitation and emission of 485 nM and 535 nM for green fluorescence to determine the final JC-1 value taking the red to green fluorescence ratio. This assay is based on change in mitochondrial membrane potential (MMP) using this lipophilic cationic dye, JC-1, by monitoring the changes in the ratio of red to green fluorescence as the MMP depolarizes. This change in MMP reflects the health of the cell with healthy, viable cells have a high JC-1 ratio and high MMP whereas apoptotic, unhealthy cells have a low JC-1 ratio or low MMP.

For the ability of compounds to reverse the stress due to serum deprivation and increase the JC-1 ratio, the percent maximal intensity in JC-1 ratio was normalized to that induced by the peak value for 10 μM dimebolin and plotted against the compound concentration to calculate $EC_{50}$ values and to control for plate-to-plate variability. Concentration-response data were analyzed using GraphPad Prism (San Diego, Calif.); the $EC_{50}$ values were derived from a single curve fit to the mean data of n=2-3, in duplicates. Selected data is shown in Table 1.

For the ability of other compounds to reverse the stress due to serum deprivation and increase the JC-1 ratio, the percent maximal intensity at a single dose, 3 μM, in JC-1 ratio was normalized to that induced by the peak value for 10 μM dimebolin (n=2-4). Data is shown in Table 2

All compounds were dissolved in dimethyl sulfoxide at 10 mM stock solutions and tested at a concentration that the dimethyl sulfoxide levels never exceeded 1%.

TABLE 1

JC-1 Mitochondrial Membrane Potential (MMP) Assay: $EC_{50}$ and Maximal JC-1 Ratio for Selected Compounds.

| Example | $EC_{50}$ (μM) | JC-1 max % |
| --- | --- | --- |
| 1 | 9.59 | 88 |
| 2 | 3.44 | 186 |
| 3 | 2.88 | 226 |
| 4 | 2.42 | 263 |
| 5 | 6.7 | 57 |
| 6 | 6.44 | 148 |
| 7 | >30 | 24 |
| 8 | 3.03 | 204 |
| 9 | 2.59 | 158 |
| 10 | 2.74 | 248 |
| 11 | 5.61 | 122 |
| 12 | 1.11 | 198 |
| 13 | 4.18 | 175 |
| 14 | 0.754 | 203 |
| 15 | 2.19 | 225 |
| 16 | 3.63 | 131 |
| 17 | 4.48 | 183 |
| 18 | 2.72 | 178 |
| 19 | 1.56 | 169 |
| 20 | 5.47 | 133 |
| 21 | 6.11 | 168 |
| 22 | 2.95 | 173 |
| 23 | 5.72 | 238 |
| 24 | 4.77 | 166 |
| 25 | 15.7 | 128 |
| 26 | 3.47 | 210 |
| 27 | 4.44 | 149 |
| 28 | 9.59 | 88 |
| 29 | 4.87 | 221 |
| 30 | 3.6 | 216 |
| 31 | 1.97 | 218 |
| 32 | 1.98 | 140 |
| 33 | 1.3 | 192 |
| 34 | 2.94 | 213 |
| 35 | 2.86 | 159 |
| 36 | 1.05 | 137 |
| 37 | 1.21 | 172 |
| 38 | >30 | 27 |
| 39 | 3.69 | 200 |
| 40 | 11.8 | 224 |
| 41 | 4.67 | 186 |
| 42 | 3.09 | 189 |
| 43 | 6.76 | 115 |
| 44 | 3 | 291 |
| 45 | 5.93 | 238 |
| 46 | 1.87 | 192 |
| 47 | 2.78 | 273 |
| 48 | 1.84 | 125 |
| 49 | 10.4 | 128 |
| 50 | 5.95 | 240 |
| 51 | 8.83 | 68 |
| 52 | 5.97 | 100 |
| 53 | 9.88 | 210 |
| 54 | 3.59 | 177 |
| 55 | 9.95 | 99 |
| 56 | 5.17 | 161 |
| 57 | 10.2 | 167 |
| 58 | 3.65 | 215 |
| 59 | 3.4 | 306 |
| 60 | 4.14 | 224 |
| 61 | 2.57 | 213 |
| 62 | 3.65 | 161 |
| 63 | 1.95 | 173 |
| 64 | 5.66 | 139 |
| 65 | 4.59 | 133 |
| 66 | 4.84 | 192 |
| 67 | 5.06 | 215 |
| 68 | 8.64 | 157 |
| 69 | 10.3 | 154 |
| 70 | 9.61 | 156 |
| 71 | 7.85 | 105 |
| 72 | 13.3 | 98 |
| 73 | 4.27 | 229 |
| 74 | 7.82 | 109 |
| 75 | >10 | 48 |
| 76 | 7.06 | 127 |
| 77 | 10.2 | 57 |
| 78 | 8.55 | 143 |
| 79 | 9.25 | 86 |
| 80 | 11.9 | 97 |
| 81 | 9.92 | 129 |
| 82 | 5.11 | 127 |
| 83 | >31.6 | 34 |
| 86 | 3.14 | 218 |
| 89 | 1.83 | 140 |
| 92 | 2.47 | 174 |
| 93 | 1.56 | 185 |
| 94 | 2.76 | 172 |
| 95 | 0.282 | 189 |
| 96 | 0.856 | 180 |
| 99 | 3.15 | 165 |
| 105 | 2.52 | 197 |
| 107 | 5.66 | 192 |
| 108 | 3.12 | 162 |
| 112 | 4.67 | 139 |
| 114 | 4.36 | 201 |
| 115 | 1.25 | 177 |

TABLE 1-continued

JC-1 Mitochondrial Membrane Potential (MMP) Assay:
EC$_{50}$ and Maximal JC-1 Ratio for Selected Compounds.

| Example | EC$_{50}$ (µM) | JC-1 max % |
|---|---|---|
| 119 | 3.95 | 172 |
| 121 | 4.21 | 167 |
| 122 | 3.4 | 133 |
| 123 | 3.44 | 186 |
| 124 | 3.49 | 193 |
| 125 | 4.26 | 98 |
| 126 | 1.89 | 150 |
| 128 | 4.25 | 168 |
| 130 | 4 | 181 |
| 131 | 3.22 | 144 |
| 132 | 3.33 | 192 |
| 133 | 3.64 | 163 |
| 134 | 3.53 | 163 |
| 135 | 4.19 | 154 |
| 136 | 2.2 | 172 |
| 137 | 3.3 | 143 |
| 138 | 1.83 | 203 |
| 139 | 3.18 | 145 |
| 140 | 3.6 | 189 |
| 144 | 3.63 | 132 |
| 145 | 3.14 | 151 |
| 146 | 2.2 | 182 |
| 151 | 1.8 | 163 |
| 152 | 3.08 | 239 |
| 156 | 2.4 | 152 |
| 158 | 1.02 | 181 |
| 160 | 0.645 | 245 |
| 161 | 3.18 | 218 |
| 166 | 0.765 | 181 |
| 169 | 0.816 | 173 |
| 171 | 2.45 | 251 |

TABLE 2

JC-1 Mitochondrial Membrane Potential (MMP) Assay:
JC-1 Ratio at 3 µM for Selected Compounds.

| Example | JC-1 max % (@ 3 µM) |
|---|---|
| 84 | 183 |
| 85 | 80 |
| 87 | 83 |
| 88 | 139 |
| 90 | 114 |
| 91 | 78 |
| 97 | 32 |
| 98 | 107 |
| 100 | 118 |
| 101 | 149 |
| 102 | 110 |
| 103 | 42 |
| 104 | 178 |
| 106 | 81 |
| 109 | 65 |
| 110 | 97 |
| 111 | 162 |
| 113 | 51 |
| 116 | 198 |
| 117 | 70 |
| 118 | 84 |
| 120 | −5 |
| 127 | 26 |
| 129 | 40 |
| 141 | 12 |
| 142 | 13 |
| 143 | 30 |
| 147 | 1.7 |
| 148 | 38 |
| 149 | 218 |
| 150 | 212 |
| 153 | 68 |
| 154 | 49 |
| 155 | 75 |
| 157 | 264 |
| 159 | 64 |
| 162 | 194 |
| 163 | 183 |
| 164 | 93 |
| 165 | 251 |
| 167 | 63 |
| 168 | 259 |
| 170 | 273 |
| 172 | 0 |
| 173 | 68 |
| 174 | 41 |
| 175 | 40 |
| 176 | 40 |

(iv) In Vivo Models of Procognitive Effects

A range of animal models capturing diverse cognitive domains may be utilized for assessing procognitive effects of compounds. Examples of these models are provided in Bitner et al., (Bitner, R. S.; Bunnelle, W. H.; et al. Broad-spectrum efficacy across cognitive domains by α7 nicotinic acetylcholine receptor agonism correlates with activation of ERK1/2 and CREB phosphorylation pathways. *J. Neurosci.* 2007, 27(39), 10578-10587.). Various transgenic animal models that are relevant of neurodegenerative diseases of interest may also be utilized to assess effects of test compounds (Goetz, J.; Ittner, L. M. Animal models of Alzheimer's disease and frontotemporal dementia. *Nat. Rev. Neurosci.* 2008, 9(7), 532-544.).

Inhibitory Avoidance in Mouse: The inhibitory avoidance task involves the uses of a two-compartment step through apparatus (Ugo Basile, Collegeville, Pa.) that measures the animal's ability to remember a brief noxious stimulus (foot shock), and is considered a measure of trial learning, and memory consolidation. Briefly, mice were placed in a lighted compartment of the apparatus where the latency to enter into the preferred dark compartment is recorded. Entry into a dark compartment results in the immediate delivery of a mild foot shock (0.2 mA, 1-second duration). Retention testing is conducted 24 hours later with the animal again placed in the lighted compartment where its latency to reenter the dark side of the apparatus is measured (no shock). Increasing retention latency is regarded as an index of memory consolidation (Bitner, R. S.; Bunnelle, W. H.; et al. Broad-spectrum efficacy across cognitive domains by α7 nicotinic acetylcholine receptor agonism correlates with activation of ERK1/2 and CREB phosphorylation pathways. *J. Neurosci.* 2007, 27(39), 10578-10587.).

Social Recognition in Rat: The social recognition test measures short-term memory on the basis of olfactory cues, and depends on the hippocampus. Adult (350-450 g) rats are allowed to interact with a juvenile (60-80 g) rat for a 5 minute interaction trial (T1) in which the adult exhibits behaviors that included close following, grooming and/or sniffing of the juvenile for as much as 40-50% of the trial duration. The juvenile rat is then removed and the adult rat immediately administered various doses of test compound. A second 5 minute recognition trial (T2) is conducted 120 minutes later where interactive behavior of the adult rat is again monitored.

If recognition memory is lost over the 120 minute interval between trials, the interactive behavior would be similar for the two trials; however, if memory is retained, the recognition ratio (T2:T1) would decline, i.e. deceasing T2:T1 ratio is regarded as an index of improved short-term recognition memory (Bitner, R. S.; Bunnelle, W. H.; et al. Broad-spectrum efficacy across cognitive domains by α7 nicotinic acetylcholine receptor agonism correlates with activation of ERK1/2 and CREB phosphorylation pathways. *J. Neurosci.* 2007, 27(39), 10578-10587. Timmermann, D. B.; Groenlien, J. H.; et al. An allosteric modulator of the α7 nicotinic acetylcholine receptor possessing cognition-enhancing properties in vivo. *J. Pharmacol. Exp. Ther.* 2007, 323(1), 294-307.).

Delayed Matching-to-Sample (DMTS) Titration in Monkey: Studies can be conducted in Rhesus monkeys that were initially trained in the DMTS procedure (Buccafusco, J. J.; Terry, A. V.; et al. Profile of nicotinic acetylcholine receptor agonists ABT-594 and A-582941, with differential subtype selectivity, on delayed matching accuracy by young monkeys. *Biochem. Pharmacol.* 2007, 74(8), 1202-1211.). Using a touch-sensitive screen in the animals home-cage, trial initiation consists of presentation of one of three colored stimuli (red, blue, or yellow rectangles) that remain in view (sample stimuli) until touched by subject. Following a delay interval, two choice rectangles are presented, one being the previous sample stimulus, in which correct (matching) choice-touch to the sample stimuli is food reinforced. For standard DMTS testing, the duration for each delay interval is adjusted for each subject until three levels of performance accuracy were approximated: zero delay (85-100% of trials answered correctly); short delay interval (75-84% correct); medium delay interval (65-74% correct); and long delay interval (55-64% correct). The titration version of the DMTS task used in the present studies requires the animals to perform a 96 trial session that begins with a 0 sec delay interval. If the trial is answered correctly, a 1 second delay interval is presented during the next trial presented. The 1 second incremental progression is maintained until the subject made an incorrect match. The delay interval for the trial after an incorrect match is always decreased by 1 second. After an incorrect match, if the next trial is answered correctly, then the subsequent trial presented a delay interval 1 second longer in duration. Dependent variables include the overall % of trials answered correctly, the number of trials to reach the maximal delay interval attained, and the maximum and average delay interval attained (in seconds). Compounds are administered prior to DMTS testing.

(v) Determination of Analgesic Effect Against Neuropathic Pain

Animals were prepared for testing, by use of a surgical procedure that induces neuropathic pain in one paw. Male Sprague Dawley rats were purchased from Charles River (Portage, Mich.). Prior to surgery, animals were housed in groups and maintained in a temperature-regulated environment. Following nerve ligation surgery, animals were housed in groups, and had access to food and water ad libitum.

The L5 and L6 spinal nerves of anesthetized rats were tightly ligated in a manner described previously (see Kim and Chung, Pain (1992) vol. 50 pp. 355-363). An incision was made on the dorsal portion of the hip and the muscle was blunt-dissected to reveal the spinal processes. The L6 transverse process was removed, and the left side L5 and L6 spinal nerves were tightly ligated with 5.0 braided silk suture. The wound was cleaned, the membrane sewn with 4.0 dissolvable Vicryl suture and the skin closed with wound clips. The paw affected by the surgical procedure (the left paw) develops an allodynic response, a hypersensitivity to mechanical and other stimuli; neuropathic pain is assessed as an increased sensitivity in the surgically affected (left) allodynic paw compared to the control paw on the right side, and measured by comparing the response of the (left side) allodynic paw to the response of the unaffected right side control paw.

For the assessment of neuropathic pain, mechanical allodynia in the affected paw of animals that had undergone spinal nerve ligation was evaluated using testing with von Frey filaments. As described previously by S. R. Chaplan, et al ("Quantitative assessment of tactile allodynia in the rat paw" J. Neurosci. Meth. (1994) vol. 53 pp. 55-63), two weeks following surgery rats were acclimated to a testing box constructed of plexiglass with a wire mesh floor which allowed access to the plantar surface of the animal's hindpaws. Using an Up-Down method (Dixon, Annual Rev. Pharmacol. Toxicol. (1980) vol. 20, pp. 441-462; Chaplan et al. "Quantitative assessment of tactile allodynia in the rat paw" J. Neuroscience Methods (1994) vol. 53 pp. 55-63), von Frey filaments of increasing stiffness were applied to the plantar surface of the hindpaws and the withdrawal response of the animals was observed; for the surgically affected paw with neuropathic pain (the left side paw) the baseline level of allodynia has a withdrawal threshold of ≤4 g of pressure. By comparison, for the control paw without allodynia (in this case the right side paw), the typical withdrawal pressure is around 15 g. Representative compounds of the invention, administered intraperitoneally 30 minutes before testing, are able to reduce the symptoms of neuropathic pain and induce a dose-dependent increase in the withdrawal threshold for allodynic (left side) limb, up to a maximum effect of 15 g. The efficacy of the compound in reducing neuropathic pain at different doses is determined by comparing response in the surgery-affected paw versus the response in the control paw. This is expressed as the MPE (maximum potential effect).

(vi) Animal Pharmacokinetics

The pharmacokinetic properties of test compounds can be assessed in mouse, rat, dog and monkey to obtain various parameters including clearance (Clp), volume of distribution and bioavailability. For the determination of plasma and brain concentrations of the parent compound, naïve rats or mice can be dosed with the compounds i.p. and sacrificed at various time points post-dosing. For the determination of plasma concentrations, blood is collected into heparinized tubes and then centrifuged, and the separated plasma is frozen at −20° C. until analysis. For analysis, compounds are extracted from the samples via liquid-liquid extraction and quantified by liquid chromatography/mass spectroscopy.

d. METHODS OF USING THE COMPOUNDS

In still yet another embodiment, the present invention provides a method for preventing or treating a disease condition in a subject in need of treatment thereof. The subject in need of treatment thereof can be a mammal, such as, but not limited to, a human.

In one aspect, the disease condition is a neurodegeneration disorder. A neurodegeneration disorder refers to a type of neurological disease marked by the loss of nerve cells in the brain or central nervous system. Examples of neurodegeneration disorders include, but are not limited to, Alzheimer's disease (AD), mild cognitive impairment (MCI), age-associated memory impairment (AAMI), multiple sclerosis, Parkinson's disease, vascular dementia, senile dementia, AIDS dementia, Pick's disease, dementia caused by cerebrovascular disorders, corticobasal degeneration, amyotrophic lateral sclerosis (ALS), Huntington's disease, diminished CNS function associated with traumatic brain injury or any combinations thereof.

In another aspect, the disease condition is a neuropsychiatric disorder. A neuropsychiatric disorder is a behavioral or psychological problem associated with a known neurological condition, and typically defined as a cluster of symptoms that co-exist. Examples of neuropsychiatric disorders include, but are not limited to, schizophrenia, cognitive deficits in schizophrenia, attention deficit disorder, attention deficit hyperactivity disorder, bipolar and manic disorders, depression or any combinations thereof.

In a further aspect, the present invention relates to methods of preventing or treating a pain including neuropathic and nociceptive pain, chronic or acute, such as, without limitation, allodynia, inflammatory pain, inflammatory hyperalgesia, post herpetic neuralgia, neuropathies, neuralgia, diabetic neuropathy, HIV-related neuropathy, nerve injury, rheumatoid arthritic pain, osteoarthritic pain, burns, back pain, ocular pain, visceral pain, cancer pain, dental pain, headache, migraine, carpal tunnel syndrome, fibromyalgia, neuritis, sciatica, pelvic hypersensitivity, pelvic pain, post operative pain, post stroke pain, and menstrual pain.

Cognitive deficits are recognized in various forms of neurodegeneration and neuropsychiatric disorders (such as, but not limited to, dementia, including Alzheimer's disease, (AD) and neuropsychiatric diseases, particularly schizophrenia and bipolar disorders). For example, in AD, current therapies offer modest efficacy, and therefore, there is need for an agent that offers a superior clinical benefit. One such agent, dimebolin, has been shown to inhibit neuronal death in models of neurodegenerative diseases suggestive of modification of disease processes (Lermontova, N. N.; Lukoyanov, N. V.; et al. Dimebon improves learning in animals with experimental Alzheimer's disease. *Bull. Exp. Biol. Med.* 2000, 129(6), 544-546. Bachurin, S.; Bukatina, E.; et al. Antihistamine agent dimebon as a novel neuroprotector and a cognition enhancer. *Ann. N.Y. Acad. Sci.* 2001, 939 (Neuroprotective Agents), 425-435.) and more recently, shown to possess beneficial effect in cognition in patients with Alzheimer's disease (Burns, A.; Jacoby, R. Dimebon in Alzheimer's disease: old drug for new indication. *Lancet* 2008, 372(9634), 179-80. Doody, R. S.; Gavrilova, S. I.; et al. Effect of dimebon on cognition, activities of daily living, behaviour, and global function in patients with mild-to-moderate Alzheimer's disease: a randomised, double-blind, placebo-controlled study. *Lancet* 2008, 372(9634), 207-215.). Patients with mild-to-moderate Alzheimer's disease administered with 20 mg three times a day (60 mg/day) showed significant improvement in the clinical course of disease, as reflected in improvement over baseline for ADAS-Cog (Alzheimer's disease assessment scale—cognitive subscale) (Cummings, J.; Doody, R.; Gavrilova, S.; Sano, M.; Aisen, P.; Seely, L.; Hung, D. 18-month data from an open-label extension of a one-year controlled trial of dimebon in patients with mild-to-moderate Alzheimer's disease. Presented at the International Conference on Alzheimer's Disease (ICAD), Chicago, Ill., USA, July 2008; paper P4-334). Patients with mild-to-moderate Alzheimer's disease who had earlier received the drug for 12 months had preservation of function close to their starting baseline on key symptoms of Alzheimer's disease indicated the ability of dimebolin to alter disease progression. Patients originally on placebo who received dimebolin in the extension study showed stabilization across all key measures.

Beneficial effects of agents such as dimebolin have been linked to diverse mechanisms of action including effects at the level of mitochondria. In particular, dimebolin has been reported to improve neuronal function by enhancing neuronal outgrowth and affecting mitochondrial function. For example, Hung and coworkers (Hung, D. Dimebon: A phase 3 investigational agent for Alzheimer's disease with a novel mitochondrial mechanism of action. Presented at the International Conference on Alzheimer's Disease, Chicago, Ill., USA, July 2008; paper S4-04-05.) reported that dimebolin can protect cells from excitotoxic damage and improve neurite outgrowth in in vitro model systems. Other mechanisms of action may also contribute to its beneficial effects of compounds with a "dimebolin-like" profile. Indeed, multi-targeted mechanisms have been proposed as viable approaches for treatment of diverse neurodegenerative diseases (Zhang, H.-Y. One-compound-multiple-targets strategy to combat Alzheimer's disease. *FEBS Lett.* 2005, 579, 5260-5264. Youdim, M.; Buccafusco, J. Multi-functional drugs for various CNS targets in the treatment of neurodegenerative disorders. *Trends in Pharm. Sci.* 2005, 26(1), 27-35. Csermely, P.; Agoston, V.; Pongor, S. The efficiency of multi-target drugs: the network approach might help drug design. *Trends in Pharm. Sci.* 2005, 26(4), 178-182. Cavalli, A.; Bolognesi, M. L.; Minarini, A.; Rosini, M.; Tumiatti, V.; Recanatini, M.; Melchiorre, C. Multi-target directed ligands to combat neurodegenerative diseases. *J. Med. Chem.* 2008, 51(3), 347-372.). Dimebolin is also thought to exert its cognitive enhancing effects also through inhibition of butyryl-cholinesterase, acetyl cholinesterase, NMDA receptor or L-type calcium channels (Bachurin, S.; Bukatina, E.; et al. Antihistamine agent dimebon as a novel neuroprotector and a cognition enhancer. *Ann. N.Y. Acad. Sci.* 2001, 939 (Neuroprotective Agents), 425-435. Lermontova, N. N.; Redkozubov, A. E.; et al. Dimebon and tacrine inhibit neurotoxic action of beta-amyloid in culture and block L-type Ca(2+) channels. *Bull. Exp. Biol. Med.* 2001, 132(5), 1079-1083. Grigor'ev, V. V.; Dranyi, O. A.; et al. Comparative Study of Action Mechanisms of Dimebon and Memantine on AMPA- and NMDA-Subtypes Glutamate Receptors in Rat Cerebral Neurons. *Bull. Exp. Biol. Med.* 2003, 136(5): 474-477.). Interactions at the level of select 5HT receptors have also been implicated in the beneficial cognitive of dimebolin-like analogs (Tkachenko, S. Discovery and in vivo evaluation of potent 5-HT6 receptor antagonists for cognition enhancement in treating Alzheimer's disease. Presented at the International Conference on Alzheimer's Disease (ICAD), Chicago, Ill., USA, July 2008; paper P2-478.). Thus, available preclinical and clinical data suggests that compounds exhibiting a "dimebolin-like" profile can be beneficial in treating neurodegenerative diseases such as Alzheimer's disease and other dementias. Therefore, it is believed that the compounds of the present invention exhibit at least one of the mechanisms of action exhibited by dimebolin.

For treating a neurodegenerative or a neuropsychiatric disorder, the method comprises administering to the subject in need of treatment thereof (e.g., a mammal, such as a human) a therapeutically effective amount of any of the compounds as described herein, or a pharmaceutically acceptable salt thereof. Alternatively, the method comprises administering to the subject a therapeutically effective amount of any of the compounds as described herein, or a pharmaceutically acceptable salt thereof, in combination with a therapeutically effective amount of at least one cognitive enhancing drug. A "cognitive enhancing drug", as defined herein, is a drug that improves impaired human cognitive abilities of the brain (namely, thinking, learning, and memory). Cognitive enhancing drugs work by altering the availability of neurochemicals (e.g., neurotransmitters, enzymes, and hormones), by improving oxygen supply, by stimulating nerve growth, or by inhibiting nerve damage. Examples of cognitive enhancing drugs include a compound that increases the activity of acetylcholine such as, but not limited to, an acetylcholine receptor agonist (e.g., a nicotinic α-7 receptor agonist or allosteric modulator, an α4β2 nicotinic receptor agonist or allosteric modulators), an acetylcholinesterase inhibitor (e.g., donepezil, rivastigmine, and galantamine), a butyrylcholinesterase inhibitor, an N-methyl-D-aspartate (NMDA) receptor antagonist (e.g., memantine), an activity-dependent neuroprotective protein (ADNP) agonist, a serotonin 5-HT1A receptor agonist (e.g., xaliproden), a 5-HT$_4$ receptor agonist, a 5-HT$_6$ receptor antagonist, a serotonin 1A receptor antagonist, a histamine H$_3$ receptor antagonist, a calpain inhibitor, a vascular endothelial growth factor (VEGF) protein or agonist, a trophic growth factor, an anti-apoptotic compound, an AMPA-type glutamate receptor activator, a L-type or N-type calcium channel blocker or modulator, a potassium channel blocker, a hypoxia inducible factor (HIF) activator, a HIF prolyl 4-hydroxylase inhibitor, an anti-inflammatory agent, an inhibitor of amyloid Aβ peptide or amyloid plaque, an inhibitor of tau hyperphosphorylation, a phosphodiesterase 5 inhibitor (e.g., tadalafil, sildenafil), a phosphodiesterase 4 inhibitor, a monoamine oxidase inhibitor, or pharmaceutically acceptable salt thereof. Specific examples of such cognitive enhancing drugs include, but are not limited to, cholinesterase inhibitors such as donepezil (Aricept®), rivastigmine (Exelon®), galanthamine (Reminyl®), N-methyl-D-aspartate antagonists such as memantine (Namenda®). At least one cognitive enhancing drug can be administered simultaneously with the compounds of the present invention or sequentially with the compounds of the present invention (and in any order). Additionally, it is believed that the combinations described herein may have additive or synergistic effects when used in the above-described treatment.

In still yet another embodiment, the present invention relates to a method for preventing (the development of) a disease condition, such as a neurodegeneration disorder or a neuropsychiatric disorder. As used herein, the term "prevent" a disease condition, such as a neurodegenerative disorder or a neuropsychiatric disorder by administration of any of the compounds described herein means that the detectable physical characteristics or symptoms of the disease or condition do not develop following the administration of the compound described herein. Specifically, the method of the present invention comprises administering to the subject in need of treatment thereof (e.g., a mammal, such as a human) a therapeutically effective amount of any of the compounds as described herein, or a pharmaceutically acceptable salt thereof. Alternatively, the method comprises administering to the subject a therapeutically effective amount of any of the compounds as described herein, or a pharmaceutically acceptable salt thereof, in combination with a therapeutically effective amount of at least one cognitive enhancing drug.

In still yet another embodiment, the present invention relates to a method for preventing the progression (e.g., worsening) of a disease condition, such as a neurodegeneration disorder or a neuropsychiatric disorder. The method comprises administering to the subject in need of treatment thereof (e.g., a mammal, such as a human) a therapeutically effective amount of any of the compounds as described herein, or a pharmaceutically acceptable salt thereof. Alternatively, the method comprises administering to the subject a therapeutically effective amount of any of the compounds as described herein, or a pharmaceutically acceptable salt thereof, in combination with a therapeutically effective amount of at least one cognitive enhancing drug.

In the above described methods for preventing the development or progression of a neurodegeneration disorder or a neuropsychiatric disorder one or more biomarkers, diagnostic tests or combination of biomarkers and diagnostic tests known to those skilled the art can be used to determine whether or not (1) a subject is at risk of developing one or more of neurodegeneration disorders or neuropsychiatric disorders; or (2) the neurodegeneration disorders or neuropsychiatric disorders in the subject previously diagnosed with one or more of the aforementioned disorders is progressing (e.g., worsening).

One or more biomarkers, diagnostic tests or combinations of biomarkers and diagnostic tests known in the art can be used to identify subjects who are at risk of developing a neurodegeneration disorder or a neuropsychiatric disorder. Likewise, one or more biomarkers, diagnostic tests or combinations of biomarkers and diagnostic tests known in the art can be used to determine the progression of the disease or condition of subjects who have been identified as suffering from a neurodegeneration disorder or a neuropsychiatric disorder. For example, one or more biological markers, neuroimaging markers or combination of biological or neuroimaging markers (e.g., MRI, etc.) can be used to identify subjects at risk of developing AD or, for those subjects identified as suffering AD, the progression of the disease. Biological markers that can be examined include, but are not limited to, beta-amyloid$_{1-42}$, tau, phosphorylated tau (ptau), plasma Aβ antibodies, α-antichymotrypsin, amyloid precursor protein, APP isoform ratio in platelets, β-secretase (also known as BACE), CD59, 8-hydroxy-deoxyguanine, glutamine synthetase, glial fibrillary acidic protein (GFAP), antibodies to GFAP, interleukin-6-receptor complex, kallikrein, melanotransferrin, neurofilament proteins, nitrotyrosine, oxysterols, sulphatides, synaptic markers, S100β, NPS, plasma signaling proteins, etc., or any combinations thereof (See, Shaw, L., et al., *Nature Reviews* 2007, 6, 295-303. Borroni, B., et al., *Current Med. Chem.* 2007, 14, 1171-1178. Phillips, K., et al., *Nature Reviews* 2006, 5 463-469. Bouwman, F. H., et al., *Neurology* 2007, 69, 1006-1011; Ray, S., et al., *Nature Medicine* 2007, 13(11), 1359-1362. Cummings, J., et al., *Neurology* 2007, 69, 1622-1634.).

Actual dosage levels of active ingredients in the pharmaceutical compositions of the present invention can be varied so as to obtain an amount of the active compound(s) that is effective to achieve the desired therapeutic response for a particular subject (e.g., a mammal, preferably, a human (patient)), compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the present invention can also be administered to a subject as a pharmaceutical composition comprising the compounds of interest in combination with at least one pharmaceutically acceptable carriers. The phrase "therapeutically effective amount" of the compound of the present invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a subject (namely, a mammal, such as a human) ranges from about 0.01 mg/kg body weight to about 100 mg/kg body weight. More preferable doses can be in the range of from about 0.01 mg/kg body weight to about 30 mg/kg body weight. If desired, the effective daily dose can be divided into multiple doses for purposes of administration. Consequently, single dose compositions may contain such amounts or submultiples thereof to make up the daily dose.

e. PHARMACEUTICAL COMPOSITIONS

In yet another embodiment, the present invention provides pharmaceutical compositions. The pharmaceutical compositions of the present invention comprise the compounds of the present invention or a pharmaceutically acceptable salt or solvate thereof. The pharmaceutical compositions of the present invention comprise compounds of the present invention that can be formulated together with at least one non-toxic pharmaceutically acceptable carrier.

In yet another embodiment, the present invention provides a pharmaceutical composition comprising compounds of the present invention, or a pharmaceutically acceptable salt thereof, and one or more pharmaceutically acceptable carriers, alone or in combination with one or more compounds that are not the compounds of the present invention. Examples of one or more compounds that can be combined with the compounds of the present invention in pharmaceutical compositions, include, but are not limited to, one or more cognitive enhancing drugs.

The pharmaceutical compositions of this present invention can be administered to a subject (e.g., a mammal, such as a human) orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of the present invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of the present invention include powders, sprays, ointments and inhalants. The active compound may be mixed under sterile conditions with a pharmaceutically acceptable carrier and any needed preservatives, buffers or propellants which may be required. Ophthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq.). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, piperazine and the like.

Esters can be prepared from substrates of formula (I) containing either a hydroxyl group or a carboxy group by general methods known to persons skilled in the art. The typical reactions of these compounds are substitutions replacing one of the heteroatoms by another atom, for example:

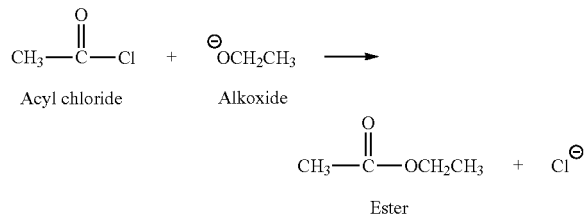

Amides can be prepared from substrates of formula (I) containing either an amino group or a carboxy group in similar fashion. Esters can also react with amines or ammonia to form amides.

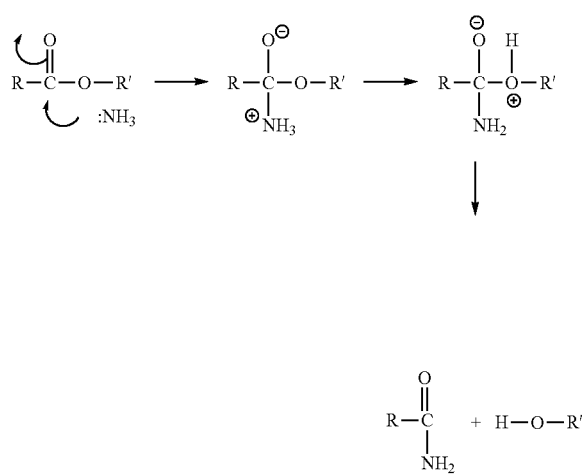

Another way to make amides from compounds of formula (I) is to heat carboxylic acids and amines together.

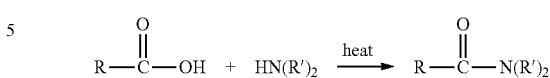

The present invention also contemplates compounds of the present invention formed by synthetic means or formed by in vivo biotransformation of a prodrug.

The compounds of the present invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. GENERAL SYNTHESIS

This invention is intended to encompass compounds of the present invention whether prepared by synthetic processes or by metabolic processes. Preparation of the compounds by metabolic processes includes those occurring in the human or animal body (in vivo) or processes occurring in vitro.

The compounds of the present invention may be prepared by a variety of processes well known for the preparation of compounds of this class. For example, the compounds of the present invention wherein the groups $R^1$, $R^2$, $R^3$, $R^4$, $X^1$, $Y^1$, $Y^2$, and $Y^3$, have the meanings as set forth in the Summary of the Invention section unless otherwise noted, can be synthesized as shown in Schemes 1-13.

Abbreviations which have been used in the descriptions of the Schemes and the Examples that follow are: Ac for acetyl; aq for aqueous; atm for atmosphere; DCC for dicyclohexylcarbodiimide; DMSO for dimethyl sulfoxide; Et for ethyl; EtOAc for ethyl acetate; EtOH for ethanol; ESI for electrospray ionization; HATU for O-(7-azabenzotriazol-1-yl)-N,N,N',N'-tetramethyluronium hexafluorophosphate; HPLC for high performance liquid chromatography; LC/MS for liquid chromatography/mass spectroscopy; Me for methyl; MeOH for methanol; MP for macroporous poly(styrene-co-divinylbenzene) resin; MP-CNBH$_3$ for cyanoborohydride reagent supported on a macroporous resin; OAc for acetate; psi for pounds per square inch; SFC for supercritical fluid chromatography; and TFA for trifluoroacetic acid.

Scheme 1

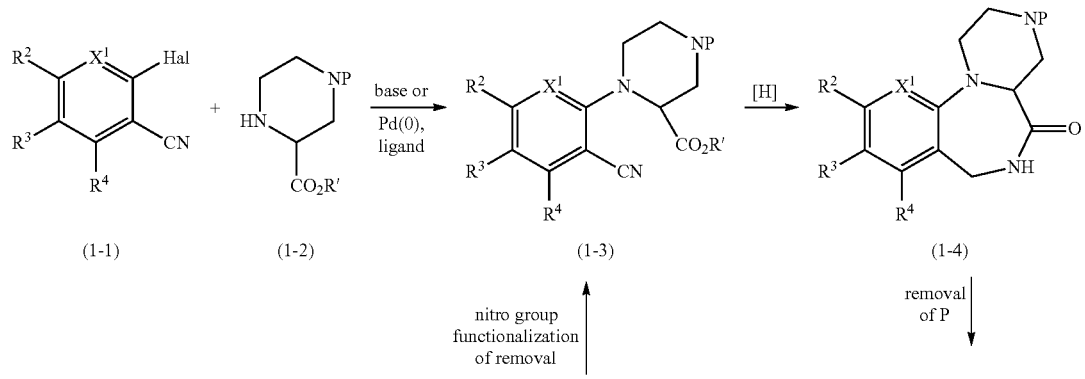

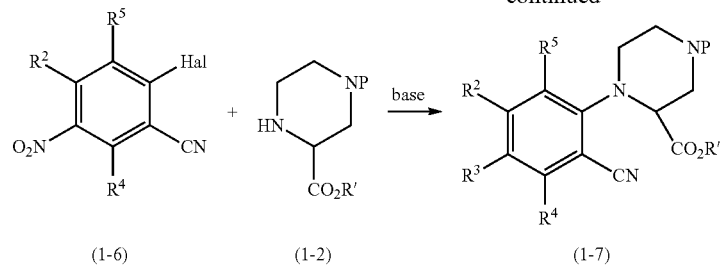

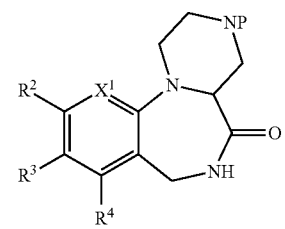

(1-6)     (1-2)     (1-7)     (1-5)

Compounds of formula (1-5), wherein $R^2$, $R^3$, $R^4$, and $X^1$ are as defined in formula (I), can be prepared as described in Scheme 1. N-Arylation of a suitably-protected piperazine-2-carboxylate of formula (1-2), wherein R' is alkyl and P is a suitable nitrogen protecting group, including, but not limited to tert-butoxycarbonyl, 9-fluorenylmethoxycarbonyl, or benzyloxycarbonyl, with a 2-haloarylnitrile of formula (1-1), wherein Hal is a halogen, can be accomplished to provide the aminonitrile of formula (1-3). The arylation reaction can be accomplished by nucleophilic aromatic substitution in the presence of a base, or alternatively using transition metal-mediated processes such as the Pd-catalyzed process developed by Hartwig and Buchwald (for a review of this process, see: J. Am. Chem. Soc. (2006), 128, 3584-3591 and references therein). For the base-mediated process, a nitro substituent on the aryl ring as shown with compounds of formula (1-6) can serve to facilitate the nucleophilic substitution giving compounds of formula (1-7). The nitro group in compounds of formula (1-7) can then be reduced to an amine, and further elaborated by acylation, reductive amination and other N-functionalization reactions known to one skilled in the art, or replaced by diazotization and captured by halogen, hydroxyl, cyano, or hydride, according to procedures well-known to one skilled in the art to provide compounds of formula (1-3). The cyano moiety of compounds of formula (1-3) can be reduced resulting in formation of cyclized compounds of formula (1-4). The nitrogen protecting group, P, can be removed with standard methods dependent on the particular protecting group to give compounds of formula (1-5). Alternatively, P can be substituent $R^1$ as defined in the claims, wherein compounds of formula (1-4) are representative of compounds of formula (I).

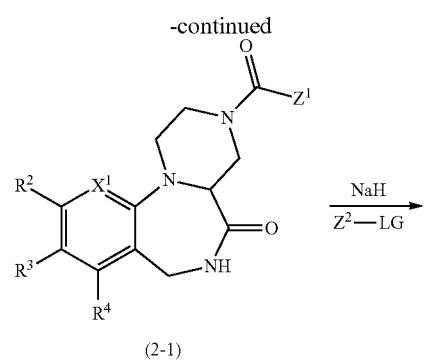

(2-1)

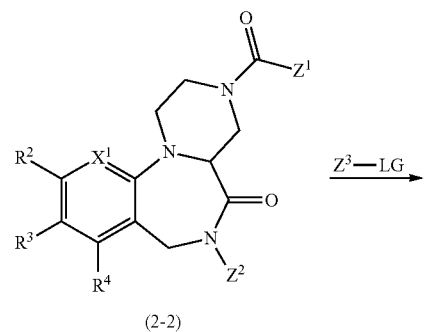

(2-2)

Scheme 2

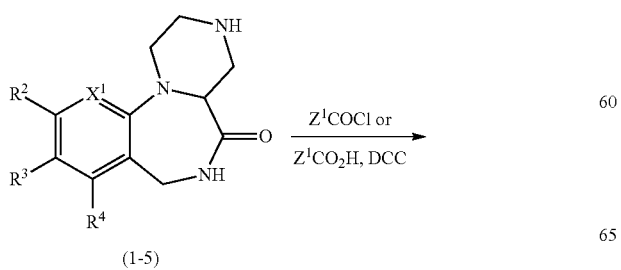

(1-5)

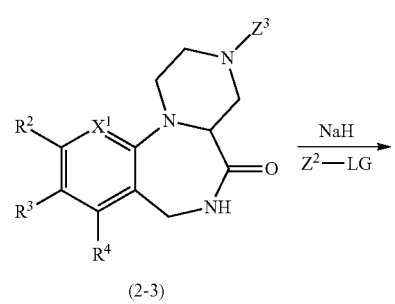

(2-3)

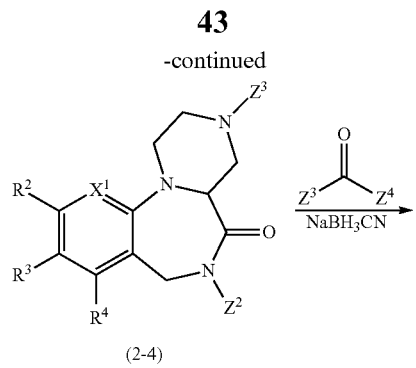

(2-4)

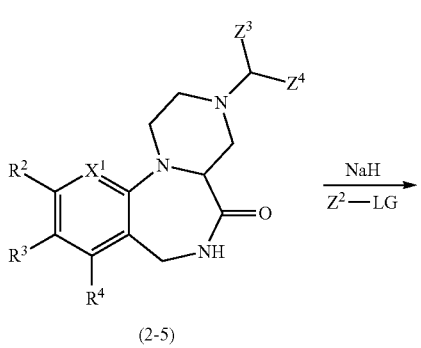

(2-5)

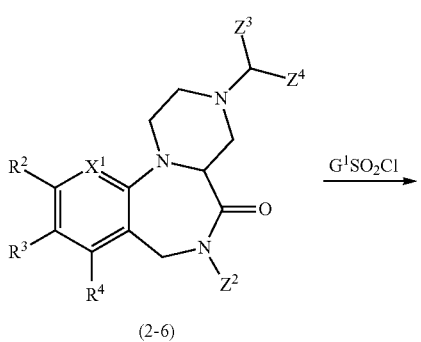

(2-6)

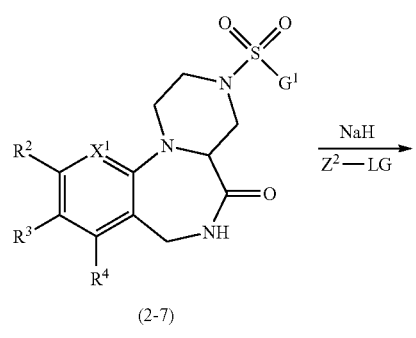

(2-7)

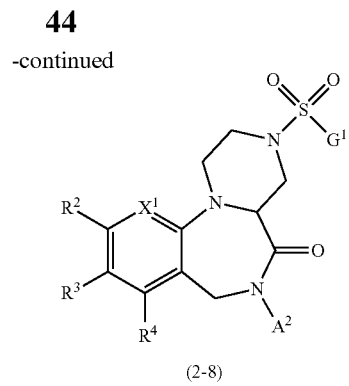

(2-8)

As shown in Scheme 2, compounds of formula (1-5) can be further elaborated to compounds of formulas (2-2), (2-4), (2-6), and (2-8). For example, compounds of formula (1-5) can be reacted with an acid chloride of formula $Z^1COCl$ to give compounds of formula (2-1) Alternatively, compounds of formula (1-5) can be reacted with a carboxylic acid of formula $Z^1CO_2H$ and an amide coupling reagent such as, but not limited to, dicyclohexylcarbodiimide (DCC) or O-(7-azabenzotriazol-1-yl)-N,N,N',N'-tetramethyluronium hexafluorophosphate (HATU), to produce compounds of formula (2-1), wherein $Z^1$ is alkyl, $G^1$, $OR^6$ or $NR^7R^8$ wherein $G^1$, $R^6$, $R^7$ and $R^8$ are as defined in the Summary of the Invention. Alternatively, alkylation of compounds of formula (1-5) with a compound of formula $Z^3$-LG gives compounds of formula (2-3). $Z^3$ is alkyl, haloalkyl or —$(CR^{4a}R^{5a})_mG^1$ wherein $R^{4a}$, $R^{5a}$, m, and $G^1$ are as defined in the Summary of the Invention, and LG is a suitable leaving group such as a halide or a sulfonate. Compounds of formula (1-5) can be reductive alkylated with a ketone or aldehyde of formula $Z^3C(O)Z^4$, wherein $Z^4$ is hydrogen or alkyl, in the presence of a reducing agent such as $NaBH_3CN$ or $H_2$ in combination with a noble metal catalyst, to form compounds of formula (2-5). Reaction of compounds of formula (1-5) with a sulfonyl chloride of formula $G^1SO_2Cl$ will provide sulfonamides of formula (2-7). Further elaboration of the lactam nitrogen of compounds of formulas (2-1), (2-3), (2-5) and (2-7) for example by deprotonation by a base such as NaH, followed by addition of an alkylating agent of formula $Z^2$-LG provides compounds of formulas (2-2), (2-4), (2-6) and (2-8), respectively. $Z^2$ is alkyl, —$(CR^{4a}R^{5a})_mG^1$, —$(CR^{4a}R^{5a})_mG^2$, wherein $R^{4a}$, $R^{5a}$, m, $G^1$, and $G^2$ are as defined in the Summary of the Invention. Compounds of formulas (2-1), (2-2), (2-3), (2-4), (2-5), (2-6), (2-7) and (2-8) are representative of compounds of formula (I).

Scheme 3

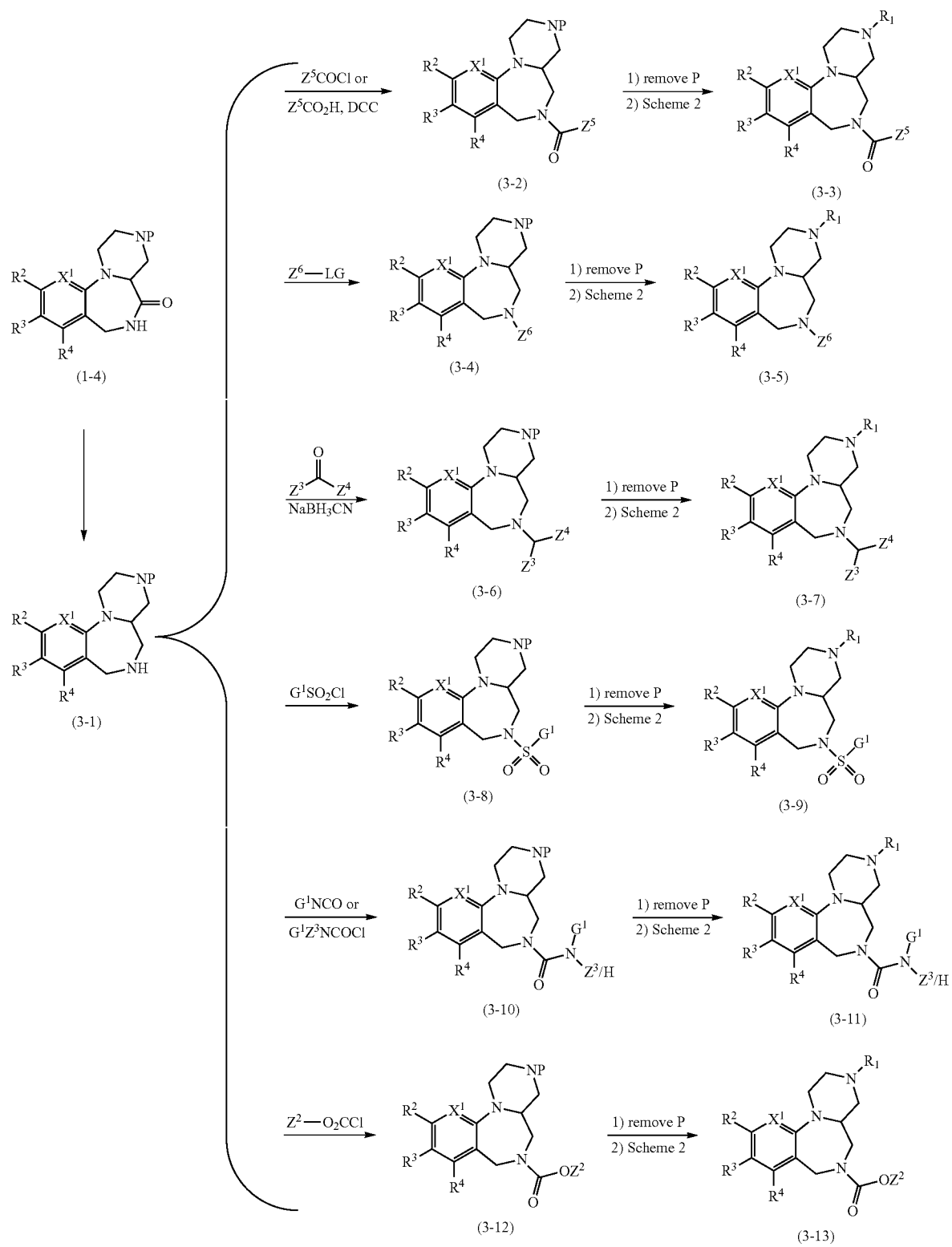

As depicted in Scheme 3, compounds of formulas (3-3), (3-5), (3-7), (3-9), (3-11), and (3-13), wherein $R^1$, $R^2$, $R^3$, $R^4$, and $X^1$ are as described in the Summary of the Invention can be prepared from compounds of formula (3-1). Compounds of formula (3-1) are in turn prepared from compounds of formula (1-4) by treatment with a suitable reducing agent, for example $BH_3$ or $AlH_3$ complexes. Compounds of formula (3-1) can be acylated with an acyl chloride of formula Z⁵COCl or coupled with a carboxylic acid of formula Z⁵CO₂H to give compounds of formula (3-2). $Z^5$ is $G^1$, $G^2$, -$G^2$-$G^1$, —$(CR^{4a}R^{5a})_m$-$G^1$, —$(CR^{4a}R^{5a})_m$-$G^2$, or —CH=CH-$G^1$, wherein $G^1$, $G^2$, $R^{4a}$, $R^{5a}$, and m are as defined in the Summary of the Invention. Reaction of Z⁵COCl and compounds of formula (3-1) in the presence of a base provides compounds of formula (3-2). Compounds of formula (3-2) are also formed by reacting compounds of formula (3-1) with Z⁵CO₂H in the presence of an amide bond forming reagent such as dicyclohexylcarbodiimide (DCC) or O-(7-azabenzotriazol-1-yl)-N,N,N',N'-tetramethyluronium hexafluorophosphate (HATU). Reaction of compounds of formula (3-1) with an alkylating reagent of formula $Z^6$-LG supplies compounds of formula (3-4), wherein $Z^6$ is —$(CR^{4a}R^{5a})_m$-$G^1$ or —$(CR^{4a}R^{5a})_m$-$G^2$ and LG is a suitable leaving group such as a halide or a sulfonate. Reductive alkylation of compounds of formula (3-1) with an aldehyde or ketone of formula $Z^3C(O)Z^4$ under conditions to reduce the intermediate imine or iminium compound, for example NaBH₃CN or hydrogen and a noble metal catalyst, will afford compounds of formula (3-6). $Z^3$ is alkyl, haloalkyl or —$(CR^{4a}R^{5a})_m G^1$ wherein $R^{4a}$, $R^{5a}$, m, and $G^1$ are as defined in the Summary of the Invention, and $Z^4$ is hydrogen or alkyl. Reaction of compounds of formula (3-1) with a sulfonyl chloride of formula $G^1SO_2Cl$ will produce compounds of formula (3-8), while reaction with isocyanates of formula $G^1NCO$ or carbamyl chlorides of formula $G^1Z^3NCOCl$ will access compounds of formula (3-10). Additionally, chloroformates of formula $Z^2O_2CCl$ react with compounds of formula (3-1) to form the carbamates of formula (3-12). $Z^2$ is alkyl, —$(CR^{4a}R^{5a})_m G^1$, —$(CR^{4a}R^{5a})_m G^2$.

The protective group P in each of the compounds of formulas (3-2), (3-4), (3-6), (3-8), (3-10), or (3-12) can be removed by methodology known to one skilled in the art. The revealed piperazine nitrogen of the compounds of formulas (3-2), (3-4), (3-6), (3-8), (3-10), or (3-12) can then be subjected to the sequences described in Scheme 2 to give compounds of formulas (3-3), (3-5), (3-7), (3-9), (3-11), and (3-13), respectively, which are representative of compounds of formula (I).

Scheme 4

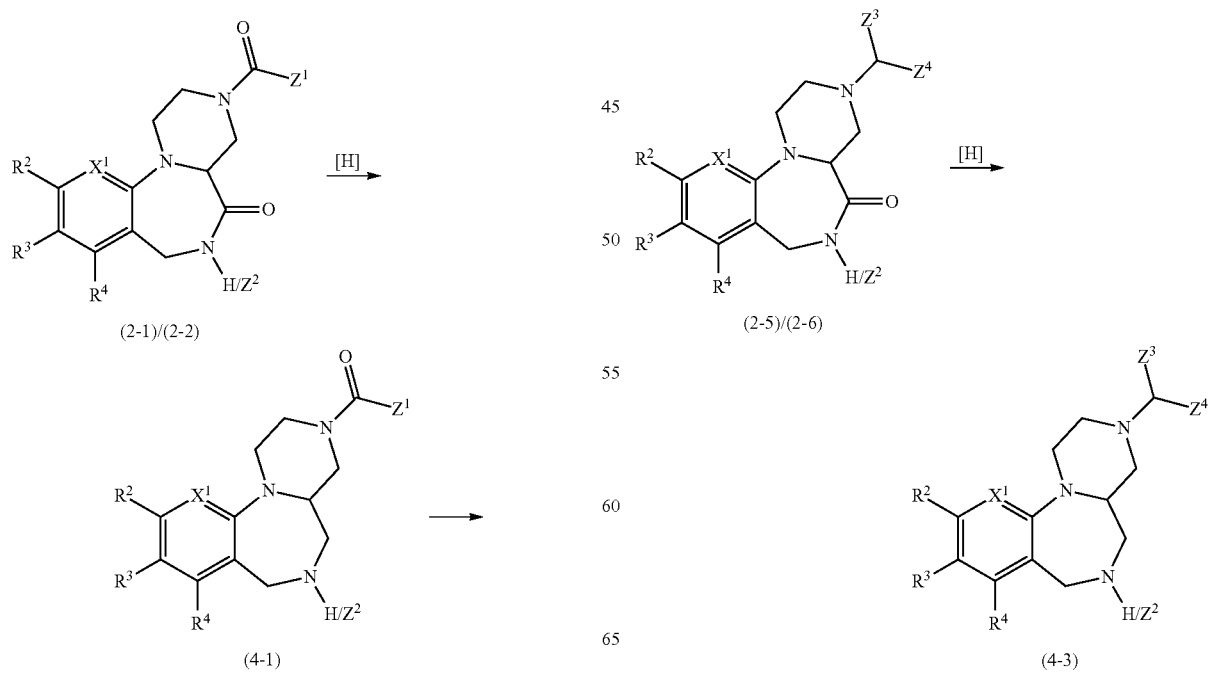

-continued

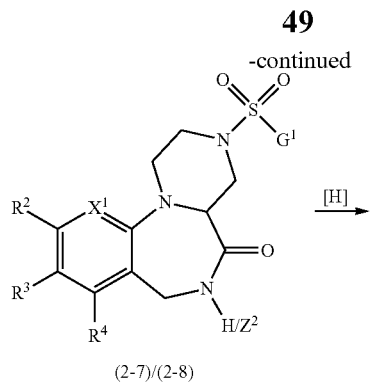

(2-7)/(2-8)

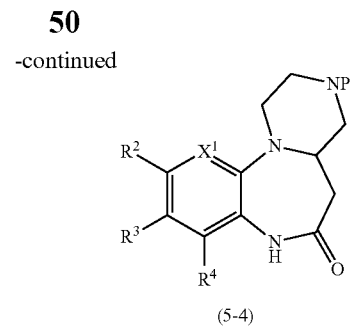

(5-4)

Compounds of formula (5-4), wherein $R^2$, $R^3$, $R^4$ and $X^1$ are as defined in the Summary of the Invention, can be prepared as outlined in Scheme 5. Nucleophilic aromatic substitution of a suitable nitroarene of formula (5-1), wherein $LG^1$ is a halogen or other leaving group, with a piperazin-2-yl acetate derivative of formula (5-2), wherein $Z^4$ is hydrogen or alkyl and P is a nitrogen protecting group delivers compounds of formula (5-3). A two-step sequence of reduction followed by cyclization transforms compounds of formula (5-3) to compounds of formula (5-4). Reduction of the nitro group in compounds of formula (5-3) can be achieved using hydrogenation in the presence of a noble metal catalyst or, alternatively, iron, tin or $SnCl_2$ in the presence of acid as known to one skilled in the art. In the case where $Z^4$ is H, cyclization to provide compounds of formula (5-4) can be accomplished by reaction with an amide coupling reagent such as dicyclohexylcarbodiimide (DCC) or O-(7-azabenzotriazol-1-yl)-N,N,N',N'-tetramethyluronium hexafluorophosphate (HATU). In the case where $Z^4$ is alkyl, cyclization can be achieved by treatment with acid or with base.

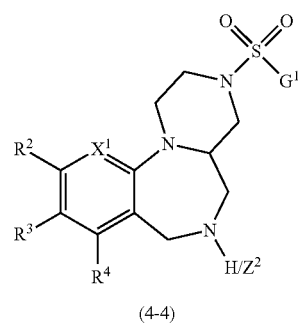

(4-4)

Compounds of formulas (2-1), (2-2), (2-3), (2-4), (2-5), (2-6), (2-7), and (2-8), wherein $G^1$, $R^1$, $R^2$, $R^3$, $R^4$, and $X^1$ are as defined in the Summary of the Invention and $Z^1$, $Z^2$, $Z^3$, and $Z^4$ are as defined in Scheme 2 can be treated with a suitable reducing agent, for example $LiAlH_4$, $BH_3$ or its complexes, or $AlH_3$ or an amine complex thereof, to effect reduction of the lactam to provide compounds of formulas (4-1), (4-2), (4-3) and (4-4), respectively. In the case of compounds of formula (4-1), the reducing agent can be used to effect further reduction of the acylamide to form the compound of formula (4-5). Compounds of formulas (4-1), (4-2), (4-3), (4-4), and (4-5) are representative of compounds of formula (I).

Scheme 6

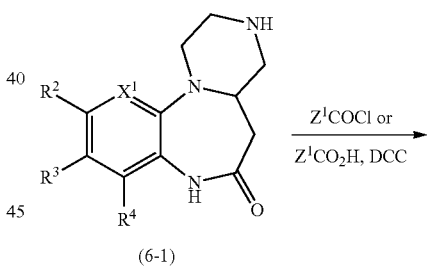

(6-1)

Scheme 5

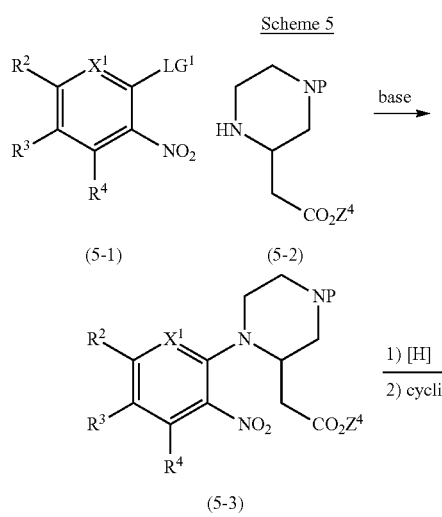

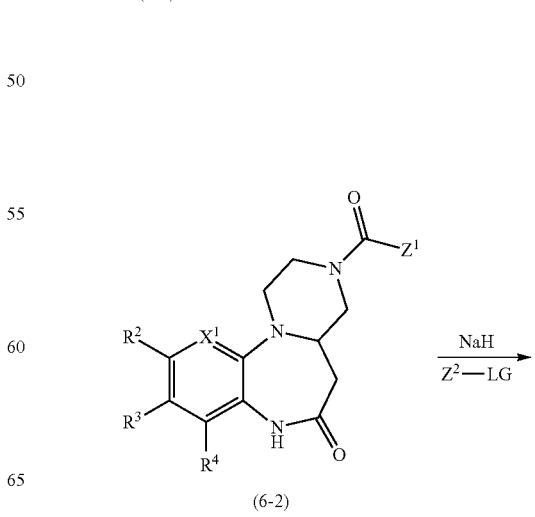

(6-2)

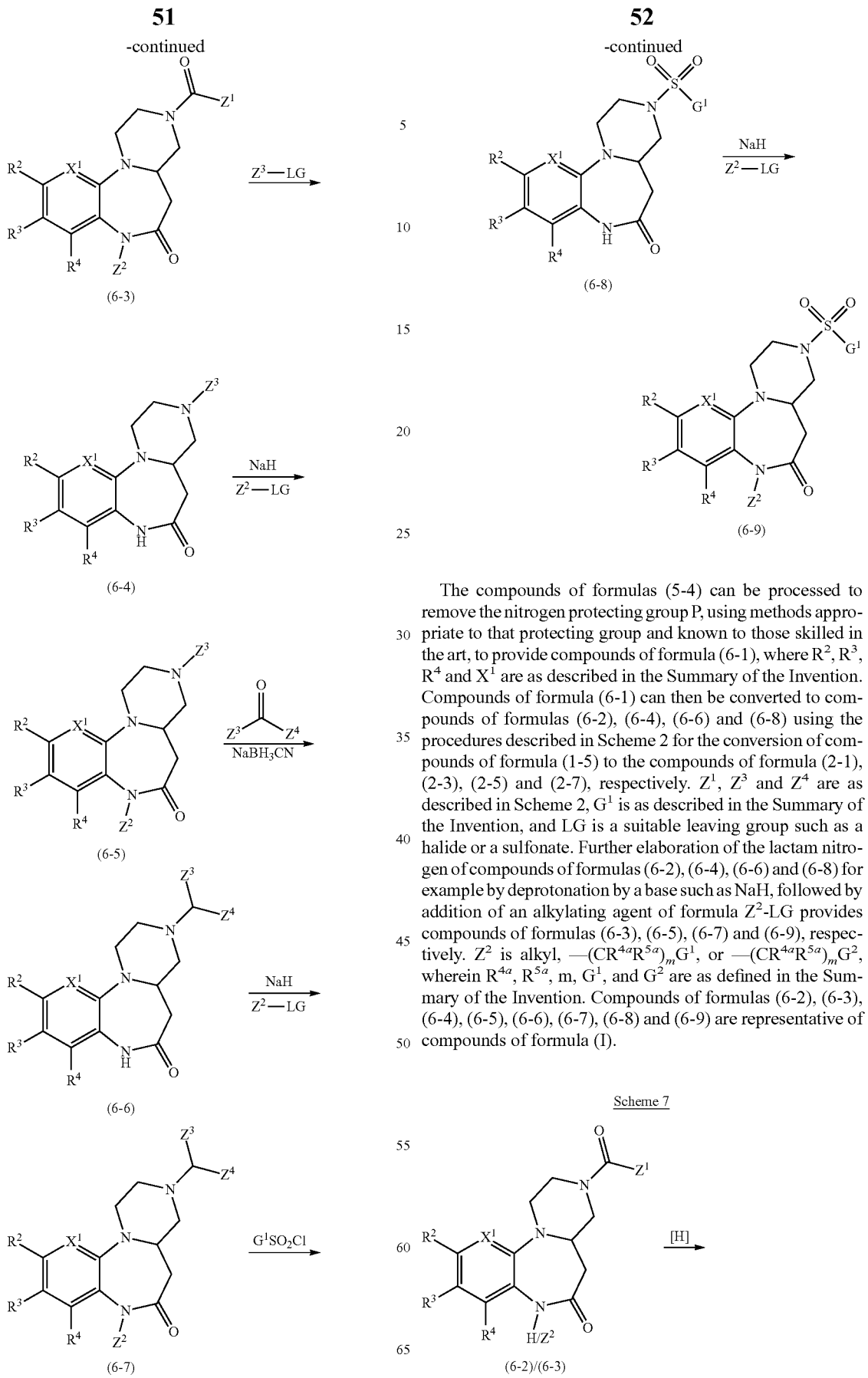

The compounds of formulas (5-4) can be processed to remove the nitrogen protecting group P, using methods appropriate to that protecting group and known to those skilled in the art, to provide compounds of formula (6-1), where $R^2$, $R^3$, $R^4$ and $X^1$ are as described in the Summary of the Invention. Compounds of formula (6-1) can then be converted to compounds of formulas (6-2), (6-4), (6-6) and (6-8) using the procedures described in Scheme 2 for the conversion of compounds of formula (1-5) to the compounds of formula (2-1), (2-3), (2-5) and (2-7), respectively. $Z^1$, $Z^3$ and $Z^4$ are as described in Scheme 2, $G^1$ is as described in the Summary of the Invention, and LG is a suitable leaving group such as a halide or a sulfonate. Further elaboration of the lactam nitrogen of compounds of formulas (6-2), (6-4), (6-6) and (6-8) for example by deprotonation by a base such as NaH, followed by addition of an alkylating agent of formula $Z^2$-LG provides compounds of formulas (6-3), (6-5), (6-7) and (6-9), respectively. $Z^2$ is alkyl, $-(CR^{4a}R^{5a})_m G^1$, or $-(CR^{4a}R^{5a})_m G^2$, wherein $R^{4a}$, $R^{5a}$, m, $G^1$, and $G^2$ are as defined in the Summary of the Invention. Compounds of formulas (6-2), (6-3), (6-4), (6-5), (6-6), (6-7), (6-8) and (6-9) are representative of compounds of formula (I).

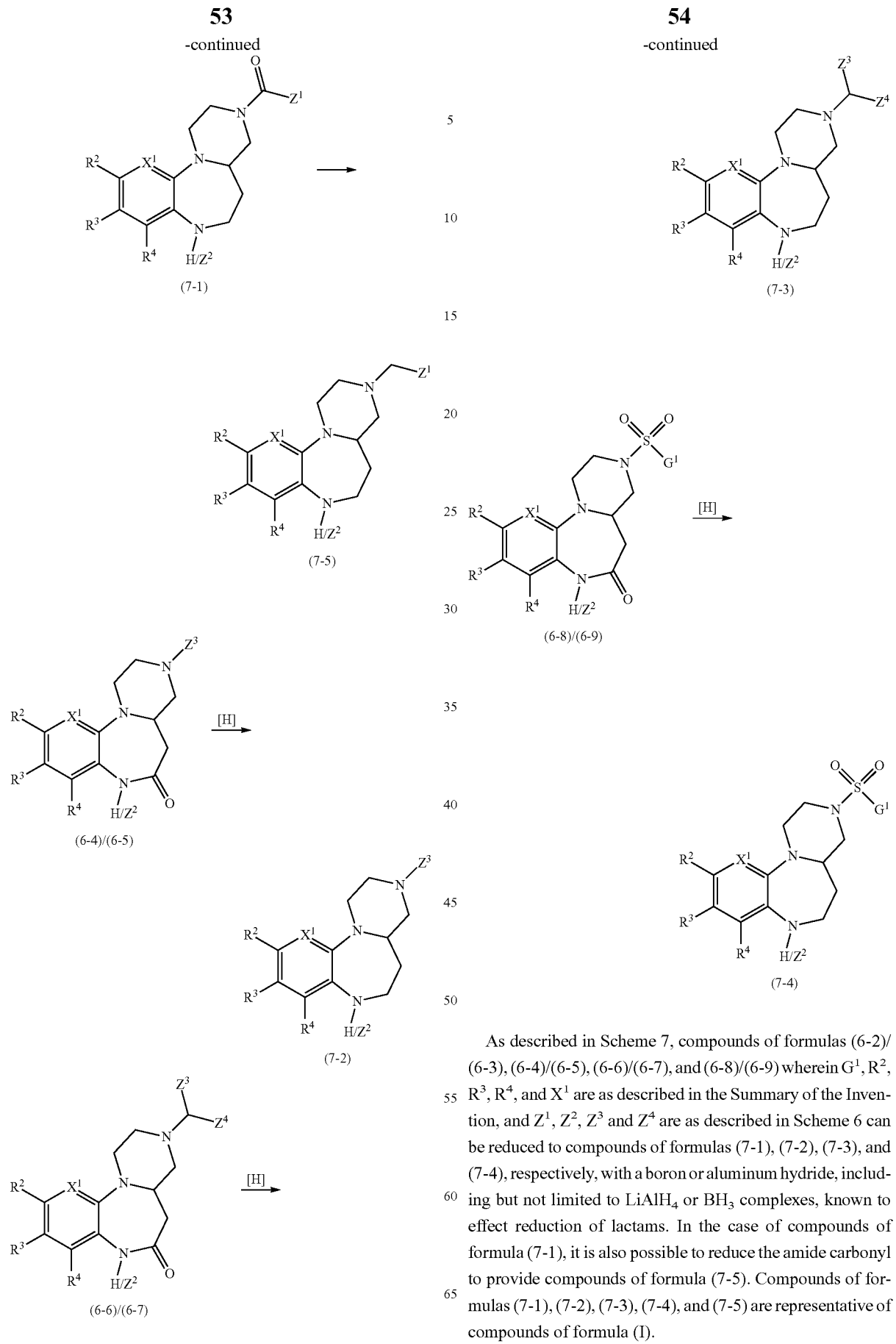

As described in Scheme 7, compounds of formulas (6-2)/(6-3), (6-4)/(6-5), (6-6)/(6-7), and (6-8)/(6-9) wherein $G^1$, $R^2$, $R^3$, $R^4$, and $X^1$ are as described in the Summary of the Invention, and $Z^1$, $Z^2$, $Z^3$ and $Z^4$ are as described in Scheme 6 can be reduced to compounds of formulas (7-1), (7-2), (7-3), and (7-4), respectively, with a boron or aluminum hydride, including but not limited to $LiAlH_4$ or $BH_3$ complexes, known to effect reduction of lactams. In the case of compounds of formula (7-1), it is also possible to reduce the amide carbonyl to provide compounds of formula (7-5). Compounds of formulas (7-1), (7-2), (7-3), (7-4), and (7-5) are representative of compounds of formula (I).

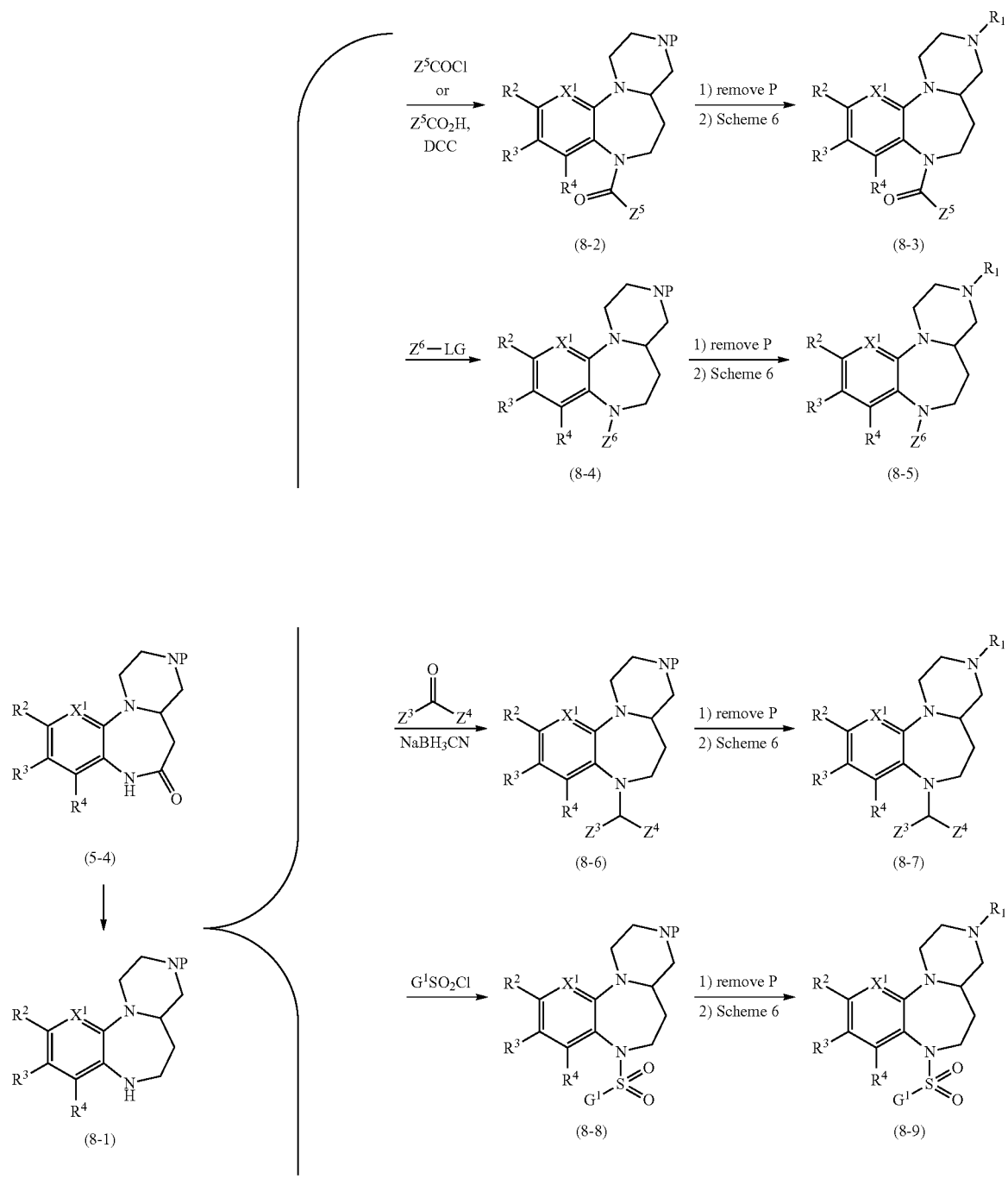

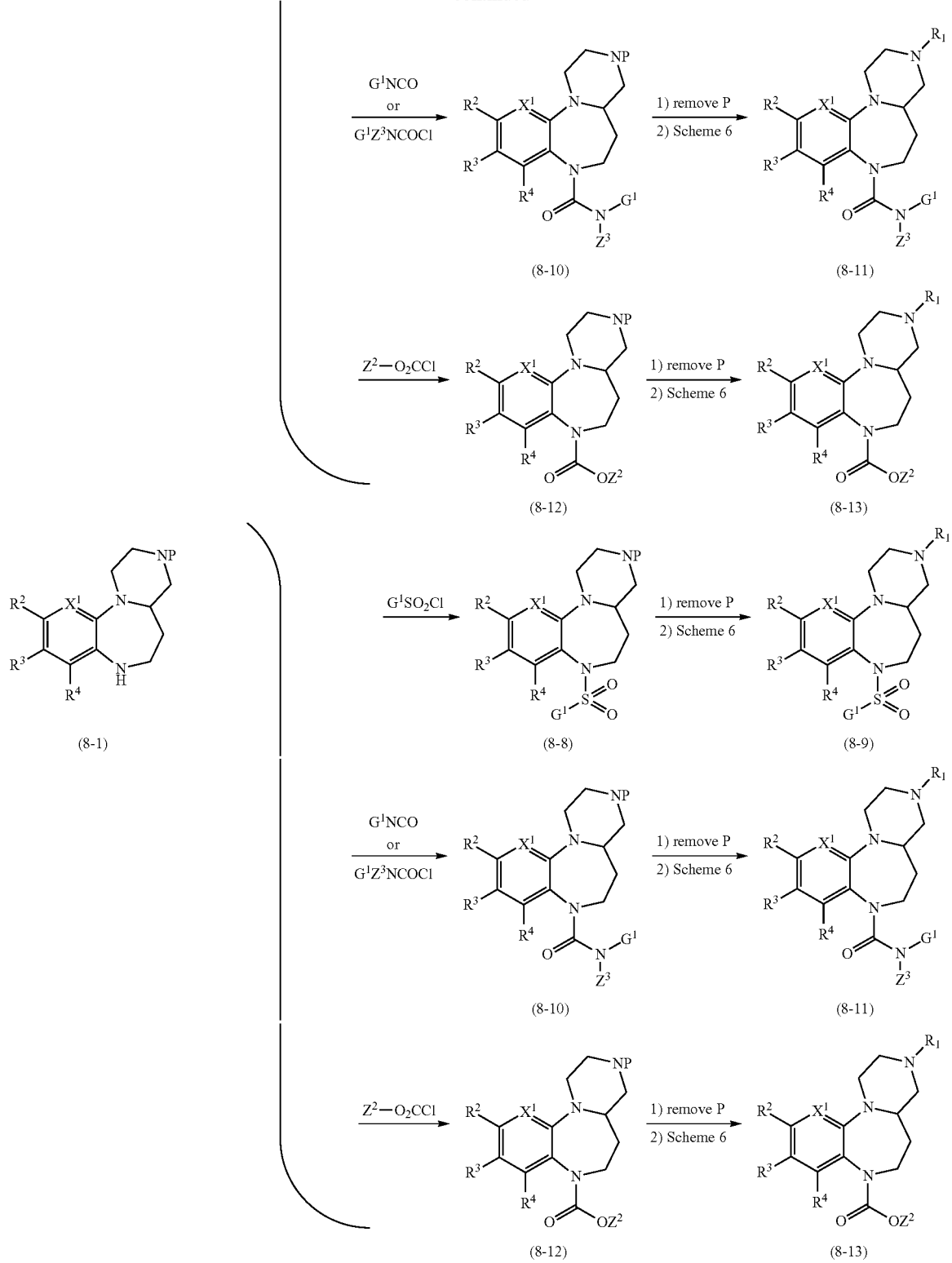

As depicted in Scheme 8, compounds of formulas (8-3), (8-5), (8-7), (8-9), (8-11), and (8-13), wherein $R^1$, $R^2$, $R^3$, $R^4$, and $X^1$ are as described in the Summary of the Invention can be prepared from compounds of formula (8-1). Compounds of formula (8-1) are in turn prepared from compounds of formula (5-4) by treatment with a suitable reducing agent, for example $BH_3$ or $AlH_3$ complexes. Compounds of formula (8-1) can be acylated with an acyl chloride of formula $Z^5COCl$ or coupled with a carboxylic acid of formula $Z^5CO_2H$ to give compounds of formula (8-2). $Z^5$ is $G^1$, $G^2$, -$G^2$-$G^1$, —$(CR^{4a}R^{5a})_m$-$G^1$, —$(CR^{4a}R^{5a})_m$-$G^2$, or —CH=CH-$G^1$, wherein $G^1$, $G^2$, $R^{4a}$, $R^{5a}$, and m are as defined in the Summary of the Invention. Reaction of $Z^5$COCl and compounds of formula (8-1) in the presence of a base provides compounds of formula (8-2). Compounds of formula (8-2) are also formed by reacting compounds of formula (8-1) with $Z^5CO_2H$ in the presence of an amide bond forming reagent such as dicyclohexylcarbodiimide (DCC) or O-(7-azabenzotriazol-1-yl)-N,N,N',N'-tetramethyluronium hexafluorophosphate (HATU). Reaction of compounds of formula (8-1) with an alkylating reagent of formula $Z^6$-LG, wherein LG is a suitable leaving group such as a halide or a sulfonate, supplies compounds of formula (8-4), wherein $Z^6$ is —$(CR^{4a}R^{5a})_m$-$G^1$ or —$(CR^{4a}R^{5a})_m$-$G^2$. Reductive alkylation of compounds of formula (8-1) with an aldehyde or ketone of formula $Z^3C(O)Z^4$ under conditions to reduce the intermediate imine or iminium compound, for example $NaBH_3CN$ or hydrogen and a noble metal catalyst, will afford compounds of formula (8-6). $Z^3$ is alkyl, haloalkyl or —$(CR^{4a}R^{5a})_mG^1$ wherein $R^{4a}$, $R^{5a})_m$, and $G^1$ are as defined in the Summary of the Invention, and $Z^4$ is hydrogen or alkyl. Reaction of compounds of formula (8-1) with a sulfonyl chloride of formula $G^1SO_2Cl$ will produce compounds of formula (8-8), while reaction with isocyanates of formula $G^1$NCO or carbamyl chlorides of formula $G^1Z^3$NCOCl will access compounds of formula (8-10). Additionally, chloroformates of formula $Z^2O_2CCl$ react with compounds of formula (8-1) to form the carbamates of formula (8-12). $Z^2$ is alkyl, —$(CR^{4a}R^{5a})_mG^2$.

The protective group P in each of the compounds of formulas (8-2), (8-4), (8-6), (8-8), (8-10), or (8-12) can be removed by methodology known to one skilled in the art. The revealed piperazine nitrogen of the compounds of formulas (8-2), (8-4), (8-6), (8-8), (8-10), or (8-12) can then be reacted with the sequences described in Scheme 6 to give compounds of formulas (8-3), (8-5), (8-7), (8-9), (8-11), and (8-13), respectively, which are representative of compounds of formula (I).

As shown in Scheme 9, compounds of formula (9-1) which can be prepared with the methodology described in Scheme 7 can be converted to compounds of formula (9-3), wherein $R^1$, $R^2$, $R^3$, $R^4$, and $X^1$ are as defined in the Summary of the Invention. Compounds of formula (9-1) can be heated in the presence of a base such as diisopropylethylamine with compounds of formula (9-2), wherein $Hal^1$ is fluorine or chlorine, to give compounds of formula (9-3). One of $X^3$ and $X^4$ can be N, the other or both $X^3$ and $X^4$ can be CH. Compounds of formula (9-3) are representative of compounds of formula (I).

Scheme 10

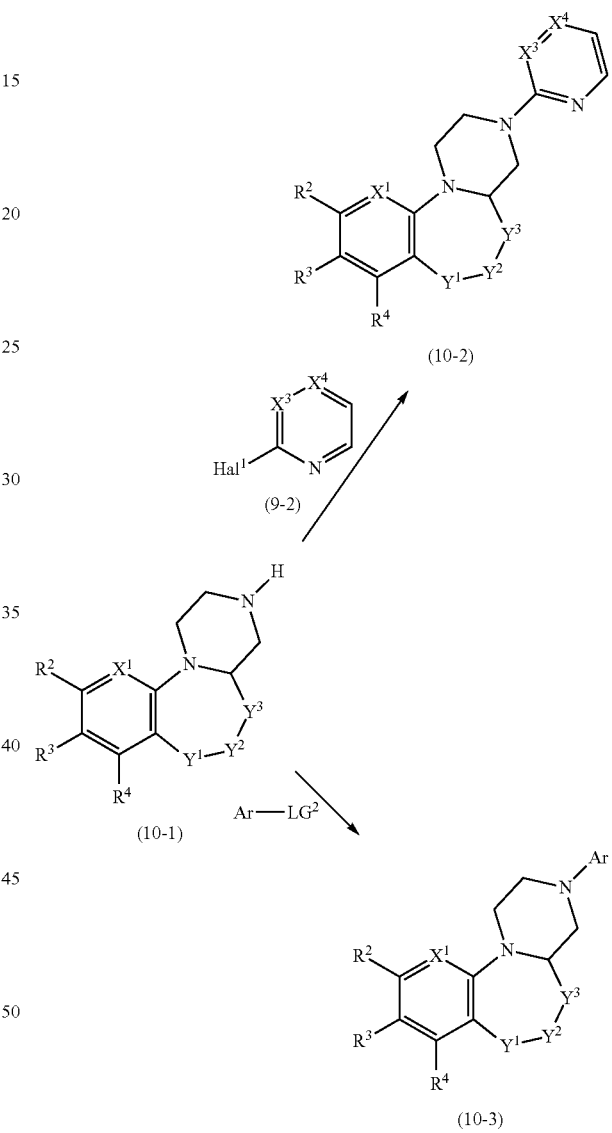

Scheme 9

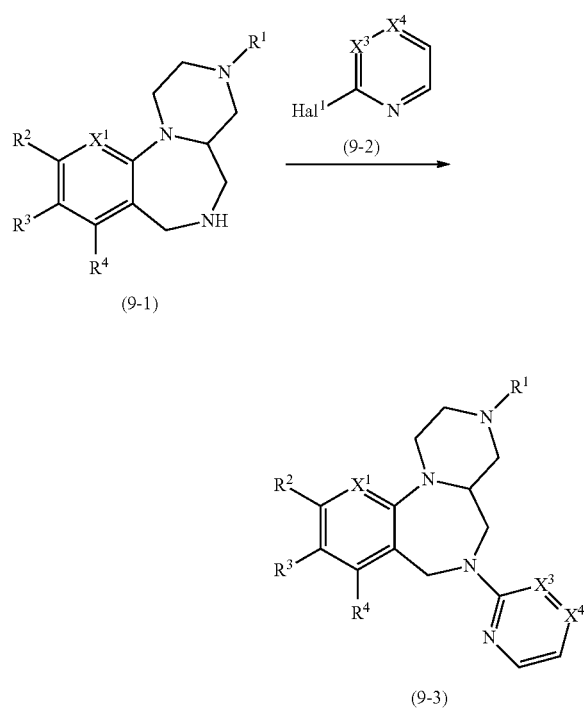

As shown in Scheme 10, Compounds of formula (10-1), wherein $R^2$, $R^3$, $R^4$, $X^1$, $Y^1$, $Y^2$ and $Y^3$ are as described in the Summary of the Invention, can be converted to compounds of formulas (10-2) and (10-3). Accordingly, compounds of formula (10-1) can be reacted with compounds of formula (9-2) using the conditions described in Scheme 9 to give compounds of formula (10-2). Compounds of formula (10-2) are representative of compounds of formula (I). Alternatively, compounds of formula (10-1) can be reacted with compounds of formula, Ar-$LG^2$, wherein Ar is an aryl or heteroaryl group and $LG^2$ is a leaving group suitable for a cross-coupling reaction or nucleophilic aromatic substitution reaction, to give compounds of formula (10-3). The arylation reaction can be accomplished by nucelophilic aromatic substitution in the presence of a base, or alternatively using transition metal-mediated processes such as the Pd-catalyzed process developed by Hartwig and Buchwald (for a review of this process, see: J. Am. Chem. Soc. (2006), 128, 3584-3591 and references therein). Compounds of formulas (10-3) are representative of compounds of formula (I).
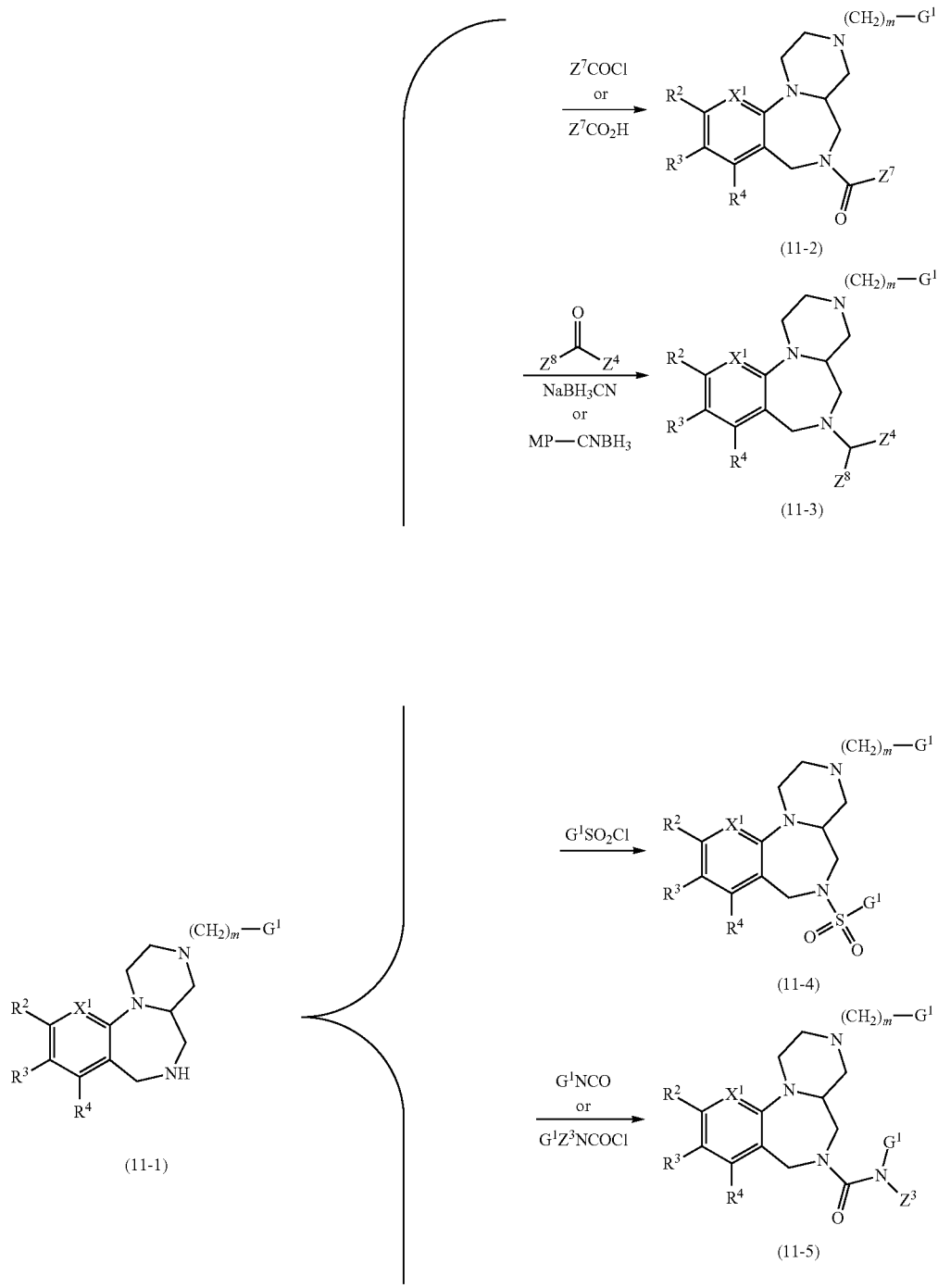
Scheme 11

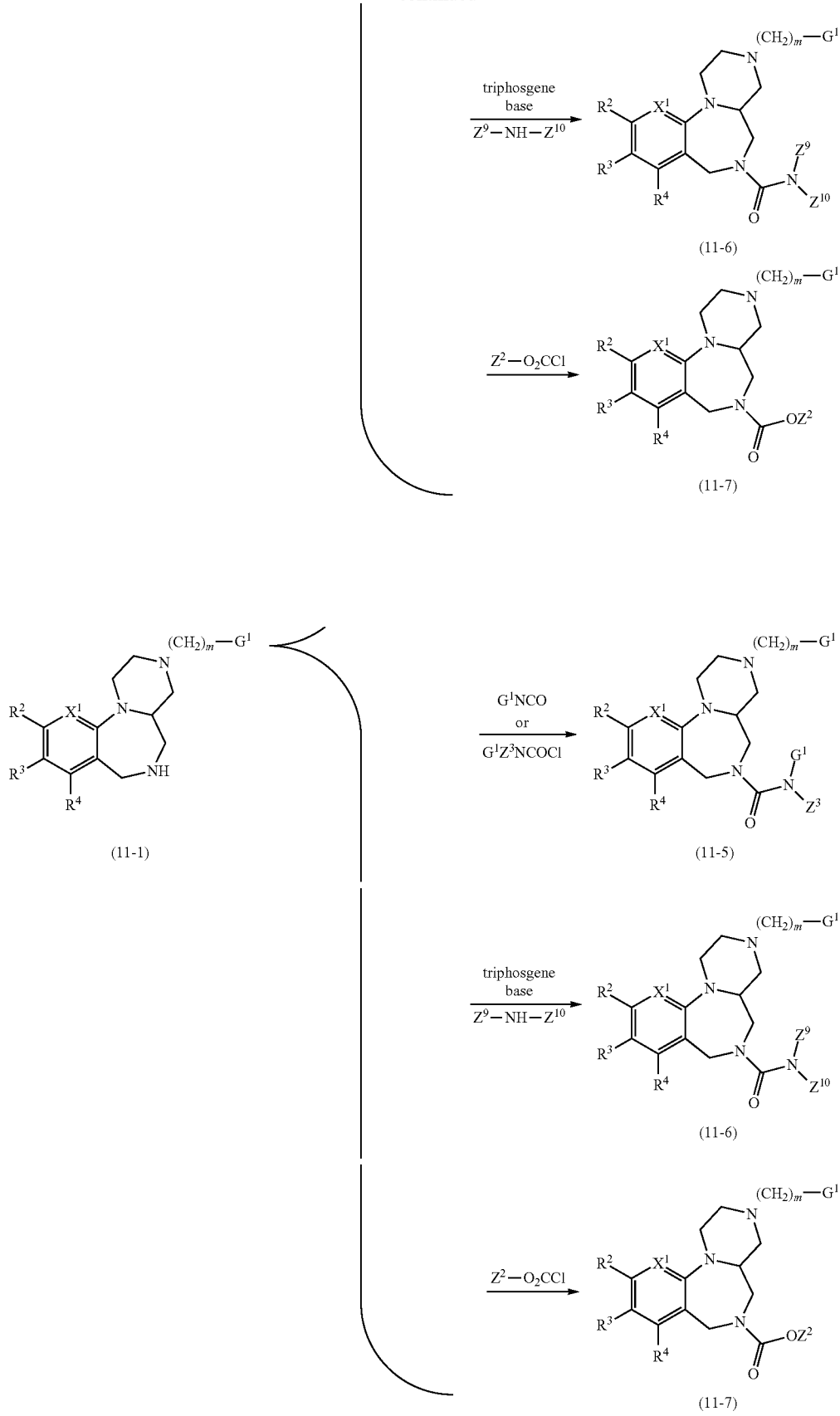

As depicted in Scheme 11, compounds of formulas (11-2), (11-3), (11-4), (11-5), (11-6), and (11-7), wherein $R^1$, $R^2$, $R^3$, $R^4$, and $X^1$ are as described in the Summary of the Invention can be prepared from compounds of formula (11-1). Compounds of formula (11-1) are in turn prepared as described in Scheme 2 for the preparation of compounds of formula (2-3). Compounds of formula (11-1) can be acylated with an acyl chloride of formula $Z^7COCl$ or coupled with a carboxylic acid of formula $Z^7CO_2H$ to give compounds of formula (11-2). $Z^7$ is $G^1$, $G^2$, $-(CR^{4a}R^{5a})_m-G^1$, $-(CR^{4a}R^{5a})_m-G^2$, $R^{2b}$, or $-(CR^{4a}R^{5a})_m-W^1$, wherein $G^1$, $G^2$, $R^{2b}$, $R^{4a}$, $R^{5a}$, m, and $W^1$ are as defined in the Summary of the Invention. Reaction of $Z^7COCl$ and compounds of formula (11-1) in the presence of a base provides compounds of formula (11-2). Compounds of formula (11-2) are also formed by reacting compounds of formula (11-1) with $Z^7CO_2H$ in the presence of an amide bond forming reagent such as dicyclohexylcarbodiimide (DCC) or O-(7-azabenzotriazol-1-yl)-N,N,N',N'-tetramethyluronium hexafluorophosphate (HATU). Reductive alkylation of compounds of formula (11-1) with an aldehyde or ketone of formula $Z^4C(O)Z^8$ under conditions to reduce the intermediate imine or iminium compound, for example $NaBH_3CN$, macroporous poly(styrene-co-divinylbenzene) cyanoborohydride resin or hydrogen and a noble metal catalyst, will afford compounds of formula (11-3). $Z^4$ is hydrogen or alkyl and $Z^8$ is alkyl, $G^1$ or $G^2$ wherein $G^1$ and $G^2$ are as defined in the Summary of the Invention, or $Z^4$ and Z8 taken together to the atom to which they are attached form a $G^2$ group. Reaction of compounds of formula (11-1) with a sulfonyl chloride of formula $G^1SO_2Cl$ will produce compounds of formula (11-4), while reaction with isocyanates of formula $G^1NCO$ or carbamyl chlorides of formula $G^1Z^3NCOCl$, wherein $Z^3$ is alkyl, haloalkyl or $-(CR^{4a}R^{5a})_mG^1$ will access compounds of formula (11-5). Compounds of formula (11-1) can also be reacted with triphosgene in the presence of a base such as but not limited to diisopropylethylamine and $Z^9-NH-Z^{10}$, wherein $Z^9$ is hydrogen, alkyl, or cyanoalkyl and $Z^{10}$ is alkyl, $G^1$, $G^2$, or $-(CR^{4a}R^{5a})_m-W^2$, wherein $W^2$ is as described in the Summary of the Invention. Additionally, chloroformates of formula $Z^2O_2CCl$ react with compounds of formula (11-1) to form the carbamates of formula (11-7). $Z^2$ is alkyl, $-(CR^{4a}R^{5a})_mG^1$, $-(CR^{4a}R^{5a})_mG^2$. Compounds of formulas (11-2), (11-3), (11-4), (11-5), (11-6), and (11-7) are representative of compounds of formula (I).

Scheme 12

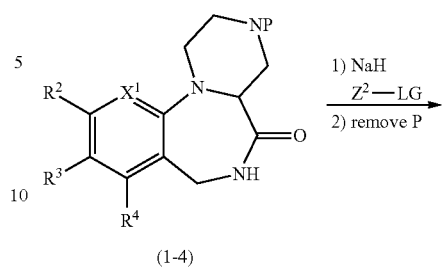

(1-4)

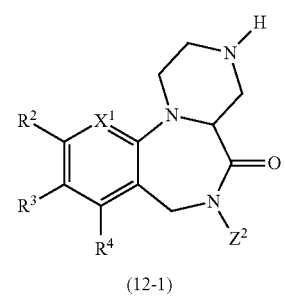

(12-1)

As shown in Scheme 12, compounds of formula (1-4), wherein $R^2$, $R^3$, $R^4$, and $X^1$ are as defined in formula (I) and P is a suitable nitrogen protecting group, including, but not limited to tert-butoxycarbonyl, 9-fluorenylmethoxycarbonyl, or benzyloxycarbonyl, can be transformed to compounds of formula (12-1). The lactam nitrogen of compounds of formulas (1-4) can be deprotonation by a base such as NaH, followed by addition of an alkylating agent of formula $Z^2$-LG provides compounds of formulas (12-1). $Z^2$ is alkyl, $-(CR^{4a}R^{5a})_m-G^1$, or $-(CR^{4a}R^{5a})_mG^2$, wherein $R^{4a}$, $R^{5a}$, m, $G^1$, and $G^2$ are as defined in the Summary of the Invention. Removal of the protecting group using conditions known to one skilled in the art delivers compounds of formulas (12-1) that are representative of compounds of formula (I).

Scheme 13

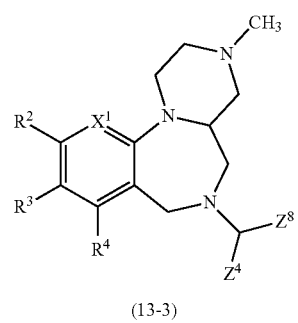

(13-3)

-continued

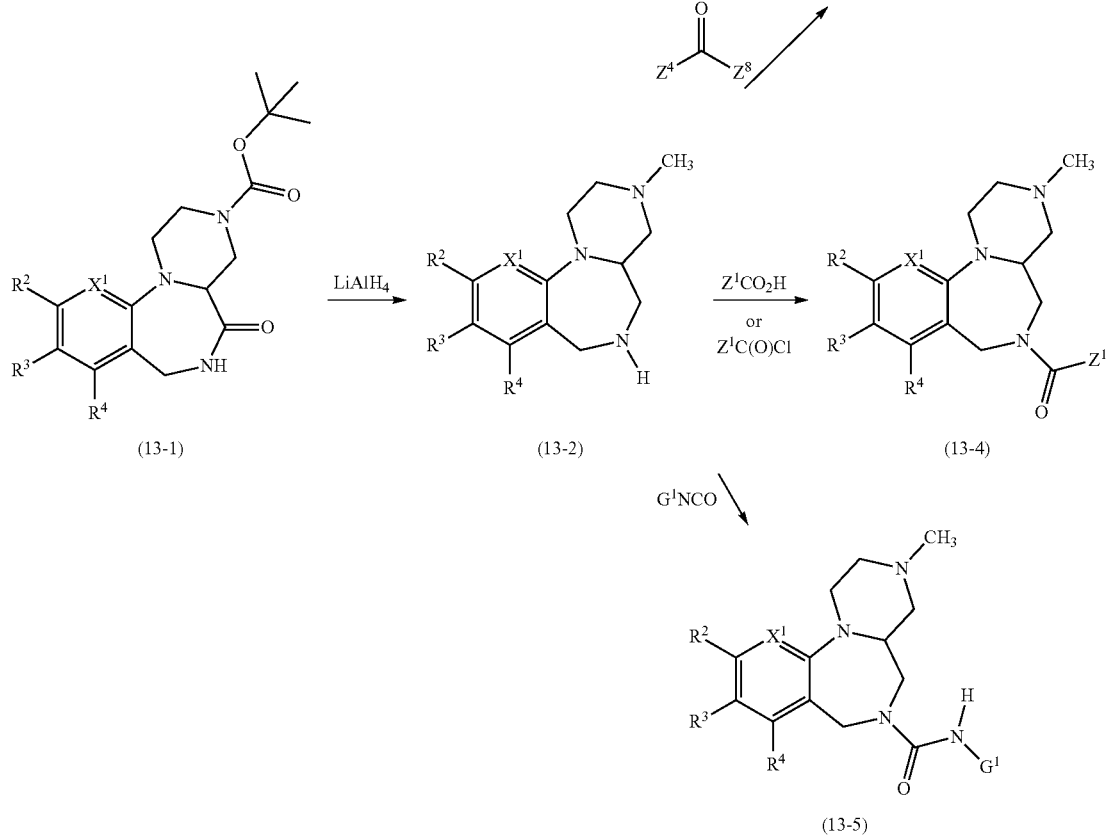

As depicted in Scheme 13, compounds of formula (13-1), wherein R2, R3, R4 and X1 are as described in the Summary of the Invention, can be reduced with lithium aluminum hydride to give compounds of formula (13-2). Reductive alkylation of compounds of formula (13-2) with an aldehyde or ketone of formula $Z^4C(O)Z^8$ under conditions to reduce the intermediate imine or iminium compound, for example $NaBH_3CN$, macroporous poly(styrene-co-divinylbenzene) cyanoborohydride resin or hydrogen and a noble metal catalyst, will afford compounds of formula (13-3). $Z^4$ is hydrogen or alkyl and $Z^8$ is alkyl, $G^1$ or $G^2$ wherein $G^1$ and $G^2$ are as defined in the Summary of the Invention, or $Z^4$ and $Z^8$ taken together to the atom to which they are attached form a $G^2$ group. Compounds of formula (13-2) can also be reacted with an acid chloride of formula $Z^1COCl$ to give compounds of formula (13-4) Alternatively, compounds of formula (13-2) can be reacted with a carboxylic acid of formula $Z^1CO_2H$ and an amide coupling reagent such as, but not limited to, dicyclohexylcarbodiimide (DCC) or O-(7-azabenzotriazol-1-yl)-N,N,N',N'-tetramethyluronium hexafluorophosphate (HATU), to produce compounds of formula (13-4), wherein $Z^1$ is alkyl, $G^1$, $OR^6$ or $NR^7R^8$ wherein $G^1$, $R^6$, $R^7$ and $R^8$ are as defined in the Summary of the Invention. Compounds of formula (13-2) can be reacted with isocyanates of formula $G^1NCO$ to produce ureas of formula (13-5). Compounds of formulas (13-3), (13-4), and (13-5) are representative of compounds of formula (I).

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g., by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protective Groups in Organic Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

g. EXAMPLES

The compounds and processes of the present invention will be better understood by reference to the following Examples, which are intended as an illustration of and not a limitation upon the scope of the application.

Example 1 tert-butyl 5-oxo-1,2,4a,5,6,7-hexahydropyrazino[1,2-a][1,4]benzodiazepine-3(4H)-carboxylate

Example 1A 1-tert-butyl 3-methyl 4-(2-cyano-4-nitrophenyl)piperazine-1,3-dicarboxylate To a solution of 1-tert-butyl 3-methyl piperazine-1,3-dicarboxylate (80 g, 328 mmol) and N,N-diisopropylethylamine (192 mL, 741 mmol) in 300 mL of dry tetrahydrofuran was added 2-fluoro-5-nitrobenzonitrile (36 g, 219 mmol) at room temperature. The reaction mixture was heated to reflux for 36 hours. The reaction was concentrated and the resulting residue was purified by silica gel chromatography (30% ethyl acetate in hexane) to give the title compound: $^1$H NMR (300 MHz, DMSO-$d_6$) δ ppm 1.41 (s, 9H), 3.01-3.15 (m, 1H), 3.29-3.36 (m, 1H), 3.34-3.36 (m, 1H), 3.48-3.55 (m, 1H), 3.66 (s, 3H), 3.72-3.76 (m, 1H), 4.43-7.48 (m, 1H), 4.96-4.98 (m, 1H), 7.30 (d, J=9.1 Hz, 1H), 8.32 (dd, J=9.5, 2.8 Hz, 1H), 8.55 (d, J=2.8 Hz, 1H); MS (DCI/NH$_3$) m/z 391 (M+H)$^+$.

Example 1B 1-tert-butyl 3-methyl 4-(2-cyanophenyl)piperazine-1,3-dicarboxylate To a solution of the product of Example 1A (66 g, 169.2 mmol) in 250 mL of methanol, was added iron dust (66 g, 1178.6 mmol) and a solution of NH$_4$Cl (81.5 g, 1523 mmol) in 250 mL of water. The solution was heated to reflux for 1 hour. The reaction was cooled and then methanol was removed in vacuo. The resulting aqueous residue was extracted with ethyl acetate (500 mL). The organic layer was washed twice with brine, dried over sodium sulfate and condensed to give crude 1-tert-butyl 3-methyl 4-(4-amino-2-cyanophenyl)piperazine-1,3-dicarboxylate (50 g), which was dissolved in 35% hypophosphorous acid (250 mL). Copper(I) oxide (1.5 g, 10.5 mmol) was added, and the reaction was chilled to 0° C. Sodium nitrite (11.6 g, 168 mmol) in water (300 mL) was added dropwise at 0° C. with stirring. After 2 hours, the reaction mixture was basified with the addition of 40% NaOH solution to pH 8 and extracted with ethyl acetate (2×500 mL). The organic layers were combined and washed with water (200 mL) and brine (100 mL). The solvent was evaporated to give the crude product which was purified by column chromatography on silica gel (ethyl acetate/petroleum ether, 1:10) to give the title compound: MS (DCI/NH$_3$) m/z 346 (M+H)$^+$.

Example 1C tert-butyl 5-oxo-1,2,4a,5,6,7-hexahydropyrazino[1,2-a][1,4]benzodiazepine-3(4H)-carboxylate A mixture of Raney®-nickel (25 g) and the product of Example 1B (35 g, 101 mmol) in 1 L of methanol saturated with NH$_3$ was stirred under a H$_2$ (40 psi) atmosphere at room temperature for 48 hours. The reaction was filtered, and the filtrate was condensed under reduced pressure to give the title compound: $^1$H NMR: (300 MHz, CDCl$_3$) δ ppm 1.49 (s, 9H), 2.99-3.25 (m, 4H), 3.47 (dd, J=10.7, 2.8 Hz, 1H), 3.78 (dd, J=13.9, 2.8 Hz, 1H), 4.18-4.20 (m, 1H), 4.36-4.40 (m, 1H), 4.87 (dd, J=13.9, 4.8 Hz, 1H), 6.14-6.18 (m, 1H) 7.02-7.08 (m, 2H), 7.17 (dd, J=7.1, 1.2 Hz, 1H), 7.30-7.36 (m, 1H); MS (DCI/NH$_3$) m/z 318 (M+H)$^+$.

Example 2

3-benzyl-1,2,3,4,4a,5,6,7-octahydropyrazino[1,2-a][1,4]benzodiazepine

Example 2A 2,3,4,4a,6,7-hexahydropyrazino[1,2-a][1,4]benzodiazepin-5(1H)-one To a solution of the product of Example 1C (32 g, 100.9 mmol) in dichloromethane (200 mL) was added trifluoroacetic acid (200 mL) at room temperature. After stirring overnight (16 hours), the reaction mixture was condensed under reduced pressure and diluted with saturated NaHCO$_3$ (100 mL). The aqueous phase was extracted with ethyl acetate (5×100 mL). The organic layer was washed with brine (100 mL), dried over magnesium sulfate and filtered. The filtrate was concentrated under reduced pressure to give the title compound: $^1$H NMR (300 MHz, C$_6$D$_6$) δ ppm 2.57-2.65 (m, 4H), 3.04-3.10 (m, 1H), 3.22 (dd, J=14.3, 7.0 Hz, 1H), 3.38-3.44 (m, 2H), 4.28 (dd, J=14.0, 4.9 Hz, 1H), 6.69-3.74 (m, 2H), 6.80 (td, J=7.4, 1.1 Hz, 1H), 7.08 (td, J=7.7, 171 Hz, 1H); MS (DCI/NH$_3$) m/z 218 (M+H)$^+$.

Example 2B 3-benzyl-2,3,4,4a,6,7-hexahydropyrazino[1,2-a][1,4]benzodiazepin-5(1H)-one Benzyl bromide (14.9 g, 87.1 mmol) was added dropwise to a mixture of the product of Example 2A (18.5 g, 82.9 mmol) and potassium carbonate (45.8 g, 331.8 mmol) in acetonitrile (200 mL) at room temperature with stirring. The reaction mixture was stirred for 3 hours under reflux. Then it was cooled, filtered, and concentrated under reduced pressure to give the crude product which was purified by column chromatography on silica gel (ethyl acetate) to give the title compound: MS (DCI/NH$_3$) m/z 308 (M+H)$^+$.

Example 2C 3-benzyl-1,2,3,4,4a,5,6,7-octahydropyrazino[1,2-a][1,4]benzodiazepine To a suspension of LiAlH$_4$ (8.9 g, 234.6 mmol) in dry tetrahydrofuran (200 mL) was added dropwise a solution of the product of Example 2B (24 g, 78.2 mmol) in dry tetrahydrofuran (200 mL) at −78° C. with stirring under a nitrogen atmosphere. Then it was allowed to warm to room temperature slowly and stirred for 60 hours. The reaction mixture was cooled to −78° C., quenched with water (20 mL), diluted with ethyl acetate (400 mL), dried over magnesium sulfate and filtered. The filtrate was washed with brine twice (2×100 mL), dried over magnesium sulfate and concentrated under reduced pressure to give the title compound: $^1$H NMR (300 MHz, DMSO-d$_6$) δ ppm 2.24-2.32 (m, 1H), 2.34-2.41 (m, 1H), 2.55-2.58 (m, 1H), 2.67-2.75 (m, 3H), 2.84-2.90 (m, 1H), 3.08-3.20 (m, 2H), 3.48-3.57 (m, 2H), 3.74 (d, J=12.6 Hz, 1H), 4.02 (d, J=12.6 Hz, 1H), 6.85-6.89 (m, 2H), 7.07 (dd, J=7.6, 1.5 Hz, 1H), 7.18 (td, J=7.6, 1.7 Hz, 1H), 7.24-7.30 (m, 1H), 7.31-7.34 (m, 4H); MS (DCI/NH$_3$) m/z 294 (M+H)$^+$.

Example 3

3-benzyl-6-(4-bromobenzyl)-1,2,3,4,4a,5,6,7-octahydropyrazino[1,2-a][1,4]benzodiazepine The product of Example 2 (344.8 mg, 1.18 mmol), was dissolved in methanol (10 mL). 4-Bromobenzaldehyde (338.8 mg, 1.56 mmol) was added to the reaction, and the mixture was stirred for 1 hour at ambient temperature. Sodium cyanoborohydride (238.9 mg, 3.80 mmol) was then added, and the reaction was stirred at ambient temperature for 20 hours. The reaction was then diluted with 1 M NaOH (50 mL) and extracted with dichloromethane (3×50 mL). The organic layers were combined, concentrated and purified by silica gel chromatography (ethyl acetate/dichloromethane 1:1, R$_f$ 0.37) to give the title compound: $^1$H NMR (500 MHz, pyridine-d$_5$) δ ppm 2.30-2.40 (m, 2H), 2.55 (dd, J=13.4, 3.1 Hz, 1H) 2.66-2.71 (m, 2H), 2.77-2.79 (m, 1H), 3.23-3.34 (m, 3H), 3.49-3.58 (m, 4H), 3.77 (d, J=13.1 Hz, 1H), 4.05 (d, J=13.1 Hz, 1H), 6.97 (dd, J=7.9, 0.9 Hz, 1H), 7.01 (td, J=7.3, 1.2 Hz, 1H), 7.13 (dd, J=7.3, 1.5 Hz, 1H), 7.30-7.36 (m, 4H), 7.39-7.43 (m, 2H), 7.48-7.50 (m, 2H), 7.53-7.57 (m, 2H); MS (DCI/NH$_3$) m/z 462 (M+H)$^+$. Elemental analysis is calculated for C$_{26}$H$_{28}$BrN$_3$: C, 67.53; H, 6.10; N, 9.09. Found: C, 67.44; H, 5.83; N, 9.08.

The title compound (270.0 mg, 0.58 mmol) was dissolve in warm methanol. Hydrochloric acid in dioxane (4 M, 0.6 mL, 2.4 mmol) was added to precipitate out the title compound as the bis-hydrochloride salt: Elemental analysis is calculated for C$_{26}$H$_{28}$N$_3$.2 HCl.2 MeOH: C, 57.16; H, 6.04; N, 7.41. Found: C, 57.29; H, 6.22; N, 7.39.

Example 4

1-(3-benzyl-1,2,3,4,4a,5-hexahydropyrazino[1,2-a][1,4]benzodiazepin-6(7H)-yl)-2-phenylethanone The product of Example 2 (154.2 mg, 0.53 mmol) was dissolved in dichloromethane (5 mL). Diisopropylethylamine (0.20 mL, 1.15 mmol) and phenylacetyl chloride (123.8 mg, 0.80 mmol) were added, and the reaction mixture was stirred for 20 hours at ambient temperature. The reaction was concentrated and purified by preparative HPLC using the general ammonium acetate method described herein on a Phenomenex® Luna® C8(2) 5 µm 100 Å AXIA column (30×75 mm). A gradient of acetonitrile (A) and 10 mM ammonium acetate in water (B) was used, at a flow rate of 50 mL/minute (0-0.5 minutes 10% A, 0.5-6.0 minutes linear gradient 10-100% A, 6.0-7.0 minutes 100% A, 7.0-8.0 minutes linear gradient 100-10% A). Samples were injected in 1.5 mL dimethyl sulfoxide:methanol (1:1). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter, IFC-PAL fraction collector/autosampler. The make-up pump for the mass spectrometer used 3:1 methanol:water with 0.1% formic acid at a flow rate of 1 mL/minute. Fraction collection was automatically triggered when the extracted ion chromatogram (EIC) for the target mass exceeded the threshold specified in the method. The system was controlled using Agilent Chemstation (Rev B.10.03), Agilent A2Prep, and Leap FractPal software, with custom Chemstation macros for data export. The desired fractions were concentrated to give the title compound: $^1$H NMR (500 MHz, pyridine-d$_5$) δ ppm 2.14-4.00 (m, 13H), 4.58 (d, J=12.5 Hz, 1H), 4.83 (d, J=12.2 Hz, 1H) 6.95-6.99 (m, 1H), 7.03-7.07 (m, 1H), 7.24-7.49 (m, 11H), 7.53-7.55 (m, 1H); MS (DCI/NH$_3$) m/z 412 (M+H)$^+$; Elemental analysis is calculated for C$_{27}$H$_{29}$N$_3$O.0.2H$_2$O: C, 78.12; H, 7.14; N, 10.12. Found: C, 78.23; H, 7.20; N, 10.02.

Example 5

(3-benzyl-1,2,3,4,4a,5-hexahydropyrazino[1,2-a][1,4]benzodiazepin-6(7H)-yl)(phenyl)methanone The product of Example 2 (130.2 mg, 0.45 mmol) and benzoyl chloride (146.6 mg, 1.04 mmol) were processed according to the procedure for Example 4 to give the title compound: $^1$H NMR (500 MHz, benzene-d$_6$) δ ppm (7:3 mixture of rotomers at 25° C.) 1.74-1.87 (m, 2H), 2.07-2.65 (m, 6H), 2.82-2.88 (m, 1.4H), 2.97-3.00 (m, 1H), 3.22 (d, J=12.8 Hz, 0.3H), 3.77 (d, J=13.2 Hz, 0.3H), 4.27 (d, J=13.1 Hz, 0.3H), 4.34 (d, J=13.7 Hz, 0.3H), 4.59 (d, J=14.0 Hz, 0.7H), 4.78 (d, J=13.7 Hz, 0.7H), 6.24-7.18 (m, 14H); MS (DCI/NH$_3$) m/z 398 (M+H)$^+$. Elemental analysis is calculated for C$_{26}$H$_{27}$N$_3$O.0.2H$_2$O: C, 77.85; H, 6.89; N, 10.48. Found: C, 77.87; H, 6.87; N, 10.53.

Example 6

3,6,6-tribenzyl-1,2,3,4,4a,5,6,7-octahydropyrazino[1,2-a][1,4]benzodiazepin-6-ium The product of Example 2 (102.2 mg, 0.35 mmol) was dissolved in acetone (5 mL). Potassium carbonate (77.3 mg, 0.56 mmol) and benzyl bromide (129.4 mg, 0.76 mmol) were added, and the reaction mixture was stirred for 2 hours at ambient temperature. The reaction was filtered, concentrated and purified by preparative HPLC (general ammonium acetate method described in Example 4, retention time 2.43 minutes) to give the title compound as the acetate salt: $^1$H NMR (300 MHz, CDCl$_3$) δ ppm 1.67 (t, J=10.0 Hz, 1H), 2.29 (td, J=10.8, 2.8 Hz, 1H), 2.46 (d, J=10.7 Hz, 1H), 2.69 (d, J=11.0 Hz, 1H), 2.93 (t, J=9.2 Hz, 1H), 3.50-3.57 (m, 2H), 2.99-3.05 (m, 1H), 3.23-3.55 (m, 5H), 7.75-7.78 (m, 2H), 4.99-5.06 (m, 2H), 5.20-5.28 (m, 2H), 6.94-6.97 (m, 2H), 7.23-7.24 (m, 2H), 7.29-7.38 (m, 6H), 7.42-7.52 (m, 7H), 7.61-7.62 (m, 2H); MS (DCI/NH$_3$) m/z 474 (M+H)$^+$.

Example 7

3,6-dibenzyl-1,2,3,4,4a,5,6,7-octahydropyrazino[1,2-a][1,4]benzodiazepine

Continued elution of Example 6 gave the title compound (retention time 2.97 minutes): $^1$H NMR (400 MHz, pyridine-d$_5$) δ ppm 2.31 (td, J=10.2, 4.0 Hz, 1H), 2.38 (t, J=10.1 Hz, 1H), 2.56-2.60 (m, 1H), 2.68-2.79 (m, 3H), 3.24-3.36 (m, 3H), 3.50-5.38 (m, 2H), 3.59-3.66 (m, 2H), 3.82 (d, J=13.1 Hz, 1H), 4.08 (d, J=12.8 Hz, 1H), 6.95-7.02 (m, 2H), 7.12 (dd, J=7.3, 1.5 Hz, 1H), 7.29-7.35 (m, 3H), 7.38-7.42 (m, 4H), 7.48-7.51 (m, 4H); MS (DCI/NH$_3$) m/z 384 (M+H)$^+$.

Example 8

3-benzyl-6-methyl-1,2,3,4,4a,5,6,7-octahydropyrazino[1,2-a][1,4]benzodiazepine

The product of Example 2 (151.1 mg, 0.52 mmol) was dissolved in formic acid (4 mL). A solution of formaldehyde (36 weight %, 1 mL) was added, and the reaction mixture was heated to 100° C. for 1 hour. The reaction was concentrated and purified by preparative HPLC (general ammonium acetate method described in Example 4) to give the title compound as the acetic acid salt: $^1$H NMR (500 MHz, CDCl$_3$) δ ppm 2.03 (s, 3H, CH$_3$CO$_2$H), 2.29-2.35 (m, 2H), 2.45 (s, 3H), 2.61 (dd, J=13.6, 3.2 Hz, 1H), 2.74-2.80 (m, 2H), 2.86-2.88 (m, 1H), 3.27-3.37 (m, 3H), 3.55-5.63 (m, 2H), 3.80 (d, J=13.1 Hz, 1H), 4.19 (d, J=12.8 Hz, 1H), 6.89-6.95 (m, 2H), 7.13-7.15 (m, 1H), 7.28-7.37 (m, 6H); $^{13}$C NMR (125 MHz, CDCl$_3$) δ ppm 22.26 (CH$_3$CO$_2$H), 43.45, 49.83, 53.15, 54.15, 56.15, 57.43, 57.46, 63.00, 118.59, 121.41, 125.18, 127.24, 128.29, 129.31, 129.63, 130.53, 137.53, 148.82, 176.00 (CH$_3$CO$_2$H); MS (DCI/NH$_3$) m/z 308 (M+H)$^+$.

Example 9

3-benzyl-6-(pyrimidin-2-yl)-1,2,3,4,4a,5,6,7-octahydropyrazino[1,2-a][1,4]benzodiazepine The product of Example 2 (108.3 mg, 0.37 mmol) was dissolved in dimethyl sulfoxide (1 mL). Diisopropylethylamine (0.12 mL, 0.69 mmol) and 2-chloropyrimidine (77.7 mg, 0.68 mmol) were added, and the reaction mixture was heated to 100° C. for 16 hours. The reaction was diluted with methanol (1 mL) and purified by preparative HPLC using the general trifluoroacetic acid method on a Phenomenex Luna C8(2) 5 µm 100 Å AXIA column (30×75 mm). A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A). Samples were injected in 1.5 mL dimethyl sulfoxide:methanol (1:1). A custom purification system was used, consisting of the following modules: Waters LC4000 preparative pump; Waters 996 diode-array detector; Waters 717+ autosampler; Waters SAT/IN module, Alltech Varex III evaporative light-scattering detector; Gilson 506C interface box; and two Gilson FC204 fraction collectors. The system was controlled using Waters Millennium32 software, automated using an Abbott developed Visual Basic application for fraction collector control and fraction tracking Fractions were collected based upon UV signal threshold and selected fractions subsequently analyzed by flow injection analysis mass spectrometry using positive APCI ionization on a Finnigan LCQ using 70:30 methanol: 10 mM NH$_4$OH(aq) at a flow rate of 0.8 mL/minute. Loop-injection mass spectra were acquired using a Finnigan LCQ running LCQ Navigator 1.2 software and a Gilson 215 liquid handler for fraction injection controlled by an Abbott developed Visual Basic application. The title compound was obtained as the bis-trifluoroacetate: $^1$H NMR (500 MHz, pyridine-d$_5$) δ ppm 2.45-2.53 (m, 2H), 3.04-3.22 (m, 5H), 3.36 (td, J=11.4, 2.6 Hz, 1H), 3.67 (d, J=12.8 Hz, 1H), 3.75 (d, J=13.1 Hz, 1H), 4.66 (dd, J=15.0, 1.5 Hz, 1H), 4.78 (d, J=13.7 Hz, 1H), 4.85 (d, J=13.7 Hz, 1H), 6.50 (t, J=4.7 Hz, 1H), 6.99 (d, J=7.9 Hz, 1H), 7.09 (t, J=7.3 Hz, 1H), 7.30-7.39 (m, 5H), 7.48 (d, J=7.0 Hz, 1H); MS (DCI/NH$_3$) m/z 372 (M+H)$^+$. Elemental analysis is calculated for C$_{23}$H$_{25}$N$_5$.2.4 TFA.H$_2$O: C, 50.35; H, 4.47; N, 10.56; F, 20.63. Found: C, 50.57; H, 4.34; N, 10.34; F, 20.60.

Example 10

(3-benzyl-1,2,3,4,4a,5-hexahydropyrazino[1,2-a][1,4]benzodiazepin-6(7H)-yl)(4-fluorophenyl)methanone The product of Example 2 (103.8 mg, 0.35 mmol) and 4-fluorobenzoyl chloride (106.6 mg, 0.67 mmol) were processed according to the procedure for Example 4 and purified by silica gel chromatography (25%→50% ethyl acetate in dichloromethane, R$_f$ 0.33→0.45) to give the title compound: $^1$H NMR (500 MHz, pyridine-d$_5$) δ ppm (mixture of rotomers at 25° C.) 2.24-3.63 (m, 11H), 4.42 (d, J=12.8 Hz, 0.3H), 4.72 (d, J=12.8 Hz, 0.3H), 4.88 (d, J=14.0 Hz, 0.7H), 5.10 (d, J=14.0 Hz, 0.7H), 6.95-7.67 (m, 13H); MS (DCI/NH$_3$) m/z 416 (M+H)$^+$. Elemental analysis is calculated for C$_{26}$H$_{26}$FN$_3$O.0.1H$_2$O: C, 74.83; H, 6.33; N, 10.07. Found: C, 74.62; H, 6.04; N, 10.03.

Example 11

3-benzyl-6-(pyrazin-2-yl)-1,2,3,4,4a,5,6,7-octahydropyrazino[1,2-a][1,4]benzodiazepine The product of Example 2 (103.8 mg, 0.35 mmol) and 2-chloropyrazine (106.7 mg, 0.93 mmol) were processed according to the procedure for Example 9. The reaction was purified by preparative HPLC as described in Example 9 to give the title compound as the tris-trifluoroacetic acid salt: $^1$H NMR (400 MHz, pyridine-d$_5$) δ ppm 2.45-2.55 (m, 2H), 3.09-3.21 (m, 5H), 3.40 (td, J=11.5, 2.9 Hz, 1H), 3.71-3.80 (m, 2H), 4.43-4.47 (m, 2H), 4.68 (d, J=12.5 Hz, 1H), 7.00 (dd, J=7.9, 0.9 Hz, 1H), 7.12 (td, J=7.4, 1.1 Hz, 1H), 7.30-7.42 (m, 5H), 7.47-7.48 (m, 2H), 8.03 (d, J=2.8 Hz, 1H), 8.15 (dd, J=2.8, 1.5 Hz, 1H), 8.35 (d, J=1.5 Hz, 1H); MS (DCI/NH$_3$) m/z 372 (M+H)$^+$. Elemental analysis calculated for C$_{23}$H$_{25}$N$_5$.3 TFA: C, 48.84; H, 3.96; N, 9.81. Found: C, 49.21; H, 4.06; N, 9.94.

Example 12

(3-benzyl-1,2,3,4,4a,5-hexahydropyrazino[1,2-a][1,4]benzodiazepin-6(7H)-yl)(pyrazin-2-yl)methanone The product of Example 2 (101.5 mg, 0.35 mmol) and 2-pyrazinecarbonyl chloride (74.8 mg, 0.53 mmol) were processed according to the procedure for Example 4 to give the title compound: $^1$H NMR (400 MHz, pyridine-d$_5$) δ ppm 2.45-2.55 (m, 2H), 3.09-3.21 (m, 5H), 3.40 (td, J=11.5, 2.9 Hz, 1H), 3.71-3.80 (m, 2H), 4.43-4.47 (m, 2H), 4.68 (d, J=12.5 Hz, 1H), 7.00 (dd, J=7.9, 0.9 Hz, 1H), 7.12 (td, J=7.4, 1.1 Hz, 1H), 7.30-7.42 (m, 5H), 7.47-7.48 (m, 2H), 8.03 (d, J=2.8 Hz, 1H), 8.15 (dd, J=2.8, 1.5 Hz, 1H), 8.35 (d, J=1.5 Hz, 1H); MS (DCI/NH$_3$) m/z 400 (M+H)$^+$. Elemental analysis calculated for C$_{24}$H$_{25}$N$_5$O.0.15H$_2$O: C, 71.67; H, 6.34; N, 17.41. Found: C, 71.61; H, 6.24; N, 17.40.

Example 13

(3-benzyl-1,2,3,4,4a,5-hexahydropyrazino[1,2-a][1,4]benzodiazepin-6(7H)-yl)(1-phenylcyclopropyl)methanone The product of Example 2 (101.8 mg, 0.35 mmol) and 1-phenyl-cyclopropanecarbonyl chloride (98.9 mg, 0.55 mmol) were processed according to the procedure for Example 4 to give the title compound: $^1$H NMR (400 MHz, pyridine-d$_5$) δ ppm (1:1 mixture of rotomers at 25° C.) 1.10-1.71 (m, 4H), 2.05-2.28 (m, 2H), 2.41-2.47 (m, 0.5H), 2.71-2.80 (m, 1.5H), 2.95-3.15 (m, 4H), 3.41-3.51 (m, 1.5H), 3.62-3.65 (m, 0.5H), 3.81-3.85 (m, 0.5H), 4.52-4.62 (m, 1.5H), 4.83 (d, J=13.4 Hz, 0.5H), 5.13 (d, J=13.7 Hz, 0.5H), 6.90-7.03 (m, 2.5H), 7.15-7.48 (m, 11.5H); (MS (DCI/NH$_3$) m/z 438 (M+H)$^+$. Elemental analysis calculated for C$_{29}$H$_{31}$N$_3$O.0.2H$_2$O: C, 78.95; H, 7.17; N, 9.52. Found: C, 78.96; H, 7.12; N, 9.56.

Example 14

(3-benzyl-1,2,3,4,4a,5-hexahydropyrazino[1,2-a][1,4]benzodiazepin-6(7H)-yl)(morpholin-4-yl)methanone The product of Example 2 (1.00 g, 3.41 mmol) was dissolved in dichloromethane (15 mL). N,N-Diisopropylethylamine (0.90 mL, 5.15 mmol) and 4-morpholinecarbonyl chloride (0.61 g, 4.09 mmol) were added, and the reaction mixture was stirred at ambient temperature for 16 hours. The reaction was concentrated and purify by silica gel chromatography (ethyl acetate, R$_f$ 0.27) to give the title compound: $^1$H NMR (300 MHz, CDCl$_3$) δ ppm 2.27-2.41 (m, 2H), 2.68-2.91 (m, 2H), 3.07-3.34 (m, 8H), 3.57-3.77 (m, 4H), 4.24 (d, J=12.6 Hz, 1H), 4.67 (d, J=12.6 Hz, 1H), 6.90-6.99 (m, 2H), 7.13-7.16 (m, 1H), 7.27-7.33 (m, 6H); MS (DCI/NH$_3$) m/z 407 (M+H)$^+$. Elemental analysis calculated for C$_{24}$H$_{30}$N$_4$O$_2$.0.25H$_2$O: C, 70.13; H, 7.48; N, 13.63. Found: C, 70.02; H, 7.34; N, 13.67.

Example 15

(3-benzyl-1,2,3,4,4a,5-hexahydropyrazino[1,2-a][1,4]benzodiazepin-6(7H)-yl)[trans-2-phenylcyclopropyl]methanone The product of Example 2 (112.0 mg, 0.38 mmol) and trans-2-phenyl-1-cyclopropanecarbonyl chloride (101.4 mg, 0.51 mmol) were processed according to the procedure for Example 4 to give the title compound: $^1$H NMR (300 MHz, CDCl$_3$) δ ppm 1.24-3.72 (m, 12H), 4.31-4.91 (m, 5H), 6.91-7.35 (m, 14H); (MS (DCI/NH$_3$) m/z 438 (M+H)$^+$.

Example 16

3-benzyl-6-(pyridin-2-yl)-1,2,3,4,4a,5,6,7-octahydropyrazino[1,2-a][1,4]benzodiazepine The product of Example 2 (100.0 mg, 0.34 mmol) and 2-fluoropyridine (73.8 mg, 0.76 mmol) were processed according to the procedure for Example 9. The reaction was purified by preparative HPLC using the method described in Example 4 to give the title compound: $^1$H NMR (400 MHz, pyridine-d$_5$) δ ppm 2.14-2.28 (m, 2H), 2.74-2.77 (m, 1H), 2.29-3.07 (m, 3H), 3.17-3.31 (m, 3H), 3.42-3.45 (m, 1H), 4.44 (d, J=12.2 Hz, 1H), 4.65 (dd, J=15.1, 2.0 Hz, 1H), 4.73 (d, J=12.5 Hz, 1H), 6.62 (dd, J=7.0, 4.9 Hz, 1H), 6.66 (d, J=8.5 Hz, 1H), 7.02 (d, J=7.9 Hz, 1H), 7.09 (td, J=7.4, 1.1 Hz, 1H), 7.28-7.42 (m, 7H), 7.50-7.54 (m, 1H), 8.34-8.35 (m, 2H); MS (DCI/NH$_3$) m/z 371 (M+H)$^+$. Elemental analysis calculated for C$_{24}$H$_{26}$N$_4$.0.3H$_2$O: C, 76.69; H, 7.13; N, 14.90. Found: C, 76.40; H, 6.76; N, 14.54.

Example 17

3-benzyl-6-(4-fluorobenzyl)-1,2,3,4,4a,5,6,7-octahydropyrazino[1,2-a][1,4]benzodiazepine The product of Example 2 (127.2 mg, 0.43 mmol) was dissolved in methanol (5 mL). 4-Fluorobenzaldehyde (85.0 mg, 0.69 mmol) was added, and the reaction mixture was stirred at ambient temperature for 1 hour. Sodium cyanoborohydride (58.1 mg, 0.93 mmol) was then added, and the reaction was stirred at ambient temperature for 20 hours. The reaction was then diluted with 1 M NaOH (25 mL) and extracted with dichloromethane (3×25 mL). The organic layers were combined, concentrated and purified by preparative HPLC using the method described in Example 9 to give the title compound as the tris-trifluoroacetic acid salt: $^1$H NMR (300 MHz, CDCl$_3$) δ ppm 2.73-2.79 (m, 1H), 3.05-3.13 (m, 2H), 3.38-3.42 (m, 2H), 3.65-3.95 (m, 5H), 4.02 (d, J=12.7 Hz, 1H), 4.15 (d, J=5.6 Hz, 1H), 4.19 (d, J=5.9 Hz, 1H), 4.33 (d, J=12.7 Hz, 1H), 4.91 (d, J=13.5 Hz, 1H), 7.93 (d, J=7.9 Hz, 1H), 7.11-7.19 (m, 2H), 7.19-7.29 (m, 2H), 7.43-7.56 (m, 8H); MS (DCI/NH$_3$) m/z 402 (M+H)$^+$. Elemental analysis is calculated for C$_{26}$H$_{28}$FN$_3$.2.65 TFA: C, 53.42; H, 4.39; N, 5.97. Found: C, 53.32; H, 4.60; N, 5.99.

Example 18

(−)-3-benzyl-6-(4-bromobenzyl)-1,2,3,4,4a,5,6,7-octahydropyrazino[1,2-a][1,4]benzodiazepine The free based product of Example 3 (200.3 mg, 0.43 mmol) was separated in to individual enantiomers by SFC purification carried out using a modified Berger Instruments PrepSFC™ system. A manual version of the Berger system was integrated with a Gilson 232 autosampler for sample injection and a Cavro MiniPrep™ pipettor customized for fraction collection at atmospheric pressure (Olson, J.; et al. *JALA* 2002, 7, 69-74). Custom designed collection shoes allowed collection into 18×150 mm tubes and a methanol wash system allows washing of shoes between fractions to maximize recovery and avoid cross-contamination of fractions. The system was controlled using SFC ProNTo™ software (version 1.5.305.15) and an Abbott developed Visual Basic application for autosampler and fraction collector control. The outlet pressure was 100 bar, oven temperature at 35° C., and mobile phase flow rate at 40 mL/minute (Daicel/Chiral Technologies Chiralpak® AD-H column, 5-50% methanol:CO$_2$ 100 bar+0.1% diethylamine). The preparative SFC system was controlled using SFC ProNTo™ software (version 1.5.305.15) and custom software for autosampler and fraction collector control. Fractions were collected based upon UV signal threshold and on-line Thermo MSQ mass spectrometry was used for molecular mass confirmation, using ESI ionization in positive mode. Mass spectra were acquired using a Navigator4.0 software and an Abbott developed Visual Basic interface to communicate with SFC controlling software. The SFC retention time was 15.60 minutes. $[\alpha]^{20}_D = -12°$ (c 0.91, CH$_2$Cl$_2$).

Example 19

(+)-3-benzyl-6-(4-bromobenzyl)-1,2,3,4,4a,5,6,7-octahydropyrazino[1,2-a][1,4]benzodiazepine The enantiomer of the above compound was obtained in the same separation procedure as described in Example 18. The SFC retention time was 16.39 minutes. $[\alpha]^{20}_D = +13°$ (c 0.94, CH$_2$Cl$_2$).

Example 20

(2E)-1-(3-benzyl-1,2,3,4,4a,5-hexahydropyrazino[1,2-a][1,4]benzodiazepin-6(7H)-yl)-3-phenylprop-2-en-1-one The product of Example 2 (98.9 mg, 0.34 mmol) and trans-cinnamoyl chloride (103.9 mg, 0.62 mmol) were processed according to the procedure for Example 4 to give the title compound: $^1$H NMR (500 MHz, benzene-d$_6$) δ ppm (1:1 mixture of rotomers at 25° C.) 2.03-2.15 (m, 1.5H), 2.41-2.51 (m, 1.5H), 2.57-2.65 (m, 1H), 2.71-2.82 (m, 2H), 2.93-2.98 (m, 3H), 4.19 (d, J=11.9 Hz, 0.5H), 4.61 (d, J=13.1 Hz, 0.5H), 4.74-4.79 (m, 1H), 5.10 (d, J=14.3 Hz, 0.5H), 6.57 (d, J=15.6 Hz, 0.5H), 6.70-6.74 (m, 1H), 6.85-6.91 (m, 2H), 6.98-6.99 (m, 0.5H), 7.05-7.35 (m, 9H), 8.12-8.17 (m, 1H); MS (DCI/NH$_3$) m/z 424 (M+H)$^+$. Elemental analysis is calculated for C$_{28}$H$_{29}$N$_3$O.0.3H$_2$O: C, 78.40; H, 6.96; N, 9.80. Found: C, 78.36; H, 6.79; N, 9.65.

Example 21

3-benzyl-6-[4-(trifluoromethyl)benzyl]-1,2,3,4,4a,5,6,7-octahydropyrazino[1,2-a][1,4]benzodiazepine The product of Example 2 (99.8 mg, 0.34 mmol) and 4-(trifluoromethyl)benzaldehyde (96.7 mg, 0.55 mmol) were processed according to the procedure for Example 17 and purified by preparative HPLC using the method described in Example 9 to give the title compound as the tris-trifluoroacetic acid salt: $^1$H NMR (300 MHz, pyridine-d$_5$) δ ppm 2.54 (dt, J=10.8, 3.4 Hz, 1H) 2.62-2.74 (m, 3H), 2.95 (d, J=10.7 Hz, 1H), 3.01 (d, J=11.0 Hz, 1H), 3.32-3.43 (m, 2H), 3.50-3.52 (m, 1H), 3.69-3.84 (m, 5H), 4.16 (d, J=13.1 Hz, 1H), 6.95 (d, J=7.9, 1H), 7.04 (t, J=7.0 Hz, 1H), 7.17 (dd, J=7.3, 1.2 Hz, 1H), 7.32-7.37 (m, 2H), 7.39-7.42 (m, 2H), 7.54-7.53 (m, 2H), 7.60-7.61 (m, 2H), 7.67-7.68 (m, 2H); MS (DCI/NH$_3$) m/z 452 (M+H)$^+$. Elemental analysis is calculated for C$_{27}$H$_{28}$F$_3$N$_3$.3 TFA: C, 49.94; H, 3.94; N, 5.29; F, 28.73. Found: C, 50.11; H, 3.83; N, 5.36; F, 28.52.

Example 22

7-(4-bromobenzyl)-3-methyl-1,2,3,4,4a,5,6,7-octahydropyrazino[1,2-a][1,5]benzodiazepine Example 22A methyl (1,4-dibenzylpiperazin-2-yl)acetate Methyl 4-bromocrotonate (Aldrich, 5.53 mL, 40 mmol) was added dropwise with stirring to an ice-cooled solution of triethylamine (11.15 mL, 80 mmol) and N,N'-dibenzylethylenediamine (Aldrich, 9.67 mL, 40 mmol) in toluene (200 mL). The solution was stirred with ice cooling for 1 hour, then allowed to warm gradually to room temperature and stirred 25 hours longer. The mixture was filtered through a pad of diatomaceous earth with an ethyl acetate (20 mL) rinse. The filtrate was concentrated to an oil, which was mixed with 10% aqueous HCl (240 mL). After 5 minutes, the mixture was filtered and the cake was rinsed with water (2×10 mL). The filtrate was washed with ethyl acetate (2×80 mL) and the aqueous phase was made basic (pH~9-10) by portionwise addition of solid K$_2$CO$_3$ (26 g), then 25% aqueous NaOH (10 mL). The turbid mixture was extracted with ethyl acetate (3×120 mL) and the combined extracts were washed with brine (100 mL), dried (MgSO$_4$) and concentrated under vacuum to leave the title compound as an oil (9.78 g): $^1$H NMR (300 MHz, CDCl$_3$) δ ppm 2.30-2.47 (m, 4H), 2.49-2.73 (m, 4H), 3.06-3.18 (m, 1H), 3.43 (d, J=13.2 Hz, 2H), 3.53 (d, J=13.2 Hz, 1H), 3.60 (s, 3H), 3.76 (d, J=13.6 Hz, 1H), 7.14-7.36 (m, 10H); MS (DCI) m/z 339 (M+H)$^+$.

Example 22B t-butyl 3-(methoxycarbonylmethyl)piperazine-1-carboxylate

The product of example 22A (9.78 g, 28.9 mmol) was combined with 20% Pd(OH)$_2$—C (wet, 1.96 g) in methanol (100 mL) and 12 M aqueous HCl (2.9 mL, 35 mmol). The mixture was stirred under hydrogen (30 psi) at room temperature for 22 hours, then filtered and concentrated under vacuum. The residue was combined with 20% aqueous K$_2$CO$_3$ (40 mL) and ethyl acetate (50 mL), and the mixture stirred with ice-cooling as 2-(tert-butoxycarbonyloxyimino)-2-phenylacetonitrile (Aldrich, 7.12 g, 28.9 mmol) was added gradually over 5 minutes. The mixture was stirred with ice cooling for 1 hour, then it was allowed to warm to room temperature for 2 hours. The mixture was extracted with ethyl acetate (2×100 mL) and the combined ethyl acetate washes were extracted with 10% aqueous HCl (40 mL). The aqueous layer was washed with ethyl acetate (30 mL), then made basic (pH~9) by gradual addition of solid K$_2$CO$_3$ (11.8 g). Ethyl acetate (80 mL) was added, and the mixture was stirred at room temperature for 30 minutes. The aqueous phase was separated, and the organic phase was washed with brine (50 mL), dried (MgSO$_4$) and concentrated under vacuum to leave the title compound: $^1$H NMR (300 MHz, CDCl$_3$) δ ppm 1.46 (s, 9H), 2.31-2.49 (m, 2H), 2.50-2.68 (m, 1H), 2.72-2.81 (m, 1H), 2.82-2.98 (m, 2H), 2.98-3.09 (m, 1H), 3.70 (s, 3H), 3.90 (d, J=9.9 Hz, 2H); MS (DCI) m/z 259 (M+H)$^+$.

Example 22C 2-(4-(t-butoxycarbonyl)-1-(2-nitrophenyl)piperazin-2-yl)acetic acid Solid $K_2CO_3$ (1070 mg, 7.74 mmol) was added to a mixture of 1-fluoro-2-nitrobenzene (655 mg, 4.65 mmol) and the product of Example 22B (1000 mg, 3.87 mmol). Dimethyl sulfoxide (40 mL) was added, and the mixture was heated at 100° C. with stirring under nitrogen. After 22 hours, additional 1-fluoro-2-nitrobenzene (350 mg) was added and heating was continued for 14 hours longer. The mixture was cooled to 40° C., diluted with water (400 mL), and aqueous 10% HCl (25 mL) was added to bring the pH~3-4. The mixture was extracted with $CHCl_3$ (4×200 mL). The combined extract was concentrated under vacuum to a residue that was purified by chromatography ($SiO_2$, eluted with hexanes-ethyl acetate, 100:0-50:50-0:100) to provide the title compound: $^1$H NMR (300 MHz, $CDCl_3$) δ ppm 1.48 (s, 9H), 2.34-2.55 (m, 1H), 2.73-2.90 (m, 1H), 3.20-3.42 (m, 2H), 3.55-3.82 (m, 4H), 3.93-4.12 (m, 1H), 7.13-7.23 (m, 2H), 7.45-7.55 (m, 1H), 7.74 (dd, J=7.9, 1.6 Hz, 1H).

Example 22D tert-butyl 6-oxo-1,2,4a,5,6,7-hexahydropyrazino[1,2-a][1,5]benzodiazepine-3(4H)-carboxylate The product of Example 22C (658 mg, 1.801 mmol) was dissolved in methanol (50 mL) and 10% Pd/C (52 mg) was added. The flask was evacuated and purged with nitrogen (3 cycles) and then with hydrogen (3 cycles), and the reaction was stirred at room temperature under hydrogen (1 atm) for 7 hours. The flask was evacuated and purged with nitrogen (3 cycles), and the reaction mixture was filtered through a pad of diatomaceous earth. The filtrate was concentrated under vacuum, and the residue was dissolved in tetrahydrofuran (25 mL). O-(7-Azabenzotriazol-1-yl)-N,N,N',N'-tetramethyluronium hexafluorophosphate (680 mg, 1.788 mmol) and diisopropylethylamine (1 mL) were added, and the mixture was stirred at room temperature for 14 hours and then concentrated under vacuum. The residue was purified by chromatography ($SiO_2$, eluted with hexanes-ethyl acetate, 100:0-50:50) to provide the title compound: $^1$H NMR (300 MHz, $CDCl_3$) δ ppm 1.48 (s, 9H), 2.18 (d, J=13.5 Hz, 1H), 2.74 (dd, J=13.3, 6.9 Hz, 1H), 2.88-3.30 (m, 5H), 4.01-4.19 (m, 2H), 6.93-6.98 (m, 1H), 7.01-7.10 (m, 2H), 7.16 (s, 1H), 7.17-7.24 (m, 1H); MS (DCI) m/z 318 (M+H)$^+$.

Example 22E 3-methyl-1,2,3,4,4a,5-hexahydropyrazino[1,2-a][1,5]benzodiazepin-6(7H)-one Formalin solution (0.3 mL, 3.92 mmol) was added to a solution of the product of Example 22D (150 mg, 0.473 mmol) in 88% formic acid (4 mL), and the solution was stirred at 100° C. under nitrogen for 30 minutes. The mixture was cooled to room temperature and concentrated under vacuum. The residue was purified by chromatography ($SiO_2$, eluted with $CH_2Cl_2$-methanol-15 M $NH_4OH$, 90:10:1) to provide the title compound: $^1$H NMR (500 MHz, DMSO-$d_6$/$D_2O$) δ ppm 2.05 (d, J=12.8 Hz, 1H), 2.66 (dd, J=13.6, 7.2 Hz, 1H), 2.90 (s, 3H), 3.08-3.19 (m, 2H), 3.32-3.39 (m, 2H), 3.53 (t, J=11.0 Hz, 2H), 3.57-3.67 (m, 1H), 7.00-7.04 (m, 1H), 7.08-7.13 (m, 1H), 7.13-7.18 (m, 1H), 7.18-7.24 (m, 1H); MS (DCI) m/z 232 (M+H)$^+$.

Example 22F 3-methyl-1,2,3,4,4a,5,6,7-octahydropyrazino[1,2-a][1,5]benzodiazepine Solid $LiAlH_4$ (100 mg, 2.63 mmol) was added to a stirred solution of the product of Example 22E (72 mg, 0.311 mmol) in tetrahydrofuran (10 mL) at room temperature. The resulting mixture was heated at reflux under nitrogen for 2 hours, then cooled in ice and quenched by successive addition of ethyl acetate (4 mL), water (0.1 mL), 15% NaOH (0.1 mL) and water (0.3 mL). The mixture was filtered through a pad of diatomaceous earth with an ethyl acetate (25 mL total) rinse. The filtrate was concentrated under vacuum to provide the title compound, sufficiently pure for use in the next step: $^1$H NMR (300 MHz, $CDCl_3$) δ ppm 2.06-2.20 (m, 2H), 2.25-2.42 (m, 2H), 2.37 (s, 3H), 2.62 (d, J=9.5 Hz, 1H), 2.77-2.87 (m, 1H), 3.08 (dt, J=11.6, 3.1 Hz, 1H), 3.18 (ddd, J=12.2, 5.3, 2.8 Hz, 1H), 3.22-3.33 (m, 1H), 3.64-3.75 (m, 2H), 6.53 (dd, J=7.5, 2.0 Hz, 1H), 6.76 (td, J=7.4, 1.8 Hz, 1H), 6.83 (td, J=7.4, 1.8 Hz, 1H), 6.92 (dd, J=7.5, 1.6 Hz, 1H); MS (DCI) m/z 218 (M+H)$^+$.

Example 22G 7-(4-bromobenzyl)-3-methyl-1,2,3,4,4a,5,6,7-octahydropyrazino[1,2-a][1,5]benzodiazepine Sodium triacetoxyborohydride (200 mg, 0.944 mmol) was added to an ice-cooled solution of 4-bromobenzaldehyde (122 mg, 0.659 mmol) and the product of Example 22F (63 mg, 0.290 mmol) in tetrahydrofuran (5 mL). A few drops of 10% HCl (aq) were added, and the mixture was allowed to warm to room temperature. After 5 hours, acetic acid (2 mL) and additional sodium triacetoxyborohydride (200 mg, 0.944 mmol) were added, and the mixture was stirred an additional 15 hours. The reaction mixture was concentrated under vacuum, and the residue was purified by flash chromatography ($SiO_2$, eluted with $CH_2Cl_2$, then $CH_2Cl_2$-methanol-15 M $NH_4OH$, 95:5:0.5-90:10:1) to provide the title compound: $^1$H NMR (300 MHz, $CD_3OD$) δ ppm 1.62 (tt, J=15.3, 5.3, 2.6 Hz, 1H), 1.84-2.00 (m, 1H), 2.33 (t, J=10.9 Hz, 1H), 2.42-2.51 (m, 1H), 2.43 (s, 3H), 2.77 (dt, J=10.7, 2.0 Hz, 1H), 2.85 (ddd, J=11.1, 5.2, 3.6 Hz, 1H), 2.89-3.04 (m, 2H), 3.13 (dt, J=11.9, 2.8 Hz, 1H), 3.30 (s, 1H), 3.45 (td, J=11.3, 2.8 Hz, 1H), 4.22 (d, J=15.1 Hz, 1H), 4.46 (d, J=15.1 Hz, 1H), 6.77-6.96 (m, 4H), 7.27 (d, J=8.3 Hz, 2H), 7.44 (d, J=8.3 Hz, 2H); MS (DCI) m/z 386/388 (M+H)$^+$.

Example 23

3-benzyl-6-(4-bromo-3-fluorobenzyl)-1,2,3,4,4a,5,6,7-octahydropyrazino[1,2-a][1,4]benzodiazepine The product of Example 2 (149.5 mg, 0.51 mmol) and 4-bromo-3-fluorobenzaldehyde (155.2 mg, 0.77 mmol) were processed according to the procedure for Example 17 and purified by preparative HPLC according to the method in Example 9 to give the title compound as the tris-trifluoroacetic acid salt: $^1$H NMR (500 MHz, pyridine-$d_5$) δ ppm 2.52 (dt, J=10.8, 3.4 Hz, 1H) 2.59-2.70 (m, 3H), 2.92 (d, J=10.7 Hz, 1H), 2.99 (d, J=11.0 Hz, 1H), 3.31-3.41 (m, 2H), 3.45-3.47 (m, 1H), 3.56-3.64 (m, 2H), 3.74-3.80 (m, 3H), 4.11 (d, J=13.1 Hz, 1H), 6.94-6.95 (m, 1H), 7.03 (t, J=7.3 Hz, 1H), 7.13 (d, J=8.2 Hz, 1H), 7.16 (d, J=7.0 Hz, 1H), 7.32-7.36 (m, 3H), 7.39-7.42 (m, 2H), 7.54-7.55 (m, 2H), 7.57-7.58 (m, 1H); MS (DCI/$NH_3$) m/z 480 (M+H)$^+$. Elemental analysis is calculated for $C_{26}H_{27}BrFN_3 \cdot 3$ TFA: C, 46.73; H, 3.68; N, 5.11. Found: C, 47.07; H, 3.81; N, 5.23.

Example 24

3-benzyl-6-(3,5-difluorobenzyl)-1,2,3,4,4a,5,6,7-octahydropyrazino[1,2-a][1,4]benzodiazepine The product of Example 2 (99.6 mg, 0.34 mmol) and 3,5-difluorobenzaldehyde (91.7 mg, 0.65 mmol) were processed according to the procedure for Example 17 and purified by preparative HPLC using the method described in Example 9 to give the title compound as the tris-trifluoroacetic acid salt: $^1$H NMR (300 MHz, benzene-$d_6$) δ ppm 1.71-1.74 (m, 1H), 2.13-2.23 (m, 2H), 2.35 (d, J=12.8 Hz, 1H) 2.86-2.89 (m, 2H), 2.95-3.04 (m, 2H), 3.15-3.23 (m, 2H), 3.30-3.52 (m, 3H), 3.65 (d, J=12.8 Hz, 1H), 4.44 (d, J=13.1 Hz, 1H), 6.33-6.39 (m, 2H), 6.53 (dd, J=7.3, 0.9 Hz, 1H), 6.64-6.65 (m, 2H), 6.73 (td, J=7.5, 0.9 Hz, 1H), 7.02-7.07 (m, 2H), 7.14-7.18 (m, 2H), 7.33-7.34 (m, 2H); MS (DCI/NH$_3$) m/z 420 (M+H)$^+$. Elemental analysis is calculated for $C_{26}H_{27}F_2N_3 \cdot 3.45$ TFA: C, 48.61; H, 3.78; N, 5.17. Found: C, 48.65; H, 3.75; N, 5.28.

Example 25

3-benzyl-6-(3,4-difluorobenzyl)-1,2,3,4,4a,5,6,7-octahydropyrazino[1,2-a][1,4]benzodiazepine The product of Example 2 (102.4 mg, 0.35 mmol) and 3,4-difluorobenzaldehyde (121.3 mg, 0.85 mmol) were processed according to the procedure for Example 17 and purified by preparative HPLC using the method described in Example 4 to give the title compound: $^1$H NMR (500 MHz, benzene-$d_6$) δ ppm 2.17 (td, J=10.2, 3.7 Hz, 1H), 2.26 (d, J=9.9 Hz, 1H), 2.31-2.40 (m, 2H), 2.50-2.52 (m, 1H) 2.59-2.64 (m, 2H), 3.05-3.19 (m, 5H), 3.35-3.41 (m, 2H), 3.54 (d, J=13.1 Hz, 1H), 3.97 (d, J=12.8 Hz, 1H), 6.69-6.72 (m, 2H), 6.75 (d, J=7.9 Hz, 1H), 7.03-7.07 (m, 1H), 7.11-7.19 (m, 2H), 7.23 (t, J=7.6 Hz, 1H), 7.37 (d, J=7.3 Hz, 2H); MS (DCI/NH$_3$) m/z 420 (M+H)$^+$. Elemental analysis is calculated for $C_{26}H_{27}F_2N_3$: C, 74.44; H, 6.49; N, 10.02. Found: C, 74.65; H, 6.12; N, 9.99.

Example 26

3-benzyl-1,2,3,4,4a,5,6,7-octahydropyrazino[1,2-a][1,5]benzodiazepine

Example 26A methyl 4-benzylpiperazinyl-2-acetate

A solution of trityl chloride (37.6 g, 132 mmol) in CH$_2$Cl$_2$ (188 mL) was added dropwise over 1 hour to an ice-cooled solution of N-benzylethane-1,2-diamine (20.0 g, 133 mmol) and triethylamine (19.6 mL, 140 mmol) in acetonitrile (25 mL). The mixture was allowed to warm to room temperature over 1 hour and the precipitated solids were removed by filtration and washed with CH$_2$Cl$_2$ (25 mL). The combined filtrate was concentrated under vacuum. The residue (64.11 g) was combined with acetonitrile (320 mL) and stirred vigorously as solid K$_2$CO$_3$ (36.8 g, 266 mmol) and KI (0.78 g, 4.70 mmol) were added. Finally, (E)-methyl 4-bromocrotanoate (Aldrich, 28.0 g, 133 mmol) was added, followed by an acetonitrile (10 mL) rinse, and the suspension was stirred at room temperature for 13 hours. The mixture was filtered, and the cake rinsed with CH$_3$CN (60 mL) and then with CH$_2$Cl$_2$ (100 mL). The filtrate was concentrated under vacuum at a bath temperature of 55° C. to leave a light amber semisolid (72.4 g). This material was dissolved in methanol (100 mL) and a solution of HCl in dioxane (4 M, 40 mL) was added. The resulting solution was heated at reflux for 90 minutes, then cooled to room temperature and concentrated under vacuum. The residue was diluted with water (250 mL) and made acidic (pH~3) by the addition of 10% HCl (10 mL). The mixture was washed with ethyl acetate (2×120 mL), and the aqueous phase was made basic (pH~9) by cautious addition of solid K$_2$CO$_3$ (22 g), followed by 25% aqueous NaOH (10 mL). The mixture was extracted with CHCl$_3$ (3×110 mL) and the combined organic phase was washed with saturated brine, dried over Na$_2$SO$_4$ and concentrated under vacuum to leave the title compound of sufficient purity for use in the next reaction: $^1$H NMR (300 MHz, CDCl$_3$) δ ppm 1.85 (dd, J=11.1, 9.9 Hz, 1H), 2.11 (ddd, J=11.5, 9.1, 4.8 Hz, 1H), 2.32-2.45 (m, 2H), 2.69-2.77 (m, 2H), 2.86-2.99 (m, 2H), 3.14-3.26 (m, 1H), 3.49 (s, 2H), 3.67 (s, 3H), 7.23-7.35 (m, 5H); MS (DCI) m/z 249 (M+H)$^+$.

Example 26B 2-(4-benzyl-1-(2-nitrophenyl)piperazin-2-yl)acetic acid

The product of Example 26A (5.0 g, 20.14 mmol), K$_2$CO$_3$ (10.02 g, 72.5 mmol), 1-fluoro-2-nitrobenzene (2.84 g, 20.14 mmol) and 18-crown-6 (0.25 g, 0.946 mmol) were combined with acetonitrile (72 mL) and water (18 mL), and the mixture was heated at 100° C. under nitrogen for 29 hours. The reaction mixture was cooled to room temperature and concentrated under vacuum. The aqueous residue was diluted with water (150 mL) and washed with CH$_2$Cl$_2$ (100 mL). The aqueous phase was made acidic (pH~4) by cautious addition of 10% aqueous HCl (approximately 40 mL), then extracted with CH$_2$Cl$_2$ (3×100 mL). The combined organic phases were dried (MgSO$_4$) and concentrated to provide the title compound of sufficient purity for the next step: $^1$H NMR (300 MHz, CD$_3$OD) δ ppm 2.29 (d, J=5.6 Hz, 2H), 2.90-3.31 (m, 3H), 3.36-3.44 (m, 1H), 3.50-3.62 (m, J=13.9, 1.2 Hz, 1H), 3.79-3.90 (m, 1H), 4.20-4.36 (m, 2H), 7.41 (t, J=7.7 Hz, 1H), 7.45-7.58 (m, 6H), 7.64 (td, J=7.7, 1.6 Hz, 1H), 7.73 (dd, J=7.9, 1.6 Hz, 1H); MS (DCI) m/z 365 (M+H)$^+$.

Example 26C 3-benzyl-1,2,3,4,4a,5-hexahydropyrazino[1,2-a][1,5]benzodiazepin-6(7H)-one Platinum on carbon (5%, 30 mg) was added to a solution of the product of Example 26B (0.67 g, 1.88 mmol) in methanol (100 mL). The reaction flask was evacuated and purged with nitrogen (5 cycles) and then with hydrogen (5 cycles), and the suspension was stirred under hydrogen (1 atm) for 18 hours. The reaction flask was evacuated and purged with nitrogen (5 cycles), and the mixture was filtered through diatomaceous earth with ethyl acetate (50 mL) and methanol (50 mL) rinses. The filtrate was concentrated under vacuum and the residue was dissolved in N,N-dimethylformamide (8 mL). O-(7-Azabenzotriazol-1-yl)-N,N,N',N'-tetramethyluronium hexafluorophosphate (720 mg, 1.89 mmol) and diisopropylethylamine (0.395 mL, 2.262 mmol) were added, and the solution was stirred at room temperature for 3 hours. The mixture was diluted with water (50 mL) and extracted with ethyl acetate (2×50 mL). The combined extracts were washed successively with 1 N NaOH (50 mL) and brine (40 mL), and then concentrated under vacuum. The residue was purified by flash chromatography (SiO$_2$ eluted with CH$_2$Cl$_2$-CH$_3$OH, 100:0-95:5) to provide the title compound: $^1$H NMR (300 MHz, CD$_3$OD) δ ppm 1.98 (dd, J=13.4, 1.2 Hz, 1H), 2.27 (dt, J=11.4, 3.1 Hz, 1H), 2.40 (t, J=10.9 Hz, 1H), 2.67 (dd, J=13.2, 7.5 Hz, 1H), 2.82-2.89 (m, 1H), 2.89-2.97 (m, 1H), 3.01-3.09 (m, 1H), 3.22 (dd, J=11.5, 2.7 Hz, 1H), 3.35-3.44 (m, 1H), 3.61 (s, 2H), 6.98 (dd, J=8.1, 1.7 Hz, 1H), 7.03 (td, J=7.3, 1.7 Hz, 1H), 7.10-7.22 (m, 2H), 7.25-7.39 (m, 5H); MS (DCI) m/z 308 (M+H)$^+$.

Example 26D 3-benzyl-1,2,3,4,4a,5,6,7-octahydropyrazino[1,2-a][1,5]benzodiazepine Solid LiAlH$_4$ (180 mg, 4.74 mmol) was added at room temperature to a stirring solution of the product of Example 26C (280 mg, 0.911 mmol) in tetrahydrofuran (10 mL). The resulting mixture was stirred at room temperature under nitrogen for 12 hours, then heated at 60° C. for 1 hour. The reaction mixture was cooled in ice and quenched by successive addition of ethyl acetate (4 mL), water (0.18 mL), 15% NaOH (0.18 mL) and water (0.54 mL). The mixture was filtered through diatomaceous earth with an ethyl acetate (25 mL) rinse. The filtrate was concentrated and the residue was purified by preparative HPLC (30×100 mm, C18, Waters XBridge™ column eluted with 0.1 M (NH$_4$)$_2$CO$_{3(aq)}$-methanol (95:5-10:90) over 18 minutes) to provide the title compound: $^1$H NMR (400 MHz, CD$_3$OD) δ ppm 1.53-1.63 (m, 1H), 1.94-2.06 (tddd, J=12.0, 12.0, 6.1, 3.2, 3.1 Hz, 1H), 2.29 (t, J=10.4 Hz, 1H), 2.37 (td, J=10.8, 3.1 Hz, 1H), 2.63 (dd, J=10.5, 2.6, 2.2 Hz, 1H), 2.85 (dq, J=11.0, 2.7 Hz, 1H), 2.90-3.01 (m, 2H), 3.09 (ddd, J=12.2, 5.2, 2.7 Hz, 1H), 3.21 (td, J=11.1, 2.9 Hz, 1H), 3.53 (td, J=12.1, 1.5 Hz, 1H), 3.58 (s, 2H), 6.62 (dd, J=7.6, 1.5 Hz, 1H), 6.73 (td, J=7.6, 1.7 Hz, 1H), 6.80 (td, J=7.6, 1.7 Hz, 1H), 6.89 (dd, J=7.9, 1.5 Hz, 1H), 7.23-7.29 (m, 1H), 7.29-7.39 (m, 4H); MS (ESI) m/z 294 (M+H)$^+$.

Example 27

1-(3-benzyl-2,3,4,4a,5,6-hexahydropyrazino[1,2-a][1,5]benzodiazepin-7(1H)-yl)-2-(4-chlorophenyl)ethanone To a solution of the product of Example 26 (40 mg, 0.136 mmol) in CH$_2$Cl$_2$ (4 mL) was added 2-(4-chlorophenyl)acetyl chloride (118 mg, 0.624 mmol), and the solution was stirred at room temperature for 2 hours and then concentrated under vacuum. The residue was crystallized from ethanol (4 mL) and water (0.2 mL) to provide the title compound: $^1$H NMR (400 MHz, pyridine-d$_5$) δ ppm 1.33-1.39 (m, 1H), 1.44-1.63 (m, 1H), 2.17 (t, J=11.9 Hz, 1H), 2.24-2.43 (m, 1H), 2.64-2.79 (m, 2H), 2.82-2.90 (m, 1H), 2.92-3.03 (m, 1H), 3.07-3.30 (m, 2H), 3.34-3.58 (m, 2H), 3.56-3.73 (m, 2H), 4.32-4.56 (m, 1H), 6.86-7.20 (m, 5H), 7.23-7.52 (m, 8H); MS (DCI) m/z 446/448 (M+H)$^+$. Elemental analysis is calculated for C$_{27}$H$_{28}$N$_3$OCl HCl 0.24 EtOH 0.3H$_2$O: C, 66.17; H, 6.26; N, 8.43. Found: C, 66.03; H, 6.22; N, 8.38.

Example 28

3-benzyl-6-(pyridin-3-ylmethyl)-1,2,3,4,4a,5,6,7-octahydropyrazino[1,2-a][1,4]benzodiazepine The product of Example 2 (106.8 mg, 0.36 mmol) and 3-pyridinecarboxaldehyde (66.1 mg, 0.62 mmol) were processed according to the procedure for Example 17 and purified by preparative HPLC using the method described in Example 4 to give the title compound: $^1$H NMR (500 MHz, pyridine-d$_5$) δ ppm 2.32 (dt, J=10.2, 3.7 Hz, 1H), 2.37 (t, J=10.1 Hz, 1H), 2.57 (dd, J=13.4, 3.4 Hz, 1H), 2.68-2.72 (m, 2H), 2.76-2.78 (m, 2H), 3.23-3.34 (m, 3H), 3.50-3.62 (m, 4H), 3.77 (d, J=13.1 Hz, 1H), 4.05 (d, J=13.1 Hz, 1H), 6.95-7.01 (m, 2H), 7.11 (d, J=6.1 Hz, 1H), 7.26 (dd, J=7.6, 4.6 Hz, 1H), 7.32-7.34 (m, 2H), 7.39-7.42 (m, 2H), 7.74-7.76 (m, 1H), 8.69 (dd, J=4.7, 1.4 Hz, 1H), 8.85 (d, J=1.8 Hz, 1H); MS (DCI/NH$_3$) m/z 385 (M+H)$^+$. Elemental analysis is calculated for C$_{25}$H$_{28}$N$_4$.0.25H$_2$O: C, 77.19; H, 7.38; N, 14.40. Found: C, 77.24; H, 7.30; N, 14.34.

Example 29

3-benzyl-6-(pyridin-2-ylmethyl)-1,2,3,4,4a,5,6,7-octahydropyrazino[1,2-a][1,4]benzodiazepine The product of Example 2 (120.9 mg, 0.41 mmol) and 2-pyridinecarboxaldehyde (75.8 mg, 0.71 mmol) were processed according to the procedure for Example 17 and purified by preparative HPLC using the method described in Example 9 to give the title compound as the tetra-trifluoroacetic acid salt: $^1$H NMR (400 MHz, pyridine-d$_5$) δ ppm 2.46-2.53 (m, 1H) 2.69 (t, J=10.5 Hz, 1H), 2.88-3.03 (m, 4H), 3.28-3.40 (m, 2H), 3.57-3.59 (m, 1H), 3.73-3.81 (m, 2H), 4.09-4.15 (m, 2H), 4.37 (d, J=12.8 Hz, 1H), 6.91-6.93 (m, 1H), 6.98-7.02 (m, 1H), 7.16-7.18 (m, 1H), 7.27 (dd, J=7.6, 1.5 Hz, 1H), 7.31-7.35 (m, 2H), 7.38-7.42 (m, 2H), 7.53-7.54 (m, 2H), 7.62-7.68 (m, 2H), 8.65-8.67 (m, 1H); MS (DCI/NH$_3$) m/z 385 (M+H)$^+$. Elemental analysis is calculated for C$_{25}$H$_{28}$N$_4$.4 TFA: C, 47.15; H, 3.84; N, 6.67. Found: C, 47.44; H, 4.01; N, 6.80.

Example 30

3-benzyl-6-(pyridin-4-ylmethyl)-1,2,3,4,4a,5,6,7-octahydropyrazino[1,2-a][1,4]benzodiazepine The product of Example 2 (122.4 mg, 0.42 mmol) and 4-pyridinecarboxaldehyde (80.3 mg, 0.75 mmol) were processed according to the procedure for Example 17 and purified by preparative HPLC using the method described in Example 4 to give the title compound: $^1$H NMR (500 MHz, pyridine-d$_5$) δ ppm 2.34 (dt, J=10.2, 3.8 Hz, 1H), 2.41 (t, J=9.9 Hz, 1H), 2.34 (dd, J=13.4, 3.1 Hz, 1H), 2.68-2.72 (m, 2H), 2.78-2.80 (m, 1H), 3.25-3.34 (m, 3H), 3.53-3.61 (m, 4H), 3.75 (d, J=12.8 Hz, 1H), 4.06 (d, J=13.1 Hz, 1H), 6.97-7.03 (m, 2H), 7.12 (dd, J=7.3, 1.5 Hz, 1H), 7.31-7.43 (m, 6H), 7.49-7.50 (m, 2H), 8.74-8.75 (m, 2H); MS (DCI/NH$_3$) m/z 385 (M+H)$^+$.

Example 31

(3-benzyl-1,2,3,4,4a,5-hexahydropyrazino[1,2-a][1,4]benzodiazepin-6(7H)-yl)(4-bromophenyl)methanone The product of Example 2 (109.9 mg, 0.37 mmol) and 4-bromobenzoyl chloride (152.3 mg, 0.69 mmol) were processed according to the procedure for Example 4 to give the title compound: $^1$H NMR (500 MHz, benzene-d$_6$) δ ppm (7:3 mixture of rotamers at 25° C.) 1.98-2.06 (m, 2.1H), 2.16-2.20 (m, 0.3H), 2.38-2.39 (m, 1H), 2.56-2.58 (m, 1H), 2.71-2.73 (m, 1H), 2.82-2.92 (m, 3.3H), 3.10-3.12 (m, 0.7H), 3.29-3.32 (m, 1H), 3.50 (d, J=12.8 Hz, 0.3H), 3.94 (d, J=12.5 Hz, 0.3H), 4.40 (d, J=13.4 Hz, 0.3H), 4.56 (d, J=12.5 Hz, 0.3H), 4.79 (d, J=14.0 Hz, 0.7H), 5.02 (d, J=14.0 Hz, 0.7H), 6.56-6.57 (m, 0.3H), 6.65-6.70 (m, 1H), 3.74-6.77 (m, 0.3H), 6.85-6.89 (m, 2.1H), 7.05-7.21 (m, 8.6H), 7.31-7.36 (m, 0.7H); MS (DCI/NH$_3$) m/z 476 (M+H)$^+$. Elemental analysis is calculated for C$_{26}$H$_{26}$BrN$_3$O.0.15H$_2$O: C, 65.18; H, 5.53; N, 8.77. Found: C, 64.91; H, 5.22; N, 8.62.

Example 32

3-benzyl-6-[(6-methylpyridin-3-yl)methyl]-1,2,3,4,4a,5,6,7-octahydropyrazino[1,2-a][1,4]benzodiazepine The product of Example 2 (102.9 mg, 0.35 mmol) and 5-formyl-2-picoline (68.4 mg, 0.57 mmol) were processed according to the procedure for Example 17 and purified by preparative HPLC using the method described in Example 4 to give the title compound: $^1$H NMR (500 MHz, pyridine-d$_5$) δ ppm 2.32 (dt, J=10.2, 3.7 Hz, 1H), 2.37 (t, J=10.1 Hz, 1H), 2.53-2.58 (m, 4H), 2.68-2.73 (m, 2H), 2.76-2.79 (m, 2H), 3.26-3.35 (m, 3H), 3.50-3.59 (m, 4H), 3.80 (d, J=13.1 Hz, 1H), 4.06 (d, J=13.1 Hz, 1H), 6.96-7.01 (m, 2H), 7.11-7.13 (m, 2H), 7.30-7.34 (m, 2H), 7.39-7.42 (m, 2H), 7.48-7.49 (m, 2H), 7.65 (dd, J=7.6, 2.1 Hz, 1H), 8.71 (d, J=1.8 Hz, 1H); MS (DCI/NH$_3$) m/z 399 (M+H)$^+$. Elemental analysis is calculated for C$_{26}$H$_{30}$N$_4$: C, 78.35; H, 7.59; N, 14.06. Found: C, 78.02; H, 7.35; N, 14.05.

Example 33

3-benzyl-6-(quinolin-3-ylmethyl)-1,2,3,4,4a,5,6,7-octahydropyrazino[1,2-a][1,4]benzodiazepine The product of Example 2 (99.7 mg, 0.34 mmol) and quinoline-3-carboxaldehyde (84.6 mg, 0.54 mmol) were processed according to the procedure for Example 17 and purified by preparative HPLC using the method described in Example 9 to give the title compound as the tris-trifluoroacetic acid salt: $^1$H NMR (500 MHz, pyridine-d$_5$) δ ppm 2.54 (dt, J=10.8, 3.1 Hz, 1H), 2.66-2.79 (m, 2H), 2.75-2.79 (m, 1H), 2.96 (d, J=10.7 Hz, 1H), 3.02 (d, J=10.7 Hz, 1H), 3.31-3.34 (m, 1H), 3.39-3.43 (m, 1H), 3.52-3.54 (m, 1H), 3.77-3.91 (m, 5H), 4.22 (d, J=13.1 Hz, 1H), 6.95 (d, J=7.9 Hz, 1H), 7.03 (t, J=7.3 Hz, 1H), 7.19-7.20 (m, 1H), 7.32-7.40 (m, 4H), 7.53-7.57 (m, 3H), 7.71-7.74 (m, 1H), 7.91 (d, J=7.9 Hz, 1H), 8.24 (d, J=1.5 Hz, 1H), 8.36 (d, J=8.6 Hz, 1H), 9.23 (d, J=2.1 Hz, 1H); MS (DCI/NH$_3$) m/z 435 (M+H)$^+$. Elemental analysis is calculated for C$_{29}$H$_{30}$N$_4$.3.2 TFA.1.25H$_2$O: C, 51.73; H, 4.38; N, 6.82. Found: C, 51.78; H, 4.48; N, 6.84.

Example 34

3-benzyl-6-[(6-chloropyridin-3-yl)methyl]-1,2,3,4,4a,5,6,7-octahydropyrazino[1,2-a][1,4]benzodiazepine The product of Example 2 (113.4 mg, 0.39 mmol) and 6-chloronicotinaldehyde (81.7 mg, 0.58 mmol) were processed according to the procedure for Example 17 and purified by preparative HPLC using the method described in Example 9 to give the title compound as the tris-trifluoroacetic acid salt: $^1$H NMR (500 MHz, pyridine-d$_5$) δ ppm 2.84 (dt, J=10.5, 3.8 Hz, 1H), 2.91-2.95 (m, 2H), 3.02-3.06 (m, 1H), 3.22 (d, J=10.4 Hz, 1H), 3.30 (d, J=11.0 Hz, 1H), 3.67-3.80 (m, 3H), 3.90-3.98 (m, 2H), 4.05-4.13 (m, 3H), 4.44 (d, J=13.1 Hz, 1H), 7.32 (d, J=7.9 Hz, 1H), 7.39 (t, J=7.3 Hz, 1H), 7.51 (dd, J=7.3, 1.5 Hz, 1H), 7.68-7.79 (m, 5H), 7.89-7.90 (m, 2H), 8.11 (dd, J=8.1, 2.3 Hz, 1H), 8.89 (d, J=2.4 Hz, 1H); MS (DCI/NH$_3$) m/z 419 (M+H)$^+$. Elemental analysis is calculated for C$_{25}$H$_{27}$ClN$_4$.3 TFA: C, 48.92; H, 3.97; N, 7.36. Found: C, 49.03; H, 4.13; N, 7.40.

Example 35

3-benzyl-6-{[6-(trifluoromethyl)pyridin-3-yl]methyl}-1,2,3,4,4a,5,6,7-octahydropyrazino[1,2-a][1,4]benzodiazepine The product of Example 2 (117.0 mg, 0.40 mmol) and 6-(trifluoromethyl)pyridine-3-carboxaldehyde (102.9 mg, 0.59 mmol) were processed according to the procedure for Example 17 and purified by preparative HPLC using the method described in Example 4 to give the title compound: $^1$H NMR (500 MHz, pyridine-d$_5$) δ ppm 2.31-3.40 (m, 2H) 2.58 (dd, J=13.2, 3.2 Hz, 1H), 2.68-2.71 (m, 2H), 2.77-2.79 (m, 1H), 3.25-3.34 (m, 3H), 3.52-3.58 (m, 2H), 3.61-3.69 (m, 2H), 3.76 (d, J=13.1 Hz, 1H), 4.05 (d, J=13.1 Hz, 1H), 6.97-7.03 (m, 2H), 7.13 (dd, J=7.3, 1.2 Hz, 1H), 7.33-7.37 (m, 2H), 7.39-7.42 (m, 2H), 7.48-7.50 (m, 2H), 7.72 (d, J=7.6, Hz, 1H), 7.95 (d, J=7.6, Hz, 1H), 8.87 (s, 1H); MS (DCI/NH$_3$) m/z 453 (M+H)$^+$. Elemental analysis is calculated for C$_{26}$H$_{27}$F$_3$N$_4$.0.6H$_2$O: C, 67.40; H, 6.13; N, 12.09. Found: C, 67.30; H, 6.04; N, 12.12.

Example 36

3-benzyl-6-(quinolin-4-ylmethyl)-1,2,3,4,4a,5,6,7-octahydropyrazino[1,2-a][1,4]benzodiazepine The product of Example 2 (155.3 mg, 0.53 mmol) and quinoline-4-carboxaldehyde (132.9 mg, 0.85 mmol) were processed according to the procedure for Example 17 and purified by preparative HPLC using the method described in Example 4 to give the title compound: $^1$H NMR (500 MHz, pyridine-d$_5$) δ ppm 2.33 (dt, J=10.2, 3.7 Hz, 1H), 2.40 (t, J=10.1 Hz, 1H), 2.67-2.71 (m, 2H), 2.76-2.80 (m, 2H), 3.26-3.33 (m, 2H), 3.37-3.40 (m, 1H), 3.50-3.57 (m, 2H), 3.85 (d, J=13.1 Hz, 1H), 4.00-4.10 (m, 2H), 4.13 (d, J=12.8 Hz, 1H), 6.98-7.04 (m, 2H), 7.17 (dd, J=7.0, 1.2 Hz, 1H), 7.32-7.42 (m, 4H), 7.48-7.49 (m, 2H), 7.56-7.61 (m, 2H), 7.73-7.76 (m, 1H), 8.36-8.41 (m, 2H), 9.05 (d, J=4.3 Hz, 1H); MS (DCI/NH$_3$) m/z 435 (M+H)$^+$. Elemental analysis is calculated for C$_{29}$H$_{30}$N$_4$.0.35H$_2$O: C, 79.00; H, 7.02; N, 12.71. Found: C, 79.07; H, 7.01; N, 12.66.

Example 37

3-benzyl-6-(isoquinolin-4-ylmethyl)-1,2,3,4,4a,5,6,7-octahydropyrazino[1,2-a][1,4]benzodiazepine The product of Example 2 (152.2 mg, 0.52 mmol) and isoquinoline-4-carboxaldehyde (101.8 mg, 0.65 mmol) were processed according to the procedure for Example 17 and purified by preparative HPLC using the method described in Example 9 to give the title compound as the tris-trifluoroacetic acid salt: $^1$H NMR (500 MHz, pyridine-d$_5$) δ ppm 2.47-2.52 (m, 1H), 2.58-2.62 (m, 1H), 2.65-2.74 (m, 2H), 2.87-2.89 (m, 1H), 3.00-3.02 (m, 1H), 3.29-3.32 (m, 1H), 3.36-3.41 (m, 1H), 3.47-3.48 (m, 1H), 3.72-3.77 (m, 2H), 3.85 (d, J=13.1 Hz, 1H), 3.95-4.02 (m, 2H), 4.14 (d, J=13.1 Hz, 1H), 6.92-7.04 (m, 2H), 7.19-7.20 (m, 1H), 7.33-7.34 (m, 2H), 7.39-7.42 (m, 2H), 7.51-7.53 (m, 2H), 7.63 (t, J=7.5 Hz, 1H), 7.76 (t, J=7.5 Hz, 1H), 8.05 (d, J=8.2 Hz, 1H), 8.43 (d, J=8.2

Hz, 1H), 8.75 (s, 1H), 9.45 (s, 1H); MS (DCI/NH$_3$) m/z 435 (M+H)$^+$. Elemental analysis is calculated for C$_{29}$H$_{30}$N$_4$.3TFA.0.2H$_2$O: C, 53.88; H, 4.31; N, 7.18. Found: C, 54.23; H, 4.70; N, 7.39.

Example 38

3-(4-fluorobenzyl)-2,3,4,4a,6,7-hexahydropyrazino[1,2-a][1,4]benzodiazepin-5(1H)-one 2,3,4,4a,6,7-Hexahydropyrazino[1,2-a][1,4]benzodiazepin-5(1H)-one (680.0 mg, 3.13 mmol, Example 2A) was dissolve in methanol (15 mL). 4-Fluorobenzaldehyde (653.5 mg, 5.27 mmol) was added to the reaction and stirred at ambient temperature for 1 hour. Sodium cyanoborohydride (565.3 mg, 9.00 mmol) was then added, and the reaction was stirred at ambient temperature for 17 hours. The reaction was then diluted with 1 M NaOH (50 mL) and extract with dichloromethane (3×50 mL). The organic layers were combined, and purified by silica gel chromatography (ethyl acetate, R$_f$ 0.40) to give the title compound: $^1$H NMR (400 MHz, benzene-d$_6$) δ ppm 1.93 (td, J=11.0, 2.8 Hz, 1H), 2.42 (t, J=10.6 Hz, 1H), 2.49-2.51 (m, 1H), 2.60 (dt, J=11.0, 2.6 Hz, 1H), 2.85 (td, J=11.2, 2.9 Hz, 1H), 3.02-3.10 (m, 2H), 3.30 (d, J=13.2 Hz, 1H), 3.50 (dt, J=10.7, 2.3 Hz, 1H), 3.75 (dd, J=10.4, 2.8 Hz, 1H), 4.51 (dd, J=13.6, 4.0 Hz, 1H), 6.72-6.73 (d, J=8.1 Hz, 1H), 6.75 (dd, J=7.3, 1.5 Hz, 1H), 6.81-6.84 (m, 3H), 7.02-7.09 (m, 3H); MS (DCI/NH$_3$) m/z 326 (M+H)$^+$.

Example 39

3-benzyl-6-[(6-bromopyridin-3-yl)methyl]-1,2,3,4,4a,5,6,7-octahydropyrazino[1,2-a][1,4]benzodiazepine The product of Example 2 (166.8 mg, 0.57 mmol) and 6-bromonicotinaldehyde (154.9 mg, 0.83 mmol) were processed according to the procedure for Example 17 and purified by preparative HPLC using the method described in Example 9 to give the title compound as the tris-trifluoroacetic acid salt: $^1$H NMR (500 MHz, pyridine-d$_5$) δ ppm 2.46 (td, J=10.4, 4.0 Hz, 1H), 2.50-2.58 (m, 2H), 2.64-2.68 (m, 1H), 2.83-2.85 (m, 1H), 2.91-2.93 (m, 1H), 3.30-3.35 (m, 2H), 3.40-3.42 (m, 1H), 3.50-3.58 (m, 2H), 3.67-3.70 (m, 2H), 3.74 (d, J=13.1 Hz, 1H), 4.07 (d, J=13.1 Hz, 1H), 6.95 (d, J=7.9 Hz, 1H), 7.02 (td, J=7.3, 0.9 Hz, 1H), 7.13 (dd, J=7.3, 1.5 Hz, 1H), 7.32-7.35 (m, 2H), 7.39-7.42 (m, 2H), 7.51-7.53 (m, 3H), 7.64 (dd, J=8.2, 2.4 Hz, 1H), 8.50 (d, J=2.1 Hz, 1H); MS (DCI/NH$_3$) m/z 463 (M+H)$^+$. Elemental analysis is calculated for C$_{25}$H$_{27}$BrN$_4$.2.5 TFA: C, 48.14; H, 3.97; N, 7.49. Found: C, 48.02; H, 4.08; N, 7.54.

Example 40

3-(4-fluorobenzyl)-1,2,3,4,4a,5,6,7-octahydropyrazino[1,2-a][1,4]benzodiazepine

The product of Example 38 was dissolve in tetrahydrofuran (13 mL). The reaction was chilled to 0° C. with an ice bath and LiAlH$_4$ (148.3, 3.91 mmol) was added. The reaction was allowed to warm to ambient temperature, then heated to reflux for 16 hours. The reaction mixture was then treated with the dropwise addition of water (150 μL), 15% NaOH(aq) (150 μL) and water (450 μL). The resulting precipitate was filtered off. The filtrate was concentrated to give the title compound: $^1$H NMR (400 MHz, benzene-d$_6$) δ ppm 2.05 (td, J=10.7, 3.1 Hz, 1H), 2.28 (t, J=10.2 Hz, 1H), 2.39-2.41 (m, 1H), 2.46-2.53 (m, 2H), 2.71-2.73 (m, 1H), 2.77-2.80 (m, 1H), 2.91 (dt, J=11.0, 3.1 Hz, 1H), 3.02-3.05 (m, 1H), 3.20-3.30 (m, 2H), 3.89 (d, J=12.8 Hz, 1H), 4.23 (d, J=12.5 Hz, 1H), 6.64 (d, J=7.6 Hz, 1H), 6.84-6.89 (m, 3H), 7.07-7.13 (m, 4H); MS (DCI/NH$_3$) m/z 312 (M+H)$^+$.

Example 41

(3-benzyl-2,3,4,4a,5,6-hexahydropyrazino[1,2-a][1,5]benzodiazepin-7(1H)-yl)(4-bromophenyl)methanone 4-Bromobenzoyl chloride (80 mg, 0.365 mmol) was added to a solution of the product of Example 26 (80 mg, 0.273 mmol) in CH$_2$Cl$_2$ (4 mL) at room temperature, and the mixture was stirred for 1 hour and then concentrated under vacuum. The residue was crystallized from ethanol (4 mL) to provide the title compound: $^1$H NMR (500 MHz, pyridine-d$_5$) δ ppm 1.52 (d, J=16.2 Hz, 1H), 1.66-1.77 (m, 1H), 2.55 (t, J=10.4 Hz, 1H), 2.62 (t, J=10.4 Hz, 1H), 2.93 (d, J=10.4 Hz, 1H), 3.11 (d, J=9.2 Hz, 1H), 3.16 (d, J=11.0 Hz, 1H), 3.50 (t, J=10.5 Hz, 1H), 3.58 (d, J=13.4 Hz, 1H), 3.62-3.75 (m, J=7.0 Hz, 1H), 3.79 (s, 2H), 4.30 (t, J=13.1 Hz, 1H), 6.71-6.79 (m, 2H), 7.01 (d, J=7.6 Hz, 1H), 7.13-7.20 (m, 1H), 7.29-7.40 (m, 5H), 7.43 (t, J=7.5 Hz, 2H), 7.68 (d, J=7.0 Hz, 2H); MS (DCI) m/z 476/478 (M+H)$^+$. Elemental analysis is calculated for C$_{26}$H$_{26}$N$_3$OBr HCl 0.67EtOH 0.6H$_2$O: C, 59.21; H, 5.86; N, 7.58. Found: C, 59.16; H, 5.69; N, 7.59.

Example 42

3-benzyl-6-[(5-bromopyridin-2-yl)methyl]-1,2,3,4,4a,5,6,7-octahydropyrazino[1,2-a][1,4]benzodiazepine The product of Example 2 (103.1 mg, 0.35 mmol) and 5-bromo-2-formylpyridine (100.6 mg, 0.54 mmol) were processed according to the procedure for Example 17 and purified by preparative HPLC using the method described in Example 9 to give the title compound as the tris-trifluoroacetic acid salt: $^1$H NMR (500 MHz, pyridine-d$_5$) δ ppm 2.36-2.43 (m, 1H), 2.49-2.53 (m, 1H), 2.69-2.72 (m, 1H), 2.76-2.87 (m, 3H), 3.30-3.32 (m, 1H), 3.38-3.41 (m, 1H), 3.60-3.66 (m, 2H), 3.84-3.91 (m, 3H), 4.17 (d, J=13.1 Hz, 1H), 6.95 (d, J=7.6 Hz, 1H), 7.00 (t, J=7.3, 0.9 Hz, 1H), 7.19 (dd, J=7.3, 1.5 Hz, 1H), 7.31-7.34 (m, 2H), 7.39-7.42 (m, 2H), 7.50-7.53 (m, 3H), 7.84 (dd, J=8.4, 2.3 Hz, 1H), 8.77 (d, J=2.4 Hz, 1H); MS (DCI/NH$_3$) m/z 463 (M+H)$^+$. Elemental analysis is calculated for C$_{25}$H$_{27}$BrN$_4$.3.35 TFA.0.75H$_2$O: C, 44.33; H, 3.75; N, 6.52; F, 22.23. Found: C, 44.19; H, 3.57; N, 6.68; F, 22.20.

Example 43

(3-benzyl-2,3,4,4a,5,6-hexahydropyrazino[1,2-a][1,5]benzodiazepin-7(1H)-yl)(pyridin-4-yl)methanone The product of Example 26 (218 mg, 0.74 mmol) was combined with isonicotinoyl chloride hydrochloride (132 mg, 0.74 mmol) in CH$_2$Cl$_2$ (5 mL), and the mixture was stirred at room temperature for 14 hours and then concentrated under vacuum. The residue was purified by HPLC (30×100 mm, C18, Waters XBridge™ column eluted with aqueous 0.1 M (NH$_4$)$_4$CO$_3$-methanol (95:5-5:95 over 18 minutes)) and then by chromatography on silica gel (CH$_2$Cl$_2$-methanol-15 M NH$_4$OH, 95:5:0.5) to provide the title compound: $^1$H NMR (400 MHz, DMSO-d$_6$, 90° C.) δ ppm 1.74 (s, 2H), 2.28-2.38 (m, 2H), 2.74 (d, J=10.4 Hz, 1H), 2.81-2.93 (m, 1.0 Hz, 2H), 3.10-3.37 (m, 3H), 3.51-3.63 (m, 2H), 3.75-4.23 (m, 1H), 6.60-6.73 (m, 2H), 6.97 (d, J=4.6 Hz, 2H), 6.98-7.02 (m, 1H), 7.13 (t, J=6.9 Hz, 1H), 7.20-7.28 (m, 1H), 7.29-7.38 (m, 4H), 8.36 (d, J=5.8 Hz, 2H); MS (DCI) m/z 399 (M+H

Example 44

3-benzyl-7-[2-(4-chlorophenyl)ethyl]-1,2,3,4,4a,5,6,7-octahydropyrazino[1,2-a][1,5]benzodiazepine A mixture of the product of Example 27 (99 mg, 0.205 mmol) in tetrahydrofuran (9 mL) was stirred under nitrogen with ice cooling as alane-N,N-dimethylethylamine complex (Aldrich, 0.5 M in toluene, 2.0 mL, 1.00 mmol) was added dropwise from a syringe. The mixture was stirred with ice cooling for 30 minutes, and then it was allowed to warm to room temperature for 12 hours. The reaction mixture was quenched by addition of methanol (2 mL) and concentrated under vacuum. The residue was purified by chromatography ($SiO_2$, eluted with hexanes-ethyl acetate, 83:17) to provide the title compound: $^1$H NMR (400 MHz, $CD_3OD$) δ ppm 1.53 (dddd, J=15.2, 4.9, 2.8, 2.6 Hz, 1H), 1.79 (dddd, J=15.2, 11.9, 5.9, 3.4 Hz, 1H), 2.19 (t, J=10.7 Hz, 1H), 2.29 (td, J=11.1, 2.8 Hz, 1H), 2.65 (dt, J=10.3, 2.0 Hz, 1H), 2.74-2.91 (m, 5H), 2.98 (dt, J=11.5, 2.8 Hz, 1H), 3.15-3.27 (m, 2H), 3.45-3.55 (m, 2H), 3.56-3.62 (m, 2H), 6.77-6.97 (m, 4H), 7.14-7.23 (m, 4H), 7.24-7.40 (m, 5H); MS (ESI) m/z 432/434 (M+H)$^+$.

Example 45

3,7-dibenzyl-1,2,3,4,4a,5,6,7-octahydropyrazino[1,2-a][1,5]benzodiazepine

Solid $LiAlH_4$ (116 mg, 3.06 mmol) was added gradually to a mixture of the product of Example 41 (52.0 mg, 0.11 mmol) in tetrahydrofuran (6 mL) at room temperature. The resulting mixture was heated at 60° C. under nitrogen for 3 hours, and then it was cooled in ice and quenched by successive addition of ethyl acetate (1 mL), water (0.12 mL), 15% NaOH (0.12 mL), and water (0.36 mL). Diatomaceous earth (approximately 200 mg) was added, and the resulting slurry was filtered with an ethyl acetate (25 mL) rinse. The filtrate was concentrated under vacuum and the residue was purified by preparative HPLC on a Phenomenex® Luna® C8(2) 5 µm 100 Å AXIA column (30×75 mm) eluted with acetonitrile:0.1% trifluoroacetic acid in water (10:90-95:5) to provide the title compound as the bis-trifluoroacetic acid salt: $^1$H NMR (500 MHz, pyridine-$d_5$) δ ppm 1.38-1.45 (m, 1H), 1.81-1.90 (m, 1H), 2.42 (t, J=10.4 Hz, 1H), 2.55 (td, J=10.8, 2.6 Hz, 1H), 2.73-2.82 (m, 2H), 3.00-3.09 (m, 2H), 3.11-3.18 (m, J=6.5, 6.5, 2.9 Hz, 1H), 3.45 (td, J=11.1, 2.1 Hz, 1H), 3.50 (td, J=11.6, 1.8 Hz, 1H), 3.76 (s, 2H), 4.30 (d, J=15.6 Hz, 1H), 4.49 (d, J=15.6 Hz, 1H), 6.90 (dd, J=7.8, 1.4 Hz, 1H), 6.94 (td, J=7.5, 1.5 Hz, 1H), 6.98-7.05 (m, 2H), 7.29 (t, J=7.3 Hz, 1H), 7.32-7.46 (m, 7H), 7.54 (d, J=7.0 Hz, 1H); MS (ESI) m/z 384 (M+H)$^+$.

Example 46

3-benzyl-6-(4-iodobenzyl)-1,2,3,4,4a,5,6,7-octahydropyrazino[1,2-a][1,4]benzodiazepine The product of Example 2 (153.3 mg, 0.52 mmol) and 4-iodobenzaldehyde (119.7 mg, 0.52 mmol) were processed according to the procedure for Example 17 and purified by preparative HPLC using the method described in Example 9 to give the title compound as the tris-trifluoroacetic acid salt: $^1$H NMR (500 MHz, pyridine-$d_5$) δ ppm 2.38-2.41 (m, 1H), 2.47 (t, J=10.1 Hz, 1H) 2.58-2.61 (m, 1H), 2.69-2.73 (m, 1H), 2.78-2.80 (m, 1H), 2.58-2.87 (m, 1H), 3.31 (dd, J=6.9, 2.6 Hz, 1H), 3.40-3.42 (m, 2H), 3.56-3.66 (m, 4H), 3.83 (d, J=13.1 Hz, 1H), 4.11 (d, J=13.1 Hz, 1H), 6.95 (d, J=7.3, 1H), 7.02 (td, J=7.3, 1.2 Hz, 1H), 7.15 (dd, J=7.5, 1.4 Hz, 1H), 7.23-7.24 (m, 2H), 7.31-7.36 (m, 2H), 7.39-7.42 (m, 2H), 7.50-7.51 (m, 2H), 7.76-7.77 (m, 2H); MS (DCI/$NH_3$) m/z 510 (M+H)$^+$. Elemental analysis is calculated for $C_{26}H_{28}IN_3$.3 TFA: C, 45.14; H, 3.67; N, 4.93. Found: C, 45.33; H, 3.63; N, 4.99.

Example 47

3-benzyl-7-(4-bromobenzyl)-1,2,3,4,4a,5,6,7-octahydropyrazino[1,2-a][1,5]benzodiazepine A solution of alane-N,N-dimethylethylamine complex in toluene (Aldrich, 0.5 M, 1.5 mL, 0.750 mmol) was added to an ice-cooled mixture of the product of Example 41 (58.7 mg, 0.114 mmol) in tetrahydrofuran (5 mL). The mixture was stirred for 30 minutes, and then it was allowed to warm to room temperature for 50 minutes before being quenched by the addition of methanol (1.5 mL) and concentrated under vacuum. The residue was taken up with 1 M NaOH (3 mL) and extracted with $CH_2Cl_2$ (2×10 mL). The combined organic phases were concentrated under vacuum, and the residue was purified by purified by preparative HPLC on a Phenomenex® Luna® C8(2) 5 µm 100 Å AXIA column (30 mm×75 mm) eluting with acetonitrile:0.1% trifluoroacetic acid in water (10:90-95:5) to provide the title compound as the bis-trifluoroacetic acid salt: $^1$H NMR (500 MHz, pyridine-$d_5$) δ ppm 1.38-1.47 (m, 1H), 1.77-1.89 (m, 1H), 2.40 (t, J=10.4 Hz, 1H), 2.54 (td, J=10.8, 2.6 Hz, 1H), 2.72 (ddd, J=11.3, 4.9, 3.7 Hz, 1H), 2.80 (d, J=10.7 Hz, 1H), 3.00-3.09 (m, 2H), 3.09-3.16 (m, 1H), 3.40-3.48 (m, 2H), 3.76 (s, 2H), 4.18 (d, J=15.6 Hz, 1H), 4.42 (d, J=15.6 Hz, 1H), 6.87 (dd, J=7.9, 1.2 Hz, 1H), 6.96 (td, J=7.4, 1.4 Hz, 1H), 7.00 (dd, J=7.9, 1.8 Hz, 1H), 7.05 (td, J=7.5, 1.8 Hz, 1H), 7.30 (d, J=8.5 Hz, 2H), 7.32-7.38 (m, 1H), 7.42 (t, J=7.3 Hz, 2H), 7.53 (d, J=8.2 Hz, 2H), 7.53-7.56 (m, 2H); MS (ESI) m/z 462/464 (M+H)$^+$.

Example 48

3-benzyl-7-(pyridin-4-ylmethyl)-1,2,3,4,4a,5,6,7-octahydropyrazino[1,2-a][1,5]benzodiazepine A solution of alane-N,N-dimethylethylamine complex (Aldrich, 0.5 M in toluene, 3.1 mL, 1.55 mmol) was added dropwise with stirring to an ice-cooled solution of the product of Example 43 (123 mg, 0.309 mmol) in tetrahydrofuran (10 mL). The mixture was stirred under nitrogen as the ice bath was allowed to expire over 2.5 hours. The reaction was quenched by addition of methanol (2 mL) and concentrated under vacuum. The residue was purified by flash chromatography ($SiO_2$, eluted with $CH_2Cl_2$-methanol-15 M $NH_4OH$) and then by HPLC (30×100 mm, C18, Waters XBridge™ column eluting with aqueous 0.1 M $(NH_4)_2CO_3$-methanol (80:20-0:100 over 15 minutes)) to provide the title compound: $^1$H NMR (300 MHz, $CD_3OD$) δ ppm 1.60 (ddt, J=15.3, 2.4 Hz, 1H), 1.85-2.03 (m, 1H), 2.26 (t, J=10.7 Hz, 1H), 2.37 (td, J=11.1, 3.2 Hz, 1H), 2.70 (br d, J=10.7 Hz, 1H), 2.86-2.98 (m, 3H), 3.06 (dt, J=11.5, 2.8 Hz, 1H), 3.25-3.35 (m, 1H), 3.55 (td, J=11.4, 2.2 Hz, 1H), 3.61 (s, 2H), 4.32 (d, J=16.7 Hz, 1H), 4.61 (d, J=16.7 Hz, 1H), 6.75 (dd, J=6.8, 2.4 Hz, 1H), 6.78-6.92 (m, 2H), 6.94 (dd, J=7.1, 2.1 Hz, 1H), 7.24-7.39 (m, 5H), 7.42 (d, J=5.9 Hz, 2H), 8.40 (d, J=6.3 Hz, 2H); MS (ESI) m/z 385 (M+H)$^+$.

Example 49

3-benzyl-7-methyl-1,2,3,4,4a,5,6,7-octahydropyrazino[1,2-a][1,5]benzodiazepine

The product of Example 26 (241 mg, 0.821 mmol) was dissolved in 88% formic acid (5 mL), and 36% formalin solution (0.55 mL, 7.2 mmol) was added. The mixture was heated at 100° C. for 1 hour and then cooled to room temperature. The mixture was concentrated under vacuum and the residue purified by HPLC (30×100 mm, C18, Waters XBridge™ column eluting with aqueous 0.1 M (NH$_4$)$_2$CO$_3$— methanol (80:20-0:100 over 15 minutes)) to provide the title compound: $^1$H NMR (300 MHz, CD$_3$OD) δ ppm 1.51 (dddd, J=15.3, 4.9, 2.7, 2.5 Hz, 1H), 1.76 (dddd, J=15.5, 12.0, 6.1, 4.1 Hz, 1H), 2.34 (t, J=10.7 Hz, 1H), 2.42 (td, J=11.4, 3.4 Hz, 1H), 2.66-2.76 (m, 2H), 2.79 (s, 3H), 2.80-2.85 (m, 1H), 2.85-2.93 (m, 1H), 3.02 (dt, J=11.5, 2.7 Hz, 1H), 3.20-3.29 (m, 1H), 3.50 (td, J=11.7, 3.1 Hz, 1H), 3.61 (s, 2H), 6.82 (dd, J=7.8, 1.4 Hz, 1H), 6.84-7.01 (m, 3H), 7.22-7.40 (m, 5H); MS (ESI) m/z 308 (M+H)$^+$.

Example 50

4-[(3-benzyl-1,2,3,4,4a,5-hexahydropyrazino[1,2-a][1,4]benzodiazepin-6(7H)-yl)methyl]phenol The product of Example 2 (101.8 mg, 0.35 mmol) and 4-hydroxybenzaldehyde (58.8 mg, 0.48 mmol) were processed according to the procedure for Example 17 and purified by preparative HPLC using the method described in Example 9 to give the title compound as the tris-trifluoroacetic acid salt: $^1$H NMR (500 MHz, pyridine-d$_5$) δ ppm 2.31-2.36 (m, 1H), 2.47 (t, J=10.1 Hz, 1H) 2.83-2.88 (m, 2H), 2.95-3.05 (m, 2H), 3.30-3.31 (m, 2H), 3.57-3.60 (m, 1H), 3.65-3.68 (m, 2H), 4.07-4.15 (m, 2H), 4.31 (d, J=13.1 Hz, 1H), 4.47 (d, J=13.1 Hz, 1H), 6.95-7.96 (m, 13H); MS (DCI/NH$_3$) m/z 400 (M+H)$^+$.

Example 51

9-benzyl-7,7a,8,9,10,11-hexahydropyrazino[1,2-d]pyrido[3,2-b][1,4]diazepin-6(5H)-one Example 51A methyl 2-(4-benzyl-1-(3-nitropyridin-2-yl)piperazin-2-yl)acetate The product of Example 26A (1.46 g, 4.70 mmol) and 2-chloro-3-nitropyridine (0.746 g, 4.70 mmol) were combined with diisopropylethylamine (0.82 mL, 4.7 mmol) and dimethyl sulfoxide (5 mL), and the mixture was heated under nitrogen at 95° C. for 13 hours. The mixture was cooled to room temperature and partitioned between water (50 mL) and ethyl acetate (50 mL). The aqueous layer was extracted with CH$_2$Cl$_2$ (2×50 mL) and the extracts were combined with the ethyl acetate phase and concentrated under vacuum. The residue was purified by chromatography (SiO$_2$, eluted with hexanes-ethyl acetate 90:10-80:20) to provide the title compound: $^1$H NMR (300 MHz, CD$_3$OD) δ ppm 2.17 (td, J=11.7, 3.2 Hz, 1H), 2.33 (dd, J=11.7, 3.4 Hz, 1H), 2.75-2.84 (m, 3H), 2.84-3.01 (m, 2H), 3.03-3.13 (m, 1H), 3.38-3.51 (m, 1H), 3.43 (d, J=13.2 Hz, 1H), 3.47 (s, 3H), 3.59 (d, J=13.1 Hz, 1H), 6.84 (dd, J=8.1, 4.6 Hz, 1H), 7.19-7.38 (m, 5H), 8.16 (dd, J=7.9, 1.6 Hz, 1H), 8.33 (dd, J=4.8, 1.6 Hz, 1H); MS (ESI) m/z 371 (M+H)$^+$.

Example 51B 9-benzyl-7,7a,8,9,10,11-hexahydropyrazino[1,2-d]pyrido[3,2-b][1,4]diazepin-6(5H)-one Platinum(IV) oxide (35 mg, 0.154 mmol) was added to a solution of the product of Example 51A (1.20 g, 2.92 mmol) in methanol (150 mL), and the suspension was stirred under hydrogen (1 atm) for 1 hour. The reaction flask was evacuated and purged with nitrogen (4 cycles), and the mixture was filtered through a pad of diatomaceous earth with a methanol (30 mL) rinse. A solution of 25% sodium methoxide in methanol (Aldrich, 1.83 g, 8.47 mmol) was added to the filtrate, and the solution was stirred at reflux under nitrogen for 41 hours and then cooled to room temperature. The reaction mixture was concentrated under vacuum, and the residue was purified by chromatography (SiO$_2$, eluted with CH$_2$Cl$_2$—CH$_3$OH, 95:5), followed by crystallization from ethanol (2 mL) to provide the title compound: $^1$H NMR (300 MHz, CD$_3$OD) δ ppm 2.15 (dd, J=13.7, 3.0 Hz, 1H), 2.22-2.32 (m, 1H), 2.31 (t, J=10.7 Hz, 1H), 2.75 (dd, J=13.7, 6.5 Hz, 1H), 2.83-2.96 (m, 2H), 3.23 (td, J=12.7, 2.8 Hz, 1H), 3.51-3.59 (m, 1H), 3.60 (s, 2H), 3.64-3.74 (m, 1H), 6.99 (dd, J=7.7, 5.0 Hz, 1H), 7.22-7.40 (m, 6H), 8.08 (dd, J=4.8, 1.6 Hz, 1H); MS (DCI) m/z 309 (M+H)$^+$.

Example 52

9-benzyl-5,6,7,7a,8,9,10,11-octahydropyrazino[1,2-d]pyrido[3,2-b][1,4]diazepine

Solid LiAlH$_4$ (255 mg, 6.72 mmol) was added gradually to a stirred suspension of the product of Example 51B (337 mg, 1.093 mmol) in tetrahydrofuran (25 mL). The resulting mixture was heated at reflux under nitrogen for 1 hour, then cooled in ice and quenched by successive addition of ethyl acetate (3 mL), water (0.25 mL), 15% NaOH (0.25 mL) and water (0.75 mL). The gray slurry was filtered through diatomaceous earth with an ethyl acetate (30 mL total) rinse. The filtrate was concentrated under vacuum and the residue was purified by HPLC (30×100 mm, C18, XBridge™ column eluting with aqueous 0.1 M (NH$_4$)$_2$CO$_3$— methanol, 80:20-0:100 over 15 minutes) to provide the title compound: $^1$H NMR (300 MHz, CD$_3$OD) δ ppm 1.75-1.89 (m, 1H), 1.90-2.04 (m, 1H), 2.30 (dd, J=11.0, 9.0 Hz, 1H), 2.44 (ddd, J=10.9, 9.6, 3.2 Hz, 1H), 2.59 (ddd, J=10.9, 2.8, 1.2 Hz, 1H), 2.72-2.83 (m, 1H), 3.17 (ddd, J=12.5, 5.4, 3.7 Hz, 1H), 3.26-3.34 (m, 1H), 3.33-3.53 (m, 3H), 3.52-3.63 (m, 2H), 6.73 (dd, J=7.8, 4.7 Hz, 1H), 6.91 (dd, J=7.6, 1.5 Hz, 1H), 7.20-7.40 (m, 5H), 7.61 (dd, J=4.9, 1.5 Hz, 1H); MS (ESI) m/z 295 (M+H)$^+$.

Example 53

1-(9-benzyl-7,7a,8,9,10,11-hexahydropyrazino[1,2-d]pyrido[3,2-b][1,4]diazepin-5 (6H)-yl)-2-(4-chlorophenyl)ethanone A solution of the product of Example 52 (135 mg, 0.367 mmol) in CH$_2$Cl$_2$ (3 mL) was added to 4-chlorophenylacetyl chloride (Aldrich, 0.058 mL, 0.38 mmol), and the resulting solution was stirred at room temperature for 45 minutes.

Methanol (0.5 mL) was added and the mixture was stirred for 10 minutes and then concentrated under vacuum. The residue was crystallized from ethanol (4 mL) and water (0.2 mL) to provide the title compound as the HCl salt: $^1$H NMR (400 MHz, pyridine-$d_5$) δ ppm 2.57-2.86 (m, 3H), 2.92-3.31 (m, 2H), 3.32-3.59 (m, 7H), 4.29-4.66 (m, 2H), 6.69-6.88 (m, 1H), 6.91-7.04 (m, 2H), 7.21 (d, J=8.2 Hz, 2H), 7.25 (d, J=7.3 Hz, 1H), 7.27-7.36 (m, J=7.3, 7.3 Hz, 3H), 7.37-7.44 (m, 2H), 8.23-8.33 (m, 1H), one proton obscured by solvent; MS (ESI) m/z 447/449 (M+H)$^+$. Elemental analysis is calculated for $C_{26}H_{27}N_4OCl·HCl·0.4H_2O$: C, 63.65; H, 5.92; N, 11.42. Found: C, 63.72; H, 5.75; N, 11.26.

Example 54

9-benzyl-5-[2-(4-chlorophenyl)ethyl]-5,6,7,7a,8,9,10,11-octahydropyrazino[1,2-d]pyrido[3,2-b][1,4]diazepine The product of Example 53 (44 mg, 0.1 mmol) was partitioned with $CH_2Cl_2$ (25 mL) and 20% $Na_2CO_{3(aq)}$ (5 mL). The organic layer was dried ($Na_2SO_4$) and concentrated under vacuum. The residue was dissolved in tetrahydrofuran (3 mL) and cooled in ice under nitrogen. A solution of alane-N,N-dimethylethylamine complex in toluene (Aldrich, 0.5 M, 1.0 mL, 0.50 mmol) was added, and the turbid mixture warmed gradually to room temperature and stirred for 12 hours. Methanol (2 mL) was added, and the mixture was concentrated under vacuum. The residue was partitioned between $CH_2Cl_2$ (5 mL) and 1 M NaOH (5 mL), and the organic phase was applied to a column of silica gel and eluted with hexanes-ethyl acetate (80:20-0:100) to provide the title compound: $^1$H NMR (300 MHz, $CD_3OD$) δ ppm 1.61-1.87 (m, 2H), 2.07 (t, J=10.3 Hz, 1H), 2.23 (td, J=10.9, 3.2 Hz, 1H), 2.61 (d, J=10.3 Hz, 1H), 2.74-2.82 (m, 1H), 2.81 (t, J=6.7 Hz, 2H), 2.92-3.04 (m, 1H), 3.11-3.21 (m, 1H), 3.22-3.29 (m, 2H), 3.32-3.52 (m, 3H), 3.54 (s, 2H), 6.85 (dd, J=7.7, 5.0 Hz, 1H), 7.08-7.16 (m, 3H), 7.18-7.39 (m, 7H), 7.69 (dd, J=5.0, 1.4 Hz, 1H); MS (ESI) m/z 433/435 (M+H)$^+$.

Example 55

9-benzyl-5-methyl-5,6,7,7a,8,9,10,11-octahydropyrazino[1,2-d]pyrido[3,2-b][1,4]diazepine Formic acid (88%, 3 mL) was added to a solution of the product of Example 52 (97 mg, 0.231 mmol) in $CH_2Cl_2$ (2 mL). Aqueous formalin (0.5 mL, 6.5 mmol) was added, and the mixture was heated at 110° C. for 45 minutes, then cooled to room temperature and concentrated under vacuum. The residue was purified by HPLC (30×100 mm XBridge™ column eluting with aqueous 0.1 M$(NH_4)_2CO_3$-methanol, 80:20-0:100 over 15 minutes) to provide the title compound: $^1$H NMR (300 MHz, $CD_3OD$) δ ppm 1.62-1.74 (m, 1H), 1.77-1.91 (m, 1H), 2.23 (t, J=10.5 Hz, 1H), 2.39 (td, J=11.0, 3.1 Hz, 1H), 2.70 (ddd, J=10.8, 2.4, 1.9 Hz, 1H), 2.79 (s, 3H), 2.80-2.88 (m, 1H), 2.96 (ddd, J=11.1, 6.5, 4.4 Hz, 1H), 3.23-3.29 (m, 1H), 3.32-3.40 (m, 2H), 3.50 (dt, J=12.9, 3.1 Hz, 1H), 3.59 (s, 2H), 6.87 (dd, J=7.8, 4.7 Hz, 1H), 7.08 (dd, J=7.8, 1.4 Hz, 1H), 7.22-7.39 (m, 5H), 7.71 (dd, J=4.9, 1.5 Hz, 1H); MS (ESI) m/z 309 (M+H)$^+$.

Example 56

6-(4-bromobenzyl)-3-(4-fluorobenzyl)-1,2,3,4,4a,5,6,7-octahydropyrazino[1,2-a][1,4]benzodiazepine The product of Example 40 (385.7 mg, 1.24 mmol), was dissolved in methanol (10 mL). 4-Bromobenzaldehyde (360.5 mg, 1.95 mmol) was added to the reaction and stirred for 1 hour at ambient temperature. Sodium cyanoborohydride (238.9 mg, 3.80 mmol) was then added, and the reaction was stirred at ambient temperature for 20 hours. The reaction was then diluted with 1 M NaOH (50 mL) and extracted with dichloromethane (3×50 mL). The organic layers were combined, concentrated and purified by silica gel chromatography (ethyl acetate/dichloromethane 1:1, $R_f$ 0.33) to give the title compound: $^1$H NMR (500 MHz, pyridine-$d_5$) δ ppm 2.31 (td, J=10.4, 3.4 Hz, 1H), 2.37 (t, J=9.9 Hz, 1H), 2.57 (dd, J=13.3, 3.2 Hz, 1H), 2.67-2.76 (m, 3H), 3.24-3.35 (m, 3H), 3.45-3.57 (m, 4H), 3.79 (d, J=12.8 Hz, 1H), 4.06 (d, J=13.1 Hz, 1H), 6.98 (d, J=7.9 Hz, 1H), 7.02 (td, J=7.3, 0.9 Hz, 1H), 7.13-7.19 (m, 3H), 7.33-7.36 (m, 3H), 7.40-7.43 (m, 2H), 7.54-7.56 (m, 2H); MS (DCI/$NH_3$) m/z 480 (M+H)$^+$. Elemental analysis is calculated for $C_{26}H_{27}BrFN_3$: C, 65.00; H, 5.66; N, 8.75. Found: C, 64.74; H, 5.51; N, 8.59.

Example 57

6-(4-bromobenzyl)-3-methyl-1,2,3,4,4a,5,6,7-octahydropyrazino[1,2-a][1,4]benzodiazepine Example 57A 3-methyl-1,2,3,4,4a,5,6,7-octahydropyrazino[1,2-a][1,4]benzodiazepine The product of Example 1 (148.7 mg, 0.47 mmol) was dissolved in tetrahydrofuran (14 mL). The reaction was chilled to 0° C. with an ice bath and lithium aluminum hydride (57.8 mg, 1.52 mmol) was added. The reaction was allowed to warm to ambient temperature and stirred for 20 hours. The reaction was diluted with ethyl acetate (2 mL), then water (60 μL), 15% NaOH (60 μL) and water (180 μL) were added dropwise producing a precipitate. The precipitate was filtered off and the filtrated concentrated to give the title compound: MS (DCI/$NH_3$) m/z 218 (M+H)$^+$.

Example 57B 6-(4-bromobenzyl)-3-methyl-1,2,3,4,4a,5,6,7-octahydropyrazino[1,2-a][1,4]benzodiazepine The product of Example 57A (97.8 mg, 0.48 mmol) and 4-bromobenzaldehyde (128.8 mg, 0.70 mmol) were processed according to the procedure for Example 17 and purified by preparative HPLC as described in Example 9 to give the title compound as the tris-trifluoroacetic acid salt: $^1$H NMR (500 MHz, pyridine-$d_5$) δ ppm 2 2.50 (dd, J=13.7, 3.4 Hz, 1H), 2.57 (dd, J=13.7, 4.1 Hz, 1H), 2.79 (s, 3H), 2.92 (td, J=11.6, 3.4 Hz, 1H), 3.14 (t, J=11.0 Hz, 1H), 3.31-3.37 (m, 2H), 3.46-3.48 (m, 2H), 3.53-3.64 (m, 4H), 4.14 (d, J=13.1 Hz, 1H), 6.83 (d, J=7.6 Hz, 1H), 7.03 (td, J=7.4, 1.1 Hz, 1H), 7.13 (dd, J=7.3, 1.5 Hz, 1H), 7.28-7.32 (m, 3H), 7.52-7.54 (m, 2H); MS (DCI/$NH_3$) m/z 386 (M+H)$^+$. Elemental analysis is calculated for $C_{20}H_{24}BrN_3·3.35$ TFA: C, 41.74; H, 3.59; N, 5.47. Found: C, 41.80; H, 3.47; N, 5.55.

Example 58

(9-benzyl-7,7a,8,9,10,11-hexahydropyrazino[1,2-d]pyrido[3,2-b][1,4]diazepin-5(6H)-yl)(2,2,3,3-tetramethylcyclopropyl)methanone O-(7-Azabenzotriazol-1-yl)-N,N,N',N'-tetramethyluronium hexafluorophosphate (254 mg, 0.668 mmol) and 2,2,3, 3-tetramethylcyclopropanecarboxylic acid (95 mg, 0.668 mmol) were added to a solution of the product of Example 52 (164 mg, 0.45 mmol) and diisopropylethylamine (0.16 mL, 0.89 mmol) in $CH_2Cl_2$ (5 mL). The mixture was stirred at room temperature for 45 hours, and then concentrated under vacuum. The residue was purified by preparative HPLC on a Phenomenex® Luna® C8(2) 5 μm 100 Å AXIA column (30×75 mm), eluting with methanol: 10 mM ammonium acetate in water (10:90-95:5) to provide the title compound: $^1$H NMR (400 MHz, pyridine-$d_5$, 110° C.) δ ppm 0.90 (s, 6H), 1.33 (s, 3H), 1.35 (s, 3H), 1.69 (q, J=6.1 Hz, 2H), 2.04 (s, 1H), 2.03-2.13 (m, 1H), 2.40 (td, J=10.8, 2.9 Hz, 1H), 2.64 (d, J=11.0 Hz, 1H), 2.78 (d, J=10.7 Hz, 1H), 3.33-3.44 (m, 1H), 3.43 (ddd, J=13.1, 11.0, 3.0 Hz, 1H), 3.49 (s, 2H), 3.57-3.72 (m, 2H), 4.03-4.13 (m, 1H), 6.80 (dd, J=7.5, 4.7 Hz, 1H), 7.22 (t, J=7.3 Hz, 1H), 7.27-7.33 (m, J=7.3, 7.3 Hz, 3H), 7.35-7.40 (m, 2H), 8.26 (dd, J=4.6, 1.8 Hz, 1H); MS (ESI) m/z 419 $(M+H)^+$.

Example 59

9-benzyl-5-[(2,2,3,3-tetramethylcyclopropyl)methyl]-5,6,7,7a,8,9,10,11-octahydropyrazino[1,2-d]pyrido[3,2-b][1,4]diazepine A solution of alane-N,N-dimethylethylamine complex (Aldrich, 0.5 M in toluene, 1.4 mL, 0.70 mmol) was added to an ice-cooled solution of the product of Example 58 (59 mg, 0.141 mmol) in tetrahydrofuran (5 mL). The mixture was stirred with ice cooling under nitrogen for 90 minutes, and then it was warmed to room temperature. After 4 hours, methanol (5 mL) was added, and the mixture was concentrated under vacuum. The residue was purified by HPLC (30×100 mm XBridge™ column eluted with aqueous 0.1 M $(NH_4)_2CO_3$— methanol, 80:20-0:100 over 15 minutes) to provide the title compound: $^1$H NMR (300 MHz, $CDCl_3$) δ ppm 0.95 (s, 3H), 0.96 (s, 3H), 1.08 (s, 3H), 1.09 (s, 3H), 1.53-1.61 (m, 1H), 1.65-1.79 (m, 1H), 1.80-1.94 (m, 1H), 2.16-2.29 (m, 1H), 2.33-2.52 (m, 1H), 2.57-2.74 (m, 1H), 2.78-2.93 (m, 1H), 2.99 (dd, J=12.1, 6.3 Hz, 1H), 2.97-3.11 (m, 1H), 3.07 (dd, J=13.4, 5.9 Hz, 1H), 3.24-3.73 (m, 6H), 6.77 (dd, J=7.5, 4.8 Hz, 1H), 6.96 (dd, J=7.5, 1.6 Hz, 1H), 7.27-7.45 (m, 5H), 7.80 (dd, J=4.6, 1.4 Hz, 1H); MS (ESI) m/z 405 $(M+H)^+$.

Example 60

1-(3-benzyl-1,2,3,4,4a,5-hexahydropyrazino[1,2-a][1,4]benzodiazepin-6(7H)-yl)-2-(6-chloropyridin-3-yl)ethanone The product of Example 2 (98.3 mg, 0.34 mmol) was dissolved in dichloromethane (3 mL). (6-Chloropyridin3-yl) acetic acid (99.2 mg, 0.58 mmol), 1-hydroxybenzotriazole hydrate (62.8 mg, 0.41 mmol), (13.8 mg, 0.11 mmol) and N-(3-dimethylaminopropyl)-N-ethylcarbodiimide hydrochloride (95.7 mg, 0.58 mmol) were added, and the reaction was stirred at ambient temperature for 16 hours. The reaction was concentrated and purified by preparative HPLC using the method described in Example 4 to give the title compound: $^1$H NMR (300 MHz, methanol-$d_4$) δ ppm 2.09-2.23 (m, 4H), 2.40 (s, 3H), 3.19-3.45 (m, 5H), 4.36 (s, 2H), 4.98 (s, 2H), 6.96-7.00 (m, 1H), 7.14 (s, 1H), 7.19-7.23 (m, 3H), 7.61-7.65 (m, 2H); MS (DCI/$NH_3$) m/z 447 $(M+H)^+$. Elemental analysis is calculated for $C_{26}H_{27}ClN_4O \cdot 0.25H_2O$: C, 69.17; H, 6.14; N, 12.41. Found: C, 69.11; H, 6.08; N, 12.55.

Example 61

(+)-(4aS)-6-(4-bromobenzyl)-3-(4-fluorobenzyl)-1,2,3,4,4a,5,6,7-octahydropyrazino[1,2-a][1,4]benzodiazepine The product of Example 56 (298.3 mg, 0.96 mmol) was separated in to individual enantiomers by SFC purification carried out using a modified Berger Instruments PrepSFC™ system. A manual version of the Berger system was integrated with a Gilson 232 autosampler for sample injection and a Cavro MiniPrep™ pipettor customized for fraction collection at atmospheric pressure (Olson, J.; Pan, J.; Hochlowski, J.; Searle, P.; Blanchard, D. JALA 2002, 7, 69-74). Custom designed collection shoes allowed collection into 18×150 mm tubes and a methanol wash system allows washing of shoes between fractions to maximize recovery and avoid cross-contamination of fractions. The system was controlled using SFC ProNTo™ software (version 1.5.305.15) and an Abbott developed Visual Basic application for autosampler and fraction collector control. The outlet pressure was 100 bar, oven temperature at 35° C., and mobile phase flow rate at 40 mL/minute (Daicel/Chiral Technologies Chiralpak® AD-H column, 5-50% methanol:$CO_2$ 100 bar+0.1% diethylamine). The preparative SFC system was controlled using SFC ProNTo™ software (version 1.5.305.15) and custom software for autosampler and fraction collector control. Fractions were collected based upon UV signal threshold and on-line Thermo MSQ mass spectrometry was used for molecular mass confirmation, using ESI ionization in positive mode. Mass spectra were acquired using a Navigator4.0 software and an Abbott developed Visual Basic interface to communicate with SFC controlling software. The first eluting isomer (retention time 15.29 minutes) was crystallized from methanol. The stereochemistry of the first eluting isomer (S configuration) was determined by single crystal X-ray analysis. $[\alpha]^{20}_D$=+ 20° (c 0.93, $CH_2Cl_2$).

Example 62

(−)-(4aR)-6-(4-bromobenzyl)-3-(4-fluorobenzyl)-1,2,3,4,4a,5,6,7-octahydropyrazino[1,2-a][1,4]benzodiazepine Continued elution (retention time 19.05 minutes) of the procedure in Example 61 afforded the enantiomer of Example 61. The stereochemistry of the second eluting isomer (R configuration) was assigned based on this compound being the enantiomer of Example 61. $[\alpha]^{20}_D$=−19° (c 0.94, $CH_2Cl_2$).

Example 63

3-benzyl-6-[2-(6-chloropyridin-3-yl)ethyl]-1,2,3,4,4a,5,6,7-octahydropyrazino[1,2-a][1,4]benzodiazepine The product of Example 60 (74.4 mg, 0.17 mmol) was dissolved in tetrahydrofuran (5 mL). The reaction was chilled to 0° C. with an ice bath and the lithium aluminum hydride (25.3 mg, 0.25 mmol) was added. The reaction was allowed to warm to ambient temperature and stirred for 4 hours. The reaction was diluted with ethyl acetate (2 mL), then water (25 μL), 15% NaOH (25 μL) and water (75 μL) were added dropwise producing a precipitate. The precipitate was filtered off, the filtrate was concentrated, and the residue was purified by preparative HPLC using the method described in Example 4 to give the title compound: $^1$H NMR (500 MHz, pyridine-$d_5$) δ ppm 2.30-2.36 (m, 2H), 2.56-2.79 (m, 8H), 3.23-3.31 (m, 3H), 3.51-3.56 (m, 2H), 3.84 (d, J=12.8 Hz, 1H), 4.12 (d, J=12.8 Hz, 1H), 6.96 (d, J=7.9, 1H), 7.02 (t, J=7.5 Hz, 1H), 7.32-7.35 (m, 3H), 7.40-7.43 (m, 2H), 7.49-7.51 (m, 2H), 7.50-7.51 (m, 2H), 7.56-7.58 (m, 2H), 8.42 (d, J=2.4 Hz, 1H); MS (DCI/NH$_3$) m/z 433 (M+H)$^+$.

Example 64

5-(cyclopropylmethyl)-9-(4-fluorobenzyl)-5,6,7,7a,8,9,10,11-octahydropyrazino[1,2-d]pyrido[3,2-b][1,4]diazepine Example 64A tert-butyl 6-oxo-6,7,7a,8,10,11-hexahydropyrazino[1,2-d]pyrido[3,2-b][1,4]diazepine-9(5H)-carboxylate Diisopropylethylamine (3.03 mL, 17.34 mmol) was added to a mixture of 2-chloro-3-nitropyridine (2.75 g, 17.34 mmol) and the product of Example 22B (4.48 g, 17.34 mmol) in dimethyl sulfoxide (20 mL). The mixture was heated at 95° C. under nitrogen for 7 hours and then cooled to room temperature. Ice water (200 mL) was added, and the mixture was extracted with ethyl acetate (2×100 mL). The organic phase was washed with saturated brine (60 mL), dried (MgSO$_4$) and concentrated under vacuum to an oil (6.81 g). This material was dissolved in methanol (400 mL), and PtO$_2$ (25 mg, 0.11 mmol) was added. The flask was evacuated and purged with nitrogen (3 cycles) and then with hydrogen (3 cycles). The suspension was stirred under hydrogen (1 atm) for 54 hours. The flask was evacuated and purged with nitrogen (3 cycles) and the black suspension was filtered through diatomaceous earth with a methanol (2×10 mL) rinse. Sodium methoxide (Aldrich, 25% in methanol, 12.01 g, 55.6 mmol) was added to the filtrate, and the mixture was heated at reflux for 41 hours. After cooling to room temperature, the reaction mixture was concentrated under vacuum. The residue was purified by chromatography (SiO$_2$, eluted with methanol-CH$_2$Cl$_2$ (0:100-5:95), followed by crystallization from ethanol (10 mL) to provide the title compound: $^1$H NMR (300 MHz, CDCl$_3$) δ ppm 1.48 (s, 9H), 2.27-2.40 (m, 1H), 2.78 (dd, J=13.5, 5.9 Hz, 1H), 2.91-3.20 (m, 3H), 3.55-3.68 (m, 1H), 3.69-3.80 (m, 1H), 3.99-4.19 (m, 2H), 6.95 (dd, J=7.7, 5.0 Hz, 1H), 7.23 (dd, J=7.7, 1.4 Hz, 1H), 7.61 (s, 1H), 8.18 (dd, J=5.0, 1.8 Hz, 1H); MS (ESI) m/z 319 (M+H)$^+$.

Example 64B 9-(4-fluorobenzoyl)-7,7a,8,9,10,11-hexahydropyrazino[1,2-d]pyrido[3,2-b][1,4]diazepin-6(5H)-one A solution of the product of Example 64A (0.50 g, 1.570 mmol) in CH$_2$Cl$_2$ (3 mL) was stirred with ice cooling as trifluoroacetic acid (2 mL) was added over 1 minute. The resulting solution was stirred at 0° C. for 50 minutes and then allowed to warm to room temperature for 1 hour. The mixture was concentrated under vacuum, and the residue was taken up in 6% NaOH (12 mL) and CH$_2$Cl$_2$ (5 mL), and p-fluorobenzoyl chloride (0.45 g, 2.8 mmol) was added. The mixture was stirred at room temperature for 13 hours and then filtered through diatomaceous earth with a CHCl$_3$ (25 mL) rinse. The aqueous layer was extracted with CHCl$_3$ (2×25 mL) and the combined extract was dried (Na$_2$SO$_4$) and concentrated under vacuum. The residue was purified by chromatography (SiO$_2$, CH$_2$Cl$_2$-methanol-15 M NH$_4$OH, 95:5:0.5) to provide the title compound: MS (DCI) m/z 341 (M+H)$^+$.

Example 64C 9-(4-fluorobenzyl)-5,6,7,7a,8,9,10,11-octahydropyrazino[1,2-d]pyrido[3,2-b][1,4]diazepine Solid LiAlH$_4$ (357 mg, 9.41 mmol) was added to a vigorously stirred solution of the product of Example 64B (528 mg, 1.55 mmol) in tetrahydrofuran (40 mL). The resulting gray suspension was heated at reflux under nitrogen for 1 hour and then cooled in ice. The reaction was quenched by successive addition of ethyl acetate (5 mL), water (0.35 ml), 15% NaOH (0.35 mL) and water (1.05 mL). The resulting slurry was stirred for 10 minutes, filtered (tetrahydrofuran (15 mL) and ethyl acetate (15 mL) rinse), and the filtrate was concentrated to provide the title compound, sufficiently pure for use in the next step: $^1$H NMR (300 MHz, CDCl$_3$) δ ppm 1.78-1.90 (m, 1H), 1.92-2.03 (m, 1H), 2.19-2.31 (m, 1H), 2.44-2.62 (m, J=8.7 Hz, 2H), 2.72-2.85 (m, J=10.7 Hz, 1H), 3.26 (ddd, J=12.1, 5.6, 3.8 Hz, 1H), 3.38-3.62 (m, 6H), 6.67 (dd, J=7.5, 4.5 Hz, 1H), 6.74 (dd, J=7.5, 2.0 Hz, 1H), 6.94-7.06 (m, 2H), 7.28-7.39 (m, 2H), 7.78 (dd, J=4.8, 1.6 Hz, 1H); MS (ESI) m/z 313 (M+H)$^+$.

Example 64D 5-(cyclopropylmethyl)-9-(4-fluorobenzyl)-5,6,7,7a,8,9,10,11-octahydropyrazino[1,2-d]pyrido[3,2-b][1,4]diazepine Cyclopropanecarbonyl chloride (0.043 ml, 0.478 mmol) was added to a solution of the product of Example 64C (97 mg, 0.31 mmol) in CH$_2$Cl$_2$ (2.0 mL). The mixture was stirred at room temperature for 2 hours and then concentrated under vacuum. The residue was taken up in 1 M NaOH (5 mL) and extracted with ethyl acetate (2×10 mL). The combined extract was washed with saturated brine (5 mL), dried (Na$_2$SO$_4$) and concentrated under vacuum. The residue was dissolved in tetrahydrofuran (5 mL) and stirred with alane-N,N-dimethylethylamine complex (Aldrich, 0.5 M in toluene, 2.9 mL, 1.45 mmol) at room temperature for 90 minutes. Methanol (1 mL) was added followed by water (5 mL) and 25% NaOH (1 mL). The mixture was stirred at room temperature for 10 minutes, and the aqueous phase was separated and extracted with ethyl acetate (2×7 mL). The combined organic was washed with saturated brine (5 mL), dried (Na$_2$SO$_4$) and concentrated under vacuum. The residue was purified by chromatography (SiO$_2$ eluted with CH$_2$Cl$_2$—CH$_3$OH 95:5) and then by HPLC (30×100 mm, C18, Waters XBridge™ column eluted with aqueous 0.1 M (NH$_4$)$_2$CO$_3$—CH$_3$OH, 80:20-0:100 over 15 minutes) to provide the title compound: $^1$H NMR (300 MHz, CDCl$_3$) δ ppm 0.15-0.23 (m, 2H), 0.51-0.61 (m, 2H), 0.94-1.06 (m, 1H), 1.66-1.80 (m, 1H), 1.80-1.95 (m, 1H), 2.19 (t, J=9.7 Hz, 1H), 2.42 (td, J=10.5, 3.1 Hz, 1H), 2.59 (d, J=10.9 Hz, 1H), 2.74-2.84 (m, 1H), 2.95 (d, J=6.4 Hz, 2H), 3.22 (ddd, J=11.5, 6.1, 4.1 Hz, 1H), 3.30-3.39 (m, 1H), 3.38-3.48 (m, 2H), 3.52 (d, J=6.4 Hz, 2H), 3.61 (dt, J=12.5, 3.4 Hz, 1H), 6.75 (dd, J=7.8, 4.7 Hz, 1H), 6.95 (dd, J=7.8, 1.7 Hz, 1H), 6.97-7.05 (m, 2H), 7.32 (dd, J=8.5, 5.8 Hz, 2H), 7.80 (dd, J=4.7, 1.7 Hz, 1H); MS (DCI) m/z 367 (M+H)$^+$.

Example 65

5-(cyclobutylmethyl)-9-(4-fluorobenzyl)-5,6,7,7a,8, 9,10,11-octahydropyrazino[1,2-d]pyrido[3,2-b][1,4] diazepine

Example 65A cyclobutyl[9-(4-fluorobenzyl)-7,7a,8,9,10,11-hexahydropyrazino[1,2-d]pyrido[3,2-b][1,4]diazepin-5(6H)-yl]methanone A solution of the product of Example 64C (97 mg, 0.31 mmol) in dichloromethane (2 mL) was added to cyclobutanecarbonyl chloride (0.048 mL, 0.42 mmol). The resulting, turbid solution was stirred at room temperature for 12 hours, and then the reaction was quenched by the addition of 20% $Na_2CO_3$ (1 mL). After 30 minutes, the mixture was made basic (pH~9) by addition of 1 M NaOH (~0.2 mL), diluted with water (3 mL) and extracted with $CHCl_3$ (3×2 mL). The combined organic phases were dried over $K_2CO_3$ and concentrated: $^1H$ NMR (300 MHz, $CD_3OD$) δ ppm 1.58-2.02 (m, 5H), 2.06-2.44 (m, 4H), 2.68-3.26 (m, 6H), 3.42-3.65 (m, 3H), 3.96-4.47 (m, 2H), 6.82-7.11 (m, 3H), 7.17-7.58 (m, 3H), 8.08-8.32 (m, 1H); MS (DCI) m/z 395 (M+H)$^+$.

Example 65B 5-(cyclobutylmethyl)-9-(4-fluorobenzyl)-5,6,7,7a,8, 9,10,11-octahydropyrazino[1,2-d]pyrido[3,2-b][1,4] diazepine A solution of alane-dimethylethylamine complex (0.5 M in toluene, 3.1 mL, 1.55 mmol) was added to a stirring solution of the product of Example 65A (122 mg, 0.31 mmol) in tetrahydrofuran (5.0 mL) at room temperature under nitrogen. The turbid solution was stirred at room temperature for 4 hours. The reaction was quenched by addition of methanol (1 mL), followed after 5 minutes by water (5 mL) and 25% NaOH (0.5 mL). The aqueous layer was separated and extracted with ethyl acetate (2×5 mL) and the combined organic phase was washed with brine (5 mL), dried ($Na_2SO_4$) and concentrated under vacuum to provide a residue that was purified by preparative HPLC on a Phenomenex® Luna® C8(2) 5 μm 100 Å AXIA column (30×75 mm), eluted with methanol: 10 mM $(NH_4)_2CO_3$ in water (50:50-95:5) to provide the title compound $^1H$ NMR (300 MHz, $CDCl_3$) δ ppm 1.62-1.94 (m, 6H), 1.97-2.12 (m, 2H), 2.13-2.26 (m, 1H), 2.30-2.49 (m, 1H), 2.51-2.69 (m, 2H), 2.72-2.87 (m, 1H), 2.91-3.03 (m, 1H), 3.02-3.15 (m, 2H), 3.17-3.70 (m, 6H), 6.74 (dd, J=7.8, 4.7 Hz, 1H), 6.92 (dd, J=7.8, 1.4 Hz, 1H), 7.01 (t, J=8.6 Hz, 2H), 7.27-7.39 (m, 2H), 7.79 (dd, J=4.7, 1.7 Hz, 1H); MS (DCI) m/z 381 (M+H)$^+$.

Example 66 tert-butyl 6-(4-bromobenzyl)-1,2,4a,5,6,7-hexahydropyrazino[1,2-a][1,4]benzodiazepine-3(4H)-carboxylate

Example 66A tert-butyl 1,2,4a,5,6,7-hexahydropyrazino[1,2-a][1,4] benzodiazepine-3(4H)-carboxylate The product of Example 1 (147.6 mg, 0.47 mmol) was dissolved in 1 M $BH_3$ in tetrahydrofuran (3 mL, 3 mmol). The reaction was heated to 60° C. for 3 hours. The reaction was concentrated, and then the residue was dissolved in propylamine (3 mL) and stirred at ambient temperature for 2 hours. The reaction mixture was concentrated again and purified by HPLC using the method described in Example 4 to give the title compound: MS ($DCI/NH_3$) m/z 304 (M+H)$^+$.

Example 66B tert-butyl 6-(4-bromobenzyl)-1,2,4a,5,6,7-hexahydropyrazino[1,2-a][1,4]benzodiazepine-3 (4H)-carboxylate The product of Example 66A (82.5 mg, 0.27 mmol) and 4-bromobenzaldehyde (77.7 mg, 0.42 mmol) were processed according to the procedure for Example 17 and purified by preparative HPLC using the method described in Example 4 to give the title compound: $^1H$ NMR (500 MHz, pyridine-$d_5$) δ ppm 1.55 (s, 9H), 2.61-2.63 (m, 1H), 2.72-2.30 (m, 1H), 3.09-3.13 (m, 1H), 3.19-3.21 (m, 1H), 3.24-3.28 (m, 1H), 3.34-3.48 (m, 3H), 3.53-3.55 (m, 2H), 3.71 (d, J=13.4 Hz, 1H), 4.01 (d, J=13.4 Hz, 1H), 6.95 (d, J=7.9 Hz, 1H), 7.02 (td, J=7.3, 0.9 Hz, 1H), 7.10 (dd, J=7.3, 1.2 Hz, 1H), 7.31-7.34 (m, 3H), 7.54-7.56 (m, 2H); MS ($DCI/NH_3$) m/z 472 (M+H)$^+$.

Example 67 tert-butyl 6-(4-bromobenzyl)-5-oxo-1,2,4a,5,6,7-hexahydropyrazino[1,2-a][1,4]benzodiazepine-3 (4H)-carboxylate Sodium hydride (60 weight %, 27.9 mg, 0.70 mmol) was washed with heptane (2 mL) and then suspended in N,N-dimethylformamide (2 mL). The product of Example 1 (149.2 mg, 0.47 mmol) was added and the reaction stirred at ambient temperature for 2 hours. 4-Bromobenzyl bromide (196.6 mg, 0.79 mmol) was added and allowed to react for 16 hours. The reaction was quenched with methanol and purify by preparative HPLC using the method described in Example 4 to give the title compound: $^1H$ NMR (500 MHz, pyridine-$d_5$) δ ppm 1.54 (s, 9H), 3.03-3.10 (m, 2H), 3.17-3.21 (m, 1H), 3.47-3.56 (m, 1H), 3.93 (dd, J=9.8, 2.8 Hz, 1H), 4.08-4.11 (m, 1H), 4.69-4.72 (m, 1H), 4.76 (d, J=14.9 Hz, 1H), 4.88 (d, J=14.3 Hz, 1H), 6.94-7.02 (m 3H), 7.22-7.24 (m, 2H), 7.29-7.33 (m, 1H), 7.48-7.50 (m, 2H); MS ($DCI/NH_3$) m/z 486 (M+H)$^+$.

Example 68

5-[(2S)-azetidin-2-ylmethyl]-9-(4-fluorobenzyl)-5,6, 7,7a,8,9,10,11-octahydropyrazino[1,2-d]pyrido[3,2-b][1,4]diazepine

Example 68A tert-butyl (2S)-2-{[9-(4-fluorobenzyl)-7,7a,8,9,10, 11-hexahydropyrazino[1,2-d]pyrido[3,2-b][1,4]diazepin-5(6H)-yl]carbonyl}azetidine-1-carboxylate O-(7-Azabenzotriazol-1-yl)-N,N,N',N'-tetramethyluronium hexafluorophosphate (177 mg, 0.465 mmol) was added to a mixture of the product of Example 64C (97 mg, 0.31 mmol) and (S)-1-(tert-butoxycarbonyl)azetidine-2-carboxylic acid (94 mg, 0.465 mmol, prepared as described in *J. Med. Chem.* 2005, 48, 7637-7647) in $CH_2Cl_2$ (2.0 mL). Diisopropylethylamine (0.108 mL, 0.620 mmol) was added, and the mixture was stirred at room temperature for 18 hours. The mixture was applied directly to a column of silica gel and eluted with 5% methanol-CH$_2$Cl$_2$ to provide the title compound: MS (DCI) m/z 496 (M+H)$^+$.

Example 68B tert-butyl (2S)-2-{[9-(4-fluorobenzyl)-7,7a,8,9,10,11-hexahydropyrazino[1,2-d]pyrido[3,2-b][1,4]diazepin-5(6H)-yl]methyl}azetidine-1-carboxylate A solution of alane-dimethylethylamine complex (0.5 M in toluene, 3.1 mL, 1.55 mmol) was added to a solution of the product of example 68A (154 mg, 0.31 mmol) in tetrahydrofuran (5.0 mL) at room temperature under nitrogen. The turbid solution was stirred at room temperature for 3 hours and then quenched by addition of methanol (1 mL), followed after 5 minutes by water (5 mL) and 25% NaOH (0.5 mL). The aqueous layer was separated and extracted with ethyl acetate (2×5 mL), and the combined organic phases were washed with brine (5 mL), dried (Na$_2$SO$_4$) and concentrated under vacuum to provide residue which was purified by preparative HPLC on a Phenomenex® Luna® C8(2) 5 μm 100 Å AXIA column (30×75 mm) eluted with methanol:10 mM (NH$_4$)$_2$CO$_3$ in water (50:50-95:5) to provide the title compound: $^1$H NMR (300 MHz, CDCl$_3$) δ ppm 1.45 (s, 9H), 1.70-1.92 (m, 2H), 1.91-2.08 (m, 1H), 2.11-2.27 (m, 2H), 2.32-2.44 (m, 1H), 2.52-2.62 (m, 1H), 2.68-2.83 (m, 1H), 3.03-3.18 (m, 1H), 3.23-3.70 (m, 8H), 3.71-3.89 (m, 2H), 4.27-4.45 (m, 1H), 6.69-6.77 (m, 1H), 6.97-7.04 (m, 1H), 7.04-7.10 (m, 1H), 7.31 (dd, J=8.3, 5.6 Hz, 2H), 7.81 (dd, J=4.7, 1.4 Hz, 1H); MS (DCI) m/z 482 (M+H)$^+$.

Example 68C

5-[(2S)-azetidin-2-ylmethyl]-9-(4-fluorobenzyl)-5,6,7,7a,8,9,10,11-octahydropyrazino[1,2-d]pyrido[3,2-b][1,4]diazepine Trifluoroacetic acid (1 mL, 13 mmol) was added to an ice-cooled solution of the product of Example 68B (51 mg, 0.106 mmol) in CH$_2$Cl$_2$ (2 mL). The solution was stirred with ice cooling for 30 minutes and then allowed to warm to room temperature. After 1 hour, the reaction solution was concentrated under vacuum to a residue that was purified by HPLC (30×100 mm, C18, Waters XBridge™ column eluted with 0.1 M aqueous (NH$_4$)$_2$CO$_3$-methanol, 80:20-0:100 over 15 minutes) to provide the title compound: $^1$H NMR (300 MHz, CD$_3$OD) δ ppm 1.64-1.90 (m, 2H), 1.98-2.14 (m, 1H), 2.15-2.27 (m, 1H), 2.27-2.42 (m, 2H), 2.67 (d, J=10.7 Hz, 1H), 2.76-2.86 (m, 1H), 2.92-3.11 (m, 1H), 3.19-3.45 (m, 6H), 3.46-3.66 (m, 4H), 4.05-4.22 (m, 1H), 6.77-6.91 (m, 1H), 7.05 (t, J=8.7 Hz, 2H), 7.15 (d, J=7.9 Hz, 1H), 7.37 (dd, J=8.3, 5.6 Hz, 2H), 7.68-7.76 (m, 1H); MS (DCI) m/z 382 (M+H)$^+$.

Example 69

5-(azetidin-3-ylmethyl)-9-(4-fluorobenzyl)-5,6,7,7a,8,9,10,11-octahydropyrazino[1,2-d]pyrido[3,2-b][1,4]diazepine

Example 69A tert-butyl 3-{[9-(4-fluorobenzyl)-7,7a,8,9,10,11-hexahydropyrazino[1,2-d]pyrido[3,2-b][1,4]diazepin-5 (6H)-yl]carbonyl}azetidine-1-carboxylate O-(7-Azabenzotriazol-1-yl)-N,N,N',N'-tetramethyluronium hexafluorophosphate (177 mg, 0.465 mmol) was added to a mixture of the product of Example 64C (97 mg, 0.31 mmol) and 1-(tert-butoxycarbonyl)azetidine-3-carboxylic acid (94 mg, 0.465 mmol) in CH$_2$Cl$_2$ (2 mL). Diisopropylethylamine (0.108 mL, 0.620 mmol) was added, and the mixture was stirred at room temperature for 18 hours. The reaction mixture was applied directly to a column of silica gel and eluted with 5% methanol-CH$_2$Cl$_2$ to provide the title compound: MS (DCI) m/z 496 (M+H)$^+$.

Example 69B tert-butyl 3-{[9-(4-fluorobenzyl)-7,7a,8,9,10,11-hexahydropyrazino[1,2-d]pyrido[3,2-b][1,4]diazepin-5 (6H)-yl]methyl}azetidine-1-carboxylate Alane-dimethylethylamine complex (0.5 M in toluene, 3.1 mL, 1.55 mmol) was added to a solution of the product of Example 69A (154 mg, 0.31 mmol) in tetrahydrofuran (5.0 mL) at room temperature under nitrogen. The cloudy solution was stirred at room temperature for 2.5 hours and then quenched by addition of methanol (1 mL), followed after minutes by water (5 mL) and 25% NaOH (0.5 mL). The aqueous layer was separated and extracted with ethyl acetate (2×6 mL). The combined organic phases were washed with brine (5 mL), dried (Na$_2$SO$_4$) and concentrated under vacuum to provide a residue that was further purified by preparative HPLC on a Phenomenex® Luna® C8(2) 5 μm 100 Å AXIA column (30×75 mm) eluted with methanol: 10 mM (NH$_4$)$_2$CO$_3$ in water (50:50-95:5) to provide the title compound: $^1$H NMR (300 MHz, CDCl$_3$) δ ppm 1.43 (s, 9H), 1.62-1.87 (m, 2H), 2.12 (t, J=10.0 Hz, 1H), 2.34 (td, J=10.7, 2.7 Hz, 1H), 2.59 (d, J=10.9 Hz, 1H), 2.72-2.86 (m, 2H), 2.89-3.00 (m, 1H), 3.14-3.26 (m, 1H), 3.28 (d, J=7.5 Hz, 2H), 3.31-3.43 (m, 2H), 3.44-3.56 (m, 2H), 3.56-3.63 (m, 2H), 3.69 (dt, J=12.8, 3.1 Hz, 1H), 3.96 (td, J=8.5, 3.7 Hz, 2H), 6.75 (dd, J=7.8, 4.7 Hz, 1H), 6.96 (dd, J=7.8, 1.4 Hz, 1H), 6.98-7.06 (m, 2H), 7.31 (dd, J=8.5, 5.4 Hz, 2H), 7.86 (dd, J=4.7, 1.7 Hz, 1H); MS (DCI) m/z 482 (M+H)$^+$.

Example 69C 5-(azetidin-3-ylmethyl)-9-(4-fluorobenzyl)-5,6,7,7a,8,9,10,11-octahydropyrazino[1,2-d]pyrido[3,2-b][1,4]diazepine Trifluoroacetic acid (1 mL, 12.98 mmol) was added to an ice-cooled solution of the product of Example 69B (75 mg, 0.156 mmol) in CH$_2$Cl$_2$ (2 mL). The solution was stirred with ice cooling for 30 minutes and then allowed to warm to room temperature and concentrated to dryness. The crude material was taken in 20% K$_2$CO$_{3(aq)}$ (20 mL) and 25% NaOH (1 mL) and extracted with CH$_2$Cl$_2$ (2×20 mL). The organic extract was dried (Na$_2$SO$_4$) and concentrated to a residue that was purified by HPLC (30×100 mm, C18, Waters XBridge™ column eluted with 0.1 M aqueous (NH$_4$)$_2$CO$_3$-methanol, 80:20-0:100 over 15 minutes) to provide the title compound: $^1$H NMR (300 MHz, CD$_3$OD) δ ppm 1.64-1.90 (m, 2H), 2.18 (t, J=10.3 Hz, 1H), 2.32 (dt, J=10.8, 3.1 Hz, 1H), 2.67 (d, J=10.5 Hz, 1H), 2.81 (d, J=10.8 Hz, 1H), 2.90-3.12 (m, 2H), 3.18-3.44 (m, 7H), 3.47-3.60 (m, 3H), 3.67 (td, J=8.4, 2.9 Hz, 2H), 6.85 (dd, J=7.8, 5.1 Hz, 1H), 7.00-7.10 (m, 2H), 7.12-7.18 (m, 1H), 7.31-7.42 (m, 2H), 7.72 (dd, J=4.9, 1.5 Hz, 1H); MS (DCI) m/z 382 (M+H)$^+$.

Example 70

6-(4-bromobenzyl)-2,3,4,4a,6,7-hexahydropyrazino[1,2-a][1,4]benzodiazepin-5(1H)-one The product of Example 67 (109.4 mg, 0.23 mmol) was dissolved in dichloromethane (3 mL), and treated with trifluoroacetic acid (0.5 mL, 6.5 mmol) for 1 hour at ambient temperature. The reaction was concentrated and purify by preparative HPLC using the method described in Example 4 to give the title compound: $^1$H NMR (500 MHz, pyridine-d$_5$) δ ppm 2.97-3.03 (m, 2H), 3.08-3.15 (m, 1H), 3.37 (dd, J=12.4, 8.4 Hz, 1H), 3.58 (dd, J=12.4, 2.6 Hz, 1H), 3.98 (dd, J=8.4, 2.9 Hz, 1H), 4.20 (d, J=14.6 Hz, 1H), 4.72-7.85 (m, 3H), 3.91-6.95 (m, 1H), 6.98-6.99 (m, 1H), 7.05 (d, J=7.6 Hz, 1H), 7.25-7.26 (m, 2H), 7.30-7.33 (m, 1H), 7.48-7.51 (m, 2H); MS (DCI/NH$_3$) m/z 386 (M+H)$^+$.

Example 71

6-(4-bromobenzyl)-1,2,3,4,4a,5,6,7-octahydropy-razino[1,2-a][1,4]benzodiazepine

The product of Example 66 (79.5 mg, 0.17 mmol) was dissolved in dichloromethane (3 mL), and treated with trifluoroacetic acid (0.5 mL, 6.5 mmol) for 1 hour at ambient temperature. The reaction was concentrated and purify by preparative HPLC using the method described in Example 9 to give the title compound as the tris-trifluoroacetic acid salt: $^1$H NMR (500 MHz, pyridine-d$_5$) δ ppm 2.57-2.67 (m, 2H), 3.43-3.51 (m, 3H), 3.58-3.61 (m, 1H), 3.66-3.76 (m, 6H), 4.24 (d, J=13.1 Hz, 1H), 6.92 (d, J=7.9 Hz, 1H), 7.09 (td, J=7.3, 0.9 Hz, 1H), 7.18 (dd, J=7.3, 1.5 Hz, 1H), 7.30-7.32 (m, 2H), 7.36 (td, J=7.6, 1.5 Hz, 1H), 7.53-7.56 (m, 2H); MS (DCI/NH$_3$) m/z 372 (M+H)$^+$. Elemental analysis calculated for $C_{19}H_{22}BrN_3$.3 TFA: C, 42.03; H, 3.53; N, 5.88; F, 23.94. Found: C, 42.10; H, 3.44; N, 5.82; F, 23.80.

Example 72 cyclopropyl(7,7a,8,9,10,11-hexahydropyrazino[1,2-d]pyrido[3,2-b][1,4]diazepin-5(6H)-yl)methanone

Example 72A tert-butyl 6,7,7a,8,10,11-hexahydropyrazino[1,2-d]pyrido[3,2-b][1,4]diazepine-9 (5H)-carboxylate A solution of alane-N,N-dimethylethylamine complex (0.5 M in toluene, 5.0 mL, 2.50 mmol) was added dropwise over 2 minutes to a solution of the product of Example 64A (506 mg, 1.59 mmol) in dry tetrahydrofuran (22 mL). The reaction was stirred at room temperature for 5 hours. Additional portions of alane-N,N-dimethylethylamine complex (0.5 M in toluene, 5.0 mL, 2.50 mmol) were added after 1 hour, and again after 4 hours. Methanol (10 mL) was added, followed after 10 minutes by water (20 mL) and 25% NaOH (3 mL). The mixture was stirred for 10 minutes, and the aqueous layer was separated and extracted with ethyl acetate (30 mL). The combined organic phases were washed with brine, dried (Na$_2$SO$_4$) and concentrated under vacuum. The residue was purified by chromatography (SiO$_2$, eluted with ethyl acetate-ethanol, 90:10) to provide the title compound: $^1$H NMR (300 MHz, CDCl$_3$) δ ppm 1.48 (s, 9H), 1.73-1.88 (m, 1H), 1.90-2.07 (m, 1H), 3.17-3.40 (m, 2H), 3.40-3.83 (m, 7H), 6.67 (dd, J=7.8, 4.8 Hz, 1H), 6.76 (d, J=7.8 Hz, 1H), 7.75 (dd, J=4.7, 1.7 Hz, 1H); MS (DCI) m/z 305 (M+H)$^+$.

Example 72B tert-butyl 5-(cyclopropylcarbonyl)-6,7,7a,8,10,11-hexahydropyrazino[1,2-d]pyrido[3,2-b][1,4]diaz-epine-9(5H)-carboxylate A solution of cyclopropylcarbonyl chloride (0.072 mL, 0.79 mmol) CH$_2$Cl$_2$ (1 mL) was added to an ice-cooled solution of the product of Example 72A (218 mg, 0.716 mmol) in CH$_2$Cl$_2$ (5 mL). The reaction was stirred with ice cooling under nitrogen for 45 minutes and then it was allowed to warm to room temperature for 4 hours. The reaction was quenched by addition of methanol (2 mL) and the solution was stirred for 10 minutes. The reaction mixture was then concentrated under vacuum. The residue was purified by HPLC (30×100 mm, C18, Waters XBridge™ column eluted with 0.1 M aqueous (NH$_4$)$_2$CO$_3$-methanol, 80:20-0:100 over 15 minutes) to provide the title compound: MS (DCI) m/z 373 (M+H)$^+$.

Example 72C cyclopropyl(7,7a,8,9,10,11-hexahydropyrazino[1,2-d]pyrido[3,2-b][1,4]diazepin-5(6H)-yl)methanone A solution of HCl (4 M in dioxane, 250 μl, 1 mmol) was added to a solution of the product of Example 72B (26.3 mg, 0.071 mmol) in CH$_2$Cl$_2$ (1.3 mL), and the mixture was stirred at room temperature for 70 hours. The mixture was concentrated under vacuum, and the residue was crystallized from ethyl acetate-ethanol (4 mL, 2:1) to provide the title compound as the bis-hydrochloride salt: $^1$H NMR (400 MHz, pyridine-d$_5$, 110° C.) δ ppm 0.41 (dd, J=7.8, 3.5 Hz, 2H), 0.85-0.97 (m, 2H), 1.06-1.21 (m, 1H), 1.51-1.64 (m, 1H), 1.66-1.77 (m, 1H), 2.91 (t, J=11.0 Hz, 1H), 3.25-3.45 (m, 3H), 3.53-4.09 (m, 5H), 6.77 (dd, J=7.6, 4.9 Hz, 1H), 7.37 (dd, J=7.6, 1.5 Hz, 1H), 8.16 (dd, J=4.6, 1.5 Hz, 1H); MS (DCI) m/z 273 (M+H)$^+$. Elemental analysis is calculated for $C_{15}H_{20}N_4O$.2 HCl.0.5H$_2$O.0.4 EtOAc: C, 51.19; H, 6.78; N, 14.38. Found: C, 51.23; H, 6.57; N, 14.12.

Example 73

6-(4-bromobenzyl)-3-(4-fluorobenzyl)-2,3,4,4a,6,7-hexahydropyrazino[1,2-a][1,4]benzodiazepin-5(1H)-one The product of Example 70 (84.2 mg, 0.22 mmol) and 4-fluorobenzaldehyde (48.7 mg, 0.39 mmol) were processed according to the procedure for Example 17 and purified by preparative HPLC using the method described in Example 9 to give the title compound as the trifluoroacetic acid salt: $^1$H NMR (400 MHz, benzene-d$_6$) δ ppm 2.29 (td, J=11.1, 2.8 Hz, 1H), 2.67 (t, J=10.5 Hz, 1H), 2.86-2.89 (m, 1H), 3.04 (dt, J=11.3, 2.6 Hz, 1H), 3.19 (td, J=11.2, 2.6 Hz, 1H), 3.48-3.51 (m, 1H), 3.57-3.62 (m, 2H), 3.96 (d, J=13.7 Hz, 1H), 4.04 (dd, J=10.4, 2.2 Hz, 1H), 4.72-7.85 (m, 2H), 5.03 (d, J=14.0 Hz, 1H), 6.95-7.01 (m, 2H), 7.06 (d, J=7.9 Hz, 1H), 7.10-7.14 (m, 2H), 7.25-7.29 (m, 2H), 7.30-7.35 (m, 1H), 7.39-7.43 (m, 2H), 7.49-7.52 (m, 2H); MS (DCI/NH$_3$) m/z 494 (M+H)$^+$. Elemental analysis calculated for $C_{26}H_{25}BrFN_3O$.1.1 TFA: C, 54.65; H, 4.24; N, 6.78. Found: C, 54.82; H, 4.01; N, 6.68.

Example 74

[5-(cyclopropylmethyl)-6,7,7a,8,10,11-hexahydropyrazino[1,2-d]pyrido[3,2-b][1,4]diazepin-9(5H)-yl](pyridin-3-yl)methanone

Example 74A 5-(cyclopropylmethyl)-5,6,7,7a,8,9,10,11-octahydropyrazino[1,2-d]pyrido[3,2-b][1,4]diazepine A solution alane-N,N-dimethylethylamine (0.5 M in toluene, 2.84 mL, 1.42 mmol) was added under nitrogen to an ice-cooled solution of the product of Example 72B (176 mg, 0.473 mmol) in tetrahydrofuran (8 mL). The reaction was stirred with ice cooling for 15 minutes and then warmed to room temperature and stirred for 30 minutes. Methanol (1 mL) was added followed after 5 minutes by addition of 25% NaOH (1 mL). The mixture was stirred for 10 minutes and then concentrated under vacuum. The residue was taken up with brine (10 mL) and extracted with $CH_2Cl_2$ (2×20 mL). The combined organic phases were dried ($Na_2SO_4$) and concentrated under vacuum. The residue was dissolved in $CH_2Cl_2$ (5 mL) and stirred with ice cooling under nitrogen for 10 minutes. Trifluoroacetic acid (1.0 mL, 13 mmol) was added gradually over 0.5 minute, and the reaction was stirred with ice cooling for 1 hour and then warmed to room temperature for 1 hour. The solution was concentrated under vacuum, and the residue was purified by HPLC (30×100 mm, C18, Waters XBridge™ column eluted with 0.1 M aqueous $(NH_4)_2CO_3$-methanol, 80:20-0:100 over 15 minutes) to provide the title compound: $^1$H NMR (300 MHz, $CD_3OD$) δ ppm 0.18-0.27 (m, 2H), 0.51-0.60 (m, 2H), 0.93-1.09 (m, 1H), 1.67-1.80 (m, 1H), 1.80-1.94 (m, 1H), 2.73-2.86 (m, 2H), 2.87-3.04 (m, 4H), 3.11-3.28 (m, 3H), 3.41-3.51 (m, 2H), 6.84 (dd, J=7.8, 5.1 Hz, 1H), 7.12 (dd, J=8.0, 1.5 Hz, 1H), 7.70 (dd, J=5.1, 1.7 Hz, 1H); MS (DCI) m/z 259 (M+H)$^+$.

Example 74B

[5-(cyclopropylmethyl)-6,7,7a,8,10,11-hexahydropyrazino[1,2-d]pyrido[3,2-b][1,4]diazepin-9(5H)-yl] (pyridin-3-yl)methanone Nicotinoyl chloride hydrochloride (58.2 mg, 0.317 mmol) was added at room temperature to a solution of the product of Example 74A (82 mg, 0.317 mmol) in $CH_2Cl_2$ (4 mL) and triethylamine (0.111 mL, 0.793 mmol). The mixture was stirred at room temperature for 30 minutes and then concentrated under vacuum. The residue was purified by HPLC (30×100 mm, C18, Waters XBridge™ column eluted with 0.1 M aqueous $(NH_4)_2CO_3$-methanol, 40:60-0:100 over 15 minutes) to provide the title compound: $^1$H NMR (400 MHz, DMSO-$d_6$) δ ppm 0.16-0.21 (m, 2H), 0.45-0.54 (m, 2H), 0.93-1.03 (m, 1H), 1.61-1.75 (m, 1H), 1.79-1.91 (m, 1H), 2.90-3.05 (m, 2H), 3.19-3.30 (m, 2H), 3.34-3.50 (m, 4H), 3.54-3.64 (m, 1H), 3.71-3.92 (m, 2H), 6.74 (dd, J=7.8, 4.7 Hz, 1H), 7.00 (dd, J=7.9, 1.5 Hz, 1H), 7.45 (ddd, J=7.9, 4.9, 0.9 Hz, 1H), 7.65 (dd, J=4.6, 1.5 Hz, 1H), 7.83 (ddd, J=8.1, 2.0, 1.8 Hz, 1H), 8.58-8.67 (m, 2H); MS (ESI) m/z 364 (M+H)$^+$.

Example 75

1,2,3,4,4a,5-hexahydropyrazino[1,2-a][1,4]benzodiazepin-6(7H)-yl(morpholin-4-yl)methanone To the product of Example 14 (1.05 g, 2.58 mmol) and ethanol (20 ml) was added 20% Pd(OH)$_2$/C, wet (0.210 g, 1.495 mmol) in a 50 mL pressure bottle. The reaction was stirred for 1 hour at 30 psi (H$_2$) and 50° C. The mixture was filtered through a nylon membrane and concentrated to give the title compound: $^1$H NMR (400 MHz, pyridine-$d_5$) δ ppm 2.95-3.05 (m, 5H), 3.12-3.14 (m, 2H), 3.18-3.24 (m, 3H), 3.34-3.40 (m, 2H), 3.64-3.68 (m, 2H), 3.72-3.84 (m, 3H), 4.48 (d, J=12.8 Hz, 1H), 4.87 (d, J=12.8 Hz, 1H), 6.95 (dd, J=7.9, 0.9 Hz, 1H), 7.03 (td, J=7.4, 1.1 Hz, 1H), 7.26 (dd, J=7.5, 1.4 Hz, 1H), 7.37 (dd, J=7.6, 1.5 Hz, 1H); (MS (DCI/NH$_3$) m/z 317 (M+H)$^+$.

Example 76

[3-(4-fluorobenzyl)-1,2,3,4,4a,5-hexahydropyrazino [1,2-a][1,4]benzodiazepin-6(7H)-yl](morpholin-4-yl) methanone The product of Example 75 (82.2 mg, 0.26 mmol) and 4-fluorobenzaldehyde (49.9 mg, 0.40 mmol) were processed according to the procedure for Example 17 and purified by preparative HPLC using the method described in Example 4 to give the title compound: $^1$H NMR (500 MHz, pyridine-$d_5$) δ ppm 2.33 (td, J=10.1=2, 3.2 Hz, 1H), 2.43-2.47 (m, 1H), 2.73-2.77 (m, 2H), 3.11-3.24 (m, 6H), 3.35-3.39 (m, 2H), 3.39-3.50 (m, 2H), 3.65-3.68 (m, 2H), 3.73-3.76 (m, 2H), 3.85 (dd, J=14.5, 3.8 Hz, 1H), 4.50 (d, J=13.2 Hz, 1H), 4.86 (d, J=12.8 Hz, 1H), 6.98 (d, J=7.6 Hz, 1H), 7.04 (td, J=7.5, 0.9 Hz, 1H), 7.14-7.18 (m, 2H), 7.27 (dd, J=7.3, 1.2 Hz, 1H), 7.36 (td, J=7.7, 1.4 Hz, 1H), 7.39-7.41 (m, 2H); MS (DCI/NH$_3$) m/z 425 (M+H)$^+$. Elemental analysis calculated for $C_{24}H_{29}FN_4O_2 \cdot 0.15H_2O$: C, 67.47; H, 6.91; N, 13.11. Found: C, 67.13; H, 6.52; N, 12.96.

Example 77

(3-methyl-1,2,3,4,4a,5-hexahydropyrazino[1,2-a][1,4]benzodiazepin-6(7H)-yl)(morpholin-4-yl)methanone The product of Example 75 (120.6 mg, 0.38 mmol) was dissolved in formic acid (4 mL). A solution of formaldehyde (36 weight %, 1 mL) was added, and the reaction was heated to 100° C. for 1 hour. The reaction was concentrated and purified by preparative HPLC using the method described in Example 4 to give the title compound: $^1$H NMR (500 MHz, pyridine-$d_5$) δ ppm 2.22 (s, 3H), 2.24-2.36 (m, 2H), 2.65-2.68 (m, 2H), 3.09-3.21 (m, 2H), 3.23-3.25 (m, 4H), 3.38-3.41 (m, 2H), 3.68-3.70 (m, 2H), 3.74-3.76 (m, 2H), 3.83-3.88 (m, 1H), 4.50 (d, J=12.8 Hz, 1H), 4.84 (d, J=12.8 Hz, 1H), 6.95-7.96 (m, 1H), 7.04 (td, J=7.4, 1.1 Hz, 1H), 7.26 (dd, J=7.3, 1.5 Hz, 1H), 7.36 (td, J=7.6, 1.5 Hz, 1H); MS (DCI/NH$_3$) m/z 331 (M+H)$^+$.

Example 78

2-[2-(3-benzyl-2,3,4,4a,5,6-hexahydropyrazino[1,2-a][1,5]benzodiazepin-7(1H)-yl)-2-oxoethyl]pyridazin-3(2H)-one A solution of the product of Example 26 (167 mg, 0.569 mmol) and 2-(6-oxopyridazin-1(6H)-yl)acetic acid (95 mg, 0.616 mmol, prepared as described in King, J. A., et al. J. Am. Chem. Soc. 1952, 74, 3222-3224) in tetrahydrofuran (15 mL) and diisopropylethylamine (0.151 mL, 0.867 mmol) was cooled in ice-water under nitrogen. Solid O-(7-azabenzotriazol-1-yl)-N,N,N',N'-tetramethyluronium hexafluorophosphate (302 mg, 0.794 mmol) was added all at once, and the mixture was stirred with ice cooling for 1 hour and then allowed to warm to room temperature. After 65 hours, the reaction mixture was concentrated under vacuum, and the residue was purified by HPLC (30×100 mm, C18, Waters XBridge™ column eluted with aqueous $(NH_4)_2CO_3$-methanol, 80:20-0:100 over 15 minutes) to provide the title compound: $^1$H NMR (400 MHz, pyridine-$d_5$) δ ppm 1.24-1.90 (m, 2H), 2.20-2.92 (m, 5H), 2.98-3.19 (m, 2H), 3.33-3.50 (m, 2H), 3.50-3.78 (m, 1H), 4.29-4.82 (m, 2H), 5.03-5.22 (m, 1H), 6.87-7.19 (m, 4H), 7.26-7.48 (m, 7H), 7.71-7.80 (m, 1H); MS (ESI) m/z 430 (M+H)$^+$. Elemental analysis is calculated for $C_{25}H_{27}N_5O_2 \cdot 0.1$ EtOAc: C, 69.60; H, 6.39; N, 15.98. Found: C, 69.69; H, 6.33; N, 16.02.

Example 79

(3-benzoyl-1,2,3,4,4a,5-hexahydropyrazino[1,2-a][1,4]benzodiazepin-6(7H)-yl)(morpholin-4-yl)methanone The product of Example 75 (105.8 mg, 0.33 mmol) and benzoyl chloride (69.5 mg, 0.49 mmol) were processed according to the procedure for Example 4 to give the title compound: $^1$H NMR (500 MHz, pyridine-$d_5$) δ ppm 3.02-3.37 (m, 10H), 3.49-3.53 (m, 1H), 3.64-3.88 (m, 6H), 4.48 (d, J=12.8 Hz, 1H), 4.84 (d, J=12.2 Hz, 1H), 6.96 (d, J=7.9 Hz, 1H), 7.07 (td, J=7.3, 0.9 Hz, 1H), 7.29 (d, J=7.3 Hz, 1H), 7.37 (t, J=7.8 Hz, 1H), 7.42-7.46 (m, 3H), 7.67-7.68 (m, 2H); MS (DCI/NH$_3$) m/z 421 (M+H)$^+$. Elemental analysis calculated for $C_{24}H_{28}N_4O_3 \cdot 0.25H_2O$: C, 67.82; H, 6.76; N, 13.18. Found: C, 67.66; H, 6.54; N, 13.31.

Example 80 morpholin-4-yl[3-(pyrimidin-2-yl)-1,2,3,4,4a,5-hexahydropyrazino[1,2-a][1,4]benzodiazepin-6(7H)-yl]methanone The product of Example 75 (77.6 mg, 0.33 mmol) and 2-chloropyrimidine (77.6 mg, 0.68 mmol) were processed according to the procedure for Example 9. The reaction was purified by preparative HPLC using the method described in Example 4 to give the title compound: $^1$H NMR (500 MHz, pyridine-$d_5$) δ ppm 3.06-3.08 (m, 1H), 3.17-3.26 (m, 4H), 3.27-3.38 (m, 3H), 3.45-3.49 (m, 1H), 3.60-3.72 (m, 5H), 3.86 (dd, J=14.3, 4.6 Hz, 1H), 4.52 (d, J=13.1 Hz, 1H), 4.57-4.63 (m, 2H), 4.82 (d, J=13.1 Hz, 1H), 6.52 (t, J=4.7 Hz, 1H), 6.96 (d, J=7.9 Hz, 1H), 7.06 (td, J=7.4, 1.1 Hz, 1H), 7.28 (dd, J=7.5, 1.4 Hz, 1H), 7.36 (td, J=7.6, 1.5 Hz, 1H), 8.44 (d, J=4.6 Hz, 2H); MS (DCI/NH$_3$) m/z 395 (M+H)$^+$. Elemental analysis calculated for $C_{21}H_{26}N_6O_2 \cdot 0.3H_2O$: C, 63.08; H, 6.70; N, 21.02. Found: C, 63.12; H, 6.84; N, 20.94.

Example 81 morpholin-4-yl[3-(phenylsulfonyl)-1,2,3,4,4a,5-hexahydropyrazino[1,2-a][1,4]benzodiazepin-6(7H)-yl]methanone The product of Example 75 (104.5 mg, 0.33 mmol) was dissolved in dichloromethane (3 mL). Triethylamine (0.1 mL, 0.72 mmol) and benzenesulfonyl chloride (92.0 mg, 0.52 mmol) were added, and the reaction mixture was stirred at ambient temperature for 1 hour. The reaction was concentrated and purified by preparative HPLC using the method described in Example 4 to give the title compound: $^1$H NMR (500 MHz, pyridine-$d_5$) δ ppm 2.78-2.82 (m, 1H), 2.85-2.89 (m, 1H), 3.38-3.09 (m, 1H), 3.16-3.25 (m, 5H), 3.32-3.36 (m, 2H), 3.64-3.73 (m, 2H), 3.73-3.77 (m, 3H), 3.82-3.84 (m, 1H), 3.94 (dd, J=14.7, 3.7 Hz, 1H), 4.34 (d, J=12.8 Hz, 1H), 4.63 (d, J=12.8 Hz, 1H), 6.90 (d, J=7.9 Hz, 1H), 7.04 (td, J=7.3, 0.9 Hz, 1H), 7.21-7.22 (m, 1H), 7.32 (td, J=7.6, 1.5 Hz, 1H), 7.53-7.58 (m, 3H), 7.97-7.99 (m, 2H); MS (DCI/NH$_3$) m/z 457 (M+H)$^+$.

Example 82

[3-(4-chlorophenyl)-1,2,3,4,4a,5-hexahydropyrazino[1,2-a][1,4]benzodiazepin-6(7H)-yl](morpholin-4-yl)methanone The product of Example 75 (101.4 mg, 0.32 mmol) was dissolved in toluene (3 mL). 4-Bromochlorobenzene (93.8 mg, 0.49 mmol), tris(dibenzylideneacetone)-dipalladium (15.1 mg, 0.016 mmol), 2,2'-bis(diphenylphosphino)-1,1'-binaphthyl (34.0 mg, 0.055 mmol) and sodium tert-butoxide (95.0 mg, 0.99 mmol) were added. The reaction mixture was heated to 90° C. for 23 hours under nitrogen. The reaction treated with water (35 mL) and extract with ethyl acetate (3×35 mL). The combined organic extracts were washed with brine (25 mL), dried over MgSO$_4$, filtered and concentrated. The residue was purified by preparative HPLC using the method described in Example 4 to give the title compound: $^1$H NMR (400 MHz, pyridine-$d_5$) δ ppm 2.97-3.03 (m, 1H), 3.10-3.16 (m, 2H), 3.22-3.34 (m, 5H), 3.38-3.44 (m, 2H), 3.54-3.57 (m, 1H), 3.60-3.62 (m, 1H), 3.66-3.71 (m, 2H), 3.73-3.78 (m, 2H), 3.93 (dd, J=14.3, 3.4 Hz, 1H), 4.53 (d, J=12.8 Hz, 1H), 4.83 (d, J=12.5 Hz, 1H), 6.93-6.99 (m, 3H), 7.07 (td, J=7.3, 0.9 Hz, 1H), 7.29 (dd, J=7.5, 1.4 Hz, 1H), 7.35-7.41 (m, 3H); MS (DCI/NH$_3$) m/z 427 (M+H)$^+$. Elemental analysis calculated for $C_{23}H_{27}ClN_4O_2$: C, 64.70; H, 6.37; N, 13.12. Found: C, 64.57; H, 6.29; N, 13.24.

Example 83

1-[6-(morpholin-4-ylcarbonyl)-1,2,4a,5,6,7-hexahydropyrazino[1,2-a][1,4]benzodiazepin-3(4H)-yl]ethanone The product of Example 75 (193.9 mg, 0.61 mmol) and acetic anhydride (188.7 mg, 1.85 mmol) were processed according to the procedure for Example 4 to give the title compound: $^1$H NMR (500 MHz, pyridine-$d_5$) δ ppm (2:1 mixture of rotomers) 2.12 (s, 1H), 2.15 (s, 2H), 2.93-3.43 (m, 10H), 3.61-3.86 (m, 6H), 4.37-4.55 (m, 2H), 4.76-4.81 (m, 1H), 6.92-6.95 (m, 1H), 7.05-7.08 (m, 1H), 7.28-7.29 (m, 1H), 7.34-7.38 (m, 1H) ppm; MS (DCI/NH$_3$) m/z 359 (M+H)$^+$. Elemental analysis calculated for $C_{19}H_{26}N_4O_3 \cdot 0.5H_2O$: C, 62.11; H, 7.41; N, 15.25. Found: C, 62.11; H, 7.39; N, 15.21.

Example 84

1-{4-[(3-benzyl-1,2,3,4,4a,5-hexahydropyrazino[1,2-a][1,4]benzodiazepin-6(7H)-yl)carbonyl]piperidin-1-yl}ethanone To a solution of 3-benzyl-1,2,3,4,4a,5,6,7-octahydropyrazino[1,2-a][1,4]benzodiazepine (44 mg, 0.15 mmol, Example 2) in dimethylacetamide (1.0 mL) was added 1-acetylpiperidine-4-carboxylic acid (31 mg, 0.18 mmol) dissolved in a solution of dimethylacetamide (0.6 mL), followed by triethylamine (21 μL, 0.20 mmol) and O-(7-azabenzotriazol-1-yl)-N,N,N',N'-tetramethyluronium hexafluorophosphate (57 mg, 0.15 mmol). The reaction mixture was shaken at 60° C. overnight. The reaction was filtered, checked by LC/MS and concentrated to dryness. Purification of the residue via HPLC afforded the title compound as the trifluoroacetic acid salt. $^1$H NMR (500 MHz, pyridine-$d_5$) δ ppm 1.72-1.93 (m, 3H), 2.05 (s, 3H), 2.30-2.47 (m, 2H), 2.81-3.09 (m, 8H), 3.18-3.37 (m, 2H), 3.53-3.85 (m, 3H), 4.64 (d, J=23.50 Hz, 2H), 4.72-4.89 (m, 1H), 6.94-7.11 (m, 2H), 7.19-7.40 (m, 6H), 7.41-7.50 (m, 2H); MS (ESI+) m/z 447 (M+H)+.

Example 85

(3-benzyl-1,2,3,4,4a,5-hexahydropyrazino[1,2-a][1,4]benzodiazepin-6(7H)-yl)(1H-pyrazol-4-yl)methanone The title compound was prepared as the trifluoroacetic acid salt according to the procedure outlined in Example 84 substituting 1H-pyrazole-4-carboxylic acid for 1-acetylpiperidine-4-carboxylic acid. $^1$H NMR (500 MHz, pyridine-$d_5$) δ ppm 2.26-2.66 (m, 2H), 2.88 (d, J=10.68 Hz, 2H), 3.01-3.17 (m, 2H), 3.20-3.39 (m, 4H), 3.52-3.72 (m, 3H), 4.80 (d, J=13.12 Hz, 1H), 5.05 (d, J=13.12 Hz, 1H), 6.91-7.12 (m, 4H), 7.22-7.49 (m, 6H); MS (ESI+) m/z 388 (M+H)$^+$.

Example 86

(3-benzyl-1,2,3,4,4a,5-hexahydropyrazino[1,2-a][1,4]benzodiazepin-6(7H)-yl)(1H-pyrazol-5-yl)methanone The title compound was prepared as the trifluoroacetic acid salt according to the procedure outlined in Example 84 substituting 1H-pyrazole-5-carboxylic acid for 1-acetylpiperidine-4-carboxylic acid. $^1$H NMR (500 MHz, pyridine-$d_5$) δ ppm 2.25 (dd, 2H), 2.49 (dd, 2H), 2.81 (dd, J=10.83, 1.37 Hz, 2H), 3.12 (s, 4H), 3.27-3.61 (m, 3H), 6.87-7.13 (m, 3H), 7.20-7.35 (m, 2H), 7.27-7.48 (m, 6H), 7.79 (d, J=1.83 Hz, 1H); MS (ESI+) m/z 388 (M+H)$^+$.

Example 87

1-(3-benzyl-1,2,3,4,4a,5-hexahydropyrazino[1,2-a][1,4]benzodiazepin-6(7H)-yl)-2-(morpholin-4-yl)ethanone The title compound was prepared as the trifluoroacetic acid salt according to the procedure outlined in Example 84 substituting 2-morpholinoacetic acid for 1-acetylpiperidine-4-carboxylic acid. $^1$H NMR (500 MHz, pyridine-$d_5$) δ ppm 2.31-2.55 (m, 4H), 2.70 (s, 4H), 2.83-3.15 (m, 3H), 3.19-3.41 (m, 6H), 3.69 (d, J=49.44 Hz, 6H), 4.75 (d, 2H), 6.99 (d, J=7.93 Hz, 2H), 7.22-7.52 (m, 6H),); MS (ESI+) m/z 421 (M+H)$^+$.

Example 88

(3-benzyl-1,2,3,4,4a,5-hexahydropyrazino[1,2-a][1,4]benzodiazepin-6(7H)-yl)(1,3-thiazol-4-yl)methanone The title compound was prepared as the trifluoroacetic acid salt according to the procedure outlined in Example 84 substituting thiazole-4-carboxylic acid for 1-acetylpiperidine-4-carboxylic acid. $^1$H NMR (500 MHz, pyridine-$d_5$) δ ppm 2.40 (s, 2H), 2.91 (d, J=10.99 Hz, 2H), 3.14 (s, 2H), 3.25 (dd, J=10.99, 2.14 Hz, 2H), 3.59 (d, 4H), 4.57 (d, J=14.34 Hz, 1H), 4.77-5.01 (m, 2H), 6.90-7.12 (m, 2H), 7.22-7.46 (m, 7H); MS (ESI+) m/z 405 (M+H)$^+$.

Example 89

(3-benzyl-1,2,3,4,4a,5-hexahydropyrazino[1,2-a][1,4]benzodiazepin-6(7H)-yl)(1,3-thiazol-5-yl)methanone The title compound was prepared as the trifluoroacetic acid salt according to the procedure outlined in Example 84 substituting thiazole-5-carboxylic acid for 1-acetylpiperidine-4-carboxylic acid. $^1$H NMR (500 MHz, pyridine-$d_5$) δ ppm 2.28-2.63 (m, 2H), 2.85 (d, J=10.99 Hz, 2H), 2.92-3.18 (m, 3H), 3.18-3.37 (m, 2H), 3.50 (s, 1H), 3.56 (s, 2H), 4.76 (d, J=13.73 Hz, 1H), 4.98 (d, J=13.43 Hz, 1H), 6.91-7.13 (m, 2H), 7.22-7.50 (m, 7H); MS (ESI+) m/z 405 (M+H)$^+$.

Example 90

(3-benzyl-1,2,3,4,4a,5-hexahydropyrazino[1,2-a][1,4]benzodiazepin-6(7H)-yl)(1,2-oxazol-5-yl)methanone The title compound was prepared as the trifluoroacetic acid salt according to the procedure outlined in Example 84 substituting isooxazole-5-carboxylic acid for 1-acetylpiperidine-4-carboxylic acid. $^1$H NMR (500 MHz, pyridine-$d_5$) δ ppm 2.33 (d, 1H), 2.83 (d, 2H), 2.89-3.39 (m, 6H), 3.56 (dd, 4H), 4.57-5.03 (m, 1H), 6.81-7.10 (m, 2H), 7.22-7.52 (m, 7H); MS (ESI+) m/z 389 (M+H)$^+$.

Example 91

1-(3-benzyl-1,2,3,4,4a,5-hexahydropyrazino[1,2-a][1,4]benzodiazepin-6(7H)-yl)-3-(pyrrolidin-1-yl)propan-1-one The title compound was prepared as the trifluoroacetic acid salt according to the procedure outlined in Example 84 substituting 3-(pyrrolidin-1-yl)propanoic acid for 1-acetylpiperidine-4-carboxylic acid. $^1$H NMR (500 MHz, pyridine-$d_5$) δ ppm 1.80-2.12 (m, 4H), 2.27-2.47 (m, 2H), 2.71-3.12 (m, 5H), 3.22 (d, J=23.80 Hz, 2H), 3.40 (d, J=4.88 Hz, 4H), 3.52 (d, J=14.34 Hz, 2H), 3.59-3.78 (m, 4H), 4.59 (d, J=13.12 Hz, 1H), 4.63-4.86 (m, 1H), 6.90-7.08 (m, 2H), 7.27 (t, J=6.41 Hz, 3H), 7.29-7.41 (m, 2H), 7.43 (d, J=7.32 Hz, 2H); MS (ESI+) m/z 419 (M+H)$^+$.

Example 92

1-(3-benzyl-1,2,3,4,4a,5-hexahydropyrazino[1,2-a][1,4]benzodiazepin-6(7H)-yl)-2-cyclopropylethanone The title compound was prepared as the trifluoroacetic acid salt according to the procedure outlined in Example 84 substituting 2-cyclopropylacetic acid for 1-acetylpiperidine-4-carboxylic acid. $^1$H NMR (500 MHz, pyridine-$d_5$) δ ppm 0.24 (s, 2H), 0.54 (d, J=7.63 Hz, 2H), 1.04-1.45 (m, 1H), 2.51 (s, 4H), 2.75-3.36 (m, 6H), 3.60 (s, 3H), 4.64 (d, 2H), 6.98 (d, J=7.63 Hz, 2H), 7.27 (d, J=7.02 Hz, 2H), 7.27-7.38 (m, 2H), 7.44 (d, J=7.32 Hz, 2H); MS (ESI+) m/z 376(M+H)$^+$.

Example 93

(3-benzyl-1,2,3,4,4a,5-hexahydropyrazino[1,2-a][1,4]benzodiazepin-6(7H)-yl)(1H-pyrrol-2-yl)methanone The title compound was prepared as the trifluoroacetic acid salt according to the procedure outlined in Example 84 substituting 1H-pyrrole-2-carboxylic acid for 1-acetylpiperidine-4-carboxylic acid. $^1$H NMR (500 MHz, pyridine-d$_5$) δ ppm 2.21-2.43 (m, 1H), 2.38-2.60 (m, 2H), 2.82 (dd, J=17.55, 10.83 Hz, 2H), 3.00-3.16 (m, 2H), 3.20 (dd, J=10.38, 3.05 Hz, 2H), 3.33-3.48 (m, 1H), 3.46-3.60 (m, 2H), 4.54 (dd, J=14.65, 3.36 Hz, 1H), 4.85 (d, J=13.12 Hz, 1H), 5.11 (d, J=13.12 Hz, 1H), 6.29-6.52 (m, 1H), 6.80 (d, J=3.05 Hz, 1H), 6.91-7.08 (m, 2H), 7.22-7.36 (m, 4H), 7.33-7.48 (m, 2H); MS (ESI+) m/z 387(M+H)$^+$.

Example 94

(3-benzyl-1,2,3,4,4a,5-hexahydropyrazino[1,2-a][1,4]benzodiazepin-6(7H)-yl)(3-furyl)methanone The title compound was prepared as the trifluoroacetic acid salt according to the procedure outlined in Example 84 substituting furan-3-carboxylic acid for 1-acetylpiperidine-4-carboxylic acid. $^1$H NMR (500 MHz, pyridine-d$_5$) δ ppm 2.29-2.66 (m, 2H), 2.86 (d, J=10.99 Hz, 4H), 2.98-3.18 (m, 2H), 3.15-3.37 (m, 2H), 3.53 (d, J=26.55 Hz, 3H), 4.72 (d, J=13.43 Hz, 1H), 4.94 (d, J=13.43 Hz, 1H), 6.81 (s, 1H), 6.92-7.14 (m, 2H), 7.27 (d, J=7.32 Hz, 2H), 7.33 (t, J=7.63 Hz, 2H), 7.37-7.50 (m, 2H); MS (ESI+) m/z 388(M+H)$^+$.

Example 95

(3-benzyl-1,2,3,4,4a,5-hexahydropyrazino[1,2-a][1,4]benzodiazepin-6(7H)-yl)(1,2,5-trimethyl-1H-pyrrol-3-yl)methanone The title compound was prepared as the trifluoroacetic acid salt according to the procedure outlined in Example 84 substituting 1,2,5-trimethyl-1H pyrrole-3-carboxylic acid for 1-acetylpiperidine-4-carboxylic acid. $^1$H NMR (500 MHz, pyridine-d$_5$) δ ppm 2.07 (s, 3H), 2.30 (s, 3H), 2.34-2.55 (m, 2H), 2.71 (d, J=10.38 Hz, 1H), 2.80-2.92 (m, 1H), 3.01 (d, J=6.10 Hz, 1H), 3.01 (d, J=6.10 Hz, 1H), 3.20-3.39 (m, 6H), 3.50 (s, 1H), 3.52-3.68 (m, 2H), 4.76 (d, J=13.43 Hz, 1H), 4.98 (d, J=13.43 Hz, 1H), 5.99 (s, 1H), 6.88-7.08 (m, 2H), 7.21-7.29 (m, 2H), 7.29-7.36 (m, 2H), 7.37-7.48 (m, 2H); MS (ESI+) m/z 429 (M+H)$^+$.

Example 96

(3-benzyl-1,2,3,4,4a,5-hexahydropyrazino[1,2-a][1,4]benzodiazepin-6(7H)-yl)(2,5-dimethyl-1H-pyrrol-3-yl)methanone The title compound was prepared as the trifluoroacetic acid salt according to the procedure outlined in Example 84 substituting 1,2,5-dimethyl-1H pyrrole-3-carboxylic acid for 1-acetylpiperidine-4-carboxylic acid. $^1$H NMR (500 MHz, pyridine-d$_5$) δ ppm 2.22 (s, 3H), 2.32-2.58 (m, 6H), 2.75 (d, J=10.38 Hz, 1H), 3.03 (d, J=6.71 Hz, 1H), 3.11-3.22 (m, 2H), 3.19-3.41 (m, 2H), 3.57 (s, 1H), 4.79 (d, J=13.43 Hz, 1H), 5.03 (d, J=13.43 Hz, 1H), 6.03 (s, 1H), 6.88-7.06 (m, 2H), 7.26 (d, J=7.63 Hz, 2H), 7.32 (q, J=7.32 Hz, 3H), 7.37-7.47 (m, 2H); MS (ESI+) m/z 415 (M+H)$^+$.

Example 97

1-[(3-benzyl-1,2,3,4,4a,5-hexahydropyrazino[1,2-a][1,4]benzodiazepin-6(7H)-yl)carbonyl]cyclopropanecarboxamide The title compound was prepared as the trifluoroacetic acid salt according to the procedure outlined in Example 84 substituting 1-carbamoylcyclopropanecarboxylic acid for 1-acetylpiperidine-4-carboxylic acid. $^1$H NMR (500 MHz, pyridine-d$_5$) δ ppm 1.45 (s, 1H), 1.48-1.75 (m, 2H), 2.27-2.64 (m, 2H), 2.90 (dd, J=18.16, 11.14 Hz, 2H), 3.02-3.21 (m, 3H), 3.19-3.34 (m, 2H), 3.51-3.71 (m, 4H), 4.15 (s, 1H), 4.71-5.01 (m, 2H), 6.86-7.11 (m, 2H), 7.20-7.27 (m, 2H), 7.28-7.38 (m, 3H), 7.39-7.49 (m, 2H); MS (ESI+) m/z 405 (M+H)$^+$.

Example 98

1-(3-benzyl-1,2,3,4,4a,5-hexahydropyrazino[1,2-a][1,4]benzodiazepin-6(7H)-yl)-2-(pyridin-3-yl)ethanone The title compound was prepared as the trifluoroacetic acid salt according to the procedure outlined in Example 84 substituting 2-(pyridine-3-yl)acetic acid for 1-acetylpiperidine-4-carboxylic acid. $^1$H NMR (500 MHz, pyridine-d$_5$) δ ppm 2.39 (s, 2H), 2.87 (s, 2H), 2.99-3.17 (m, 2H), 3.24 (d, J=9.77 Hz, 2H), 3.50 (s, 1H), 3.54-3.98 (m, 5H), 4.62 (s, 1H), 4.71-4.92 (m, 1H), 6.72-7.08 (m, 2H), 7.28 (s, 2H), 7.34 (d, J=7.32 Hz, 3H), 7.42 (s, 2H), 7.75 (s, 1H), 8.56 (s, 1H), 8.77 (s, 1H); MS (ESI+) m/z 413 (M+H)$^+$.

Example 99

N-[2-(3-benzyl-1,2,3,4,4a,5-hexahydropyrazino[1,2-a][1,4]benzodiazepin-6(7H)-yl)-2-oxoethyl]-2-furamide The title compound was prepared as the trifluoroacetic acid salt according to the procedure outlined in Example 84 substituting 2-(furan-2-carboxamido) acetic acid for 1-acetylpiperidine-4-carboxylic acid. $^1$H NMR (500 MHz, pyridine-d$_5$) δ ppm 2.51 (s, 2H), 2.75-3.13 (m, 4H), 3.24 (s, 2H), 3.41-3.57 (m, 2H), 3.43-3.60 (m, 2H), 3.55-3.72 (m, 1H), 3.58-3.75 (m, 2H), 4.52 (s, 2H), 4.70-4.88 (m, 1H), 6.44 (dd, J=3.36, 1.83 Hz, 1H), 6.84-7.08 (m, 2H), 7.21-7.31 (m, 1H), 7.34 (t, J=7.02 Hz, 2H), 7.37-7.47 (m, 2H), 7.51 (s, 2H); MS (ESI+) m/z 445 (M+H)$^+$.

Example 100

1-(3-benzyl-1,2,3,4,4a,5-hexahydropyrazino[1,2-a][1,4]benzodiazepin-6(7H)-yl)-2-methylpropan-1-one The title compound was prepared as the trifluoroacetic acid salt according to the procedure outlined in Example 84 substituting isobutyric acid for 1-acetylpiperidine-4-carboxylic acid. $^1$H NMR (500 MHz, pyridine-d$_5$) δ ppm 1.22 (d, J=6.41 Hz, 6H), 2.20-2.57 (m, 3H), 2.78-3.04 (m, 4H), 3.05-3.18 (m, 1H), 3.24 (dd, J=10.83, 2.90 Hz, 2H), 3.60 (s, 3H), 4.67-4.89 (m, 1H), 6.90-7.07 (m, 1H), 7.28 (d, J=7.02 Hz, 2H), 7.34 (q, J=6.82 Hz, 3H), 7.38-7.49 (m, 2H); MS (ESI+) m/z 363 (M+H)$^+$.

Example 101

(3-benzyl-1,2,3,4,4a,5-hexahydropyrazino[1,2-a][1,4]benzodiazepin-6(7H)-yl)(3,5-dimethyl-1,2-oxazol-4-yl)methanone The title compound was prepared as the trifluoroacetic acid salt according to the procedure outlined in Example 84 substituting 3,5-dimethylisoxazole-4-carboxylic acid for 1-acetylpiperidine-4-carboxylic acid. $^1$H NMR (500 MHz, pyridine-d$_5$) δ ppm 2.20-2.38 (m, 5H), 2.34-2.57 (m, 2H), 2.55-2.80 (m, 1H), 2.87 (d, J=10.99 Hz, 1H), 3.02 (d, 1H), 3.15 (d, J=11.60 Hz, 1H), 3.18-3.34 (m, 2H), 3.50 (s, 2H), 3.59 (s, 2H), 4.64 (s, 1H), 4.80 (s, 1H), 6.84-7.12 (m, 2H), 7.26 (t, J=7.17 Hz, 2H), 7.29-7.38 (m, 3H), 7.37-7.48 (m, 2H); MS (ESI+) m/z 417 (M+H)$^+$.

Example 102

(3-benzyl-1,2,3,4,4a,5-hexahydropyrazino[1,2-a][1,4]benzodiazepin-6(7H)-yl)(5-methylpyrazin-2-yl)methanone The title compound was prepared as the trifluoroacetic acid salt according to the procedure outlined in Example 84 substituting 5-methylpyrazine-2-carboxylic acid for 1-acetylpiperidine-4-carboxylic acid. $^1$H NMR (500 MHz, pyridine-d$_5$) δ ppm 2.33-2.55 (m, 4H), 2.83-3.35 (m, 4H), 3.64 (d, J=12.82 Hz, 2H), 4.05 (s, 1H), 4.82-5.09 (m, 2H), 6.74-7.13 (m, 3H), 7.21-7.32 (m, 2H), 7.28-7.45 (m, 5H), 7.43 (s, 2H), 8.28 (s, 1H), 9.03 (s, 1H); MS (ESI+) m/z 414 (M+H)$^+$.

Example 103

1-(3-benzyl-1,2,3,4,4a,5-hexahydropyrazino[1,2-a][1,4]benzodiazepin-6(7H)-yl)-2-(4-methylpiperazin-1-yl)ethanone The title compound was prepared as the trifluoroacetic acid salt according to the procedure outlined in Example 84 substituting 2-(4-methylpiperazin-1-yl)acetic acid for 1-acetylpiperidine-4-carboxylic acid. $^1$H NMR (500 MHz, pyridine-d$_5$) δ ppm 2.27-2.61 (m, 2H), 2.66-2.83 (m, 3H), 2.83-3.43 (m, 15H), 3.49-3.85 (m, 5H), 4.75 (s, 1H), 7.00 (dd, J=11.44, 7.78 Hz, 2H), 7.19-7.27 (m, 2H), 7.25-7.38 (m, 3H), 7.39-7.51 (m, 2H); MS (ESI+) m/z 434 (M+H)$^+$.

Example 104

(3-benzyl-1,2,3,4,4a,5-hexahydropyrazino[1,2-a][1,4]benzodiazepin-6(7H)-yl)(2-furyl)methanone The title compound was prepared as the trifluoroacetic acid salt according to the procedure outlined in Example 84 substituting furan-2-carboxylic acid for 1-acetylpiperidine-4-carboxylic acid. $^1$H NMR (500 MHz, pyridine-d$_5$) δ ppm 2.19-2.54 (m, 2H), 2.88 (d, J=10.99 Hz, 2H), 3.02 (d, 2H), 3.13 (d, J=11.60 Hz, 2H), 3.16-3.33 (m, 2H), 4.81 (d, J=13.73 Hz, 1H), 5.02 (d, J=13.73 Hz, 1H), 5.18 (d, 3H), 6.50 (dd, J=3.36, 1.83 Hz, 1H), 6.88-7.07 (m, 2H), 7.21-7.30 (m, 2H), 7.28-7.36 (m, 3H), 7.36-7.47 (m, 2H); MS (ESI+) m/z 388 (M+H)$^+$.

Example 105

(3-benzyl-1,2,3,4,4a,5-hexahydropyrazino[1,2-a][1,4]benzodiazepin-6(7H)-yl)(1-methyl-1H-pyrrol-2-yl)methanone The title compound was prepared as the trifluoroacetic acid salt according to the procedure outlined in Example 84 substituting 1-methyl-1H-pyrrole-2-carboxylic acid for 1-acetylpiperidine-4-carboxylic acid. $^1$H NMR (500 MHz, pyridine-d$_5$) δ ppm 2.30-2.53 (m, 1H), 2.70 (d, J=10.38 Hz, 1H), 2.85 (d, J=10.99 Hz, 1H), 2.95-3.10 (m, 1H), 3.10-3.19 (m, 1H), 3.19-3.36 (m, 2H), 3.57 (s, 2H), 3.77 (s, 3H), 4.30 (dd, J=14.65, 3.05 Hz, 1H), 4.75 (d, J=13.73 Hz, 1H), 4.98 (d, J=13.73 Hz, 1H), 6.15 (t, J=3.20 Hz, 1H), 6.46 (d, J=3.05 Hz, 1H), 6.77 (s, 1H), 6.86-7.07 (m, 2H), 7.16 (d, J=7.32 Hz, 1H), 7.27 (d, J=7.63 Hz, 2H), 7.28-7.36 (m, 3H), 7.36-7.48 (m, 2H); MS (ESI+) m/z 401 (M+H)$^+$.

Example 106

1-(3-benzyl-1,2,3,4,4a,5-hexahydropyrazino[1,2-a][1,4]benzodiazepin-6(7H)-yl)propan-1-one The title compound was prepared as the trifluoroacetic acid salt according to the procedure outlined in Example 84 substituting propionic acid for 1-acetylpiperidine-4-carboxylic acid. $^1$H NMR (500 MHz, pyridine-d$_5$) δ ppm 1.20 (t, J=6.87 Hz, 3H), 2.46 (d, J=40.59 Hz, 4H), 2.76-2.99 (m, 4H), 3.11 (d, J=10.99 Hz, 1H), 3.25 (t, J=10.53 Hz, 2H), 3.52-3.75 (m, 3H), 4.35-4.55 (m, 1H), 4.74 (s, 1H), 6.78-7.13 (m, 2H), 7.27 (d, J=7.02 Hz, 2H), 7.27-7.39 (m, 3H), 7.44 (d, J=7.32 Hz, 2H); MS (ESI+) m/z 350 (M+H)$^+$.

Example 107

(3-benzyl-1,2,3,4,4a,5-hexahydropyrazino[1,2-a][1,4]benzodiazepin-6(7H)-yl)(pyridin-4-yl)methanone The title compound was prepared as the trifluoroacetic acid salt according to the procedure outlined in Example 84 substituting isonicotinic acid for 1-acetylpiperidine-4-carboxylic acid. $^1$H NMR (500 MHz, pyridine-d$_5$) δ ppm 2.51 (s, 3H), 2.89 (d, J=10.99 Hz, 2H), 3.26 (s, 4H), 3.50 (s, 2H), 3.64 (d, J=12.51 Hz, 2H), 4.83 (d, 1H), 6.99 (d, J=7.93 Hz, 2H), 7.18-7.32 (m, 3H), 7.29-7.49 (m, 6H); MS (ESI+) m/z 399 (M+H)$^+$.

Example 108

1-(3-benzyl-1,2,3,4,4a,5-hexahydropyrazino[1,2-a][1,4]benzodiazepin-6(7H)-yl)butan-1-one The title compound was prepared as the trifluoroacetic acid salt according to the procedure outlined in Example 84 substituting butyric acid for 1-acetylpiperidine-4-carboxylic acid. $^1$H NMR (500 MHz, pyridine-d$_5$) δ ppm 0.97 (d, 3H), 1.78 (d, J=6.41 Hz, 2H), 2.46 (t, 4H), 2.90 (dd, J=10.07 Hz, 4H), 3.13 (t, 2H), 3.26 (t, 2H), 3.50-3.74 (m, 3H), 4.48 (d, 1H), 4.75 (d, 1H), 6.98 (d, J=7.02 Hz, 2H), 7.28 (d, J=7.02 Hz, 2H), 7.33 (s, 3H); MS (ESI+) m/z 364 (M+H)$^+$.

Example 109

(3-benzyl-1,2,3,4,4a,5-hexahydropyrazino[1,2-a][1,4]benzodiazepin-6(7H)-yl)(tetrahydrofuran-3-yl)methanone The title compound was prepared as the trifluoroacetic acid salt according to the procedure outlined in Example 84 substituting tetrahydrofuran-3-carboxylic acid for 1-acetylpiperidine-4-carboxylic acid. $^1$H NMR (500 MHz, pyridine-d$_5$) δ ppm 2.09 (t, 1H), 2.39 (t, 3H), 2.88 (d, J=10.99 Hz, 3H), 3.08 (dd, 4H), 3.25 (t, J=10.83 Hz, 2H), 3.70-3.87 (m, 1H), 3.91-4.01 (m, 2H), 4.04-4.25 (m, 2H), 4.78 (s, 2H), 6.99 (d, J=7.93 Hz, 2H), 7.20-7.31 (m, 2H), 7.34 (t, J=6.71 Hz, 3H), 7.43 (d, J=7.02 Hz, 2H); MS (ESI+) m/z 392 (M+H)$^+$.

Example 110

(3-benzyl-1,2,3,4,4a,5-hexahydropyrazino[1,2-a][1,4]benzodiazepin-6(7H)-yl)(pyridin-3-yl)methanone The title compound was prepared as the trifluoroacetic acid salt according to the procedure outlined in Example 84 substituting nicotinic acid for 1-acetylpiperidine-4-carboxylic acid. $^1$H NMR (500 MHz, pyridine-d$_5$) δ ppm 2.51 (s, 3H), 2.88 (d, J=10.68 Hz, 2H), 3.11 (dd, 1H), 3.27 (dd, 2H), 3.47 (t, 1H), 3.60 (t, 2H), 6.88-7.09 (m, 3H), 7.19-7.49 (m, 8H), 7.83 (dd, J=7.93 Hz, 1H), 8.69 (t, J=4.58 Hz, 1H), 8.88 (d, 1H); MS (ESI+) m/z 399 (M+H)$^+$.

Example 111

1-(3-benzyl-1,2,3,4,4a,5-hexahydropyrazino[1,2-a] [1,4]benzodiazepin-6(7H)-yl)-3-(piperidin-1-yl)propan-1-one The title compound was prepared as the trifluoroacetic acid salt according to the procedure outlined in Example 84 substituting 3-(piperidin-1-yl) propanoic acid for 1-acetylpiperidine-4-carboxylic acid. $^1$H NMR (500 MHz, pyridine-d$_5$) δ ppm 1.45 (q, 2H), 1.79 (s, 3H), 2.23-2.66 (m, 3H), 2.72-3.37 (m, 12H), 3.43-3.63 (m, 4H), 3.68 (d, J=13.12 Hz, 2H), 4.80 (dd, 2H), 6.80-7.09 (m, 2H), 7.24-7.31 (m, 2H), 7.28-7.41 (m, 3H), 7.38-7.50 (m, 2H); MS (ESI+) m/z 433 (M+H)$^+$.

Example 112

(3-benzyl-1,2,3,4,4a,5-hexahydropyrazino[1,2-a][1, 4]benzodiazepin-6(7H)-yl)(cyclopropyl)methanone The title compound was prepared as the trifluoroacetic acid salt according to the procedure outlined in Example 84 substituting cyclopropanecarboxylic acid for 1-acetylpiperidine-4-carboxylic acid. $^1$H NMR (500 MHz, pyridine-d$_5$) δ ppm 0.73 (d, J=3.66 Hz, 2H), 1.08 (d, J=7.02 Hz, 2H), 1.30-2.05 (m, 1H), 2.17-2.52 (m, 3H), 2.90 (t, J=12.05 Hz, 2H), 3.11 (t, J=11.29 Hz, 1H), 3.15-3.38 (m, 2H), 3.61 (s, 2H), 4.59-4.79 (m, 1H), 4.87 (s, 1H), 6.77-7.12 (m, 2H), 7.19-7.29 (m, 2H), 7.23-7.38 (m, 3H), 7.36-7.50 (m, 2H); MS (ESI+) m/z 362 (M+H)$^+$.

Example 113

1-(3-benzyl-1,2,3,4,4a,5-hexahydropyrazino[1,2-a] [1,4]benzodiazepin-6(7H)-yl)-2-ethoxyethanone The title compound was prepared as the trifluoroacetic acid salt according to the procedure outlined in Example 84 substituting 2-ethoxyacetic acid for 1-acetylpiperidine-4-carboxylic acid. $^1$H NMR (500 MHz, pyridine-d$_5$) δ ppm 0.86-1.36 (m, 2H), 2.28-2.41 (m, 2H), 2.88 (dd, J=20.90, 10.83 Hz, 2H), 2.97-3.07 (m, 1H), 3.05-3.16 (m, 2H), 3.15-3.36 (m, 2H), 3.54-3.86 (m, 5H), 4.57 (s, 1H), 4.65-4.91 (m, 2H), 6.87-7.10 (m, 2H), 7.23-7.31 (m, 2H), 7.34 (q, J=6.71 Hz, 3H), 7.43 (d, J=7.02 Hz, 2H); MS (ESI+) m/z 380 (M+H)$^+$.

Example 114

(3-benzyl-1,2,3,4,4a,5-hexahydropyrazino[1,2-a][1, 4]benzodiazepin-6(7H)-yl)(1-methylcyclopropyl) methanone The title compound was prepared as the trifluoroacetic acid salt according to the procedure outlined in Example 84 substituting 1-methylcyclopropanecaboxylic acid for 1-acetylpiperidine-4-carboxylic acid. $^1$H NMR (500 MHz, pyridine-d$_5$) δ ppm 0.32-0.76 (m, 2H), 0.85-1.03 (m, 1H), 1.05-1.17 (m, 1H), 1.31 (s, 3H), 2.07-2.49 (m, 2H), 2.89 (d, J=10.99 Hz, 2H), 3.01-3.38 (m, 4H), 3.50 (s, 3H), 3.62 (d, J=1.22 Hz, 2H), 4.13 (dd, J=14.34, 2.75 Hz, 1H), 4.81 (s, 2H), 6.86-7.10 (m, 2H), 7.21-7.31 (m, 2H), 7.27-7.37 (m, 3H), 7.40-7.49 (m, 2H); MS (ESI+) m/z 376 (M+H)$^+$.

Example 115

(3-benzyl-1,2,3,4,4a,5-hexahydropyrazino[1,2-a][1, 4]benzodiazepin-6(7H)-yl)(cyclobutyl)methanone The title compound was prepared as the trifluoroacetic acid salt according to the procedure outlined in Example 84 substituting cyclobutanecarboxylic acid for 1-acetylpiperidine-4-carboxylic acid. $^1$H NMR (500 MHz, pyridine-d$_5$) δ ppm 1.86 (s, 2H), 2.12 (d, 2H), 2.22-2.60 (m, 4H), 2.88 (d, J=11.29 Hz, 4H), 3.04-3.34 (m, 3H), 3.52-3.81 (m, 2H), 4.39-4.68 (m, 1H), 4.77 (s, 1H), 6.97 (d, J=8.24 Hz, 2H), 7.18-7.27 (m, 2H), 7.22-7.38 (m, 3H), 7.44 (d, J=6.10 Hz, 2H); MS (ESI+) m/z 376(M+H)$^+$.

Example 116

(3-benzyl-1,2,3,4,4a,5-hexahydropyrazino[1,2-a][1, 4]benzodiazepin-6(7H)-yl)(2-methylcyclopropyl) methanone The title compound was prepared as the trifluoroacetic acid salt according to the procedure outlined in Example 84 substituting 2-methylcyclopranecarboxylic acid for 1-acetylpiperidine-4-carboxylic acid. $^1$H NMR (500 MHz, pyridine-d$_5$) δ ppm 0.60 (s, 1H), 1.04 (d, J=5.80 Hz, 2H), 1.11-1.64 (m, 4H), 2.15-2.50 (m, 2H), 2.91 (d, J=11.90 Hz, 4H), 3.11 (d, J=11.29 Hz, 1H), 3.19-3.39 (m, 2H), 3.59 (d, J=13.12 Hz, 2H), 4.68 (d, J=13.12 Hz, 1H), 4.82 (s, 1H), 6.71-7.13 (m, 2H), 7.24 (d, J=19.23 Hz, 2H), 7.27-7.41 (m, 3H), 7.43 (s, 2H); MS (ESI+) m/z 376 (M+H)$^+$.

Example 117

1-(3-benzyl-1,2,3,4,4a,5-hexahydropyrazino[1,2-a] [1,4]benzodiazepin-6(7H)-yl)-3,3,3-trifluoropropan-1-one The title compound was prepared as the trifluoroacetic acid salt according to the procedure outlined in Example 84 substituting 3,3,3-trifluoropropanoicacid for 1-acetylpiperidine-4-carboxylic acid. $^1$H NMR (500 MHz, pyridine-d$_5$) δ ppm 2.22-2.47 (m, 2H), 2.78-3.15 (m, 4H), 3.17-3.42 (m, 2H), 3.52-3.85 (m, 4H), 4.57 (d, J=12.51 Hz, 1H), 4.66-4.94 (m, 1H), 6.73-7.10 (m, 2H), 7.21-7.32 (m, 2H), 7.34 (d, J=6.71 Hz, 3H), 7.41 (d, J=6.41 Hz, 2H); MS (ESI+) m/z 403 (M+H)$^+$.

Example 118

(3-benzyl-1,2,3,4,4a,5-hexahydropyrazino[1,2-a][1, 4]benzodiazepin-6(7H)-yl)(tetrahydrofuran-2-yl) methanone The title compound was prepared as the trifluoroacetic acid salt according to the procedure outlined in Example 84 substituting tetrahydrofuran-2-carboxylic acid for 1-acetylpiperidine-4-carboxylic acid. $^1$H NMR (500 MHz, pyridine-d$_5$) δ ppm 1.79 (s, 1H), 1.96 (s, 2H), 2.23-2.62 (m, 2H), 2.74-3.18 (m, 4H), 3.25 (t, J=9.92 Hz, 1H), 3.51-3.69 (m, 2H), 3.62 (t, 2H), 3.93 (d, J=58.59 Hz, 3H), 4.53-5.05 (m, 3H), 6.76-7.13 (m, 2H), 7.28 (d, J=6.71 Hz, 2H), 7.28-7.39 (m, 3H), 7.43 (d, 2H); MS (ESI+) m/z 392 (M+H)$^+$.

Example 119

3-benzyl-6-(4-methoxy-3-methylbenzyl)-1,2,3,4,4a,5,6,7-octahydropyrazino[1,2-a][1,4]benzodiazepine 3-Benzyl-1,2,3,4,4a,5,6,7-octahydropyrazino[1,2-a][1,4]benzodiazepine (43 mg, 0.15 mmol) was dissolved in a 1:1 solution of dichloromethane/methanol (1.2 mL) followed by the addition of 4-methoxy-3-methylbenzaldehyde (26 mg, 0.18 mmol) dissolved in a 1:1 solution of dichloromethane/methanol (0.6 mL) followed by the addition of acetic acid (40 µL, 0.73 mmol). The reaction mixture was shaken at 50° C. for 2 hours. Then macroporous poly(styrene-co-divinylbenzene) cyanoborohydride resin (MP-CNBH$_3$) (196 mg, 0.45 mmol, 2.25 mmol/g loading) was added and the reaction mixture was shaken overnight at 50° C. The resin was removed via filtration, and the filtrate was concentrated to dryness. Purification via HPLC afforded the title compound as the trifluoroacetic acid salt. $^1$H NMR (500 MHz, pyridine-d$_5$) δ ppm 2.24 (s, 3H), 2.34-2.43 (m, 1H), 2.50 (s, 1H), 2.85-3.10 (m, 4H), 3.27-3.36 (m, 2H), 3.59-3.79 (m, 6H), 4.06-4.21 (m, 2H), 4.35 (d, J=13.12 Hz, 1H), 4.53 (d, J=13.12 Hz, 1H), 6.82 (d, J=8.24 Hz, 1H), 6.96 (d, J=7.93 Hz, 1H), 7.05 (t, J=7.17 Hz, 1H), 7.28-7.51 (m, 9H); MS (ESI+), m/z 428 (M+H)$^+$.

Example 120

3-benzyl-6-[(4,5-dimethyl-2-furyl)methyl]-1,2,3,4,4a,5,6,7-octahydropyrazino[1,2-a][1,4]benzodiazepine The title compound was prepared as the trifluoroacetic acid salt according to the procedure outlined in Example 119 substituting 4,5-dimethylfuran-2-carbaldehyde for 4-methoxy-3-methylbenzaldehyde. $^1$H NMR (500 MHz, pyridine-d$_5$) δ ppm 1.81 (s, 3H), 2.08 (s, 3H), 2.38-2.47 (m, 1H), 2.57-2.65 (m, 1H), 2.83-3.02 (m, 4H), 3.23-3.39 (m, 2H), 3.51-3.58 (m, 1H), 3.71 (s, 2H), 4.01 (d, J=4.88 Hz, 2H), 4.19 (d, J=13.12 Hz, 1H), 4.44 (d, J=12.82 Hz, 1H), 6.36 (s, 1H), 6.92 (d, J=7.63 Hz, 1H), 7.01 (t, J=7.32 Hz, 1H), 7.26 (dd, J=7.32, 1.22 Hz, 1H), 7.30-7.42 (m, 4H), 7.50 (d, J=7.32 Hz, 2H); MS (ESI+) m/z 402 (M+H)$^+$.

Example 121

3-benzyl-6-(4-ethoxybenzyl)-1,2,3,4,4a,5,6,7-octahydropyrazino[1,2-a][1,4]benzodiazepine The title compound was prepared as the trifluoroacetic acid salt according to the procedure outlined in Example 119 substituting 4-ethoxybenzaldehyde for 4-methoxy-3-methylbenzaldehyde. $^1$H NMR (500 MHz, pyridine-d$_5$) δ ppm 1.27 (t, J=7.02 Hz, 3H), 2.34-2.44 (m, 1H), 2.51-2.60 (m, 1H), 2.88-3.06 (m, 4H), 3.26-3.38 (m, 2H), 3.61-3.77 (m, 3H), 3.90 (q, J=6.81 Hz, 2H), 4.11 (q, J=13.43 Hz, 2H), 4.30 (d, 1H), 4.46 (d, 1H), 6.93-7.01 (m, 3H), 7.04 (t, J=7.32 Hz, 1H), 7.28-7.33 (m, 2H), 7.39 (t, J=7.48 Hz, 3H), 7.50 (d, J=7.32 Hz, 2H), 7.58-7.61 (m, 2H); MS (ESI+) m/z 428 (M+H)$^+$.

Example 122

3-benzyl-6-[(5-methyl-2-thienyl)methyl]-1,2,3,4,4a,5,6,7-octahydropyrazino[1,2-a][1,4]benzodiazepine The title compound was prepared as the trifluoroacetic acid salt according to the procedure outlined in Example 119 substituting 5-methylthiophene-2-carbaldehyde for 4-methoxy-3-methylbenzaldehyde. $^1$H NMR (500 MHz, pyridine-d$_5$) δ ppm 2.34 (s, 3H), 2.46-2.54 (m, 1H), 2.62-2.75 (m, 2H), 2.84 (dd, J=13.58, 5.03 Hz, 1H), 2.99 (dd, J=20.29, 10.83 Hz, 2H), 3.26-3.42 (m, 2H), 3.49-3.55 (m, 1H), 3.75-3.84 (m, 2H), 3.91-4.06 (m, 3H), 4.31 (d, J=13.12 Hz, 1H), 6.67 (d, J=2.14 Hz, 1H), 6.89-6.97 (m, 2H), 7.02 (t, J=7.32 Hz, 1H), 7.20 (s, 1H), 7.30-7.36 (m, 2H), 7.40 (t, J=7.32 Hz, 2H), 7.54 (d, J=7.32 Hz, 2H); MS (ESI+) m/z 404 (M+H)$^+$.

Example 123

3-benzyl-6-(4-bromobenzyl)-1,2,3,4,4a,5,6,7-octahydropyrazino[1,2-a][1,4]benzodiazepine The title compound was prepared as the trifluoroacetic acid salt according to the procedure outlined in Example 119 substituting 4-bromobenzaldehyde for 4-methoxy-3-methylbenzaldehyde. $^1$H NMR (500 MHz, pyridine-d$_5$) δ ppm 2.48-2.57 (m, 1H) 2.62-2.81 (m, 3H), 3.00 (dd, J=21.21, 10.83 Hz, 2H), 3.29-3.44 (m, 2H), 3.53-3.59 (m, 1H), 3.67-3.84 (m, 4H), 3.91 (d, J=13.12 Hz, 1H), 4.23 (d, J=13.12 Hz, 1H), 6.93 (d, J=7.93 Hz, 1H), 7.03 (t, J=7.32 Hz, 1H), 7.19 (dd, J=7.48, 1.37 Hz, 1H), 7.30-7.43 (m, 6H), 7.51-7.57 (m, 4H); MS (ESI+) m/z 462 (M+H)$^+$.

Example 124

3-benzyl-6-(2-naphthylmethyl)-1,2,3,4,4a,5,6,7-octahydropyrazino[1,2-a][1,4]benzodiazepine The title compound was prepared as the trifluoroacetic acid salt according to the procedure outlined in Example 119 substituting 2-naphthaldehyde for 4-methoxy-3-methylbenzaldehyde. $^1$H NMR (500 MHz, pyridine-d$_5$) δ ppm 2.44-2.56 (m, 1H), 2.65 (t, J=9.92 Hz, 1H), 2.78-2.91 (m, 2H), 2.98 (dd, J=15.71, 11.75 Hz, 2H), 3.28-3.45 (m, 2H), 3.61-3.67 (m, 1H), 3.72-3.82 (m, 2H), 4.00-4.13 (m, 3H), 4.37 (d, J=12.82 Hz, 1H), 6.95 (d, J=7.93 Hz, 1H), 7.04 (t, J=7.32 Hz, 1H), 7.25-7.42 (m, 5H), 7.48-7.56 (m, 4H), 7.77 (dd, J=8.54, 1.53 Hz, 1H), 7.88-7.96 (m, 3H), 8.01 (s, 1H); MS (ESI+) m/z 434 (M+H)$^+$.

Example 125

3-benzyl-6-(cyclopentylmethyl)-1,2,3,4,4a,5,6,7-octahydropyrazino[1,2-a][1,4]benzodiazepine The title compound was prepared as the trifluoroacetic acid salt according to the procedure outlined in Example 119 substituting cyclopentanecarbaldehyde for 4-methoxy-3-methylbenzaldehyde. $^1$H NMR (500 MHz, pyridine-d$_5$) δ ppm 1.15-1.58 (m, 6H), 1.84 (dd, J=12.66, 6.87 Hz, 2H), 2.21-2.44 (m, 3H), 2.94-3.17 (m, 6H), 3.34 (d, J=6.71 Hz, 2H), 3.57-3.69 (m, 2H), 3.82-3.91 (m, 1H), 4.51 (d, J=55.23 Hz, 2H), 6.98 (d, J=7.93 Hz, 1H), 7.03 (t, J=7.48 Hz, 1H), 7.32 (t, J=7.32 Hz, 1H), 7.35-7.43 (m, 4H), 7.49 (d, J=7.32 Hz, 2H); MS (ESI+) m/z 376 (M+H)$^+$.

Example 126

3-benzyl-6-(quinolin-2-ylmethyl)-1,2,3,4,4a,5,6,7-octahydropyrazino[1,2-a][1,4]benzodiazepine The title compound was prepared as the trifluoroacetic acid salt according to the procedure outlined in Example 119 substituting quinoline-2-carbaldehyde for 4-methoxy-3-methylbenzaldehyde. $^1$H NMR (500 MHz, pyridine-$d_5$) δ ppm 2.49-2.60 (m, 1H), 2.72 (t, J=10.37 Hz, 1H), 2.82-2.91 (m, 2H), 3.01 (d, J=10.07 Hz, 2H), 3.28-3.44 (m, 2H), 3.52-3.59 (m, 1H), 3.81 (d, J=14.65 Hz, 2H), 4.06 (d, J=12.82 Hz, 1H), 4.15-4.27 (m, 2H), 4.34 (d, J=12.82 Hz, 1H), 6.93 (d, J=7.63 Hz, 1H), 7.01 (t, J=7.32 Hz, 1H), 7.26-7.29 (m, 1H), 7.33 (t, J=7.63 Hz, 2H), 7.40 (t, J=7.48 Hz, 2H), 7.51-7.56 (m, 3H), 7.70-7.75 (m, 1H), 7.81 (d, J=8.54 Hz, 2H), 8.18 (d, J=8.54 Hz, 1H), 8.28 (d, J=8.54 Hz, 1H); MS (ESI+), m/z 434 (M+H)$^+$.

Example 127

3-benzyl-6-[(5-ethyl-2-furyl)methyl]-1,2,3,4,4a,5,6,7-octahydropyrazino[1,2-a][1,4]benzodiazepine The title compound was prepared as the trifluoroacetic acid salt according to the procedure outlined in Example 119 substituting 5-ethylfuran-2-carbaldehyde for 4-methoxy-3-methylbenzaldehyde. $^1$H NMR (500 MHz, pyridine-$d_5$) δ ppm 1.10 (t, J=7.48 Hz, 3H), 2.40-2.49 (m, 1H), 2.49-2.57 (m, 2H), 2.64 (t, J=10.22 Hz, 1H), 2.84-3.02 (m, 4H), 3.22-3.41 (m, 2H), 3.49-3.58 (m, 1H), 3.73 (s, 2H), 3.96-4.07 (m, 2H), 4.14 (d, J=13.12 Hz, 1H), 4.41 (d, J=12.82 Hz, 1H), 6.03 (d, J=3.05 Hz, 1H), 6.48 (d, J=3.05 Hz, 1H), 6.91 (d, J=7.93 Hz, 1H), 7.01 (t, J=7.32 Hz, 1H), 7.28-7.43 (m, 5H), 7.51 (d, J=7.32 Hz, 2H); MS (ESI+) m/z 402 (M+H)$^+$.

Example 128

4-[(3-benzyl-1,2,3,4,4a,5-hexahydropyrazino[1,2-a][1,4]benzodiazepin-6(7H)-yl)methyl]benzonitrile The title compound was prepared as the trifluoroacetic acid salt according to the procedure outlined in Example 119 substituting 4-formylbenzonitrile for 4-methoxy-3-methylbenzaldehyde. $^1$H NMR (500 MHz, pyridine-$d_5$) δ ppm 2.57-2.71 (m, 3H), 2.77 (t, J=10.37 Hz, 1H), 3.05 (d, J=10.98 Hz, 1H), 3.10 (d, J=10.98 Hz, 1H), 3.31-3.38 (m, 1H), 3.41-3.48 (m, 1H), 3.51-3.57 (m, 1H), 3.63-3.79 (m, 3H), 3.90 (s, 2H), 4.15 (d, J=13.12 Hz, 1H), 6.94 (d, J=7.93 Hz, 1H), 7.04 (t, J=7.02 Hz, 1H), 7.16 (d, J=6.10 Hz, 1H), 7.30-7.37 (m, 2H), 7.40 (t, J=7.48 Hz, 2H), 7.51 (d, J=8.24 Hz, 2H), 7.55-7.58 (m, 2H), 7.61-7.69 (m, 2H); MS (ESI+) m/z 409 (M+H)$^+$.

Example 129

3-benzyl-6-butyl-1,2,3,4,4a,5,6,7-octahydropyrazino[1,2-a][1,4]benzodiazepine

The title compound was prepared as the trifluoroacetic acid salt according to the procedure outlined in Example 119 substituting butyraldehyde for 4-methoxy-3-methylbenzaldehyde. $^1$H NMR (500 MHz, pyridine-$d_5$) δ ppm 0.79 (t, J=7.32 Hz, 3H) 1.15-1.29 (m, 2H), 1.63-1.85 (m, 2H), 2.24-2.33 (m, 1H), 2.39 (d, 1H), 2.80 (d, J=10.98 Hz, 1H), 2.87-3.13 (m, 5H), 3.22-3.38 (m, 2H), 3.51-3.73 (m, 3H), 4.37 (s, 1H), 4.54 (s, 1H), 6.98 (d, J=7.93 Hz, 1H), 7.04 (t, J=7.32 Hz, 1H), 7.30-7.37 (m, 2H), 7.40 (t, J=7.63 Hz, 3H), 7.48 (d, J=7.02 Hz, 2H); MS (ESI+) m/z 350 (M+H)$^+$.

Example 130

3-benzyl-6-(4-chlorobenzyl)-1,2,3,4,4a,5,6,7-octahydropyrazino[1,2-a][1,4]benzodiazepine The title compound was prepared as the trifluoroacetic acid salt according to the procedure outlined in Example 119 substituting 4-chlorobenzaldehyde for 4-methoxy-3-methylbenzaldehyde. $^1$H NMR (500 MHz, pyridine-$d_5$) δ ppm 2.52-2.59 (m, 1H), 2.63-2.81 (m, 3H), 3.01 (dd, J=18.31, 10.98 Hz, 2H), 3.27-3.35 (m, 1H), 3.36-3.45 (m, 1H), 3.58 (d, J=4.27 Hz, 1H), 3.70-3.85 (m, 4H), 3.93 (d, J=13.12 Hz, 1H), 4.24 (d, J=12.82 Hz, 1H), 6.94 (d, J=7.93 Hz, 1H), 7.03 (t, J=7.32 Hz, 1H), 7.20 (d, J=7.32 Hz, 1H), 7.30-7.42 (m, 6H), 7.44-7.47 (m, 2H), 7.55 (d, J=7.32 Hz, 2H); MS (ESI+) m/z 418 (M+H)$^+$.

Example 131

3-benzyl-6-(2-methylbenzyl)-1,2,3,4,4a,5,6,7-octahydropyrazino[1,2-a][1,4]benzodiazepine The title compound was prepared as the trifluoroacetic acid salt according to the procedure outlined in Example 119 substituting 2-methylbenzaldehyde for 4-methoxy-3-methylbenzaldehyde. $^1$H NMR (500 MHz, pyridine-$d_5$) δ ppm 2.36 (s, 3H), 2.53-2.62 (m, 1H), 2.64-2.76 (m, 3H), 2.99 (d, J=10.68 Hz, 1H), 3.08 (d, J=10.68 Hz, 1H), 3.29-3.37 (m, 1H), 3.37-3.49 (m, 1H), 3.54-3.60 (m, 1H), 3.64-3.77 (m, 2H), 3.81-3.90 (m, 3H), 4.18 (d, J=13.12 Hz, 1H), 6.91 (d, J=7.93 Hz, 1H), 7.03 (t, J=7.17 Hz, 1H), 7.19-7.21 (m, 2H), 7.24-7.28 (m, 2H), 7.34 (t, J=7.17 Hz, 2H), 7.39 (q, J=7.12 Hz, 2H), 7.46-7.50 (m, 1H), 7.56 (d, J=7.32 Hz, 2H); MS (ESI+) m/z 398 (M+H)$^+$.

Example 132

3-benzyl-6-(2-bromobenzyl)-1,2,3,4,4a,5,6,7-octahydropyrazino[1,2-a][1,4]benzodiazepine The title compound was prepared as the trifluoroacetic acid salt according to the procedure outlined in Example 119 substituting 2-bromobenzaldehyde for 4-methoxy-3-methylbenzaldehyde. $^1$H NMR (500 MHz, pyridine-$d_5$) δ ppm 2.61-2.67 (m, 1H) 2.69 (d, J=3.97 Hz, 2H) 2.85 (t, J=10.53 Hz, 1H) 3.12 (dd, J=32.04, 10.68 Hz, 2H) 3.29-3.37 (m, 1H) 3.43-3.56 (m, 2H) 3.68-3.84 (m, 3H) 3.95 (s, 2H) 4.16 (d, J=13.12 Hz, 1H) 6.90 (d, J=7.93 Hz, 1H) 7.03 (t, J=7.32 Hz, 1H) 7.13-7.18 (m, 1H) 7.20 (s, 1H) 7.30-7.37 (m, 3H) 7.41 (t, J=7.48 Hz, 2H) 7.60 (s, 2H) 7.65 (d, J=7.63 Hz, 2H); MS (ESI+) m/z 462 (M+H)$^+$.

Example 133

3-benzyl-6-(2-methoxybenzyl)-1,2,3,4,4a,5,6,7-octahydropyrazino[1,2-a][1,4]benzodiazepine The title compound was prepared as the trifluoroacetic acid salt according to the procedure outlined in Example 119 substituting 2-methoxybenzaldehyde for 4-methoxy-3-methylbenzaldehyde. $^1$H NMR (500 MHz, pyridine-$d_5$) δ ppm 2.26-2.44 (m, 2H), 2.87 (dd, J=27.31, 10.83 Hz, 2H), 2.97-3.10 (m, 2H), 3.37 (d, J=5.80 Hz, 2H), 3.59-3.69 (m, 5H), 3.82-3.89 (m, 1H), 4.21-4.38 (m, 3H), 4.54 (d, J=12.82 Hz, 1H), 6.89 (d, J=8.24 Hz, 1H), 6.94 (d, J=7.93 Hz, 1H), 7.00 (t, J=7.48 Hz, 2H), 7.29-7.43 (m, 6H), 7.49 (d, J=7.02 Hz, 2H), 7.78 (dd, J=7.48, 1.37 Hz, 1H); MS (ESI+) m/z 414 (M+H)$^+$.

Example 134

3-benzyl-6-(4-methoxybenzyl)-1,2,3,4,4a,5,6,7-octahydropyrazino[1,2-a][1,4]benzodiazepine The title compound was prepared as the trifluoroacetic acid salt according to the procedure outlined in Example 119 substituting 4-methoxybenzaldehyde for 4-methoxy-3-methylbenzaldehyde. $^1$H NMR (500 MHz, pyridine-$d_5$) δ ppm 2.34-2.46 (m, 1H), 2.56 (s, 1H), 2.87-3.09 (m, 4H), 3.24-3.50 (m, 2H), 3.64-3.68 (m, 3H), 3.68-3.77 (m, 3H), 4.04-4.17 (m, 2H), 4.28 (d, J=13.12 Hz, 1H), 4.48 (d, J=13.12 Hz, 1H), 6.92-6.99 (m, 3H), 7.04 (t, J=7.32 Hz, 1H), 7.31 (t, J=7.17 Hz, 2H), 7.39 (t, J=7.48 Hz, 3H), 7.50 (d, J=7.32 Hz, 2H), 7.58-7.62 (m, 2H); MS (ESI+) m/z 414 (M+H)$^+$.

Example 135

3-benzyl-6-(3-methoxybenzyl)-1,2,3,4,4a,5,6,7-octahydropyrazino[1,2-a][1,4]benzodiazepine The title compound was prepared as the trifluoroacetic acid salt according to the procedure outlined in Example 119 substituting 3-methoxybenzaldehyde for 4-methoxy-3-methylbenzaldehyde. $^1$H NMR (500 MHz, pyridine-$d_5$) δ ppm 2.42-2.50 (m, 1H), 2.55-2.67 (m, 1H), 2.81-3.01 (m, 4H), 3.23-3.40 (m, 2H), 3.63-3.69 (m, 1H), 3.70-3.79 (m, 5H), 3.95-4.09 (m, 2H), 4.15 (d, J=13.12 Hz, 1H), 4.39 (d, J=13.12 Hz, 1H), 6.93 (d, J=7.93 Hz, 1H), 6.98 (dd, J=8.24, 2.14 Hz, 1H), 7.03 (t, J=7.32 Hz, 1H), 7.16 (d, J=7.32 Hz, 1H), 7.25 (d, J=7.32 Hz, 1H), 7.29-7.42 (m, 6H), 7.52 (d, J=7.32 Hz, 2H); MS (ESI+) m/z 414 (M+H)$^+$.

Example 136

3-benzyl-6-(3-bromobenzyl)-1,2,3,4,4a,5,6,7-octahydropyrazino[1,2-a][1,4]benzodiazepine The title compound was prepared as the trifluoroacetic acid salt according to the procedure outlined in Example 119 substituting 3-bromobenzaldehyde for 4-methoxy-3-methylbenzaldehyde. $^1$H NMR (500 MHz, pyridine-$d_5$) δ ppm 2.51-2.56 (m, 1H), 2.58-2.77 (m, 3H), 2.81 (none, 1H), 2.95 (d, J=10.68 Hz, 1H), 3.02 (d, J=10.98 Hz, 1H), 3.26-3.33 (m, 1H), 3.36-3.42 (m, 1H), 3.46-3.53 (m, 1H), 3.68 (q, J=13.73 Hz, 2H), 3.76-3.87 (m, 3H), 4.18 (d, J=13.12 Hz, 1H), 6.92 (d, J=7.93 Hz, 1H), 7.02 (t, J=7.32 Hz, 1H), 7.16 (d, J=7.32 Hz, 1H), 7.21-7.26 (m, 1H), 7.31-7.36 (m, 2H), 7.40 (t, J=7.48 Hz, 3H), 7.50 (d, J=7.93 Hz, 1H), 7.55 (d, J=7.32 Hz, 2H), 7.76 (s, 1H); MS (ESI+) m/z 462 (M+H)$^+$.

Example 137

3-benzyl-6-(4-methylbenzyl)-1,2,3,4,4a,5,6,7-octahydropyrazino[1,2-a][1,4]benzodiazepine The title compound was prepared as the trifluoroacetic acid salt according to the procedure outlined in Example 119 substituting 4-methylbenzaldehyde for 4-methoxy-3-methylbenzaldehyde. $^1$H NMR (500 MHz, pyridine-$d_5$) δ ppm 2.22 (s, 3H), 2.38-2.48 (m, 1H), 2.58 (s, 1H), 2.83-3.04 (m, 4H), 3.25-3.45 (m, 2H), 3.64-3.77 (m, 3H), 4.05 (q, J=12.92 Hz, 2H), 4.21 (d, J=13.12 Hz, 1H), 4.42 (d, J=13.12 Hz, 1H), 6.94 (d, J=7.93 Hz, 1H), 7.04 (t, J=7.32 Hz, 1H), 7.15 (d, J=7.93 Hz, 2H), 7.25-7.34 (m, 2H), 7.35-7.41 (m, 3H), 7.51 (d, J=7.63 Hz, 4H); MS (ESI+) m/z 398 (M+H)$^+$.

Example 138

3-benzyl-6-(1-naphthylmethyl)-1,2,3,4,4a,5,6,7-octahydropyrazino[1,2-a][1,4]benzodiazepine The title compound was prepared as the trifluoroacetic acid salt according to the procedure outlined in Example 119 substituting 1-naphthaldehyde for 4-methoxy-3-methylbenzaldehyde. $^1$H NMR (500 MHz, pyridine-$d_5$) δ ppm 2.56-2.63 (m, 1H), 2.67-2.77 (m, 3H), 2.97 (d, J=10.68 Hz, 1H), 3.14 (d, J=10.68 Hz, 1H), 3.32 (d, J=12.51 Hz, 1H), 3.41-3.49 (m, 1H), 3.52-3.59 (m, 1H), 3.82-3.92 (m, 3H), 4.10 (q, J=13.12 Hz, 2H), 4.19 (d, J=12.82 Hz, 1H), 6.90 (d, J=7.93 Hz, 1H), 7.04 (t, J=7.32 Hz, 1H), 7.20 (s, 1H), 7.30-7.37 (m, 2H), 7.40 (t, J=7.32 Hz, 2H), 7.47-7.57 (m, 4H), 7.59-7.63 (m, 2H), 7.90 (d, J=8.24 Hz, 1H), 7.97 (d, J=7.93 Hz, 1H), 8.46 (d, J=8.24 Hz, 1H); MS (ESI+) m/z 398 (M+H)$^+$.

Example 139

3-benzyl-6-(2-chlorobenzyl)-1,2,3,4,4a,5,6,7-octahydropyrazino[1,2-a][1,4]benzodiazepine The title compound was prepared as the trifluoroacetic acid salt according to the procedure outlined in Example 119 substituting 2-chlorobenzaldehyde for 4-methoxy-3-methylbenzaldehyde. $^1$H NMR (500 MHz, pyridine-$d_5$) δ ppm 2.56-2.66 (m, 1H), 2.70 (d, J=3.66 Hz, 2H), 2.80 (t, J=10.37 Hz, 1H), 3.09 (dd, J=27.92, 10.83 Hz, 2H), 3.28-3.38 (m, 1H), 3.41-3.48 (m, 1H), 3.50-3.56 (m, 1H), 3.69-3.94 (m, 5H), 4.18 (d, J=12.82 Hz, 1H), 6.91 (d, J=7.93 Hz, 1H), 7.03 (t, J=7.32 Hz, 1H), 7.20 (s, 1H), 7.24 (dd, J=7.78, 1.68 Hz, 1H), 7.26-7.37 (m, 3H), 7.37-7.47 (m, 3H), 7.57 (s, 2H), 7.64-7.69 (m, 1H); MS (ESI+) m/z 418 (M+H)$^+$.

Example 140

3-benzyl-6-(3-chlorobenzyl)-1,2,3,4,4a,5,6,7-octahydropyrazino[1,2-a][1,4]benzodiazepine The title compound was prepared as the trifluoroacetic acid salt according to the procedure outlined in Example 119 substituting 3-chlorobenzaldehyde for 4-methoxy-3-methylbenzaldehyde. $^1$H NMR (500 MHz, pyridine-$d_5$) δ ppm 2.47-2.77 (m, 4H), 2.99 (d, J=10.68 Hz, 1H), 3.05 (d, J=10.98 Hz, 1H), 3.26-3.34 (m, 1H), 3.37-3.46 (m, 1H), 3.49-3.57 (m, 1H), 3.65-3.78 (m, 2H), 3.80-3.88 (m, 3H), 4.20 (d, J=13.12 Hz, 1H), 6.92 (d, J=7.93 Hz, 1H), 7.03 (t, J=7.17 Hz, 1H), 7.17 (d, J=6.10 Hz, 1H), 7.26-7.43 (m, 7H), 7.56 (d, J=7.32 Hz, 2H), 7.60 (s, 1H); MS (ESI+) m/z 418 (M+H)$^+$.

Example 141

3-benzyl-6-(2,2-dimethylpropyl)-1,2,3,4,4a,5,6,7-octahydropyrazino[1,2-a][1,4]benzodiazepine The title compound was prepared as the trifluoroacetic acid salt according to the procedure outlined in Example 119 substituting pivalaldehyde for 4-methoxy-3-methylbenzaldehyde. $^1$H NMR (500 MHz, pyridine-$d_5$) δ ppm 0.92 (s, 9H), 2.27-2.36 (m, 1H), 2.39-2.45 (m, 1H), 2.48-2.65 (m, 2H), 2.75-2.90 (m, 2H), 2.96 (d, J=10.07 Hz, 2H), 3.31-3.43 (m, 2H), 3.44-3.54 (m, 1H), 3.71-3.85 (m, 2H), 3.96 (d, J=12.21 Hz, 1H), 4.24 (d, J=12.51 Hz, 1H), 6.94 (d, J=7.93 Hz, 1H), 7.03 (t, J=7.32 Hz, 1H), 7.26 (d, J=7.32 Hz, 1H), 7.33 (t, J=7.48 Hz, 2H), 7.40 (t, J=7.48 Hz, 2H), 7.56 (d, J=7.32 Hz, 2H); MS (ESI+) m/z 364 (M+H)$^+$.

Example 142

3-benzyl-6-[(3-methyl-2-thienyl)methyl]-1,2,3,4,4a,5,6,7-octahydropyrazino[1,2-a][1,4]benzodiazepine The title compound was prepared as the trifluoroacetic acid salt according to the procedure outlined in Example 119 substituting 3-methylthiophene-2-carbaldehyde for 4-methoxy-3-methylbenzaldehyde. $^1$H NMR (500 MHz, pyridine-$d_5$) δ ppm 2.11-2.19 (m, 3H), 2.52-2.81 (m, 4H), 3.02 (dd, J=37.38, 11.14 Hz, 2H), 3.28-3.34 (m, 1H), 3.37-3.44 (m, 1H), 3.48-3.54 (m, 1H), 3.75-3.93 (m, 5H), 4.25 (d, J=13.12 Hz, 1H), 6.84-6.93 (m, 2H), 7.02 (t, J=7.48 Hz, 1H), 7.18 (d, J=6.10 Hz, 1H), 7.29-7.37 (m, 3H), 7.40 (t, J=7.32 Hz, 2H), 7.55 (t, J=6.71 Hz, 2H); MS (ESI+) m/z 404 (M+H)$^+$.

Example 143

3-benzyl-6-(3-methylbutyl)-1,2,3,4,4a,5,6,7-octahydropyrazino[1,2-a][1,4]benzodiazepine The title compound was prepared as the trifluoroacetic acid salt according to the procedure outlined in Example 119 substituting 3-methylbutanal for 4-methoxy-3-methylbenzaldehyde. $^1$H NMR (500 MHz, pyridine-$d_5$) δ ppm 0.81 (dd, J=6.56, 1.98 Hz, 6H), 1.46-1.56 (m, 1H), 1.70-1.77 (m, 2H), 2.26-2.34 (m, 1H), 2.42 (d, 1H), 2.82 (d, J=10.68 Hz, 1H), 2.97 (d, J=10.68 Hz, 1H), 3.01-3.20 (m, 4H), 3.26-3.33 (m, 2H), 3.51-3.80 (m, 3H), 4.38-4.69 (m, 2H), 6.98 (d, J=7.93 Hz, 1H), 7.05 (t, J=7.32 Hz, 1H), 7.32 (t, J=7.32 Hz, 1H), 7.38-7.44 (m, 4H), 7.48 (d, J=7.32 Hz, 2H); MS (ESI+) m/z 364 (M+H)$^+$.

Example 144

3-benzyl-6-(cyclohexylmethyl)-1,2,3,4,4a,5,6,7-octahydropyrazino[1,2-a][1,4]benzodiazepine The title compound was prepared as the trifluoroacetic acid salt according to the procedure outlined in Example 119 substituting cyclohexanecarbaldehyde for 4-methoxy-3-methylbenzaldehyde. $^1$H NMR (500 MHz, pyridine-$d_5$) δ ppm 0.88-1.21 (m, 5H), 1.44-1.61 (m, 3H), 1.74-2.04 (m, 3H), 2.24-2.36 (m, 2H), 2.75-2.89 (m, 3H), 2.93-3.11 (m, 3H), 3.26-3.40 (m, 2H), 3.54-3.70 (m, 2H), 3.76-3.90 (m, 1H), 4.51 (s, 2H), 6.97 (d, J=7.93 Hz, 1H), 7.04 (t, J=7.32 Hz, 1H), 7.29-7.43 (m, 5H), 7.49 (d, J=7.32 Hz, 2H); MS (ESI+) m/z 390 (M+H)$^+$.

Example 145

3-benzyl-6-(3-methylbenzyl)-1,2,3,4,4a,5,6,7-octahydropyrazino[1,2-a][1,4]benzodiazepine The title compound was prepared as the trifluoroacetic acid salt according to the procedure outlined in Example 119 substituting 3-methylbenzaldehyde for 4-methoxy-3-methylbenzaldehyde. $^1$H NMR (500 MHz, pyridine-$d_5$) δ ppm 2.26 (s, 3H), 2.42-2.49 (m, 1H), 2.60 (s, 1H), 2.82-2.98 (m, 4H), 3.22-3.42 (m, 2H), 3.66-3.79 (m, 3H), 3.96-4.09 (m, 2H), 4.19 (d, J=13.12 Hz, 1H), 4.41 (d, J=12.82 Hz, 1H), 6.94 (d, J=7.93 Hz, 1H), 7.04 (t, J=7.17 Hz, 1H), 7.13 (d, J=7.32 Hz, 1H), 7.26-7.44 (m, 8H), 7.51 (d, J=7.32 Hz, 2H); MS (ESI+) m/z 398 (M+H)$^+$.

Example 146

3-[(3-benzyl-1,2,3,4,4a,5-hexahydropyrazino[1,2-a][1,4]benzodiazepin-6(7H)-yl)methyl]benzonitrile The title compound was prepared as the trifluoroacetic acid salt according to the procedure outlined in Example 119 substituting 3-formylbenzonitrile for 4-methoxy-3-methylbenzaldehyde. $^1$H NMR (500 MHz, pyridine-$d_5$) δ ppm 2.55-2.75 (m, 4H), 2.99 (d, J=10.68 Hz, 1H), 3.07 (d, J=10.98 Hz, 1H), 3.28-3.36 (m, 1H), 3.38-3.46 (m, 1H), 3.46-3.54 (m, 1H), 3.60-3.78 (m, 3H), 3.81-3.88 (m, 2H), 4.15 (d, J=12.82 Hz, 1H), 6.93 (d, J=7.93 Hz, 1H), 7.04 (t, J=7.17 Hz, 1H), 7.16 (d, J=7.02 Hz, 1H), 7.29-7.45 (m, 5H), 7.57 (d, J=7.32 Hz, 2H), 7.63 (dd, J=17.55, 7.78 Hz, 2H), 7.81 (s, 1H); MS (ESI+) m/z 409 (M+H)$^+$.

Example 147

3-benzyl-6-(2-thienylmethyl)-1,2,3,4,4a,5,6,7-octahydropyrazino[1,2-a][1,4]benzodiazepine The title compound was prepared as the trifluoroacetic acid salt according to the procedure outlined in Example 119 substituting thiophene-2-carbaldehyde for 4-methoxy-3-methylbenzaldehyde. $^1$H NMR (500 MHz, pyridine-$d_5$) δ ppm 2.53-2.60 (m, 1H), 2.63-2.85 (m, 3H), 3.04 (dd, J=29.90, 10.98 Hz, 2H), 3.25-3.33 (m, 1H), 3.36-3.46 (m, 1H), 3.48-3.55 (m, 1H), 3.78-3.89 (m, 2H), 3.93-4.04 (m, 3H), 4.28 (d, J=13.12 Hz, 1H, 6.90 (d, J=7.93 Hz, 1H), 6.99-7.05 (m, 2H), 7.12-7.18 (m, 2H), 7.29-7.46 (m, 5H), 7.56 (d, J=7.32 Hz, 2H); MS (ESI+) m/z 390 (M+H)$^+$.

Example 148

3-benzyl-6-isobutyl-1,2,3,4,4a,5,6,7-octahydropyrazino[1,2-a][1,4]benzodiazepine The title compound was prepared as the trifluoroacetic acid salt according to the procedure outlined in Example 119 substituting isobutyraldehyde for 4-methoxy-3-methylbenzaldehyde. $^1$H NMR (500 MHz, pyridine-$d_5$) δ ppm 0.95 (d, J=6.41 Hz, 6H), 1.92-2.06 (m, 1H), 2.29-2.44 (m, 2H), 2.63-2.76 (m, 2H), 2.81-3.03 (m, 4H), 3.29-3.36 (m, 2H), 3.58-3.70 (m, 2H), 3.71-3.81 (m, 1H), 4.17-4.52 (m, 2H), 6.97 (d, J=7.93 Hz, 1H), 7.02 (t, J=7.32 Hz, 1H), 7.32 (t, J=6.71 Hz, 2H), 7.36-7.42 (m, 3H), 7.50 (d, J=7.32 Hz, 2H); MS (ESI+) m/z 350 (M+H)$^+$.

Example 149

3-benzyl-N-(2-methoxyethyl)-N-methyl-1,2,3,4,4a,5-hexahydropyrazino[1,2-a][1,4]benzodiazepine-6(7H)-carboxamide To a solution of triphosgene (22 mg, 0.074 mmol) in tetrahydrofuran (1 mL) was added 3-benzyl-1,2,3,4,4a,5,6,7-octahydropyrazino[1,2-a][1,4]benzodiazepine (66 mg, 0.22 mmol, Example 2) in a tetrahydrofuran (1.0 mL) and diisopropylethylamine(118 μL, 0.68 mmol). The reaction mixture was shaken at room temperature for fifteen minutes. To the reaction mixture was added 2-methoxy-N-methylethanamine (30 mg, 0.33 mmol). The reaction mixture was allowed to stir at room temperature overnight. The reaction was filtered, checked by LC/MS and concentrated to dryness. Purification of the residue via reverse phase HPLC afforded the title compound as the trifluoroacetic acid salt. $^1$H NMR (500 MHz, pyridine-$d_5$) δ ppm 2.53 (t, 1H), 2.69 (t, J=10.22 Hz, 1H), 2.86 (s, 3H), 3.00 (d, J=10.07 Hz, 2H), 3.13-3.27 (m, 7H), 3.33 (t, 1H), 3.44-3.59 (m, 2H), 3.65-3.84 (m, 4H), 4.39 (d, J=12.51 Hz, 1H), 4.85 (d, J=12.51 Hz, 1H), 6.91 (d, J=7.63 Hz, 1H), 7.03 (t, J=7.48 Hz, 1H), 7.23 (d, J=6.41 Hz, 1H), 7.30-7.36 (m, 2H), 7.39 (t, J=7.32 Hz, 2H), 7.53 (d, J=7.32 Hz, 2H); MS (ESI+) m/z 409 (M+H)$^+$.

Example 150

3-benzyl-N-[2-(pyridin-3-yl)ethyl]-1,2,3,4,4a,5-hexahydropyrazino[1,2-a][1,4]benzodiazepine-6(7H)-carboxamide The title compound was prepared as the trifluoroacetic acid salt according to the procedure outlined in Example 149 substituting 2-(pyridine-3-yl)-ethanamine for 2-methoxy-N-methylethanamine. $^1$H NMR (500 MHz, pyridine-$d_5$) δ ppm 2.58-2.69 (m, 1H), 2.85 (t, J=10.83 Hz, 1H), 2.91-3.06 (m, 3H), 3.06-3.20 (m, 3H), 3.32-3.47 (m, 2H), 3.66-3.79 (m, 2H), 3.84-3.92 (m, 1H), 3.94-4.03 (m, 1H), 4.31 (d, J=14.95 Hz, 1H), 4.52 (d, J=11.60 Hz, 1H), 4.84 (d, J=11.60 Hz, 1H), 6.95 (d, J=7.63 Hz, 1H), 7.04 (t, J=7.17 Hz, 2H), 7.17-7.21 (m, 2H), 7.29-7.40 (m, 4H), 7.55-7.57 (m, 3H), 8.63 (dd, J=4.88, 1.53 Hz, 1H); MS (ESI+) m/z 442 (M+H)$^+$.

Example 151

3-benzyl-N-[2-(pyridin-2-yl)ethyl]-1,2,3,4,4a,5-hexahydropyrazino[1,2-a][1,4]benzodiazepine-6(7H)-carboxamide The title compound was prepared as the trifluoroacetic acid salt according to the procedure outlined in Example 149 substituting 2-(pyridine-2-yl)-ethanamine for 2-methoxy-N-methylethanamine. $^1$H NMR (500 MHz, pyridine-$d_5$) δ ppm 2.56-2.65 (m, 1H), 2.89 (t, J=10.83 Hz, 1H), 2.98 (dd, J=14.95, 3.97 Hz, 1H), 3.07-3.31 (m, 5H), 3.33-3.47 (m, 2H), 3.84 (d, J=13.43 Hz, 1H), 3.90-4.02 (m, 3H), 4.31 (d, J=14.95 Hz, 1H), 4.52 (d, J=11.60 Hz, 1H), 4.84 (d, J=11.60 Hz, 1H), 6.95 (d, J=7.93 Hz, 1H), 7.05 (t, J=7.17 Hz, 2H), 7.09 (dd, J=7.17, 5.34 Hz, 1H), 7.20 (d, J=3.97 Hz, 1H), 7.27-7.41 (m, 4H), 7.50-7.57 (m, 3H), 8.63 (d, J=4.58 Hz, 1H); MS (ESI+) m/z 442 (M+H)$^+$.

Example 152

3-benzyl-N-[2-(pyridin-4-yl)ethyl]-1,2,3,4,4a,5-hexahydropyrazino[1,2-a][1,4]benzodiazepine-6(7H)-carboxamide The title compound was prepared as the trifluoroacetic acid salt according to the procedure outlined in Example 149 substituting 2-(pyridine-4-yl)-ethanamine for 2-methoxy-N-methylethanamine. $^1$H NMR (500 MHz, pyridine-$d_5$) δ ppm 2.54-2.63 (m, 1H) 2.77 (t, J=10.83 Hz, 1H) 2.91-3.04 (m, 3H), 3.04-3.16 (m, 3H), 3.27-3.46 (m, 2H), 3.69-3.79 (m, 2H), 3.80-3.85 (m, 1H), 3.90-3.96 (m, 1H), 4.32 (d, J=14.95 Hz, 1H), 4.53 (d, J=11.60 Hz, 1H), 4.85 (d, J=11.60 Hz, 1H), 6.97 (d, J=7.93 Hz, 1H), 7.04 (t, J=7.17 Hz, 2H), 7.17-7.21 (m, 2H), 7.29-7.41 (m, 4H), 7.56 (d, J=7.32 Hz, 2H), 8.67 (d, J=5.80 Hz, 2H); MS (ESI+) m/z 442 (M+H)$^+$.

Example 153

3-benzyl-N-(2-cyanoethyl)-N-cyclopropyl-1,2,3,4,4a,5-hexahydropyrazino[1,2-a][1,4]benzodiazepine-6(7H)-carboxamide The title compound was prepared as the trifluoroacetic acid salt according to the procedure outlined in Example 149 substituting 3-(cyclopropylamino)propanenitrile for 2-methoxy-N-methylethanamine. $^1$H NMR (500 MHz, pyridine-$d_5$) δ ppm 0.63 (s, 2H) 0.67-0.90 (m, 4H) 2.46 (d, J=3.05 Hz, 1H), 2.66 (t, J=10.07 Hz, 1H), 2.72-2.88 (m, 4H), 2.99 (dd, 2H), 3.08-3.26 (m, 2H), 3.20-3.37 (m, 2H), 3.72-3.90 (m, 2H), 4.65 (d, J=12.51 Hz, 1H), 4.92 (d, J=12.51 Hz, 1H), 6.93 (d, J=7.63 Hz, 1H), 7.04 (t, J=7.32 Hz, 1H), 7.28-7.37 (m, 2H), 7.34-7.48 (m, 3H), 7.52 (d, J=7.32 Hz, 2H); MS (ESI+) m/z 430 (M+H)$^+$.

Example 154

[4-(2-aminoethyl)-1H-imidazol-1-yl](3-benzyl-1,2,3,4a,5-hexahydropyrazino[1,2-a][1,4]benzodiazepin-6(7H)-yl)methanone The title compound was prepared as the trifluoroacetic acid salt according to the procedure outlined in Example 149 substituting 2-(1H-imidazol-4-yl)ethanamine propanenitrile for 2-methoxy-N-methylethanamine. $^1$H NMR (500 MHz, pyridine-$d_5$) δ ppm 2.31 (s, 2H), 2.52-2.79 (m, 2H), 2.86-3.08 (m, 2H), 3.06-3.29 (m, 4H), 3.26-3.54 (m, 4H), 3.82 (s, 4H), 4.55 (s, 2H), 4.57-4.77 (m, 2H), 6.87-7.00 (m, 1H), 7.00-7.11 (m, 1H), 7.23-7.32 (m, 2H), 7.29-7.41 (m, 3H), 7.38-7.52 (m, 2H); MS (ESI+) m/z 431 (M+H)$^+$.

Example 155

3-benzyl-N-(pyridin-4-ylmethyl)-1,2,3,4,4a,5-hexahydropyrazino[1,2-a][1,4]benzodiazepine-6(7H)-carboxamide The title compound was prepared as the trifluoroacetic acid salt according to the procedure outlined in Example 149 substituting pyridine-4-ylmethanamine propanenitrile for 2-methoxy-N-methylethanamine. $^1$H NMR (500 MHz, pyridine-$d_5$) δ ppm 2.44-2.49 (m, 1H), 2.73 (t, J=10.53 Hz, 1H), 2.98-3.15 (m, 4H), 3.20 (d, J=10.37 Hz, 1H), 3.28-3.39 (m, 1H), 3.63-3.83 (m, 2H), 4.35 (d, J=14.65 Hz, 1H), 4.62-4.82 (m, 3H), 4.98-5.07 (m, 1H), 6.96-7.02 (m, 1H), 7.06 (t, J=7.48 Hz, 1H), 7.26-7.32 (m, 2H), 7.33-7.39 (m, J=7.53, 7.53, 7.53 Hz, 3H), 7.42-7.46 (m, 2H), 7.47-7.51 (m, J=7.17, 7.17 Hz, 3H), 7.72-7.76 (m, 1H); MS (ESI+) m/z 428 (M+H)$^+$.

Example 156

3-benzyl-N-[(5-methyl-2-furyl)methyl]-1,2,3,4,4a,5-hexahydropyrazino[1,2-a][1,4]benzodiazepine-6(7H)-carboxamide The title compound was prepared as the trifluoroacetic acid salt according to the procedure outlined in Example 149 substituting (5-methylfuran-2-yl)methanamine propanenitrile for 2-methoxy-N-methylethanamine. $^1$H NMR (500 MHz, pyridine-$d_5$) δ ppm 2.13 (s, 3H), 2.28-2.37 (m, 1H), 2.63 (t, J=10.53 Hz, 1H), 2.91 (t, J=11.60 Hz, 2H), 3.00-3.14 (m, 3H), 3.17-3.29 (m, 1H), 3.52 (d, J=13.12 Hz, 1H), 3.61-3.67 (m, 1H), 4.32 (d, J=14.65 Hz, 1H), 4.59-4.71 (m, 2H), 4.79-4.88 (m, 1H), 4.97 (d, J=11.59 Hz, 1H), 6.97 (d, J=7.93 Hz, 1H), 7.03 (t, J=7.48 Hz, 1H), 7.19 (s, 1H), 7.28-7.42 (m, 6H), 7.47 (d, J=7.32 Hz, 2H); MS (ESI+) m/z 431 (M+H)$^+$.

Example 157

3-benzyl-N-ethyl-N-(2-methoxyethyl)-1,2,3,4,4a,5-hexahydropyrazino[1,2-a][1,4]benzodiazepine-6(7H)-carboxamide The title compound was prepared as the trifluoroacetic acid salt according to the procedure outlined in Example 149 substituting N-ethyl-2-methoxyethanamine propanenitrile for 2-methoxy-N-methylethanamine. $^1$H NMR (500 MHz, pyridine-d$_5$) δ ppm 0.97-1.39 (m, 3H), 2.67 (s, 2H), 2.96 (dd, J=29.29, 10.37 Hz, 3H), 3.20-3.36 (m, 4H), 3.35-3.55 (m, 4H), 3.55-3.91 (m, 6H), 4.57-4.79 (m, 1H), 4.87 (d, J=12.82 Hz, 1H), 6.61-7.00 (m, 1H), 6.97-7.11 (m, 2H), 7.24 (t, J=6.10 Hz, 2H), 7.27-7.38 (m, 3H), 7.36-7.47 (m, 2H); MS (ESI+) m/z 423 (M+H)$^+$.

Example 158

3-benzyl-N,N-diethyl-1,2,3,4,4a,5-hexahydropyrazino[1,2-a][1,4]benzodiazepine-6 (7H)-carboxamide The title compound was prepared as the trifluoroacetic acid salt according to the procedure outlined in Example 149 substituting diethylamine for 2-methoxy-N-methylethanamine. $^1$H NMR (500 MHz, pyridine-d$_5$) δ ppm 1.09 (t, J=7.02 Hz, 6H), 2.30-2.52 (m, 2H), 2.89 (dd, J=20.75, 10.98 Hz, 2H), 3.03 (dd, J=14.04, 7.02 Hz, 2H), 3.06-3.22 (m, 4H), 3.22-3.37 (m, 4H), 3.57-3.74 (m, 4H), 4.40 (d, J=12.82 Hz, 1H), 4.85 (d, J=12.51 Hz, 1H), 7.24-7.37 (m, 2H), 7.32-7.45 (m, 3H), 7.49 (d, J=7.32 Hz, 2H); MS (ESI+) m/z 393 (M+H)$^+$.

Example 159

3-benzyl-N-(1,3-thiazol-2-yl)-1,2,3,4,4a,5-hexahydropyrazino[1,2-a][1,4]benzodiazepine-6(7H)-carboxamide The title compound was prepared as the trifluoroacetic acid salt according to the procedure outlined in Example 149 substituting thiazole-2-amine for 2-methoxy-N-methylethanamine. $^1$H NMR (500 MHz, pyridine-d$_5$) δ ppm 2.26 (t, 2H), 2.85 (t, 1H), 3.05 (d, J=11.29 Hz, 2H), 3.08-3.33 (m, 4H), 3.38-3.73 (m, 4H), 4.76 (s, 1H), 6.27 (d, J=5.19 Hz, 1H), 6.64 (d, J=3.66 Hz, 1H), 6.95 (d, J=7.93 Hz, 1H), 6.97-7.12 (m, 1H), 7.32 (s, 2H), 7.30-7.45 (m, 3H), 7.43-7.55 (m, 2H); MS (ESI+) m/z 420 (M+H)$^+$.

Example 160

3-benzyl-N-(cyclopropylmethyl)-1,2,3,4,4a,5-hexahydropyrazino[1,2-a][1,4]benzodiazepine-6(7H)-carboxamide The title compound was prepared as the trifluoroacetic acid salt according to the procedure outlined in Example 149 substituting cyclopropylmethanamine for 2-methoxy-N-methylethanamine. $^1$H NMR (500 MHz, pyridine-d$_5$) δ ppm 0.10-0.53 (m, 4H), 1.20 (s, 1H), 2.34-2.60 (m, 2H), 2.72-3.12 (m, 4H), 3.10-3.43 (m, 4H), 3.62-3.88 (m, 4H), 4.18-4.42 (m, 1H), 4.51-4.73 (m, 1H), 4.92 (d, J=11.59 Hz, 1H), 6.88-7.00 (m, 1H), 7.00-7.10 (m, 1H), 7.23-7.35 (m, 2H), 7.29-7.45 (m, 3H), 7.53 (d, J=7.32 Hz, 2H); MS (ESI+) m/z 391 (M+H)$^+$.

Example 161

(3-benzyl-1,2,3,4,4a,5-hexahydropyrazino[1,2-a][1,4]benzodiazepin-6(7H)-yl)(4-isopropylpiperazin-1-yl)methanone The title compound was prepared as the trifluoroacetic acid salt according to the procedure outlined in Example 149 substituting 1-isopropylpiperazine for 2-methoxy-N-methylethanamine. $^1$H NMR (500 MHz, pyridine-d$_5$) δ 1.20 (d, J=6.41 Hz, 6H), 2.33-2.65 (m, 2H), 2.80-2.98 (m, 2H), 3.06-3.20 (m, 4H), 3.17-3.31 (m, 4H), 3.29-3.48 (m, 2H), 3.63-3.78 (m, 4H), 3.77-3.89 (m, 2H), 4.45 (d, J=12.82 Hz, 1H), 4.83 (d, J=12.82 Hz, 1H), 6.93 (d, J=7.63 Hz, 1H), 7.03 (t, J=7.48 Hz, 1H), 7.24-7.38 (m, 2H), 7.34-7.46 (m, 3H), 7.49 (d, J=7.02 Hz, 2H); MS (ESI+) m/z 448 (M+H)$^+$.

Example 162

3-benzyl-N-isobutyl-1,2,3,4,4a,5-hexahydropyrazino[1,2-a][1,4]benzodiazepine-6(7H)-carboxamide The title compound was prepared as the trifluoroacetic acid salt according to the procedure outlined in Example 149 substituting 2-methylpropan-1-amine for 2-methoxy-N-methylethanamine. $^1$H NMR (500 MHz, pyridine-d$_5$) δ ppm 0.94 (t, J=7.02 Hz, 6H), 1.82-2.12 (m, 1H), 2.28-2.55 (m, 1H), 2.70 (t, J=10.68 Hz, 1H), 2.95-3.23 (m, 4H), 3.20-3.52 (m, 4H), 3.52-3.87 (m, 2H), 4.34 (d, J=14.95 Hz, 1H), 4.64 (d, J=11.59 Hz, 1H), 4.95 (d, J=11.90 Hz, 1H), 6.90-7.04 (m, 1H), 7.05 (t, J=7.48 Hz, 1H), 7.20-7.31 (m, 2H), 7.31-7.44 (m, 3H), 7.50 (d, J=7.02 Hz, 2H); MS (ESI+) m/z 393 (M+H)$^+$.

Example 163

3-benzyl-N-(pyridin-3-ylmethyl)-1,2,3,4,4a,5-hexahydropyrazino[1,2-a][1,4]benzodiazepine-6(7H)-carboxamide The title compound was prepared as the trifluoroacetic acid salt according to the procedure outlined in Example 149 substituting pyridine-3-ylmethanamine for 2-methoxy-N-methylethanamine. $^1$H NMR (500 MHz, pyridine-d$_5$) δ ppm 2.35-2.61 (m, 1H), 2.75 (t, J=10.53 Hz, 1H), 2.93-3.20 (m, 4H), 3.15-3.44 (m, 2H), 3.68-4.01 (m, 2H), 4.31 (d, J=13.43 Hz, 1H), 4.56-4.70 (m, 2H), 4.71-4.86 (m, 1H), 4.97 (d, J=11.59 Hz, 1H), 6.97 (d, J=7.93 Hz, 1H), 7.05 (t, J=7.32 Hz, 1H), 7.23-7.28 (m, 2H), 7.28-7.45 (m, 3H), 7.45-7.59 (m, 3H), 7.68 (t, J=5.80 Hz, 1H), 7.85 (d, J=7.93 Hz, 1H), 8.65 (dd, J=4.73, 1.37 Hz, 1H), 8.95 (d, J=1.53 Hz, 1H); MS (ESI+) m/z 428 (M+H)$^+$.

Example 164

3-benzyl-N-[3-(dimethylamino)propyl]-1,2,3,4,4a,5-hexahydropyrazino[1,2-a][1,4]benzodiazepine-6(7H)-carboxamide The title compound was prepared as the trifluoroacetic acid salt according to the procedure outlined in Example 149 substituting N,N-dimethylpropane-1,3-diamine for 2-methoxy-N-methylethanamine. $^1$H NMR (500 MHz, pyridine-d$_5$) δ ppm 1.96-2.32 (m, 2H), 2.33-2.63 (m, 1H), 2.67-2.85 (m, 7H), 2.93-3.15 (m, 4H), 3.16-3.42 (m, 4H), 3.47-3.75 (m, 4H), 3.82 (s, 1H), 4.30 (d, 1H), 4.63 (d, J=11.90 Hz, 1H), 4.92 (d, J=11.90 Hz, 1H), 6.97 (d, J=7.93 Hz, 1H), 7.04 (t, J=7.48 Hz, 1H), 7.23-7.30 (m, 2H), 7.32-7.45 (m, 3H), 7.53 (d, J=7.02 Hz, 2H); MS (ESI+) m/z 422 (M+H)$^+$.

Example 165

3-benzyl-N-butyl-N-(cyanomethyl)-1,2,3,4,4a,5-hexahydropyrazino[1,2-a][1,4]benzodiazepine-6(7H)-carboxamide The title compound was prepared as the trifluoroacetic acid salt according to the procedure outlined in Example 149 substituting 2-(butylamino)acetonitrile for 2-methoxy-N-methylethanamine. ¹H NMR (500 MHz, pyridine-d₅) δ ppm 0.83 (t, J=7.32 Hz, 3H), 1.06-1.26 (m, 2H), 1.49-1.70 (m, 2H), 2.40 (d, J=2.14 Hz, 1H), 2.54 (dd, J=10.37, 8.85 Hz, 1H), 2.67-2.91 (m, 2H), 3.03-3.42 (m, 6H), 3.48-3.67 (m, 2H), 3.85 (s, 1H), 4.15-4.41 (m, 2H), 4.39-4.60 (m, 1H), 4.84 (d, J=13.12 Hz, 1H), 6.96 (d, J=7.32 Hz, 2H), 7.25-7.40 (m, 2H), 7.34-7.41 (m, 3H), 7.49 (d, J=7.32 Hz, 2H); MS (ESI+) m/z 432 (M+H)⁺.

Example 166

3-benzyl-N-(3-methoxypropyl)-1,2,3,4,4a,5-hexahydropyrazino[1,2-a][1,4]benzodiazepine-6(7H)-carboxamide The title compound was prepared as the trifluoroacetic acid salt according to the procedure outlined in Example 149 substituting 1-methoxypropane for 2-methoxy-N-methylethanamine. ¹H NMR (500 MHz, pyridine-d₅) δ ppm 1.82-2.08 (m, 2H), 2.49 (d, J=2.44 Hz, 1H), 2.76 (s, 1H), 2.92-3.13 (m, 4H), 3.13-3.32 (m, 3H), 3.31-3.48 (m, 4H), 3.50-3.65 (m, 2H), 3.62-3.89 (m, 2H), 4.57 (d, J=11.60 Hz, 1H), 4.90 (d, J=11.90 Hz, 1H), 6.97 (d, J=7.93 Hz, 1H), 7.05 (t, J=7.48 Hz, 1H), 7.28 (dd, J=41.65, 6.87 Hz, 2H), 7.32-7.44 (m, 3H), 7.52 (d, J=7.32 Hz, 2H); MS (ESI+) m/z 409 (M+H)⁺.

Example 167

3-benzyl-N-(2-methoxyethyl)-1,2,3,4,4a,5-hexahydropyrazino[1,2-a][1,4]benzodiazepine-6(7H)-carboxamide The title compound was prepared as the trifluoroacetic acid salt according to the procedure outlined in Example 149 substituting 2-methoxyethanamine for 2-methoxy-N-methylethanamine. ¹H NMR (500 MHz, pyridine-d₅) δ ppm 2.34-2.64 (m, 1H), 2.78 (s, 1H), 2.85-3.14 (m, 4H), 3.16-3.40 (m, 4H), 3.45-3.68 (m, 4H), 3.68-3.91 (m, 4H), 4.31 (d, 1H), 4.57 (d, J=11.90 Hz, 1H), 6.96 (d, J=7.93 Hz, 1H), 6.99-7.09 (m, 1H), 7.31 (d, 2H), 7.37 (q, J=7.22 Hz, 3H), 7.52 (d, J=7.32 Hz, 2H); MS (ESI+) m/z 395 (M+H)⁺.

Example 168

3-benzyl-N-(pyridin-2-ylmethyl)-1,2,3,4,4a,5-hexahydropyrazino[1,2-a][1,4]benzodiazepine-6(7H)-carboxamide The title compound was prepared as the trifluoroacetic acid salt according to the procedure outlined in Example 149 substituting pyridin-2-ylmethanamine for 2-methoxy-N-methylethanamine. ¹H NMR (500 MHz, pyridine-d₅) δ ppm 2.32-2.63 (m, 1H), 2.67-2.92 (m, 1H), 2.96-3.24 (m, 4H), 3.24-3.48 (m, 2H), 3.69-3.96 (m, 2H), 4.35 (d, J=14.34 Hz, 1H), 4.53-4.72 (m, 1H), 4.79-5.08 (m, 2H), 6.98 (d, J=7.93 Hz, 1H), 7.06 (t, J=7.32 Hz, 1H), 7.03-7.16 (m, 1H), 7.24-7.34 (m, 3H), 7.31-7.50 (m, 3H), 7.50-7.59 (m, 5H); MS (ESI+) m/z 428 (M+H)⁺.

Example 169

3-benzyl-N-cyclobutyl-1,2,3,4,4a,5-hexahydropyrazino[1,2-a][1,4]benzodiazepine-6 (7H)-carboxamide The title compound was prepared as the trifluoroacetic acid salt according to the procedure outlined in Example 149 substituting cyclobutanamine for 2-methoxy-N-methylethanamine. ¹H NMR (500 MHz, pyridine-d₅) δ ppm 1.22-1.62 (m, 4H), 1.71-1.94 (m, 1H), 1.94-2.11 (m, 1H), 2.18-2.48 (m, 4H), 2.55-3.39 (m, 6H), 3.46-3.82 (m, 2H), 4.50-4.68 (m, 1H), 4.91 (d, J=11.60 Hz, 1H), 6.97 (t, J=7.93 Hz, 1H), 6.97-7.10 (m, 1H), 7.28-7.38 (m, 2H), 7.34-7.45 (m, 3H), 7.42-7.53 (m, 2H); MS (ESI+) m/z 391 (M+H)⁺.

Example 170

3-benzyl-N-methyl-N-propyl-1,2,3,4,4a,5-hexahydropyrazino[1,2-a][1,4]benzodiazepine-6(7H)-carboxamide The title compound was prepared as the trifluoroacetic acid salt according to the procedure outlined in Example 149 substituting N-methylpropan-1-amine for 2-methoxy-N-methylethanamine. ¹H NMR (500 MHz, pyridine-d₅) δ ppm 0.80 (t, J=7.32 Hz, 3H), 1.27-1.60 (m, 1H), 2.46 (d, J=3.05 Hz, 1H), 2.52-2.65 (m, 1H), 2.74 (s, 3H), 2.79-3.06 (m, 4H), 3.10-3.25 (m, 4H), 3.29 (s, 2H), 3.38 (s, 2H), 3.54-3.76 (m, 3H), 4.84 (d, J=12.51 Hz, 1H), 6.93 (d, J=7.63 Hz, 1H), 7.03 (t, J=7.48 Hz, 1H), 7.25-7.37 (m, 2H), 7.33-7.44 (m, 3H), 7.49 (s, 2H); MS (ESI+) m/z 393 (M+H)⁺.

Example 171

(3-benzyl-1,2,3,4,4a,5-hexahydropyrazino[1,2-a][1,4]benzodiazepin-6(7H)-yl)(piperidin-1-yl)methanone The title compound was prepared as the trifluoroacetic acid salt according to the procedure outlined in Example 149 substituting piperidine for 2-methoxy-N-methylethanamine. ¹H NMR (500 MHz, DMSO-d₆) δ=10.39 (s, 4H), 7.50 (dt, J=6.5, 3.4, 28H), 7.50 (dt, J=6.5, 3.4, 26H), 7.35 (t, J=7.5, 6H), 7.35 (t, J=7.5, 5H), 7.28 (d, J=7.1, 6H), 7.28 (d, J=7.1, 5H), 7.02 (m, 11H), 7.02 (m, 11H), 4.60 (d, J=12.2, 6H), 4.60 (d, J=12.2, 5H), 4.45 (s, 11H), 4.45 (s, 10H), 4.13 (d, J=12.3, 5H), 4.13 (d, J=12.3, 9H), 3.83 (s, 57H), 3.61 (m, 96H), 3.30 (m, 68H), 3.21 (m, 30H), 2.99 (m, 19H), 2.94 (d, J=14.9, 5H), 2.50 (m, 6H), 1.51 (d, J=48.7, 29H), 1.51 (d, J=48.7, 30H), 1.30 (d, J=7.0, 3H), 1.06 (t, J=7.0, 1H); MS (ESI+) m/z 405.1 (M+H)⁺.

Example 172

6-(cyclopropylmethyl)-2,3,4,4a,6,7-hexahydropyrazino[1,2-a][1,4]benzodiazepin-5(1H)-one To a solution of tert-butyl 5-oxo-1,2,4a,5,6,7-hexahydropyrazino[1,2-a][1,4]benzodiazepine-3(4H)-carboxylate (100 mg, 0.315 mmol, Example 1) in anhydrous N,N-dimethylformamide (2 mL) was added sodium hydride (13.86 mg, 0.347 mmol). After stirring for 1 hour at room temperature, (bromomethyl)cyclopropane (102 mg, 0.756 mmol) was added to the reaction mixture. The reaction was stirred for 20 hours. The reaction was then quenched carefully with water and extracted with ethyl acetate. The organic layer was separated, dried with MgSO₄, and concentrated. The residue was purified via flash chromatography (0-40% ethyl acetate/hexanes). The material obtained was dissolved in 1,4-dioxane (0.8 mL) and 4 M HCl in 1,4-dioxane (0.8 mL). The mixture was stirred for 20 hours. at room temperature. The title compound was collected by filtration as the hydrochloric acid salt. ¹H NMR (500 MHz, DMSO-d₆) δ 9.44 (s, 1H), 8.19 (s, 1H), 7.07-6.94 (m, 1H), 6.89 (d, J=7.9 Hz, 1H), 6.70 (t, J=7.2 Hz, 1H), 4.73 (d, J=16.0 Hz, 1H), 4.43 (s, 1H), 4.17 (d, J=16.1 Hz, 1H), 3.51-2.79 (m, 8H), 0.66 (m, 1H), 0.15-0.05 (m, 1H), 0.05-0.08 (m, J=4.1 Hz, 1H); MS (DCI) m/z 221.1 (M+H)+.

Example 173

[4-(3-methyl-1,2,3,4,4a,5-hexahydropyrazino[1,2-a]
[1,4]benzodiazepin-6(7H)-yl)piperidin-1-yl](phenyl)
methanone Example 173A 3-methyl-1,2,3,4,4a,5,6,7-octahydrobenzo[f]pyrazino
[1,2-a][1,4]diazepine To a solution of tert-butyl 5-oxo-1,2,4a,5,6,7-hexahydropyrazino[1,2-a][1,4]benzodiazepine-3(4H)-carboxylate (3 g, 9.45 mmol, Example 1) in tetrahydrofuran (95 mL) was added LiAlH$_4$ in tetrahydrofuran (14.18 mL, 28.4 mmol), and the mixture was stirred at room temperature for 24 hours. Water was added carefully and the product was extracted once with dichloromethane. The organic phase was dried over Na$_2$SO$_4$ and concentrated to provide crude product which was purified by reverse phase HPLC to afford the title compound as the trifluoroacetic acid salt. $^1$H NMR (500 MHz, DMSO-d$_6$) δ ppm 10.43 (s, 1H), 9.29 (s, 2H), 7.46 (t, J=7.7, 1H), 7.33 (d, J=7.0, 1H), 7.13 (t, J=8.7, 2H), 4.33 (d, J=11.8, 1H), 4.21 (d, J=7.5, 1H), 3.41-2.93 (m, 9H), 2.90 (s, 3H); MS (ESI+) m/z 218.0 (M+H)+.

Example 173B

[4-(3-methyl-1,2,3,4,4a,5-hexahydropyrazino[1,2-a]
[1,4]benzodiazepin-6(7H)-yl)piperidin-1-yl](phenyl)
methanone To a solution of Example 173A (0.128 g, 0.589 mmol) in dichloromethane (4.53 mL) was added acetic acid (0.438 mL, 7.66 mmol), 1-benzoylpiperidin-4-one (0.120 g, 0.589 mmol) and MP-cyanoborohydride resin (1.414 g, 1.767 mmol), and the mixture was stirred at room temperature for 24 hours. The reaction mixture was filtered and the resin beads were washed with methanol. The filtrate was concentrated and purified by reverse phase HPLC to afford the title compound as the trifluoroacetic acid salt. $^1$H NMR (500 MHz, DMSO-d$_6$) δ ppm 10.35 (br s, 1H), 7.58-7.33 (m, 7H), 7.20-6.99 (m, 5H), 5.02-3.96 (m, 7H), 3.13 (m, 5H), 2.86 (s, 3H), 2.17 (br s, 1H), 1.69 (br s, 1H); MS (ESI+) m/z 405.1 (M+H)+.

Example 174

(2-chlorophenyl)(3-methyl-1,2,3,4,4a,5-hexahydro-
pyrazino[1,2-a][1,4]benzodiazepin-6(7H)-yl)metha-
none To a solution of Example 173A (0.128 g, 0.589 mmol) in dichloromethane (3 mL) was added 2-chlorobenzoic acid (101 mg, 0.645 mmol), diisopropylethylamine (0.309 mL, 1.767 mmol) and O-(7-azabenzotriazol-1-yl)-N,N,N',N'-tetramethyluronium hexafluorophosphate (0.336 g, 0.884 mmol), and the reaction mixture was stirred at room temperature for 24 hours. The reaction mixture was filtered, the filtrate was concentrated, and the crude residue was purified by reverse phase HPLC to afford the title compound as the trifluoroacetic acid salt. $^1$H NMR (500 MHz, DMSO-d$_6$) δ ppm 9.81 (br s, 1H), 7.67-7.33 (m, 6H), 7.10 (m, 2H), 4.82-4.52 (m, 1H), 4.49-4.20 (m, 1H), 3.77-3.48 (m, 1H), 3.32-2.74 (m, 11H); MS (ESI+) m/z 356.0 (M+H)+.

Example 175

(3-chlorophenyl)(3-methyl-1,2,3,4,4a,5-hexahydro-
pyrazino[1,2-a][1,4]benzodiazepin-6(7H)-yl)metha-
none The title compound was prepared as the trifluoroacetic acid salt according to the procedure outlined in Example 174 substituting 3-chlorobenzoic acid for 2-chlorobenzoic acid. $^1$H NMR (500 MHz, DMSO-d$_6$) δ ppm 10.02-9.54 (m, 1H), 7.65-6.99 (m, 8H), 4.71-4.52 (m, 2H), 4.38-4.15 (m, 1H), 3.63-3.37 (m, 3H), 3.19-2.71 (m, 8H); MS (ESI+) m/z 356.0 (M+H)+.

Example 176

(4-chlorophenyl)(3-methyl-1,2,3,4,4a,5-hexahydro-
pyrazino[1,2-a][1,4]benzodiazepin-6(7H)-yl)metha-
none The title compound was prepared as the trifluoroacetic acid salt according to the procedure outlined in Example 174 substituting 4-chlorobenzoic acid for 2-chlorobenzoic acid. $^1$H NMR (500 MHz, DMSO-d$_6$) δ ppm 7.76-6.99 (m, 8H), 4.62 (dd, J=21.8, 7.7, 2H), 4.30-4.12 (m, 1H), 3.49 (m, 2H), 3.32-2.76 (m, 9H); MS (ESI+) m/z 356.0 (M+H)+.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:
1. A compound of formula (I):

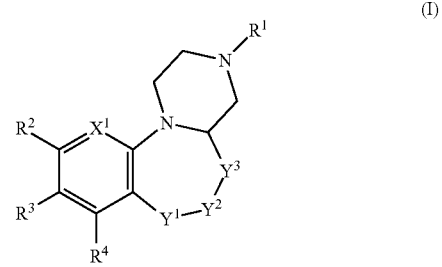

or a pharmaceutically acceptable salt thereof, wherein
R$^1$ is selected from the group consisting of alkylcarbonyl, haloalkyl, G$^1$, —(CR$^{4a}$R$^{5a}$)$_m$-G$^1$, —C(O)-G$^1$, —S(O)$_2$G$^1$, —C(O)OR$^6$ and —C(O)NR$^7$R$^8$; wherein R$^1$ is other than alkylcarbonyl, or haloalkyl when one of Y$^1$ or Y$^2$ is CH$_2$ and the other is NR$^9$;
R$^2$, R$^3$, and R$^4$ are each independently hydrogen, alkyl, alkenyl, alkynyl, halogen, cyano, —NO$_2$, —OR$^{1a}$, —S(O)$_2$R$^{2a}$, —C(O)OR$^{1a}$, or haloalkyl;
R$^5$ is hydrogen;
R$^6$ is alkyl or —(CR$^{4a}$R$^{5a}$)$_m$-G$^1$;

R⁷ and R⁸ are independently hydrogen, alkyl, G¹, or —(CR$^{4a}$R$^{5a}$)$_m$-G¹;

R⁹ is hydrogen or alkyl;

R$^{1a}$, at each occurrence, is independently hydrogen, alkyl, haloalkyl, or —(CR$^{4a}$R$^{5a}$)$_m$-G¹;

R$^{2a}$, at each occurrence, is independently alkyl, haloalkyl, or G¹;

R$^{4a}$ and R$^{5a}$, at each occurrence, are each independently hydrogen, halogen, alkyl, or haloalkyl, or R$^{4a}$ and R$^{5a}$ together with the carbon to which they are attached form a cycloalkyl;

R$^{1b}$, at each occurrence, is independently hydrogen, alkyl, or haloalkyl;

R$^{2b}$, at each occurrence, is independently alkyl, cyanoalkyl or haloalkyl;

G¹, at each occurrence, is independently aryl or heteroaryl, wherein each G¹ is independently unsubstituted or substituted with 1, 2, 3, 4, or 5 substituents selected from the group consisting of alkyl, alkenyl, halogen, cyano, —NO₂, —OR$^{1b}$, —S(O)₂R$^{2b}$, —C(O)OR$^{1b}$, —(CR$^{4a}$R$^{5a}$)$_m$—N(R$^{1b}$)₂, and haloalkyl;

G², at each occurrence, is independently cycloalkyl or heterocycle, wherein each G² is independently unsubstituted or substituted with 1, 2, 3, 4, or 5 substituents selected from the group consisting of alkyl, alkenyl, halogen, cyano, —NO₂, —OR$^{1b}$, —S(O)₂R$^{2b}$, —C(O)OR$^{1b}$, —C(O)R$^{2b}$, —C(O)N(R$^{1b}$)₂, haloalkyl, and oxo;

m, at each occurrence, is independently 1, 2, 3, 4, or 5;

X¹ is CR⁵;

Y¹ is CH₂;

Y² is selected from the group consisting of NR⁹, N-G¹, N—(CR$^{4a}$R$^{5a}$)$_m$-G¹, N⁺-[(CR$^{4a}$R$^{5a}$)$_m$-G¹]₂, NC(O)—(CR$^{4a}$R$^{5a}$)$_m$-G¹, NC(O)—CH=CH-G¹, NC(O)-G¹, NC(O)-G²-G¹, N-G², N—(CR$^{4a}$R$^{5a}$)$_m$-G², NC(O)—(CR$^{4a}$R$^{5a}$)$_m$-G², and NC(O)-G²; wherein W¹ is NHC(O)G¹ or —O—(CR$^{4a}$R$^{5a}$)$_m$—R$^{1b}$; and Y³ is C(O).

2. The compound of claim 1, wherein R¹ is selected from the group consisting of —(CR$^{4a}$R$^{5a}$)$_m$-G¹ and —C(O)OR⁶; and Y² is NR⁹, N—(CR$^{4a}$R$^{5a}$)$_m$-G¹ or N—(CR$^{4a}$R$^{5a}$)$_m$-G².

3. A compound of formula (I)

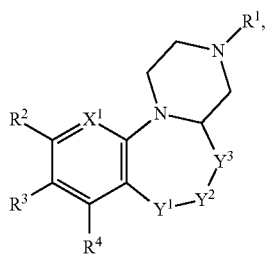

(I)

or a pharmaceutically acceptable salt thereof, wherein

R¹ is selected from the group consisting of alkylcarbonyl, haloalkyl, G¹, —(CR$^{4a}$R$^{5a}$)$_m$-G¹, —C(O)-G¹, —S(O)₂G¹, —C(O)OR⁶ and —C(O)NR⁷R⁸; wherein R¹ is other than alkylcarbonyl, or haloalkyl when one of Y¹ or Y² is CH₂ and the other is NR⁹;

R², R³, and R⁴ are each independently hydrogen, alkyl, alkenyl, alkenyl, halogen, cyano, —NO₂, —OR$^{1a}$, —S(O)₂R$^{2a}$, —C(O)OR$^{1a}$, or haloalkyl;

R⁵ is hydrogen;

R⁶ is alkyl or —(CR$^{4a}$R$^{5a}$)$_m$-G¹;

R⁷ and R⁸ are independently hydrogen, alkyl, G¹, or —(CR$^{4a}$R$^{5a}$)$_m$-G¹;

R⁹ is hydrogen or alkyl;

R$^{1a}$, at each occurrence, is independently hydrogen, alkyl, haloalkyl, or —(CR$^{4a}$R$^{5a}$)$_m$-G¹;

R$^{2a}$, at each occurrence, is independently alkyl, haloalkyl, or G¹;

R$^{4a}$ and R$^{5a}$, at each occurrence, are each independently hydrogen, halogen, alkyl, or haloalkyl, or R$^{4a}$ and R$^{5a}$ together with the carbon to which they are attached form a cycloalkyl;

R$^{1b}$, at each occurrence, is independently hydrogen, alkyl, or haloalkyl;

R$^{2b}$, at each occurrence, is independently alkyl, cyanoalkyl or haloalkyl;

G¹, at each occurrence, is independently aryl or heteroaryl, wherein each G¹ is independently unsubstituted or substituted with 1, 2, 3, 4, or 5 substituents selected from the group consisting of alkyl, alkenyl, halogen, cyano, —NO₂, —OR$^{1b}$, —S(O)₂R$^{2b}$, —C(O)OR$^{1b}$, —(CR$^{4a}$R$^{5a}$)$_m$—N(R$^{1b}$)₂, and haloalkyl;

G², at each occurrence, is independently cycloalkyl or heterocycle, wherein each G² is independently unsubstituted or substituted with 1, 2, 3, 4, or 5 substituents selected from the group consisting of alkyl, alkenyl, halogen, cyano, —NO₂, —OR$^{1b}$, —S(O)₂R$^{2b}$, —C(O)OR$^{1b}$, —C(O)R$^{2b}$, —C(O)N(R$^{1b}$)₂, haloalkyl, and oxo;

m, at each occurrence, is independently 1, 2, 3, 4, or 5;

X¹ is CR⁵;

Y¹ is CH₂;

Y² is selected from the group consisting of NR⁹, N-G¹, N—(CR$^{4a}$R$^{5a}$)$_m$-G¹, N⁺-[(CR$^{4a}$R$^{5a}$)$_m$-G¹]₂, NC(O)—R$^{2b}$, NC(O)—(CR$^{4a}$R$^{5a}$)$_m$-G¹; NC(O)—(CR$^{4a}$R$^{5a}$)$_m$—W¹, NC(O)—CH=CH-G¹, NC(O)-G¹, NC(O)-G²-G¹, N-G², N-G²-C(O)-G¹, N—(CR$^{4a}$R$^{5a}$)$_m$-G², NC(O)—(CR$^{4a}$R$^{5a}$)$_m$-G², NC(O)-G², NC(O)NH—W³, NC(O)N(R$^{2b}$)—W³, and NC(O)N(R$^{1b}$)—(CR$^{4a}$R$^{5a}$)$_m$—W²;

wherein

W¹ is NHC(O)G¹ or —O—(CR$^{4a}$R$^{5a}$)$_m$—R$^{1b}$;

W² is G¹, G², N(R$^{1b}$)₂, R$^{1b}$, or —O—(CR$^{4a}$R$^{5a}$)$_m$—R$^{1b}$;

W³ is R$^{1b}$, G¹ or G²; and

Y³ is CH₂.

4. The compound of claim 3, wherein R¹ is —(CR$^{4a}$R$^{5a}$)$_m$-G¹; and Y² is NR⁹.

5. The compound of claim 3, wherein R¹ is —(CR$^{4a}$R$^{5a}$)$_m$-G¹ or —C(O)OR⁶;

Y² is N—(CR$^{4a}$R$^{5a}$)$_m$-G¹, N—(CR$^{4a}$R$^{5a}$)$_m$-G², or N⁺-[(CR$^{4a}$R$^{5a}$)$_m$-G¹]₂; and m, at each occurrence, is independently 1, 2, or 3.

6. The compound of claim 3, wherein R¹ is —(CR$^{4a}$R$^{5a}$)$_m$-G¹;

Y² is N-G¹ or N-G²-C(O)-G¹; and m is independently 1, 2, or 3.

7. The compound of claim 3, wherein R¹ is alkylcarbonyl, G¹, —(CR$^{4a}$R$^{5a}$)$_m$-G¹, —C(O)-G¹, or —S(O)₂G¹; and Y² is NC(O)—(CR$^{4a}$R$^{5a}$)$_m$-G¹, NC(O)—CH=CH-G¹, NC(O)-G¹, NC(O)-G²-G¹, NC(O)—(CR$^{4a}$R$^{5a}$)$_m$-G², NC(O)—(CR$^{4a}$R$^{5a}$)$_m$—W¹, NC(O)—R$^{2b}$ or NC(O)-G².

8. The compound of claim 3, wherein R¹ is G¹, —(CR$^{4a}$R$^{5a}$)$_m$-G¹, —C(O)-G¹, or —S(O)₂G¹; and Y² is NC(O)NH—W³, NC(O)N(R$^{2b}$)—W³, or NC(O)N(R$^{1b}$)—(CR$^{4a}$R$^{5a}$)$_m$—W².

9. A compound of formula (I)

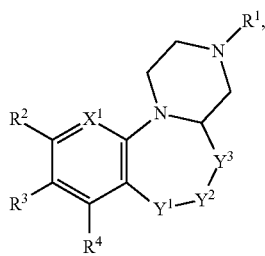

or a pharmaceutically acceptable salt thereof, wherein
$R^1$ is selected from the group consisting of alkylcarbonyl, haloalkyl, $G^1$, —$(CR^{4a}R^{5a})_m$-$G^1$, —C(O)-$G^1$, —S(O)$_2$$G^1$, —C(O)O$R^6$ and —C(O)N$R^7R^8$; wherein $R^1$ is other than alkylcarbonyl, or haloalkyl when one of $Y^1$ or $Y^2$ is $CH_2$ and the other is $NR^9$;
$R^2$, $R^3$, $R^4$, and $R^5$ are each independently hydrogen, alkyl, alkenyl, alkenyl, halogen, cyano, —NO$_2$, —O$R^{1a}$, —S(O)$_2R^{2a}$, —C(O)O$R^{1a}$, or haloalkyl;
$R^6$ is alkyl or —$(CR^{4a}R^{5a})_m$-$G^1$;
$R^7$ and $R^8$ are independently hydrogen, alkyl, $G^1$, or —$(CR^{4a}R^{5a})_m$-$G^1$;
$R^9$ is hydrogen or alkyl;
$R^{1a}$, at each occurrence, is independently hydrogen, alkyl, haloalkyl, or —$(CR^{4a}R^{5a})_m$-$G^1$;
$R^{2a}$, at each occurrence, is independently alkyl, haloalkyl, or $G^1$;
$R^{4a}$ and $R^{5a}$, at each occurrence, are each independently hydrogen, halogen, alkyl, or haloalkyl, or $R^{4a}$ and $R^{5a}$ together with the carbon to which they are attached form a cycloalkyl;
$R^{1b}$, at each occurrence, is independently hydrogen, alkyl, or haloalkyl;
$R^{2b}$, at each occurrence, is independently alkyl, cyanoalkyl or haloalkyl;
$G^1$, at each occurrence, is independently aryl or heteroaryl, wherein each $G^1$ is independently unsubstituted or substituted with 1, 2, 3, 4, or 5 substituents selected from the group consisting of alkyl, alkenyl, halogen, cyano, —NO$_2$, —O$R^{1b}$, —S(O)$_2R^{2b}$, —C(O)O$R^{1b}$, —$(CR^{4a}R^{5a})_m$—N$(R^{1b})_2$, and haloalkyl;
$G^2$, at each occurrence, is independently cycloalkyl or heterocycle, wherein each $G^2$ is independently unsubstituted or substituted with 1, 2, 3, 4, or 5 substituents selected from the group consisting of alkyl, alkenyl, halogen, cyano, —NO$_2$, —O$R^{1b}$, —S(O)$_2R^{2b}$, —C(O)O$R^{1b}$, —C(O)$R^{2b}$, —C(O)N$(R^{1b})_2$, haloalkyl, and oxo;
m, at each occurrence, is independently 1, 2, 3, 4, or 5;
$X^1$ is N or $CR^5$;
$Y^1$ is selected from the group consisting of $NR^9$, N-$G^1$, N—$(CR^{4a}R^{5a})_m$-$G^1$, $N^+$-[$(CR^{4a}R^{5a})_m$-$G^1$]$_2$, NC(O)—$R^{2b}$, NC(O)—$(CR^{4a}R^{5a})_m$-$G^1$; NC(O)—$(CR^{4a}R^{5a})_m$—$W^1$, NC(O)—CH=CH-$G^1$, NC(O)-$G^1$, NC(O)-$G^2$-$G^1$, N-$G^2$, N-$G^2$-C(O)-$G^1$, N—$(CR^{4a}R^{5a})_m$-$G^2$, NC(O)—$(CR^{4a}R^{5a})_m$-$G^2$, NC(O)-$G^2$, NC(O)NH—$W^3$, NC(O)N$(R^{2b})$—$W^3$, and NC(O)N$(R^{1b})$—$(CR^{4a}R^{5a})_m$—$W^2$;
wherein
$W^1$ is NHC(O)$G^1$ or —O—$(CR^{4a}R^{5a})_m$—$R^{1b}$;
$W^2$ is $G^1$, $G^2$, N$(R^{1b})_2$, $R^{1b}$, or —O—$(CR^{4a}R^{5a})_m$—$R^{1b}$;
$W^3$ is $R^{1b}$, $G^1$ or $G^2$;
$Y^2$ is $CH_2$; and
$Y^3$ is $CH_2$.

10. The compound of claim 9, wherein $R^1$ is —$(CR^{4a}R^{5a})_m$-$G^1$; and
$Y^1$ is $NR^9$.

11. The compound of claim 9, wherein $R^1$ is —$(CR^{4a}R^{5a})_m$-$G^1$ or —C(O)-$G^1$; and
$Y^1$ is N—$(CR^{4a}R^{5a})_m$-$G^1$, or N—$(CR^{4a}R^{5a})_m$-$G^2$.

12. The compound of claim 9, wherein $X^1$ is $CR^5$ or N;
$R^5$ is hydrogen;
$R^1$ is —$(CR^{4a}R^{5a})_m$-$G^1$; and
$Y^1$ is NC(O)—$(CR^{4a}R^{5a})_m$-$G^1$, NC(O)-$G^1$, NC(O)—$(CR^{4a}R^{5a})_m$-$G^2$, or NC(O)-$G^2$.

13. The compound according to claim 1 or a pharmaceutically acceptable salt thereof, selected from the group consisting of:
tert-butyl 5-oxo-1,2,4a,5,6,7-hexahydropyrazino[1,2-a][1,4]benzodiazepine-3(4H)-carboxylate;
3-(4-fluorobenzyl)-2,3,4,4a,6,7-hexahydropyrazino[1,2-a][1,4]benzodiazepin-5(1H)-one;
tert-butyl 6-(4-bromobenzyl)-5-oxo-1,2,4a,5,6,7-hexahydropyrazino[1,2-a][1,4]benzodiazepine-3(4H)-carboxylate; and
6-(4-bromobenzyl)-3-(4-fluorobenzyl)-2,3,4,4a,6,7-hexahydropyrazino[1,2-a][1,4]benzodiazepin-5 (1H)-one.

14. A pharmaceutical composition comprising a therapeutically effective amount of a compound of formula (I) according to claim 1 or a pharmaceutically acceptable salt thereof, in combination with a pharmaceutically acceptable carrier.

15. A pharmaceutical composition comprising a therapeutically effective amount of a compound of formula (I) according to claim 3 or a pharmaceutically acceptable salt thereof, in combination with a pharmaceutically acceptable carrier.

16. A pharmaceutical composition comprising a therapeutically effective amount of a compound of formula (I) according to claim 9 or a pharmaceutically acceptable salt thereof, in combination with a pharmaceutically acceptable carrier.

17. The compound according to claim 3 or a pharmaceutically acceptable salt thereof, selected from the group consisting of:
3-benzyl-1,2,3,4,4a,5,6,7-octahydropyrazino[1,2-a][1,4]benzodiazepine;
3-benzyl-6-(4-bromobenzyl)-1,2,3,4,4a,5,6,7-octahydropyrazino[1,2-a][1,4]benzodiazepine;
1-(3-benzyl-1,2,3,4,4a,5-hexahydropyrazino[1,2-a][1,4]benzodiazepin-6(7H)-yl)-2-phenylethanone;
(3-benzyl-1,2,3,4,4a,5-hexahydropyrazino[1,2-a][1,4]benzodiazepin-6(7H)-yl)(phenyl)methanone;
3,6,6-tribenzyl-1,2,3,4,4a,5,6,7-octahydropyrazino[1,2-a][1,4]benzodiazepin-6-ium;
3,6-dibenzyl-1,2,3,4,4a,5,6,7-octahydropyrazino[1,2-a][1,4]benzodiazepine;
3-benzyl-6-methyl-1,2,3,4,4a,5,6,7-octahydropyrazino[1,2-a][1,4]benzodiazepine;
3-benzyl-6-(pyrimidin-2-yl)-1,2,3,4,4a,5,6,7-octahydropyrazino[1,2-a][1,4]benzodiazepine;
(3-benzyl-1,2,3,4,4a,5-hexahydropyrazino[1,2-a][1,4]benzodiazepin-6(7H)-yl)(4-fluorophenyl)methanone;
3-benzyl-6-(pyrazin-2-yl)-1,2,3,4,4a,5,6,7-octahydropyrazino[1,2-a][1,4]benzodiazepine;
(3-benzyl-1,2,3,4,4a,5-hexahydropyrazino[1,2-a][1,4]benzodiazepin-6(7H)-yl)(pyrazin-2-yl)methanone;
(3-benzyl-1,2,3,4,4a,5-hexahydropyrazino[1,2-a][1,4]benzodiazepin-6(7H)-yl)(1-phenylcyclopropyl)methanone;
(3-benzyl-1,2,3,4,4a,5-hexahydropyrazino[1,2-a][1,4]benzodiazepin-6(7H)-yl)(morpholin-4-yl)methanone;

(3-benzyl-1,2,3,4,4a,5-hexahydropyrazino[1,2-a][1,4]
benzodiazepin-6(7H)-yl)[trans-2-phenylcyclopropyl]
methanone;
3-benzyl-6-(pyridin-2-yl)-1,2,3,4,4a,5,6,7-octahydropy-
razino[1,2-a][1,4]benzodiazepine;
3-benzyl-6-(4-fluorobenzyl)-1,2,3,4,4a,5,6,7-octahydro-
pyrazino[1,2-a][1,4]benzodiazepine;
(−)-3-benzyl-6-(4-bromobenzyl)-1,2,3,4,4a,5,6,7-octahy-
dropyrazino[1,2-a][1,4]benzodiazepine;
(+)-3-benzyl-6-(4-bromobenzyl)-1,2,3,4,4a,5,6,7-octahy-
dropyrazino[1,2-a][1,4]benzodiazepine;
(2E)-1-(3-benzyl-1,2,3,4,4a,5-hexahydropyrazino[1,2-a]
[1,4]benzodiazepin6(7H)-yl)-3-phenylprop-2-en-1-
one;
3-benzyl-6-[4-(trifluoromethyl)benzyl]-1,2,3,4,4a,5,6,7-
octahydropyrazino[1,2-a][1,4]benzodiazepine;
3-benzyl-6-(4-bromo-3-fluorobenzyl)-1,2,3,4,4a,5,6,7-
octahydropyrazino[1,2-a][1,4]benzodiazepine;
3-benzyl-6-(3,5-difluorobenzyl)-1,2,3,4,4a,5,6,7-octahy-
dropyrazino[1,2-a][1,4]benzodiazepine;
3-benzyl-6-(3,4-difluorobenzyl)-1,2,3,4,4a,5,6,7-octahy-
dropyrazino[1,2-a][1,4]benzodiazepine;
3-benzyl-6-(pyridin-3-ylmethyl)-1,2,3,4,4a,5,6,7-octahy-
dropyrazino[1,2-a][1,4]benzodiazepine;
3-benzyl-6-(pyridin-2-ylmethyl)-1,2,3,4,4a,5,6,7-octahy-
dropyrazino[1,2-a][1,4]benzodiazepine;
3-benzyl-6-(pyridin-4-ylmethyl)-1,2,3,4,4a,5,6,7-octahy-
dropyrazino[1,2-a][1,4]benzodiazepine;
(3-benzyl-1,2,3,4,4a,5-hexahydropyrazino[1,2-a][1,4]
benzodiazepin-6(7H)-yl)(4-bromophenyl)methanone;
3-benzyl-6-[(6-methylpyridin-3-yl)methyl]-1,2,3,4,4a,5,
6,7-octahydropyrazino[1,2-a][1,4]benzodiazepine;
3-benzyl-6-(quinolin-3-ylmethyl)-1,2,3,4,4a,5,6,7-oc-
tahydropyrazino[1,2-a][1,4]benzodiazepine;
3-benzyl-6-[(6-chloropyridin-3-yl)methyl]-1,2,3,4,4a,5,
6,7-octahydropyrazino[1,2-a][1,4]benzodiazepine;
3-benzyl-6-{[6-(trifluoromethyl)pyridin-3-yl]methyl}-1,
2,3,4,4a,5,6,7-octahydropyrazino[1,2-a][1,4]benzodi-
azepine;
3-benzyl-6-(quinolin-4-ylmethyl)-1,2,3,4,4a,5,6,7-oc-
tahydropyrazino[1,2-a][1,4]benzodiazepine;
3-benzyl-6-(isoquinolin-4-ylmethyl)-1,2,3,4,4a,5,6,7-oc-
tahydropyrazino[1,2-a][1,4]benzodiazepine;
3-benzyl-6-[(6-bromopyridin-3-yl)methyl]-1,2,3,4,4a,5,
6,7-octahydropyrazino[1,2-a][1,4]benzodiazepine;
3-(4-fluorobenzyl)-1,2,3,4,4a,5,6,7-octahydropyrazino[1,
2-a][1,4]benzodiazepine;
3-benzyl-6-[(5-bromopyridin-2-yl)methyl]-1,2,3,4,4a,5,
6,7-octahydropyrazino[1,2-a][1,4]benzodiazepine;
3-benzyl-6-(4-iodobenzyl)-1,2,3,4,4a,5,6,7-octahydropy-
razino[1,2-a][1,4]benzodiazepine;
4-[(3-benzyl-1,2,3,4,4a,5-hexahydropyrazino[1,2-a][1,4]
benzodiazepin-6(7H)-yl)methyl]phenol;
6-(4-bromobenzyl)-3-(4-fluorobenzyl)-1,2,3,4,4a,5,6,7-
octahydropyrazino[1,2-a][1,4]benzodiazepine;
1-(3-benzyl-1,2,3,4,4a,5-hexahydropyrazino[1,2-a][1,4]
benzodiazepin-6(7H)-yl)-2-(6-chloropyridin-3-yl)etha-
none;
(+)-(4aS)-6-(4-bromobenzyl)-3-(4-fluorobenzyl)-1,2,3,4,
4a,5,6,7-octahydropyrazino[1,2-a][1,4]benzodiaz-
epine;
(−)-(4aR)-6-(4-bromobenzyl)-3-(4-fluorobenzyl)-1,2,3,4,
4a,5,6,7-octahydropyrazino[1,2-a][1,4]benzodiaz-
epine;
3-benzyl-6-[2-(6-chloropyridin-3-yl)ethyl]-1,2,3,4,4a,5,
6,7-octahydropyrazino[1,2-a][1,4]benzodiazepine;

tert-butyl 6-(4-bromobenzyl)-1,2,4a,5,6,7-hexahydropy-
razino[1,2-a][1,4]benzodiazepine-3(4H)-carboxylate;
[3-(4-fluorobenzyl)-1,2,3,4,4a,5-hexahydropyrazino[1,2-
a][1,4]benzodiazepin-6(7H)-yl](morpholin-4-yl)
methanone;
(3-benzoyl-1,2,3,4,4a,5-hexahydropyrazino[1,2-a][1,4]
benzodiazepin-6(7H)yl)(morpholin-4-yl)methanone;
morpholin-4-yl[3-(pyrimidin-2-yl)-1,2,3,4,4a,5-hexahy-
dropyrazino[1,2-a][1,4]benzodiazepin-6(7H)-yl]
methanone;
morpholin-4-yl[3-(phenylsulfonyl)-1,2,3,4,4a,5-hexahy-
dropyrazino[1,2-a][1,4]benzodiazepin-6(7H)-yl]
methanone;
[3-(4-chlorophenyl)-1,2,3,4,4a,5-hexahydropyrazino[1,2-
a][1,4]benzodiazepin-6(7H)-yl](morpholin-4-yl)
methanone;
1-[6-(morpholin-4-ylcarbonyl)-1,2,4a,5,6,7-hexahydro-
pyrazino[1,2-a][1,4]benzodiazepin-3(4H)-yl]ethanone;
1-{4-[(3-benzyl-1,2,3,4,4a,5-hexahydropyrazino[1,2-a]
[1,4]benzodiazepin-6(7H)-yl)carbonyl]piperidin-1-
yl}ethanone;
(3-benzyl-1,2,3,4,4a,5-hexahydropyrazino[1,2-a][1,4]
benzodiazepin-6(7H)-yl)(1H-pyrazol-4-yl)methanone;
(3-benzyl-1,2,3,4,4a,5-hexahydropyrazino[1,2-a][1,4]
benzodiazepin-6(7H)-yl)(1H-pyrazol-5-yl)methanone;
1-(3-benzyl-1,2,3,4,4a,5-hexahydropyrazino[1,2-a][1,4]
benzodiazepin-6(7H)-yl)-2-(morpholin-4-yl)ethanone;
(3-benzyl-1,2,3,4,4a,5-hexahydropyrazino[1,2-a][1,4]
benzodiazepin-6(7H)-yl)(1,3-thiazol-4-yl)methanone;
(3-benzyl-1,2,3,4,4a,5-hexahydropyrazino[1,2-a][1,4]
benzodiazepin-6(7H)-yl)(1,3-thiazol-5-yl)methanone;
(3-benzyl-1,2,3,4,4a,5-hexahydropyrazino[1,2-a][1,4]
benzodiazepin-6(7H)-yl)(1,2-oxazol-5-yl)methanone;
1-(3-benzyl-1,2,3,4,4a,5-hexahydropyrazino[1,2-a][1,4]
benzodiazepin-6(7H)-yl)-3-(pyrrolidin-1-yl)propan-1-
one;
1-(3-benzyl-1,2,3,4,4a,5-hexahydropyrazino[1,2-a][1,4]
benzodiazepin-6(7H)-yl)-2-cyclopropylethanone;
(3-benzyl-1,2,3,4,4a,5-hexahydropyrazino[1,2-a][1,4]
benzodiazepin-6(7H)-yl)(1H-pyrrol-2-yl)methanone;
(3-benzyl-1,2,3,4,4a,5-hexahydropyrazino[1,2-a][1,4]
benzodiazepin-6(7H)-yl)(3-furyl)methanone;
(3-benzyl-1,2,3,4,4a,5-hexahydropyrazino[1,2-a][1,4]
benzodiazepin-6(7H)-yl)(1,2,5-trimethyl-1H-pyrrol-3-
yl)methanone;
(3-benzyl-1,2,3,4,4a,5-hexahydropyrazino[1,2-a][1,4]
benzodiazepin-6(7H)-yl)(2,5-dimethyl-1H-pyrrol-3-yl)
methanone;
1-[(3-benzyl-1,2,3,4,4a,5-hexahydropyrazino[1,2-a][1,4]
benzodiazepin-6(7H)-yl)carbonyl]cyclopropanecar-
boxamide;
1-(3-benzyl-1,2,3,4,4a,5-hexahydropyrazino[1,2-a][1,4]
benzodiazepin-6(7H)-yl)-2-(pyridin-3-yl)ethanone;
N-[2-(3-benzyl-1,2,3,4,4a,5-hexahydropyrazino[1,2-a][1,
4]benzodiazepin-6(7H)-yl)-2-oxoethyl]-2-furamide;
1-(3-benzyl-1,2,3,4,4a,5-hexahydropyrazino[1,2-a][1,4]
benzodiazepin-6(7H)-yl)-2-methylpropan-1-one;
(3-benzyl-1,2,3,4,4a,5-hexahydropyrazino[1,2-a][1,4]
benzodiazepin-6(7H)-yl)(3,5-dimethyl-1,2-oxazol-4-
yl)methanone;
(3-benzyl-1,2,3,4,4a,5-hexahydropyrazino[1,2-a][1,4]
benzodiazepin-6(7H)-yl)(5-methylpyrazin-2-yl)metha-
none;
1-(3-benzyl-1,2,3,4,4a,5-hexahydropyrazino[1,2-a][1,4]
benzodiazepin-6(7H)-yl)-2-(4-methylpiperazin-1-yl)
ethanone;

(3-benzyl-1,2,3,4,4a,5-hexahydropyrazino[1,2-a][1,4]
benzodiazepin-6(7H)-yl)(2-furyl)methanone;
(3-benzyl-1,2,3,4,4a,5-hexahydropyrazino[1,2-a][1,4]
benzodiazepin-6(7H)-yl)(1-methyl-1H-pyrrol-2-yl)
methanone;
1-(3-benzyl-1,2,3,4,4a,5-hexahydropyrazino[1,2-a][1,4]
benzodiazepin-6(7H)-yl)propan-1-one;
(3-benzyl-1,2,3,4,4a,5-hexahydropyrazino[1,2-a][1,4]
benzodiazepin-6(7H)-yl)(pyridin-4-yl)methanone;
1-(3-benzyl-1,2,3,4,4a,5-hexahydropyrazino[1,2-a][1,4]
benzodiazepin-6(7H)-yl)butan-1-one;
(3-benzyl-1,2,3,4,4a,5-hexahydropyrazino[1,2-a][1,4]
benzodiazepin-6(7H)-yl)(tetrahydrofuran-3-yl)methanone;
(3-benzyl-1,2,3,4,4a,5-hexahydropyrazino[1,2-a][1,4]
benzodiazepin-6(7H)-yl)(pyridin-3-yl)methanone;
1-(3-benzyl-1,2,3,4,4a,5-hexahydropyrazino[1,2-a][1,4]
benzodiazepin-6(7H)-yl)-3-(piperidin-1-yl)propan-1-
one;
(3-benzyl-1,2,3,4,4a,5-hexahydropyrazino[1,2-a][1,4]
benzodiazepin-6(7H)-yl)(cyclopropyl)methanone;
1-(3-benzyl-1,2,3,4,4a,5-hexahydropyrazino[1,2-a][1,4]
benzodiazepin-6(7H)-yl)-2-ethoxyethanone;
(3-benzyl-1,2,3,4,4a,5-hexahydropyrazino[1,2-a][1,4]
benzodiazepin-6(7H)-yl)(1-methylcyclopropyl)methanone;
(3-benzyl-1,2,3,4,4a,5-hexahydropyrazino[1,2-a][1,4]
benzodiazepin-6(7H)-yl)(cyclobutyl)methanone;
(3-benzyl-1,2,3,4,4a,5-hexahydropyrazino[1,2-a][1,4]
benzodiazepin-6(7H)-yl)(2-methylcyclopropyl)methanone;
1-(3-benzyl-1,2,3,4,4a,5-hexahydropyrazino[1,2-a][1,4]
benzodiazepin-6(7H)-yl)-3,3,3-trifluoropropan-1-one;
(3-benzyl-1,2,3,4,4a,5-hexahydropyrazino[1,2-a][1,4]
benzodiazepin-6(7H)-yl)(tetrahydrofuran-2-yl)methanone;
3-benzyl-6-(4-methoxy-3-methylbenzyl)-1,2,3,4,4a,5,6,
7-octahydropyrazino[1,2-a][1,4]benzodiazepine;
3-benzyl-6-[(4,5-dimethyl-2-furyl)methyl]-1,2,3,4,4a,5,
6,7-octahydropyrazino[1,2-a][1,4]benzodiazepine;
3-benzyl-6-(4-ethoxybenzyl)-1,2,3,4,4a,5,6,7-octahydropyrazino[1,2-a][1,4]benzodiazepine;
3-benzyl-6-[(5-methyl-2-thienyl)methyl]-1,2,3,4,4a,5,6,
7-octahydropyrazino[1,2-a][1,4]benzodiazepine;
3-benzyl-6-(4-bromobenzyl)-1,2,3,4,4a,5,6,7-octahydropyrazino[1,2-a][1,4]benzodiazepine;
3-benzyl-6-(2-naphthylmethyl)-1,2,3,4,4a,5,6,7-octahydropyrazino[1,2-a][1,4]benzodiazepine;
3-benzyl-6-(cyclopentylmethyl)-1,2,3,4,4a,5,6,7-octahydropyrazino[1,2-a][1,4]benzodiazepine;
3-benzyl-6-(quinolin-2-ylmethyl)-1,2,3,4,4a,5,6,7-octahydropyrazino[1,2-a][1,4]benzodiazepine;
3-benzyl-6-[(5-ethyl-2-furyl)methyl]-1,2,3,4,4a,5,6,7-octahydropyrazino[1,2-a][1,4]benzodiazepine;
4-[(3-benzyl-1,2,3,4,4a,5-hexahydropyrazino[1,2-a][1,4]
benzodiazepin-6(7H)-yl)methyl]benzonitrile;
3-benzyl-6-butyl-1,2,3,4,4a,5,6,7-octahydropyrazino[1,2-a][1,4]benzodiazepine;
3-benzyl-6-(4-chlorobenzyl)-1,2,3,4,4a,5,6,7-octahydropyrazino[1,2-a][1,4]benzodiazepine;
3-benzyl-6-(2-methylbenzyl)-1,2,3,4,4a,5,6,7-octahydropyrazino[1,2-a][1,4]benzodiazepine;
3-benzyl-6-(2-bromobenzyl)-1,2,3,4,4a,5,6,7-octahydropyrazino[1,2-a][1,4]benzodiazepine;
3-benzyl-6-(2-methoxybenzyl)-1,2,3,4,4a,5,6,7-octahydropyrazino[1,2-a][1,4]benzodiazepine;
3-benzyl-6-(4-methoxybenzyl)-1,2,3,4,4a,5,6,7-octahydropyrazino[1,2-a][1,4]benzodiazepine;
3-benzyl-6-(3-methoxybenzyl)-1,2,3,4,4a,5,6,7-octahydropyrazino[1,2-a][1,4]benzodiazepine;
3-benzyl-6-(3-bromobenzyl)-1,2,3,4,4a,5,6,7-octahydropyrazino[1,2-a][1,4]benzodiazepine;
3-benzyl-6-(4-methylbenzyl)-1,2,3,4,4a,5,6,7-octahydropyrazino[1,2-a][1,4]benzodiazepine;
3-benzyl-6-(1-naphthylmethyl)-1,2,3,4,4a,5,6,7-octahydropyrazino[1,2-a][1,4]benzodiazepine;
3-benzyl-6-(2-chlorobenzyl)-1,2,3,4,4a,5,6,7-octahydropyrazino[1,2-a][1,4]benzodiazepine;
3-benzyl-6-(3-chlorobenzyl)-1,2,3,4,4a,5,6,7-octahydropyrazino[1,2-a][1,4]benzodiazepine;
3-benzyl-6-(2,2-dimethylpropyl)-1,2,3,4,4a,5,6,7-octahydropyrazino[1,2-a][1,4]benzodiazepine;
3-benzyl-6-[(3-methyl-2-thienyl)methyl]-1,2,3,4,4a,5,6,
7-octahydropyrazino[1,2-a][1,4]benzodiazepine;
3-benzyl-6-(3-methylbutyl)-1,2,3,4,4a,5,6,7-octahydropyrazino[1,2-a][1,4]benzodiazepine;
3-benzyl-6-(cyclohexylmethyl)-1,2,3,4,4a,5,6,7-octahydropyrazino[1,2-a][1,4]benzodiazepine;
3-benzyl-6-(3-methylbenzyl)-1,2,3,4,4a,5,6,7-octahydropyrazino[1,2-a][1,4]benzodiazepine;
3-[(3-benzyl-1,2,3,4,4a,5-hexahydropyrazino[1,2-a][1,4]
benzodiazepin-6(7H)-yl)methyl]benzonitrile;
3-benzyl-6-(2-thienylmethyl)-1,2,3,4,4a,5,6,7-octahydropyrazino[1,2-a][1,4]benzodiazepine;
3-benzyl-6-isobutyl-1,2,3,4,4a,5,6,7-octahydropyrazino
[1,2-a][1,4]benzodiazepine;
3-benzyl-N-(2-methoxyethyl)-N-methyl-1,2,3,4,4a,5-
hexahydropyrazino[1,2-a][1,4]benzodiazepine-6(7H)-
carboxamide;
3-benzyl-N-[2-(pyridin-3-yl)ethyl]-1,2,3,4,4a,5-hexahydropyrazino[1,2-a][1,4]benzodiazepine-6(7H)-carboxamide;
3-benzyl-N-[2-(pyridin-2-yl)ethyl]-1,2,3,4,4a,5-hexahydropyrazino[1,2-a][1,4]benzodiazepine-6(7H)-carboxamide;
3-benzyl-N-[2-(pyridin-4-yl)ethyl]-1,2,3,4,4a,5-hexahydropyrazino[1,2-a][1,4]benzodiazepine-6(7H)-carboxamide;
3-benzyl-N-(2-cyanoethyl)-N-cyclopropyl-1,2,3,4,4a,5-
hexahydropyrazino[1,2-a][1,4]benzodiazepine-6(7H)-
carboxamide;
[4-(2-aminoethyl)-1H-imidazol-1-yl](3-benzyl-1,2,3,4,
4a,5-hexahydropyrazino[1,2-a][1,4]benzodiazepin-6
(7H)-yl)methanone;
3-benzyl-N-(pyridin-4-ylmethyl)-1,2,3,4,4a,5-hexahydropyrazino[1,2-a][1,4]benzodiazepine-6(7H)-carboxamide;
3-benzyl-N-[(5-methyl-2-furyl)methyl]-1,2,3,4,4a,5-
hexahydropyrazino[1,2-a][1,4]benzodiazepine-6(7H)-
carboxamide;
3-benzyl-N-ethyl-N-(2-methoxyethyl)-1,2,3,4,4a,5-
hexahydropyrazino[1,2-a][1,4]benzodiazepine-6(7H)-
carboxamide;
3-benzyl-N,N-diethyl-1,2,3,4,4a,5-hexahydropyrazino[1,
2-a][1,4]benzodiazepine-6(7H)-carboxamide;
3-benzyl-N-(1,3-thiazol-2-yl)-1,2,3,4,4a,5-hexahydropyrazino[1,2-a][1,4]benzodiazepine-6(7H)-carboxamide;
3-benzyl-N-(cyclopropylmethyl)-1,2,3,4,4a,5-hexahydropyrazino[1,2-a][1,4]benzodiazepine-6(7H)-carboxamide;
(3-benzyl-1,2,3,4,4a,5-hexahydropyrazino[1,2-a][1,4]
benzodiazepin-6(7H)-yl)(4-isopropylpiperazin-1-yl)
methanone;

3-benzyl-N-isobutyl-1,2,3,4,4a,5-hexahydropyrazino[1,2-a][1,4]benzodiazepine-6(7H)-carboxamide;
3-benzyl-N-(pyridin-3-ylmethyl)-1,2,3,4,4a,5-hexahydropyrazino[1,2-a][1,4]benzodiazepine-6(7H)-carboxamide;
3-benzyl-N-[3-(dimethylamino)propyl]-1,2,3,4,4a,5-hexahydropyrazino[1,2-a][1,4]benzodiazepine-6(7H)-carboxamide;
3-benzyl-N-butyl-N-(cyanomethyl)-1,2,3,4,4a,5-hexahydropyrazino[1,2-a][1,4]benzodiazepine-6(7H)-carboxamide;
3-benzyl-N-(3-methoxypropyl)-1,2,3,4,4a,5-hexahydropyrazino[1,2-a][1,4]benzodiazepine-6(7H)-carboxamide;
3-benzyl-N-(2-methoxyethyl)-1,2,3,4,4a,5-hexahydropyrazino[1,2-a][1,4]benzodiazepine-6(7H)-carboxamide;
3-benzyl-N-(pyridin-2-ylmethyl)-1,2,3,4,4a,5-hexahydropyrazino[1,2-a][1,4]benzodiazepine-6(7H)-carboxamide;
3-benzyl-N-cyclobutyl-1,2,3,4,4a,5-hexahydropyrazino[1,2-a][1,4]benzodiazepine-6(7H)-carboxamide;
3-benzyl-N-methyl-N-propyl-1,2,3,4,4a,5-hexahydropyrazino[1,2-a][1,4]benzodiazepine-6(7H)-carboxamide; and
(3-benzyl-1,2,3,4,4a,5-hexahydropyrazino[1,2-a][1,4]benzodiazepin-6(7H)-yl)(piperidin-1-yl)methanone.

18. The compound according to claim 9 or a pharmaceutically acceptable salt thereof, selected from the group consisting of:

3-benzyl-1,2,3,4,4a,5,6,7-octahydropyrazino[1,2-a][1,5]benzodiazepine;
1-(3-benzyl-2,3,4,4a,5,6-hexahydropyrazino[1,2-a][1,5]benzodiazepin-7(1H)-yl)-2-(4-chlorophenyl)ethanone;
(3-benzyl-2,3,4,4a,5,6-hexahydropyrazino[1,2-a][1,5]benzodiazepin7(1H)-yl)(4-bromophenyl)methanone;
(3-benzyl-2,3,4,4a,5,6-hexahydropyrazino[1,2-a][1,5]benzodiazepin-7(1H)-yl)(pyridin-4-yl)methanone;
3-benzyl-7-[2-(4-chlorophenyl)ethyl]-1,2,3,4,4a,5,6,7-octahydropyrazino[1,2-a][1,5]benzodiazepine;
3,7-dibenzyl-1,2,3,4,4a,5,6,7-octahydropyrazino[1,2-a][1,5]benzodiazepine;
3-benzyl-7-(4-bromobenzyl)-1,2,3,4,4a,5,6,7-octahydropyrazino[1,2-a][1,5]benzodiazepine;
3-benzyl-7-(pyridin-4-ylmethyl)-1,2,3,4,4a,5,6,7-octahydropyrazino[1,2-a][1,5]benzodiazepine;
3-benzyl-7-methyl-1,2,3,4,4a,5,6,7-octahydropyrazino[1,2-a][1,5]benzodiazepine;
9-benzyl-5,6,7,7a,8,9,10,11-octahydropyrazino[1,2-d]pyrido[3,2-b][1,4]diazepine;
1-(9-benzyl-7,7a,8,9,10,11-hexahydropyrazino[1,2-d]pyrido[3,2-b][1,4]diazepin-5(6H)-yl)-2-(4-chlorophenyl)ethanone;
9-benzyl-5-[2-(4-chlorophenyl)ethyl]-5,6,7,7a,8,9,10,11-octahydropyrazino[1,2-d]pyrido[3,2-b][1,4]diazepine;
9-benzyl-5-methyl-5,6,7,7a,8,9,10,11-octahydropyrazino[1,2-d]pyrido[3,2-b][1,4]diazepine;
(9-benzyl-7,7a,8,9,10,11-hexahydropyrazino[1,2-d]pyrido[3,2-b][1,4]diazepin-5(6H)-yl)(2,2,3,3-tetramethylcyclopropyl)methanone;
9-benzyl-5-[(2,2,3,3-tetramethylcyclopropyl)methyl]-5,6,7,7a,8,9,10,11-octahydropyrazino[1,2-d]pyrido[3,2-b][1,4]diazepine;
5-(cyclopropylmethyl)-9-(4-fluorobenzyl)-5,6,7,7a,8,9,10,11-octahydropyrazino[1,2-d]pyrido[3,2-b][1,4]diazepine;
5-(cyclobutylmethyl)-9-(4-fluorobenzyl)-5,6,7,7a,8,9,10,11-octahydropyrazino[1,2-d]pyrido[3,2-b][1,4]diazepine;
5-[(2S)-azetidin-2-ylmethyl]-9-(4-fluorobenzyl)-5,6,7,7a,8,9,10,11-octahydropyrazino[1,2-d]pyrido[3,2-b][1,4]diazepine;
5-(azetidin-3-ylmethyl)-9-(4-fluorobenzyl)-5,6,7,7a,8,9,10,11-octahydropyrazino[1,2-d]pyrido[3,2-b][1,4]diazepine;
[5-(cyclopropylmethyl)-6,7,7a,8,10,11-hexahydropyrazino[1,2-d]pyrido[3,2-b][1,4]diazepin-9(5H)-yl](pyridin-3-yl)methanone; and
2-[2-(3-benzyl-2,3,4,4a,5,6-hexahydropyrazino[1,2-a][1,5]benzodiazepin-7(1H)-yl)-2-oxoethyl]pyridazin-3(2H)-one.

* * * * *